(12) United States Patent
Renslo et al.

(10) Patent No.: US 7,279,494 B2
(45) Date of Patent: Oct. 9, 2007

(54) ANTIMICROBIAL [3.1.0] BICYCLOHEXYLPHENYL-OXAZOLIDINONE DERIVATIVES AND ANALOGUES

(75) Inventors: Adam Renslo, Oakland, CA (US); Mikhail Fedor Gordeev, Castro Valley, CA (US); Dinesh Vinoobhai Patel, Fremont, CA (US); Hongwu Gao, Fremont, CA (US); Vara Prasad Venkata Nagendra Josyula, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 502 days.

(21) Appl. No.: 10/815,589

(22) Filed: Apr. 1, 2004

(65) Prior Publication Data
US 2005/0192325 A1 Sep. 1, 2005

Related U.S. Application Data

(60) Provisional application No. 60/461,134, filed on Apr. 9, 2003.

(51) Int. Cl.
*A61K 31/422* (2006.01)
*A61K 31/403* (2006.01)
*C07D 413/02* (2006.01)
*C07D 49/02* (2006.01)

(52) U.S. Cl. ............ 514/376; 514/378; 514/412; 514/443; 548/229; 548/243; 548/247

(58) Field of Classification Search ............ 514/376, 514/378; 548/229, 243
See application file for complete search history.

(56) References Cited

U.S. PATENT DOCUMENTS

| 4,235,871 | A | 11/1980 | Apahadjopoulos et al. ... 424/19 |
|---|---|---|---|
| 4,501,728 | A | 2/1985 | Geho et al. .................... 424/38 |
| 4,837,028 | A | 6/1989 | Allen ......................... 424/450 |
| 6,239,152 | B1 | 5/2001 | Gordeev et al. ............ 514/340 |
| 6,313,312 | B1 | 11/2001 | Banks et al. ................ 548/452 |
| 2002/0086900 | A1 | 7/2002 | Perrault et al. ............. 514/478 |
| 2004/0044052 | A1 | 3/2004 | Thomas et al. ............. 514/364 |

FOREIGN PATENT DOCUMENTS

| WO | WO95/07271 | 3/1995 |
|---|---|---|
| WO | WO97/30995 | 8/1997 |
| WO | WO98/54161 | 12/1998 |
| WO | WO99/64417 | 12/1999 |
| WO | WO 00/21960 | 4/2000 |
| WO | WO 01/46185 | 12/2000 |
| WO | WO 01/81350 | 11/2001 |
| WO | WO 02/06278 | 1/2002 |

*Primary Examiner*—Kamal A. Saeed
(74) *Attorney, Agent, or Firm*—Steve T. Zelson; Jason G. Tebbutt

(57) ABSTRACT

The present invention provides certain [3.1.0] bicyclic oxazolidinone derivatives of formula I

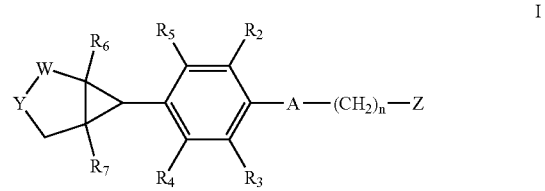

or pharmaceutically acceptable salts or prodrugs thereof that are antibacterial agents, pharmaceutical compositions containing them, methods for their use, and methods for preparing these compounds.

31 Claims, No Drawings

ANTIMICROBIAL [3.1.0] BICYCLOHEXYLPHENYL-OXAZOLIDINONE DERIVATIVES AND ANALOGUES

CROSS REFERENCE TO RELATED APPLICATIONS

This application claims the benefit of the following provisional application: Application Ser. No. 60/461,134 filed Apr. 9, 2003 under 35 U.S.C. 119(e)(1).

This Application claims benefit under 35 U.S.C. § 119 of U.S. application Ser. No. 60/461,134, filed Apr. 9, 2003.

FIELD OF THE INVENTION

This invention relates to novel [3.1.0]bicyclohexyl phenyloxazolidinone derivatives, pharmaceutical compositions thereof, methods for their use, and methods for preparing the bicyclic derivatives. These compounds display potent activities against gram-positive and/or gram-negative bacteria.

BACKGROUND

Due to ever-increasing antibiotic resistance, structurally novel antibacterials with a new mode of action have become increasingly important in the treatment of bacterial infections. Effective antibacterials should exhibit potent activity against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*. The present invention provides structurally novel pharmaceutical compounds with expanded spectrum of antibacterial activity.

Among newer antibacterial agents, oxazolidinone compounds are the most recent synthetic class of antimicrobials active against a number of pathogenic microorganisms. However, oxazolidinones generally do not demonstrate useful levels of activity against aerobic gram-negative organisms. Thus, the use of these oxazolidinone antibacterial agents is limited to infectious states caused by gram-positive bacteria. We have now discovered that [3.1.0] bicyclohexylphenyl oxazolidinone derivatives and analogues of the present invention possess enhanced anti-gram-positive activity and/or expand the spectrum of antimicrobial activity to include gram-negative organisms such as *Haemophilus influenza* and *Moraxella catarrhalis*.

SUMMARY OF THE INVENTION

The present invention relates to novel [3.1.0]bicyclohexyl phenyl-oxazolidinone derivatives that display potent activities against gram-positive and/or gram-negative bacteria. The present invention also relates pharmaceutical compositions, methods of use, and methods for preparing these [3.1.0]bicyclohexyl phenyloxazolidinone derivatives.

In one of its composition aspects, the present invention provides a compound of Formula I

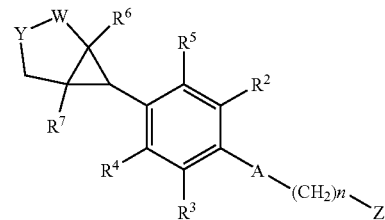

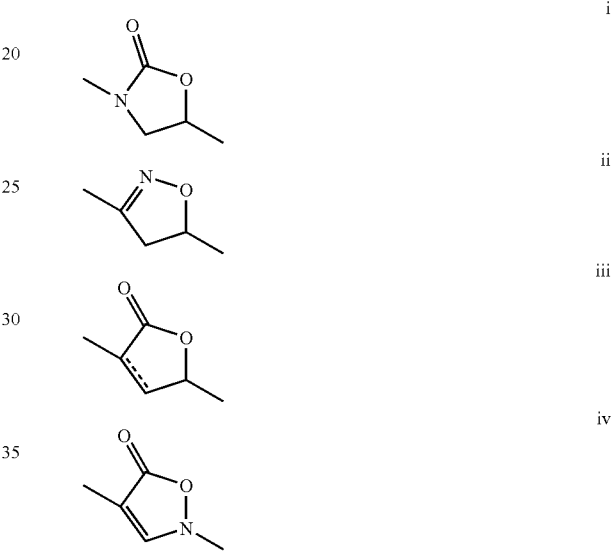

or a pharmaceutically acceptable salts thereof;
wherein A is a structure i, ii, iii, or iv wherein the dashed line in formula iii represents an optional double bond;
n is an integer equal to 0 or 1;
Y is —$SO_m$—, —O— or —$N(R^8)$—; where m is an integer equal to 0, 1, or 2;
Z is —$C(=Q)R^1$, —$NHC(=Q)R^1$, —$C(=Q)NHR^1$, —$NHC(=NCN)R^1$, —$NHC(=NNO_2)R^1$, —$SO_2R^1$, —$NH_2$, —NH-$het^1$, —O-$het^1$, —S-$het^1$, or -$het^2$;
Q is oxygen or sulfur;
W is —$CH_2$—, —C(=O)—, —C(=NOH)—, or —C(=NOC$_{1-4}$alkyl)-;
$R^1$ is —H, OH, —$NH_2$, —NHC$_{1-4}$alkyl, —C$_{1-4}$alkyl, —C$_{2-4}$alkenyl, —(CH$_2$)$_p$C(=O)C$_{1-4}$alkyl, —OC$_{1-4}$alkyl, —SC$_{1-4}$alkyl, —(CH$_2$)$_p$C$_{3-6}$cycloalkyl, —CH=CH-aryl, —CH=CH-$het^1$, —CH$_2$C(=O)-aryl, or —CH$_2$C(=O)-$het^1$;
$R^2$ and $R^3$ are independently —H or —F;
$R^4$ and $R^5$ are independently —H, —Cl, —F, —CH$_3$, —NH$_2$, or —OH;
$R^6$ and $R^7$ are independently —H or —C$_{1-4}$alkyl;
$R^8$ is independently —H, —OH, —CN, —NR$^9$R$^{10}$, —C$_{1-4}$ alkyl, —C$_{3-6}$cycloalkyl, —C$_{1-4}$heteroalkyl, -aryl, -$het^1$, —C$_{1-4}$alkylNR$^9$R$^{10}$, —(CH$_2$)$_p$C(=O)C$_{1-4}$alkyl, —(CH$_2$)$_p$C(=O)C$_{3-6}$cycloalkyl, —(CH$_2$)$_p$C(=O)C$_{1-4}$heteroalkyl, —C(=O)H, —(CH$_2$)$_p$C(=O)OR$^9$, —C(=O)(CH$_2$)$_p$OR$^9$, —(CH$_2$)$_p$C(=O)C$_{1-4}$alkylOR$^9$, —(CH$_2$)$_p$C (=O)(CH$_2$)$_p$NR$^9$R$^{10}$, —(CH$_2$)$_p$C(=O)NR$^9$OR$^{10}$, —(CH$_2$)$_p$CH(=NOC$_{1-4}$alkyl), —(CH$_2$)$_p$C(=O)het$^1$, —C(=O)(CH$_2$)$_p$het$^2$, —(CH$_2$)$_p$C(=NOC$_{1-4}$alkyl)C$_{1-4}$alkyl, —(CH$_2$)$_p$C(=NOC$_{1-4}$alkyl)het$^1$, —(CH$_2$)$_p$—SO$_2$—C$_{1-4}$alkyl, —(CH$_2$)$_p$—SO$_2$—NR$^9$R$^{10}$ —(CH$_2$)$_p$—SO$_2$-het$^1$, CONHR$^9$, or (R$^{11}$=)C—NR$^{12}$R$^{12}$;

each R$^9$ and R$^{10}$ are independently —H, —C$_{1-4}$alkyl, —C$_{3-6}$cycloalkyl, -aryl, -het, —C(=O)C$_{1-4}$alkyl, —C(=O)NHC$_{1-4}$alkyl, —C(=O)aryl, —C(=O)het$^1$, —SO$_2$C$_{1-4}$alkyl, or —SO$_2$NH$_2$;

R$^{11}$ is —NH, —NCN, or —CHNO$_2$;

each R$^{12}$ is independently H, or C$_{1-3}$alkyl;

p is an integer equal to 0, 1 or 2;

at each occurrence, —C$_{1-4}$alkyl or —C$_{3-6}$cycloalkyl is optionally substituted by one to three halo, hydroxy, —CN, —OC$_{1-2}$alkyl, aryl or a heterocyclic group;

and with the proviso that when Y is —O— or —SO$_m$—, then W is —CH$_2$—.

In another of its composition aspects, the present invention provides for pharmaceutical compositions comprising a compound of Formula I, or a pharmaceutically acceptable salt thereof, and a pharmaceutically acceptable carrier.

In one of its method aspects, the present invention provides for methods for the treatment of a microbial infection in a mammal by administering to the mammal an effective amount of the compound of Formula I. The compound of Formula I may be administered to the mammal in a pharmaceutical composition either orally, parenterally, transdermally, or topically. The compound may be administered in an amount of from about 0.1 to about 100 mg/kg of body weight/day. The compound may also be administered in an amount of from about 1 to about 50 mg/kg of body weight/day.

In another of its method aspects, the present invention provides for a method for treating gram-negative microbial infections in humans or other warm-blooded animals by administering to the subject in need thereof a therapeutically effective amount of a compound of Formula I, or a pharmaceutically acceptable salt thereof. The compound of Formula I may be administered to the mammal in a pharmaceutical composition either orally, parenterally, transdermally, or topically. The compound of Formula I may be administered in an amount of from about 0.1 to about 100 mg/kg of body weight/day, or in an amount of from about 1 to about 50 mg/kg of body weight/day.

The present invention also provides novel intermediates and processes that are useful for preparing compounds of Formula I.

DETAILED DESCRIPTION OF THE INVENTION

Unless otherwise stated, the following terms used in the specification and claims have the meanings given below:

The carbon atom content of various hydrocarbon-containing moieties is indicated by a prefix designating the minimum and maximum number of carbon atoms in the moiety, i.e., the prefix C$_{i-j}$ indicates a moiety of the integer "i" to the integer "j" carbon atoms, inclusive. Thus, for example, C$_{1-7}$ alkyl refers to alkyl of one to seven carbon atoms, inclusive.

The terms alkyl, alkenyl, etc. refer to both straight and branched groups, but reference to an individual radical such as "propyl" embraces only the straight chain radical, a branched chain isomer such as "isopropyl" being specifically referred to. Unless defined otherwise, the term "alkyl" refers to alkyl groups of from 1 to 6 carbon atoms and the term "alkenyl" refers to alkenyl groups of from 2 to 6 carbon atoms. The alkyl, alkenyl, etc. group may be optionally substituted with one, two, or three substituents, such as, halo, hydroxy, —CN, alkoxy, amino, aryl, het$^1$, or het$^2$. In addition, the functional groups on an alkyl group may optionally be protected using protecting groups well known in the art, such as Boc, Cbz, and the like. For examples of protecting groups and procedures for their introduction and removal see one of the general texts on the subject such as "Protecting Groups" by Philip J. Kocienski (publisher: Georg Thieme Verlag: Stuttgart, 1994). Representative examples of alkyl groups include, but are not limited to, difluoromethyl, 2-fluoroethyl, CF$_3$, —CH=CH-aryl, —CH=CH-het$^1$, —CH$_2$-phenyl, —CH$_2$—OH, —CH$_2$—NHCbz, and the like.

The term "alkoxy" refers to the group —O-alkyl, where alkyl is defined herein above.

The term "cycloalkyl" means a cyclic saturated monovalent hydrocarbon group of three to seven carbon atoms, e.g., cyclopropyl, cyclohexyl, and the like. The cycloalkyl group may be be optionally substituted with one, two, or three substituents, such as, halo, hydroxy, —CN, alkoxy, amino, aryl, het$^1$, or het$^2$. In addition, the functional groups on a cycloalkyl group may optionally be protected using protecting groups well known in the art, such as Boc, Cbz, and the like. For examples of protecting groups and procedures for their introduction and removal see one of the general texts on the subject such as "Protecting Groups" by Philip J. Kocienski (publisher: Georg Thieme Verlag: Stuttgart, 1994).

The term "heteroalkyl" means an alkyl or cycloalkyl group, as defined above, having at least one atom replaced by a heteroatom selected from N, O, or S(O)$_q$, where q is 0, 1 or 2. The heteroalkyl group may be be optionally substituted with one, two, or three substituents, such as, halo, hydroxy, alkoxy, amino, thio, aryl, het$^1$, or het$^2$. In addition, the functional groups on a heteroalkyl group may optionally be protected using protecting groups well known in the art, such as Boc, Cbz, and the like. For examples of protecting groups and procedures for their introduction and removal see one of the general texts on the subject such as "Protecting Groups" by Philip J. Kocienski (publisher: Georg Thieme Verlag: Stuttgart, 1994). In addition, the heteroalkyl group may be optionally substituted with substituents, including —NR$^a$R$^b$, —OR$^a$, or —S(O)$_q$R$^c$, wherein R$^a$ is hydrogen, alkyl, cycloalkyl, optionally substituted aryl, optionally substituted heterocyclic, or —COR (where R is alkyl); R$^b$ is hydrogen, alkyl, —SO$_2$R (where R is alkyl or hydroxyalkyl), —SO$_2$NRR' (where R and R' are independently of each other hydrogen or alkyl), —CONR'R" (where R' and R" are independently of each other hydrogen or alkyl); q is an integer from 0 to 2; and R$^c$ is hydrogen, alkyl, cycloalkyl, optionally substituted aryl, optionally substituted heterocyclic, or —NR$^a$R$^b$ where R$^a$ and R$^b$ are as defined above. Representative examples include, but are not limited to 2-methoxyethyl(—CH$_2$CH$_2$OCH$_3$), 2-hydroxyethyl(—CH$_2$CH$_2$OH), 2,3-dihydroxypropanoyl(—CH(OH)CH$_2$OH), hydroxymethyl(—CH$_2$OH), 2-aminoethyl(—CH$_2$CH$_2$NH$_2$), 2-dimethylaminoethyl(—CH$_2$CH$_2$NHCH$_3$), 2-morpholinoethyl, benzyloxymethyl, and the like.

The term "halo" refers to the halogens, such as fluoro (F), chloro (Cl), bromo (Br), or iodo (I).

Aryl refers to phenyl, biphenyl, or naphthyl, optionally substituted with halo, —C$_{1-4}$ alkyl, —OH, —OC$_{1-4}$ alkyl, —S(O)$_q$C$_{1-4}$alkyl wherein q is 0, 1, or 2, —C$_{1-4}$alkylNH$_2$, —C(=O)H, or —C=N—OR$^d$ wherein R$^d$ is hydrogen or alkyl.

The term heterocyclic group or ring refers to an aromatic ring or a saturated or unsaturated ring that is not aromatic of 1 to 10 carbon atoms and 1 to 4 heteroatoms selected from the group consisting of oxygen, nitrogen, and sulfur within the ring. The heterocyclic ring may be optionally substituted with halo, —$C_{1-4}$alkyl, —OH, —$OC_{1-4}$ alkyl, —$S(O)_qC_{1-4}$alkyl wherein q is 0, 1, or 2, —$C_{1-4}$alkyl$NH_2$, —C(=O)H, or —C=N—$OR^d$ wherein $R^d$ is hydrogen or alkyl. In addition, one of the carbon atoms of the heterocyclic ring may optionally be replaced by >C=O or >C=S. Examples of heterocyclic rings include, but are not limited to, azetidine, pyrrole, imidazole, pyrazole, 1,2,3-triazole, 1,3,4-triazole, oxazole, thiazole, isoxazole, isothiazole, 1,3,4-oxadiazole, 1,3,4-thiadiazole, 1,2,3-thiadiazole, tetrazole, pyridine, pyrazine, pyrimidine, pyridazine, indolizine, isoindole, indole, dihydroindole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, isoxazolinone, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazole tetrazole, thiazolidine, thiophene, benzo[b]thiophene, morpholine, thiomorpholine, (also referred to as thiamorpholine,), piperidine, pyrrolidine, tetrahydrofuran, and the like.

Specifically, het[1] refers to a C-linked five-(5) or six-(6) membered heterocyclic ring, which is optionally substituted on an available carbon atom with one or two substituents independently selected from $C_{1-4}$alkyl, $OC_{1-4}$alkyl, amino, $C_{1-4}$alkyl$NR^aR^b$, (where $R^a$ and $R^b$ are as defined above) and halogen and/or on an available nitrogen atom (provided that the ring is not thereby quaternized) with $C_{1-4}$alkyl. Representative examples of "het[1]" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxaz-olyl, 4-isoxaz-olyl, 5-isoxaz-olyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 2-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone Specifically, het[2] refers to a C-linked or N-linked five-(5) or six-(6) membered heterocyclic ring having 1 to 4 nitrogen atoms, and optionally having one oxygen or sulfur atom, and optionally substituted on an available carbon atom with one or two substituents independently selected from halogen, cyano, nitro, azido, formyl, —$C_{1-4}$alkyl, —$OC_{1-4}$alkyl, —$C_{2-4}$alkenyl, —$OC_{2-4}$alkenyl, —C(=O)$C_{1-4}$alkyl, —$C_{3-6}$cycloalkyl, —$OC_{3-6}$cycloalkyl, —$C_{1-4}$heteroalkyl, —$NR^aR^b$, —$NR^aC(=O)C_{1-4}$alkyl, or —$NR^aC(=O)OC_{1-4}$alkyl where $R^a$ and $R^b$ are as defined herein. Representative examples of "het[2]" include, but are not limited to, pyrrolyl, imidazolyl, pyrazolyl, 1,2,3-triazolyl, 1,2,4-triazolyl, 1,2,3,4-tetrazolyl, and isoxazolidinonyl group.

A C-linked heterocyclic ring is a heterocyclic group as defined above wherein the group is attached via a carbon atom of the heterocyclic ring.

An N-linked heterocyclic ring is a heterocyclic group as defined above wherein the group is attached via a nitrogen atom of the heterocyclic ring.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)- stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry i.e., an atom or group capable of being displaced by a nucleophile and includes halogen, alkylsulfonyloxy, ester, or amino such as chloro, bromo, iodo, mesyloxy, tosyloxy, trifluorosulfonyloxy, methoxy, N,O-dimethylhydroxyl-amino, and the like.

"Pro-drugs" mean any compound that releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of the subject invention, and the like.

Mammal refers to human or warm-blooded animals including livestock and companion animals.

The compounds of the present invention are generally named according to the IUPAC or CAS nomenclature systems. Abbreviations which are well known to one of ordinary skill in the art may be used (e.g. "Ph" for phenyl, "Me" for methyl, "Et" for ethyl, "Ac" for "acetyl" "h" for hour or hours and "rt" for room temperature).

ILLUSTRATIVE EMBODIMENTS

Within the broadest definition of the present invention, certain compounds of the compounds of formula I may be preferred. Specific and preferred values listed below for radicals, substituents, and ranges, are for illustration only; they do not exclude other defined values or other values within defined ranges for the radicals and substituents.

Specifically the term $C_{1-4}$alkyl can be methyl, ethyl, propyl, isopropyl, butyl, iso-butyl, sec-butyl, and their isomeric forms thereof.

Specifically, $C_{2-4}$alkenyl can be vinyl, propenyl, allyl, butenyl, and their isomeric forms thereof.

Specifically, $C_{3-6}$cycloalkyl can be cyclopropyl, cyclobutyl, cyclopentyl, cyclohexyl, and their isomeric forms thereof.

Specifically, $C_{1-4}$heteroalkyl can be hydroxymethyl, 2-hydroxyethyl, 2-methoxyethyl, 2-morpholinoethyl.

Specifically, Z is —NH(=Q)$R^1$, wherein Q is O or S.

Specifically, Z is —C(=O)$NH_2$.

Specifically, $R^1$ is $C_{1-4}$alkyl, optionally substituted with one, two, or three fluoro (F) or chloro (Cl).

Specifically, $R^1$ is $C_{1-4}$alkyl or $C_{3-6}$cycloalkyl, optionally substituted with —OH, or —CN.

Specifically, $R^1$ is —$CH_3$, —$CHF_2$, —$CF_3$, —$CHCl_2$, —$CH_2CF_3$, —$CH_2CH_3$, —$CH_2CHF_2$, or —$CH_2CH_2F$.

Specifically, $R^1$ is —CH=CH-aryl.

Specifically, $R^1$ is —CH=CH-$het^1$.

Specifically, $R^1$ is —$CH_2$C(=O)$C_{1-4}$alkyl.

Specifically, $R^2$ and $R^3$ are —H.

Specifically, $R^4$ and $R^5$ are independently —H or —F.

Specifically, $R^6$ and $R^7$ are —H.

Specifically, W is —$CH_2$—.

Specifically, Y is —N($R^8$)—.

Specifically, $R^8$ is —C(=O)$(CH_2)_p$O$R^9$.

Specifically, $R^8$ is C(=O)$C_{1-4}$alkyl, wherein alkyl is optionally substituted with one, two, or three OH, F, or CN.

Specifically, $R^8$ is —$(CH_2)_p$C(=O)$C_{3-6}$cycloalkyl, wherein $C_{3-6}$cycloalkyl is optionally substituted with one, two, or three OH, F, or CN.

Specifically, $R^8$ is —$(CH_2)_p$C(=O)$(CH_2)_p$N$R^9R^{10}$.

Specifically, $R^8$ is —C(=O)$CH_2$OH or —C(=O)CH(OH)$CH_2$OH.

Specifically, $R^8$ is H.

Specifically, $R^8$ is —C(=O)H.

Specifically, $R^8$ is —C(=O)$het^1$.

Specifically, $R^8$ is $het^1$.

Specifically, $R^8$ is —C(=O)$(CH_2)_p$$het^2$,

Specifically, $R^8$ is ($R^{11}$=)C—N$R^{12}R^{12}$;

Specifically, $R^9$ and R10 is independently H, $C_{1-4}$alkyl or —C(=O)$C_{1-4}$alkyl.

Specifically, $R^{11}$ is —NH, —NCN, or —$CHNO_2$; and each $R^{12}$ is independently H, or $C_{1-3}$alkyl.

Specifically, Y is —S—, —SO—, —$SO_2$— or —O—.

Specifically, $het^1$ is isoxazolyl, 1,2,5-thiadiazolyl, or pyridyl.

Specifically, $het^2$ is 1,2,3-triazolyl.

Specific compounds of the present invention are those wherein structure i, ii, or iii has an optical configuration as depicted below:

i

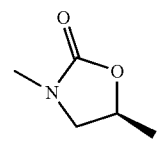

-continued

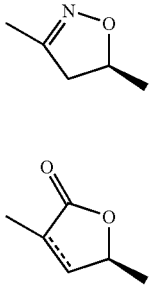

The dotted line within structure iii indicates an optional double bond at that position. It will be appreciated by those skilled in the art that compounds of the present invention may have additional chiral centers and, as such, can be isolated in optically active and racemic forms. The present invention encompasses any racemic, optically active, tautomeric, or stereoisomeric form, or mixture thereof, of a compound of the invention.

Other specific compounds of the present invention are the compounds of Formula II:

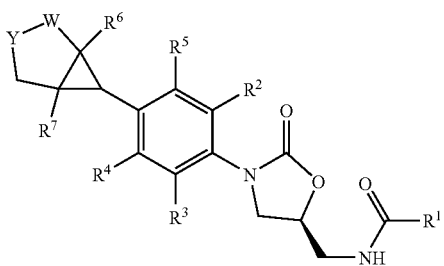

II.

Other specific compounds of the present invention are the compounds of Formula III:

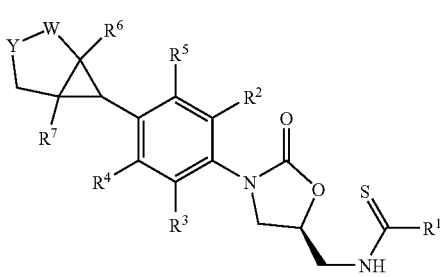

III.

Other specific compounds of the present invention are the compounds of Formula IV:

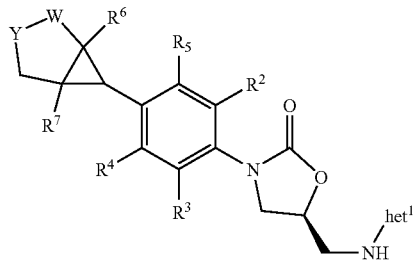

IV.

Other specific compounds of the present invention are the compounds of Formula V

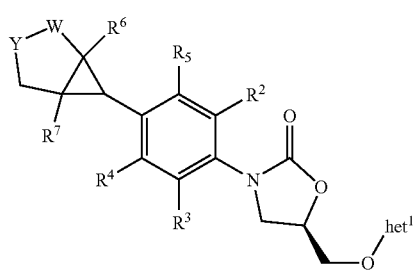

V.

Other specific compounds of the present invention are the compounds of Formula VI:

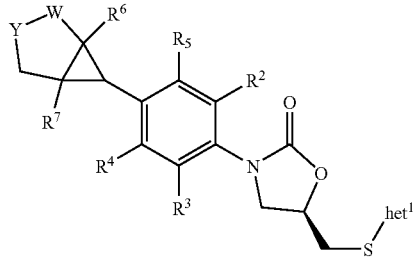

VI.

Other specific compounds of the present invention are the compounds of Formula VII:

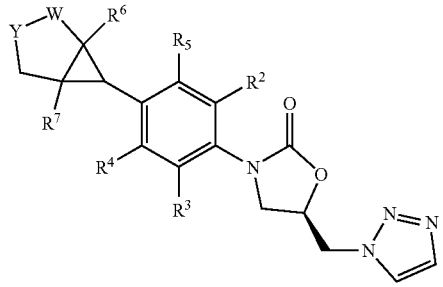

VII.

Other specific compounds of the present invention are the compounds of Formula VIII:

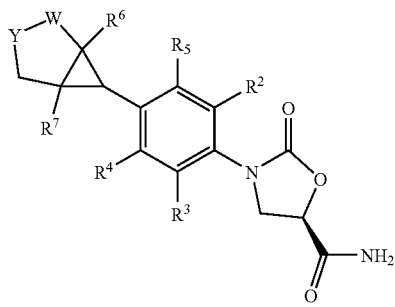

VIII.

Examples of the presention invention includes the following compounds:

N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide;

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide;

N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]acetamide;

N-[((5S)-3-{3-fluoro-4-[exo-(1R,5S)-3-oxabicyclo[3.1.0]hex-6-yl]phenyl}-2-oxo-1,3-oxazolidin-5-yl)methyl]acetamide;

N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]acetamide;

2,2-difluoro-N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]ethanethioamide;

methyl exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxylate;

N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]acetamide;

N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]acetamide;

exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxamide;

exo-(1R,5S)-6-[4-((5S)-5-{[(2,2-difluoroethanethioyl)amino]methyl}-2-oxo-1,3-oxazolidin-3-yl)-2-fluorophenyl]-3-azabicyclo[3.1.0]hexane-3-carboxamide;

N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide;

N-[((5S)-3-{4-[exo-(1R,5S)-3,3-dioxido-3-thiabicyclo[3.1.0]hex-6-yl]-3,5-difluorophenyl}-2-oxo-1,3-oxazolidin-5-yl)methyl]acetamide;

N-[((5S)-3-{3,5-difluoro-4-[exo-(1R,5S)-3-oxabicyclo[3.1.0]hex-6-yl]phenyl}-2-oxo-1,3-oxazolidin-5-yl)methyl]acetamide;

N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]acetamide;

N-[((5S)-3-{4-[exo-(1R,5S)-3-oxabicyclo[3.1.0]hex-6-yl]phenyl}-2-oxo-1,3-oxazolidin-5-yl)methyl]acetamide;

N-[((5S)-3-{4-[exo-(1R,5S)-3-glycoloyl-3-azabicyclo[3.1.0]hex-6-yl]phenyl}-2-oxo-1,3-oxazolidin-5-yl)methyl]acetamide;

N-[((5S)-3-{4-[exo-(1R,5S)-3-oxido-3-thiabicyclo[3.1.0]hex-6-yl]phenyl}-2-oxo-1,3-oxazolidin-5-yl)methyl]acetamide;

N-[((5S)-3-{4-[exo-(1R,5S)-3,3-dioxido-3-thiabicyclo[3.1.0]hex-6-yl]phenyl}-2-oxo-1,3-oxazolidin-5-yl)methyl]acetamide;

(5R)-3-{4-[exo-(1R,5S)-3,3-dioxido-3-thiabicyclo[3.1.0]hex-6-yl]-3-fluorophenyl}-2-oxo-1,3-oxazolidine-5-carboxamide;

(5R)-3-{4-[exo-(1R,5S)-3,3-dioxido-3-thiabicyclo[3.1.0]hex-6-yl]-3-fluorophenyl}-N-methyl-2-oxo-1,3-oxazolidine-5-carboxamide;

(5R)-3-{4-[exo-(1R,5S)-3,3-dioxido-3-thiabicyclo[3.1.0]hex-6-yl]-3,5-difluorophenyl}-2-oxo-1,3-oxazolidine-5-carboxamide;

(5R)-3-{4-[exo-(1R,5S)-3,3-dioxido-3-thiabicyclo[3.1.0]hex-6-yl]-3,5-difluorophenyl}-N-methyl-2-oxo-1,3-oxazolidine-5-carboxamide;

(5R)-N-ethyl-3-{4-[exo-(1R,5S)-3,3-dioxido-3-thiabicyclo[3.1.0]hex-6-yl]-3,5-difluorophenyl}-2-oxo-1,3-oxazolidine-5-carboxamide;

(5R)-N-(2-fluoroethyl)-3-{4-[exo-(1R,5S)-3,3-dioxido-3-thiabicyclo[3.1.0]hex-6-yl]-3,5-difluorophenyl}-2-oxo-1,3-oxazolidine-5-carboxamide;

(5R)-3-{4-[exo-(1R,5S)-3,3-dioxido-3-thiabicyclo[3.1.0]hex-6-yl]phenyl}-2-oxo-1,3-oxazolidine-5-carboxamide;

(5R)-3-{3-fluoro-4-[exo-(1R,5S)-3-oxido-3-thiabicyclo[3.1.0]hex-6-yl]phenyl}-2-oxo-1,3-oxazolidine-5-carboxamide;

(5R)-3-{3-fluoro-4-[exo-(1R,5S)-3-oxido-3-thiabicyclo[3.1.0]hex-6-yl]phenyl}-N-methyl-2-oxo-1,3-oxazolidine-5-carboxamide;

(5R)-3-{3,5-difluoro-4-[exo-(1R,5S)-3-oxido-3-thiabicyclo[3.1.0]hex-6-yl]phenyl}-2-oxo-1,3-oxazolidine-5-carboxamide;

(5R)-3-{3,5-difluoro-4-[exo-(1R,5S)-3-oxido-3-thiabicyclo[3.1.0]hex-6-yl]phenyl}-N-methyl-2-oxo-1,3-oxazolidine-5-carboxamide;

(5R)-N-ethyl-3-{3,5-difluoro-4-[exo-(1R,5S)-3-oxido-3-thiabicyclo[3.1.0]hex-6-yl]phenyl}-2-oxo-1,3-oxazolidine-5-carboxamide;

(5R)-3-{4-[exo-(1R,5S)-3-oxido-3-thiabicyclo[3.1.0]hex-6-yl]phenyl}-2-oxo-1,3-oxazolidine-5-carboxamide;

(5R)-3-{3-fluoro-4-[exo-(1R,5S)-3-thiabicyclo[3.1.0]hex-6-yl]phenyl}-2-1,3-oxazolidine-5-carboxamide;

(5R)-3-{3,5-difluoro-4-[exo-(1R,5S)-3-thiabicyclo[3.1.0]hex-6-yl]phenyl}-2-oxo-1,3-oxazolidine-5-carboxamide;

(5R)-3-{4-[exo-(1R,5S)-3-thiabicyclo[3.1.0]hex-6-yl]phenyl}-2-oxo-1,3-oxazolidine-5-carboxamide;

(5R)-3-{3-fluoro-4-[exo-(1R,5S)-3-glycoloyl-3-azabicyclo[3.1.0]hex-6-yl]phenyl}-2-oxo-1,3-oxazolidine-5-carboxamide;

(5R)-3-{3-fluoro-4-[exo-(1R,5S)-3-glycoloyl-3-azabicyclo[3.1.0]hex-6-yl]phenyl}-N-methyl-2-oxo-1,3-oxazolidine-5-carboxamide;

(5R)-3-{3,5-difluoro-4-[exo-(1R,5S)-3-glycoloyl-3-azabicyclo[3.1.0]hex-6-yl]phenyl}-2-oxo-1,3-oxazolidine-5-carboxamide;

(5R)-3-{3,5-difluoro-4-[exo-(1R,5S)-3-glycoloyl-3-azabicyclo[3.1.0]hex-6-yl]phenyl}-N-methyl-2-oxo-1,3-oxazolidine-5-carboxamide;

(5R)-3-{3-fluoro-4-[exo-(1R,5S)-3-oxabicyclo[3.1.0]hex-6-yl]phenyl}-2-oxo-1,3-oxazolidine-5-carboxamide;

(5R)-3-{3-fluoro-4-[exo-(1R,5S)-3-oxabicyclo[3.1.0]
hex-6-yl]phenyl}-N-methyl-2-oxo-1,3-oxazolidine-5-carboxamide;

(5R)-3-{3,5-difluoro-4-[exo-(1R,5S)-3-oxabicyclo[3.1.0]
hex-6-yl]phenyl}-2-oxo-1,3-oxazolidene-5-carboxamide;

(5R)-3-{3,5-difluoro-4-[exo-(1R,5S)-3-oxabicyclo[3.1.0]
hex-6-yl]phenyl}-N-methyl-2-oxo-1,3-oxazolidine-5-carboxamide;

N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]propanamide;

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide;

N-[((5S)-3-{4-[exo-(1R,5S)-3,3-dioxido-3-thiabicyclo[3.1.0]hex-6-yl]-3,5-difluorophenyl}-2-oxo-1,3-oxazolidin-5-yl)methyl]propanamide;

N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]propanamide;

N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]propanamide;

N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]propanamide;

N-[((5S)-3-{3,5-difluoro-4-[exo-(1R,5S)-3-oxabicyclo[3.1.0]hex-6-yl]phenyl}-2-oxo-1,3-oxazolidin-5-yl)methyl]propanamide;

N-[((5S)-3-{3-fluoro-4-[exo-(1R,5S)-3-oxabicyclo[3.1.0]hex-6-yl]phenyl}-2-oxo-1,3-oxazolidin-5-yl)methyl]propanamide;

(5R)-3-{3-fluoro-4-[exo-(1R,5S)-3-oxido-3-thiabicyclo[3.1.0]hex-6-yl]phenyl}-5-(1H-1,2,3-triazol-1-ylmethyl)-1,3-oxazolidin-2-one;

(5R)-3-{3,5-difluoro-4-[exo-(1R,5S)-3-oxido-3-thiabicyclo[3.1.0]hex-6-yl]phenyl}-5-(1H-1,2,3-triazol-1-ylmethyl)-1,3-oxazolidin-2-one;

(5R)-3-{4-[exo-(1R,5S)-3,3-dioxido-3-thiabicyclo[3.1.0]hex-6-yl]-3-fluorophenyl}-5-(1H-1,2,3-triazol-1-ylmethyl)-1,3-oxazolidin-2-one;

(5R)-3-{4-[exo-(1R,5S)-3,3-dioxido-3-thiabicyclo[3.1.0]hex-6-yl]-3,5-difluorophenyl}-5-(1H-1,2,3-triazol-1-ylmethyl)-1,3-oxazolidin-2-one;

(5R)-3-{3-fluoro-4-[exo-(1R,5S)-3-glycoloyl-3-azabicyclo[3.1.0]hex-6-yl]phenyl}-5-(1H-1,2,3-triazol-1-ylmethyl)-1,3-oxazolidin-2-one;

(5R)-3-{3,5-difluoro-4-[exo-(1R,5S)-3-glycoloyl-3-azabicyclo[3.1.0]hex-6-yl]phenyl}-5-(1H-1,2,3-triazol-1-ylmethyl)-1,3-oxazolidin-2-one;

(5R)-3-{3-fluoro-4-[exo-(1R,5S)-3-oxabicyclo[3.1.0]hex-6-yl]phenyl}-5-(1H-1,2,3-triazol-1-ylmethyl)-1,3-oxazolidin-2-one;

(5R)-3-{3,5-difluoro-4-[exo-(1R,5S)-3-oxabicyclo[3.1.0]hex-6-yl]phenyl}-5-(1H-1,2,3-triazol-1-ylmethyl)-1,3-oxazolidin-2-one;

N-[((5S)-3-{3-fluoro-4-[(1S,5R,6R)-2-oxo-3-azabicyclo[3.1.0]hex-6-yl]phenyl}-2-oxo-1,3-oxazolidin-5-yl)methyl]acetamide;

N-[((5S)-3-{3,5-difluoro-4-[(1S,5R,6R)-2-oxo-3-azabicyclo[3.1.0]hex-6-yl]phenyl}-2-oxo-1,3-oxazolidin-5-yl)methyl]acetamide;

(5R)-3-{3-fluoro-4-[(1S,5R,6R)-2-oxo-3-azabicyclo[3.1.0]hex-6-yl]phenyl}-2-oxo-1,3-oxazolidine-5-carboxamide;

(5R)-3-{3,5-difluoro-4-[(1S,5R,6R)-2-oxo-3-azabicyclo[3.1.0]hex-6-yl]phenyl}-2-oxo-1,3-oxazolidine-5-carboxamide;

(1S,5R,6R)-6-{2-fluoro-4-[(5R)-2-oxo-5-(1H-1,2,3-triazol-1-ylmethyl)-1,3-oxazolidin-3-yl]phenyl}-3-azabicyclo[3.1.0]hexan-2-one;

(1S,5R,6R)-6-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexan-2-one;

N-{[4-{4-[exo-(1R,5S)-3,3-dioxido-3-thiabicyclo[3.1.0]hex-6-yl]-3,5-difluorophenyl}-5-oxoisoxazol-2(5H)-yl]methyl}acetamide;

and pharmaceutically acceptable salts thereof.

Particularly, examples of the present invention includes the following compounds:

(1) N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide, (2) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide, (3) N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]acetamide, (4) N-[((5S)-3-{3-fluoro-4-[exo-(1R,5S)-3-oxabicyclo[3.1.0]hex-6-yl]phenyl}-2-oxo-1,3-oxazolidin-5-yl)methyl]acetamide, (5) N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]acetamide, (6) 2,2-difluoro-N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]ethanethioamide, (7) methyl exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxylate, (8) N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]acetamide, (9) N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]acetamide,

(10) exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxamide,

(11) exo-(1R,5S)-6-[4-((5S)-5-{[(2,2-difluoroethanethioyl)amino]methyl}-2-oxo-1,3-oxazolidin-3-yl)-2-fluorophenyl]-3-azabicyclo[3.1.0]hexane-3-carboxamide,

(12) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide,

(13) N-[((5S)-3-{4-[exo-(1R,5S)-3,3-dioxido-3-thiabicyclo[3.1.0]hex-6-yl]-3,5-difluorophenyl}-2-oxo-1,3-oxazolidin-5-yl)methyl]acetamide,

(14) N-[((5S)-3-{3,5-difluoro-4-[exo-(1R,5S)-3-oxabicyclo[3.1.0]hex-6-yl]phenyl}-2-oxo-1,3-oxazolidin-5-yl)methyl]acetamide,

(15) N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]acetamide,

(16) N-[((5S)-3-{4-[exo-(1R,5S)-3-oxabicyclo[3.1.0]hex-6-yl]phenyl}-2-oxo-1,3-oxazolidin-5-yl)methyl]acetamide,

(17) N-[((5S)-3-{4-[exo-(1R,5S)-3-glycoloyl-3-azabicyclo[3.1.0]hex-6-yl]phenyl}-2-oxo-1,3-oxazolidin-5-yl)methyl]acetamide,

(18) N-[((5S)-3-{4-[exo-(1R,5S)-3-oxido-3-thiabicyclo[3.1.0]hex-6-yl]phenyl}-2-oxo-1,3-oxazolidin-5-yl)methyl]acetamide,
(19) N-[((5S)-3-{4-[exo-(1R,5S)-3,3-dioxido-3-thiabicyclo[3.1.0]hex-6-yl]phenyl}-2-oxo-1,3-oxazolidin-5-yl)methyl]acetamide,
(20) (5R)-3-{4-[exo-(1R,5S)-3,3-dioxido-3-thiabicyclo[3.1.0]hex-6-yl]-3-fluorophenyl}-2-oxo-1,3-oxazolidine-5-carboxamide,
(21) N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide,
(22) N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]propanamide,
(23) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-carboxamide,
(24) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-methylcarboxamide,
(25) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-ethylcarboxamide,
(26) N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]propanamide,
(27) N-[((5S)-3-{3-fluoro-4-[exo-(1R,5S)-3-methoxyacetyl-3-azabicyclo[3.1.0]hex-6-yl]phenyl}-2-oxo-1,3-oxazolidin-5-yl)methyl]propanamide,
(28) N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]propanamide,
(29) N-[((5S)-3-{3-fluoro-4-[exo-(1R,5S)-3-(2-(S)-hydroxypropanoyl)-3-azabicyclo[3.1.0]hex-6-yl]phenyl}-2-oxo-1,3-oxazolidin-5-yl)methyl]acetamide,
(30) N-[((5S)-3-{3-fluoro-4-[exo-(1R,5S)-3-cyclopropanecarbonyl-3-azabicyclo[3.1.0]hex-6-yl]phenyl}-2-oxo-1,3-oxazolidin-5-yl)methyl]acetamide,
(31) N-[((5S)-3-{3-fluoro-4-[exo-(1R,5S)-3-(1-hydroxy-cyclopropanecarbonyl)-3-azabicyclo[3.1.0]hex-6-yl]phenyl}-2-oxo-1,3-oxazolidin-5-yl)methyl]acetamide,
(32) N-[((5S)-3-{3-fluoro-4-[exo-(1R,5S)-3-(2-hydroxy-2-methyl-propanoyl)-3-azabicyclo[3.1.0]hex-6-yl]phenyl}-2-oxo-1,3-oxazolidin-5-yl)methyl]acetamide,
(33) N-[((5S)-3-{3-fluoro-4-[exo-(1R,5S)-3-(3,3,3-trifluoro-2-(S)-hydroxypropanoyl)-3-azabicyclo[3.1.0]hex-6-yl]phenyl}-2-oxo-1,3-oxazolidin-5-yl)methyl]acetamide,
(34) N-[((5S)-3-{3-fluoro-4-[exo-(1R,5S)-3-difluoroacetyl-3-azabicyclo[3.1.0]hex-6-yl]phenyl}-2-oxo-1,3-oxazolidin-5-yl)methyl]acetamide,
(35) N-[((5S)-3-{3-fluoro-4-[exo-(1R,5S)-3-aminoacetyl-3-azabicyclo[3.1.0]hex-6-yl]phenyl}-2-oxo-1,3-oxazolidin-5-yl)methyl]acetamide,
(36) N-[((5S)-3-{3-fluoro-4-[exo-(1R,5S)-3-acetylaminoacetyl-3-azabicyclo-[3.1.0]hex-6-yl]phenyl}-2-oxo-1,3-oxazolidin-5-yl)methyl]acetamide,
(37) N-[((5S)-3-{3-fluoro-4-[exo-(1R,5S)-3-(isoxazole-5-carbonyl)-3-azabicyclo[3.1.0]hex-6-yl]phenyl}-2-oxo-1,3-oxazolidin-5-yl)methyl]acetamide,
(38) N-[((5S)-3-{3-fluoro-4-[exo-(1R,5S)-3-(1H-pyrazole-3-carbonyl)-3-azabicyclo[3.1.0]hex-6-yl]phenyl}-2-oxo-1,3-oxazolidin-5-yl)methyl]acetamide,
(39) N-[((5S)-3-{3-fluoro-4-[exo-(1R,5S)-3-(1H-imidazole-4-carbonyl)-3-azabicyclo[3.1.0]hex-6-yl]phenyl}-2-oxo-1,3-oxazolidin-5-yl)methyl]acetamide,
(40) N-[((5S)-3-{3-fluoro-4-[exo-(1R,5S)-3-(1H-pyrazole-4-carbonyl)-3-azabicyclo[3.1.0]hex-6-yl]phenyl}-2-oxo-1,3-oxazolidin-5-yl)methyl]acetamide,
(41) N-[((5S)-3-{3-fluoro-4-[exo-(1R,5S)-3-(tetrahydrofuran-2-(R)-carbonyl)-3-azabicyclo[3.1.0]hex-6-yl]phenyl}-2-oxo-1,3-oxazolidin-5-yl)methyl]acetamide,
(42) N-[((5S)-3-{3-fluoro-4-[exo-(1R,5S)-3-(tetrahydrofuran-2-(S)-carbonyl)-3-azabicyclo[3.1.0]hex-6-yl]phenyl}-2-oxo-1,3-oxazolidin-5-yl)methyl]acetamide,
(43) N-[((5S)-3-{3-fluoro-4-[exo-(1R,5S)-3-(pyrimidin-2-yl)-3-azabicyclo[3.1.0]hex-6-yl]phenyl}-2-oxo-1,3-oxazolidin-5-yl)methyl]acetamide,
(44) N-[((5S)-3-{3-fluoro-4-[exo-(1R,5S)-3-(2H-tetrazol-5-yl)-3-azabicyclo[3.1.0]hex-6-yl]phenyl}-2-oxo-1,3-oxazolidin-5-yl)methyl]acetamide,
(45) N-[((5S)-3-{3-fluoro-4-[exo-(1R,5S)-3-(1-methyl-1H-tetrazol-5-yl)-3-azabicyclo[3.1.0]hex-6-yl]phenyl}-2-oxo-1,3-oxazolidin-5-yl)methyl]acetamide,
(46) N-[((5S)-3-{3-fluoro-4-[exo-(1R,5S)-3-(2-fluoroethyl)-3-azabicyclo[3.1.0]hex-6-yl]phenyl}-2-oxo-1,3-oxazolidin-5-yl)methyl]acetamide,
(47) N-[((5S)-3-{3-fluoro-4-[exo-(1R,5S)-3-(2-hydroxyethyl)-3-azabicyclo[3.1.0]hex-6-yl]phenyl}-2-oxo-1,3-oxazolidin-5-yl)methyl]acetamide,
(48) N-[((5S)-3-{3-fluoro-4-[exo-(1R,5S)-3-(2-cyanoethyl)-3-azabicyclo[3.1.0]hex-6-yl]phenyl}-2-oxo-1,3-oxazolidin-5-yl)methyl]acetamide,
(49) N-[((5S)-3-{3-fluoro-4-[exo-(1R,5S)-3-dimethylamino-3-azabicyclo[3.1.0]hex-6-yl]phenyl}-2-oxo-1,3-oxazolidin-5-yl)methyl]acetamide,
(50) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide,
(51) N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]propanamide,
(52) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide,
(53) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide,
(54) 2,2-difluoro-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide,
(55) 2,2-difluoro-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(56) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclobutanecarboxamide,
(57) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclobutanecarboxamide,
(58) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]propanamide,
(59) N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(60) 2,2-difluoro-N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(61) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide,

(62) N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide,

(63) exo-(1R,5S)-6-(4-{(5S)-5-[(propanoylamino)methyl]-2-oxo-1,3-oxazolidin-3-yl}-2,6-difluorophenyl)-3-azabicyclo[3.1.0]hexane-3-carboxamide,

(64) N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]propanamide,

(65) exo-(1R,5S)-6-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexane-3-carboxamide,

(66) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]-2-hydroxyacetamide,

(67) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]-2-hydroxyacetamide,

(68) 2-cyano-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide,

(69) 2-cyano-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]acetamide,

(70) 2-cyano-N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide,

(71) 2-cyano-N-[((5S)-3-{3,5-difluoro-4-[exo-(1R,5S)-3,3-dioxide-3-thiabicyclo[3.1.0]hex-6-yl]phenyl}-2-oxo-1,3-oxazolidin-5-yl)methyl]acetamide,

(72) N-{[(5S)-3-(4-{exo-(1R,5S)-3-[amino(imino)methyl]-3-azabicyclo[3.1.0]hex-6-yl}-3-fluorophenyl)-2-oxo-1,3-oxazolidin-5-yl]methyl}acetamide,

(73) exo-(1R,5S)-N'-cyano-6-(4-{(5S)-5-[(acetylamino)methyl]-2-oxo-1,3-oxazolidin-3-yl}-2-fluorophenyl)-N-methyl-3-azabicyclo[3.1.0]hexane-3-carboximidamide,

(74) exo-(1R,5S)-N'-cyano-6-(4-{(5S)-5-[(acetylamino)methyl]-2-oxo-1,3-oxazolidin-3-yl}-2-fluorophenyl)-3-azabicyclo[3.1.0]hexane-3-carboximidamide, or

(75) N-[((5S)-3-{3-fluoro-4-[exo-(1R,5S)-3-((E)-1-{methylamino}-2-nitrovinyl)-3-azabicyclo[3.1.0]hex-6-yl]phenyl}-2-oxo-1,3-oxazolidin-5-yl)methyl]acetamide.

The compounds discussed herein are named according to one of the structures set forth below in which the ring positions are numbered according to convention:

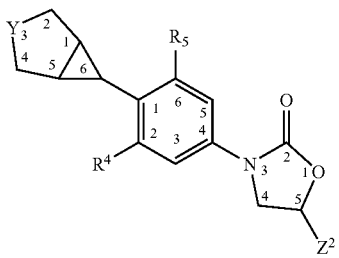

6-(4-{5-[$Z^2$]-2-oxo-1,3-oxazolidin-3-yl}-2,6-($R^4$ and/or $R^5$)-phenyl)-3-Y-bicyclo[3.1.0]hexane-3-($R^8$);

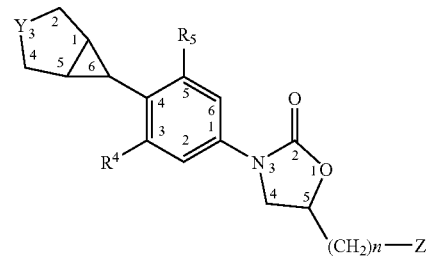

N-[(3-{3,5-($R^4$ and/or $R^5$)-4-[3-($R^8$)-3-Y-bicyclo[3.1.0]hex-6-yl]-phenyl}-2-oxo-1,3-oxazolidin-5-yl)($CH_2$)$_n$]-(Z).

or

3-{3,5-($R^4$ and/or $R^5$)-4-[3-($R^8$)-3-Y-bicyclo[3.1.0]hex-6-yl]-phenyl}-2-oxo-1,3-oxazolidin-5-(Z).

General Synthetic Schemes

The compounds of this invention can be prepared in accordance with one or more of the Schemes discussed below. Further discussions can be found in International Publication WO 02/06278, which is incorporated herein by reference.

The starting materials, intermediates, and final compounds described in this invention were prepared using common procedures and techniques that are well known to persons of ordinary skill in organic chemistry. These compounds were prepared in accordance with one or more of the following Schemes as described below.

It will be appreciated that some of the processes described herein require the use of protective groups to prevent the undesired reactivity of certain substituents. A person skilled in organic chemistry will recognize when such protection may be required and how such groups may be installed and subsequently removed. For examples of protecting groups and procedures for their introduction and removal see one of the general texts on the subject such as "Protecting Groups" by Philip J. Kocienski (publisher: Georg Thieme Verlag: Stuttgart, 1994).

Chiral intermediates of enantiomeric purity may be prepared using various asymmetric reaction methodologies or, alternatively, by resolution of the racemic mixtures. It is known that the bicyclo[3.1.0]hexyl ring systems described herein can exist as either endo or exo diastereomers. When products comprised of bicyclo[3.1.0]hexyl ring systems form as mixtures, these diastereomers can be separated by standard techniques of organic chemistry, for example, by silica gel chromatography.

Scheme I illustrates three methods for preparing benzaldehyde starting materials required for the preparation of the compounds of this invention. In the first method, a substituted 5-nitrotoluene analog is oxidized to the corresponding benzaldehyde (step 1). This oxidation can be accomplished according to the procedure reported by Gordeev et. al. in U.S. Pat. No. 6,239,152, incorporated herein in its entirety.

Step 2 of Scheme I involves reduction of the nitro substituent to an amino substituent. This reduction is generally accomplished by reacting the nitro intermediate with iron metal. The reaction is carried out at temperatures between 60° C. and 90° C. in mixtures of water and alcohol (methanol, ethanol, etc.) as solvent, and in the presence of ammonium chloride. Optionally, reductions of this type are conducted by reaction with other metals such as tin or zinc or by hydrogenation using a palladium or platinum catalyst (see Rylander *Hydrogenation Methods;* Academic Press:

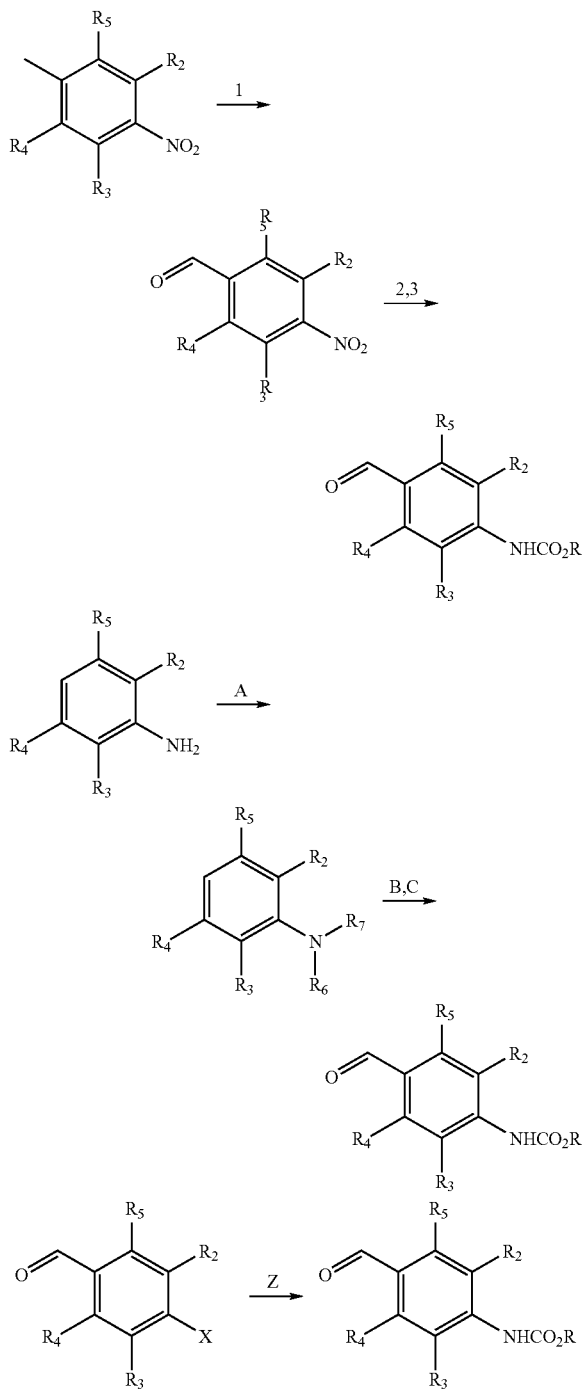

SCHEME I

Step 3 of Scheme I involves the introduction of carbamate protection (e.g., benzyloxycarbonyl (Cbz) or t-butoxycarbonyl (Boc)) on the aniline formed in step 2. This is a standard transformation that is typically carried out by reaction of the amine with benzyl chloroformate, di-tert-butyl dicarbonate, or an equivalent reagent (see Kocienski *Protecting Groups;* Georg Thieme Verlag: Stuttgart, 1994, pp. 195-199). The reaction is typically conducted at temperatures between 0° C. and 25° C. in organic solvents such as dichloromethane in the presence of amines such as triethylamine or pyridine and is run until substantially complete, usually 2 hours to 16 hours. Optionally the reaction may be performed in aqueous solutions in the presence of inorganic bases such as sodium hydroxide or sodium bicarbonate.

A second method for preparing the benzaldehyde starting material begins with a substituted aniline. Step A of Scheme I involves protection of the amino group as a carbamate (e.g., isopropoxycarbonyl or t-butoxycarbonyl (Boc)). This is a standard transformation that is typically carried out by reaction of the amine with isopropyl chloroformate, di-tert-butyl dicarbonate, or an equivalent reagent (see Kocienski *Protecting Groups;* Georg Thieme Verlag: Stuttgart, 1994, pp. 195-199). The reaction is typically conducted at temperatures between 0° C. and 25° C. in organic solvents such as tetrahydrofuran and using a base such as lithium bis(trimethylsilyl) amide and is run until complete, usually 2 hours to about 24 hours. Alternatively, protection of the aniline function may be accomplished using silyl protecting groups. Reagents including but not limited to trimethylsilyl chloride and 1,2-bis(chlorodimethylsilyl)ethane have been used for this purpose (see patent application WO 97/30995).

Step B of Scheme I illustrates the introduction of a formyl group para to the protected aniline intermediate. This reaction is accomplished by formation of the aryl lithium species and subsequent reaction with dimethylformamide or equivalent formylating reagent. The lithiation reaction is typically carried out at temperatures below −50° C. using strong bases such as n-butyllithium or tert-butyllithium, optionally in the presence of additives such as TMEDA (N,N,N',N'-tetramethylethylenediamine). The formylating reagent may be added at temperatures below −50° C. and the reaction allowed to warm to room temperature. The reaction is run until complete, usually 1 hours to about 3 hours. For silyl-protected aniline intermediates, an aqueous work-up is likely to re-generate the free aniline. For these cases, an additional step (Step C) will be required to convert the free aniline into a carbamate. The product of each step in Scheme I may be used as collected or may be purifed using conventional techniques such as preparative TLC or HPLC, chromatography, precipitation, crystallization and the like.

A third method for preparation of substituted benzaldehyde intermediates is shown in Scheme I. Step Z of Scheme I involves for example the transition metal catalyzed reaction of a 4-bromo benzaldehyde compound with an alkyl carbamate, for example benzyl carbamate. The benzaldehyde starting material is substituted in the para position with a halogen atom or a triflate, nonaflate or similar sulfonate ester. Reactions of this type are well known to those skilled in the art (see for example Buchwald et.al. J. Am. Chem. Soc. 2002, 124, 7421-7428) and are typically carried out with palladium or copper catalysts and employing ligands such as BINAP or related phosphine or arsine ligands. The reaction is favorably carried out in solvents such as toluene or benzene and at temperatures of about 50° C. up to 110° C. The reaction is run until complete, usually 3 hours to about 20 hours. The product may be used as collected or may be purified using conventional techniques such as preparative TLC or HPLC, chromatography, precipitation, crystallization and the like.

Scheme II illustrates the conversion of the benzaldehyde starting materials (described in Scheme I) into bis-hydroxymethylcyclopropane intermediates. These intermediates can, in turn, be used to prepare bicyclo[3.1.0]hexane analogs with various heteroatoms at the 3 position of the bicyclic ring.

Step 1 of Scheme It involves the reaction of the benzaldehyde starting material with a phosphonate ylide. This reaction, the Horner-Wadsworth-Emmons reaction, is well known to those skilled in the art (for reviews, see Wadsworth in Organic Reactions 1977, 25, pp. 73-253). The ylide is first formed by reaction of a phosphonate (e.g. trimethyl phosphonoacetate) with a strong base such as sodium hydride or n-butyllithium in solvents such as dimethylformamide or tetrahydrofuran. After formation of the ylide, it is reacted with the aldehyde in solvents such as DMSO or DMF for about 4 hours to 20 hours at about 0° C. to about 30° C. to form the desired unsaturated ester product. The product may be used as collected or may first be purifed using conventional techniques such as preparative TLC or HPLC, chromatography, precipitation, crystallization and the like.

Step 2 of Scheme II involves the reduction of the unsaturated ester to an allylic alcohol. This is a very common reaction that will be well known to those skilled in the art. The reduction is carried out with reducing agents such as lithium aluminum hydride or sodium borohydride (or an equivalent reagent). The reaction may be conducted for about 1 hour to about 4 hours in ethereal solvents such as tetrahydrofuran or diethyl ether at temperatures between –40 and 25° C. The product may be used as collected or may first be purifed using conventional techniques such as preparative TLC or HPLC, chromatography, precipitation, crystallization and the like.

Step 3 of Scheme II in involves the formation of a diazoester. This is accomplished using glyoxylic acid chloride p-toluenesulfonylhydrazone (prepared as described by C. J. Blankley, F. J. Sauter and H. O. House, *Organic Syntheses*, Coll. Vol. V, p. 258; John Wiley, New York (1973)). Reaction of this reagent with the allylic alcohol may be carried out according to the procedure described by Myers and Corey (Tetrahedron Letters, 1984, pp. 3559-3562). The product may be used as collected or may first be purifed using conventional techniques such as preparative TLC or HPLC, chromatography, precipitation, crystallization and the like.

SCHEME II

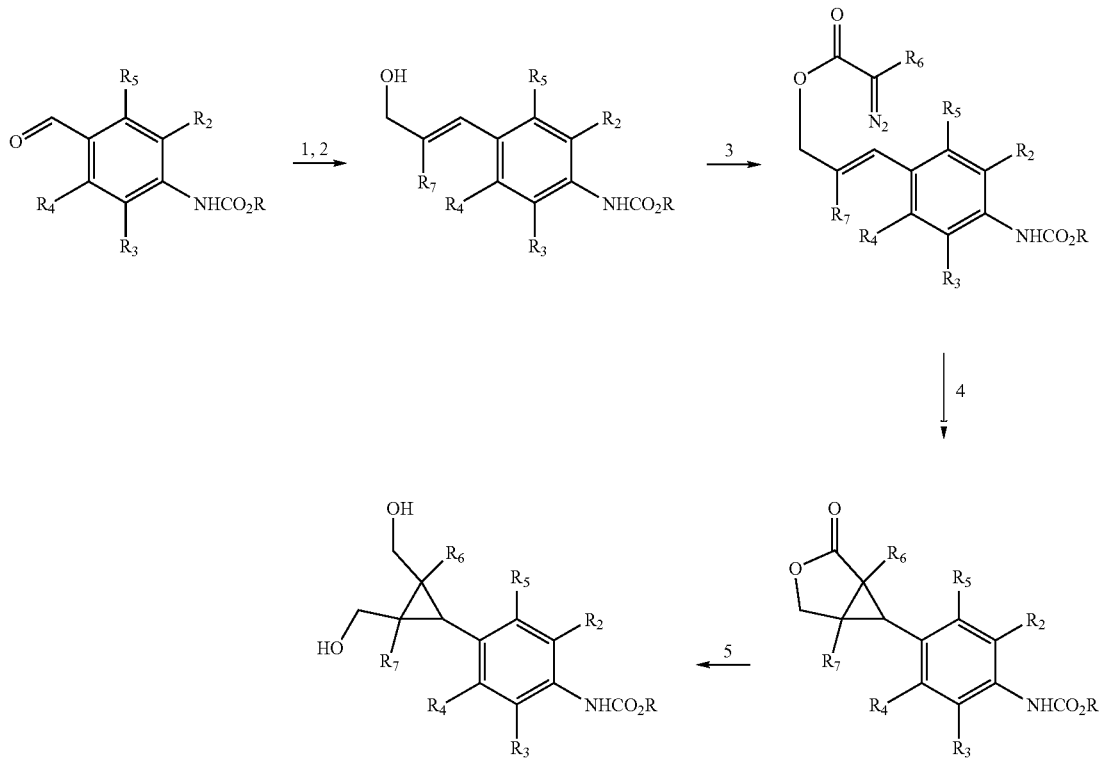

Step 4 of Scheme II involves an intramolecular cyclopropanation reaction. This transformation is usually accomplished with a suitable transition metal catalyst, typically of copper or rhodium (e.g. bis-(N-t-butylsalicyl-aldiminato) copper(II), prepared as described by R. G. Charles in *J. Org. Chem.* 1957, 22, 677). A solution of the diazoester in toluene, dichloromethane or mixtures thereof is added slowly using a dropping funnel or syringe pump to a refluxing solution of the catalyst in toluene or similar solvent. The reaction may be conducted at concentrations below 0.05M to avoid dimerization of the diazoester and is run until substantially complete, usually from about 12 hours to about 36 hours. The product may be used as collected or may first be purifed using conventional techniques such as preparative TLC or HPLC, chromatography, precipitation, crystallization and the like.

Step 5 of Scheme II involves reduction of the lactone ring to a diol. This reduction can be accomplished using conditions similar to those described above for step 2 of Scheme II. The product may be used as collected or may first be purifed using conventional techniques such as preparative TLC or HPLC, chromatography, precipitation, crystallization and the like.

Scheme III describes the preparation of thiabicyclo[3.1.0]hexyl-substituted phenyloxazolidinones starting from the diol intermediate described in Scheme II. Step 1 involves conversion of the alcohol substituents into leaving groups (such as mesylates). These transformations are well known to those skilled in the art and may be performed with reagents such as methanesulfonic anhydride, methanesulfonyl chloride, p-toluenesulfonyl chloride, or equivalent reagents. The reactions may be carried out for about 0.5 hours to about 2 hours in organic solvents such as dichloromethane or tetrahydrofuran, and in the presence of acid-scavenging amines such as triethylamine or N,N-diisopropylethylamine a temperature of about 0° C. to 40° C. The product of this reaction may be used in the next reaction as collected or may first be purifed using conventional techniques such as preparative TLC or HPLC, chromatography, precipitation, crystallization and the like.

Step 2 of Scheme III describes a cyclization reaction in which the bis-mesylate prepared in step 1 is reacted with a nucleophilic sulfur source to form the thiabicyclo[3.1.0]hexane ring. This reaction is generally conducted with sodium sulfide in dipolar aprotic solvents such as dimethylsulfoxide.

Step 3 of Scheme III illustrates the construction of the oxazolidinone ring from the aryl carbamate. Transformations of this type are known art (see, e.g., International Publication WO 95/07271, published on 16 Mar. 1995). In step 3 the oxazolidinone synthesis is performed with S-acetic acid 2-acetylamino-1-chloromethyl-ethyl. This reagent is prepared from (S)-epichlorohydrin in three steps (epoxide ring opening with benzaldehyde imine, imine hydrolysis, and peracylation with acetic anyhdride) according to the procedure described in U.S. patent application Ser. No. 09/982,157, which is incorporated herein in its entirety. The reaction of this reagent with aryl carbamates is to afford the acetylaminomethyl-substituted oxazolidinone. The reaction is performed in the presence of an organic base such as lithium tert-butoxide, in a polar organic solvent such as dimethylformamide, at temperatures of about 0° C. to 25° C.

SCHEME III

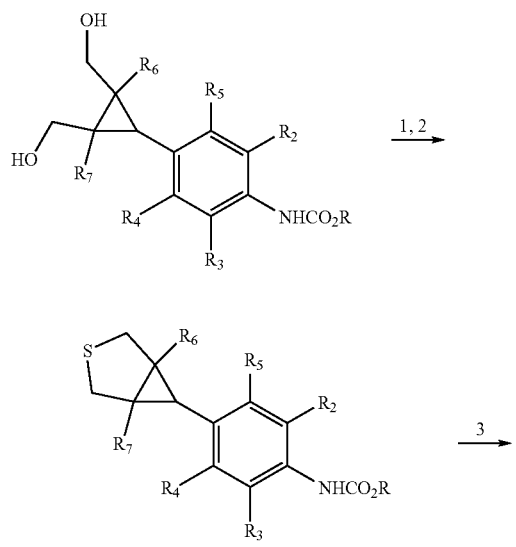

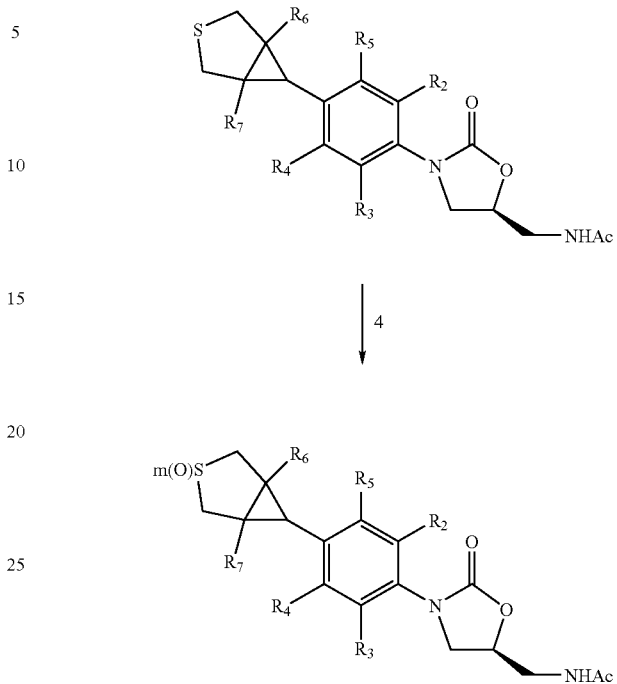

Step 4 of Scheme III involves an optional oxidation of the sulfur atom to form a sulfoxide or sulfone. These transformations will be well known to one skilled in the art and a variety of reagents are available (for a review see Hudlicky in *Oxidations in Organic Chemistry;* American Chemical Society: Washington, 1990, pp 252-263). Sulfoxides are formed as a pair of diastereomers that are often separable using flash column or preparative thin layer chromatography. The oxidation to sulfoxide may be conducted with sodium periodate in water-alcohol mixtures. Oxidation to sulfone may be carried out with peracetic acid in aqueous tetrahydrofuran. These reactions are typically carried out at temperatures of about 0° C. to 25° C.

Scheme IV describes the preparation of azabicyclo[3.1.0]hexyl-substituted phenyloxazolidinones starting from the diol intermediate described in Scheme II. Step 1 involves conversion of the alcohol substituents into leaving groups (such as mesylates). This transformation is conducted as described above for step 1 of Scheme III.

Step 2 of Scheme IV describes a cyclization reaction in which the bis-mesylate prepared in step 1 is reacted with a nucleophilic amine source such as 4-methoxybenzylamine or similar amine. This reaction is conducted neat, using the amine as solvent and at temperatures of around 0 to 30° C. The choice of amine is important in that the subsequent deprotection step (step 4) should be facile.

Step 3 of Scheme IV involves construction of the oxazolidinone ring. This transformation is conducted as described above for step 3 of Scheme III.

SCHEME IV

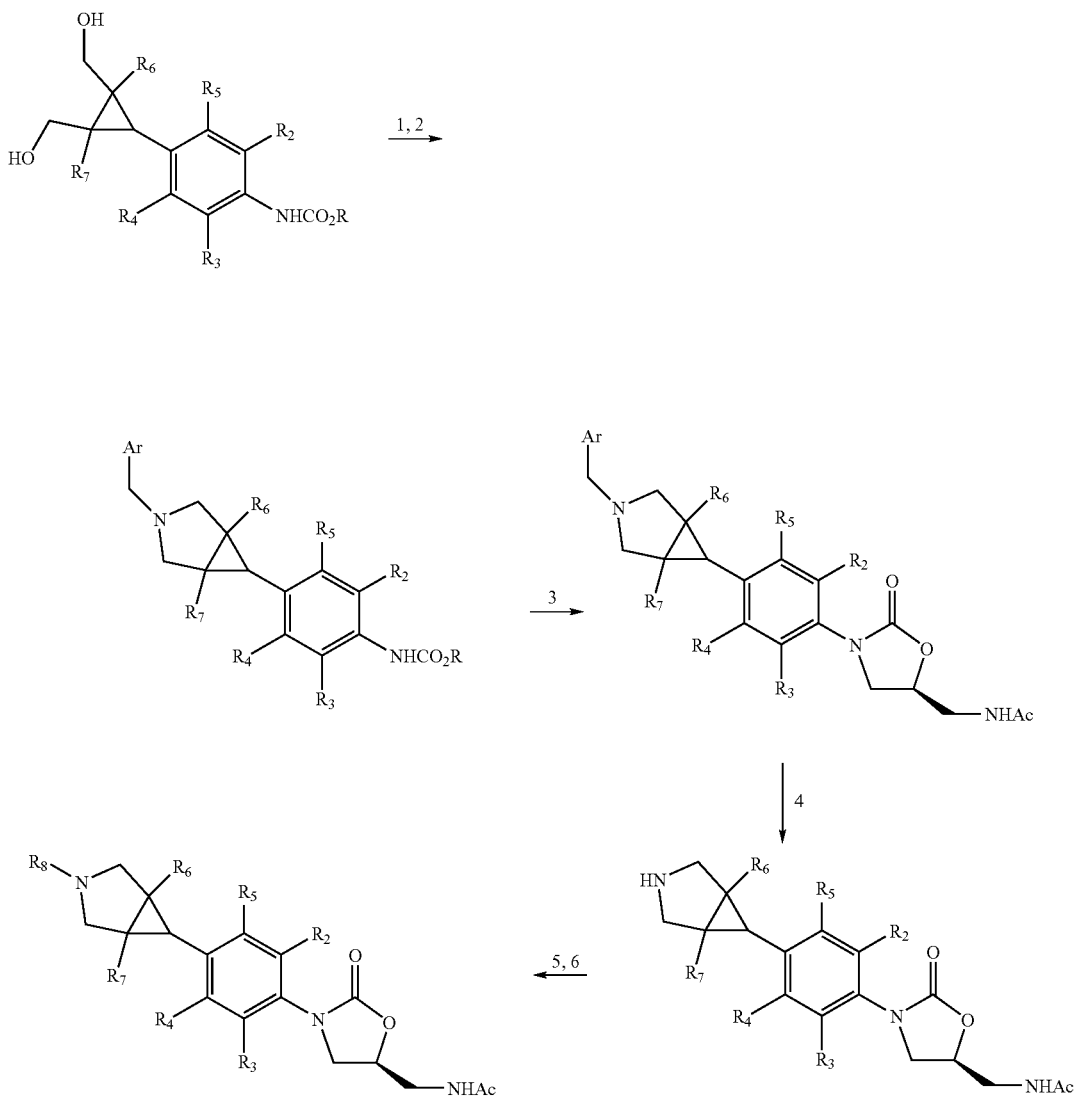

Step 4 of Scheme IV involves deprotection of the tertiary amine to reveal the free secondary azabicyclic amine. The choice of reagent for this deprotection will depend on the amine used for cyclization in step 2. It is understood that a person skilled in the art will select the appropriate deprotection conditions for the amine chosen. In this example, removal of the 4-methoxybenzylamine group can be accomplished by hydrogenolysis. Hydrogenolysis reactions are well known and are typically carried out using palladium catalysts, of which several varieties are available, and under an atmosphere of hydrogen gas. Removal of the p-methoxybenzyl group may be conducted using palladium hydroxide on carbon as catalyst and a solvent system of methanol, ethanol, ethyl acetate, or mixtures thereof. These reactions are typically carried out at temperatures of about 15° C. to 35° C. For analogs lacking fluorine substitution on the aromatic ring, an alternate procedure may be employed, involving reaction with 1-chloroethyl chloroformate or similar reagent in the presence of amine scavenging bases such as triethylamine and in solvents such as dichloromethane (see Olofson et al. in *J. Org. Chem.* 1984, pp 2081-2082 and Yang et al. in *Synlett,* 1993, pp 195-196). This alternative procedure circumvents the problem of cyclopropane ring-opening that is sometimes encountered in the des-fluoro aromatic analogs.

Step 5 of Scheme IV represents a coupling step in which the free secondary amine is reacted with alkylating, acylating, sulfonylating, or other reagents to introduce substituents represented generically as $R^8$. Coupling reactions of amines are very common reactions in synthetic organic chemistry and will be well known to those of average ability in the art. In an illustrative example leading to a preferred structure, the amine is reacted with benzyloxyacetyl chloride in dichloromethane and triethylamine to form the benzyloxyacetamide.

Step 6 of Scheme IV represents an optional step or steps that may involve a deprotection step or other reaction to further elaborate the $R^8$ substituent introduced in step 5. Those skilled in the art will be able to select appropriate conditions for removing given protecting groups or for further elaboration of a given $R^8$ substituent. As an illustrative example, the benzyloxyacetamide formed in step 5 is subjected to hydrogenolysis with a palladium catalyst to reveal the desired hydroxyacetamide-substituted azabicyclic phenyloxazolidinone.

Scheme V describes the preparation of oxabicyclo[3.1.0] hexyl-substituted phenyloxazolidinones starting from the diol intermediate described in Scheme II. Conceptually this reaction involves the conversion of one of the hydroxy substituents into a suitable leaving group and subsequent intramolecular displacement of the leaving group by the other hydroxy group or its alkoxide form. A person skilled in the art will recognize possible strategies for this cyclization including activation of the alcohol under Mitsunobu conditions. This reaction can be accomplished in a one-pot reaction (step 1). Initial reaction with about two equivalents of a base such as n-butyllithium is followed by reaction with one to two equivalents of an activating reagent, such as, methanesulfonyl chloride. Additional base is then added (about one equivalent) to effect cyclization and form the oxabicyclic ring. This reaction is typically conducted in ethereal solvent such as THF and at temperature of about −30 to −60° C. for about 1 hour to 3 hours. The product may be used as collected or may first be purifed using conventional techniques such as preparative TLC or HPLC, chromatography, precipitation, crystallization and the like.

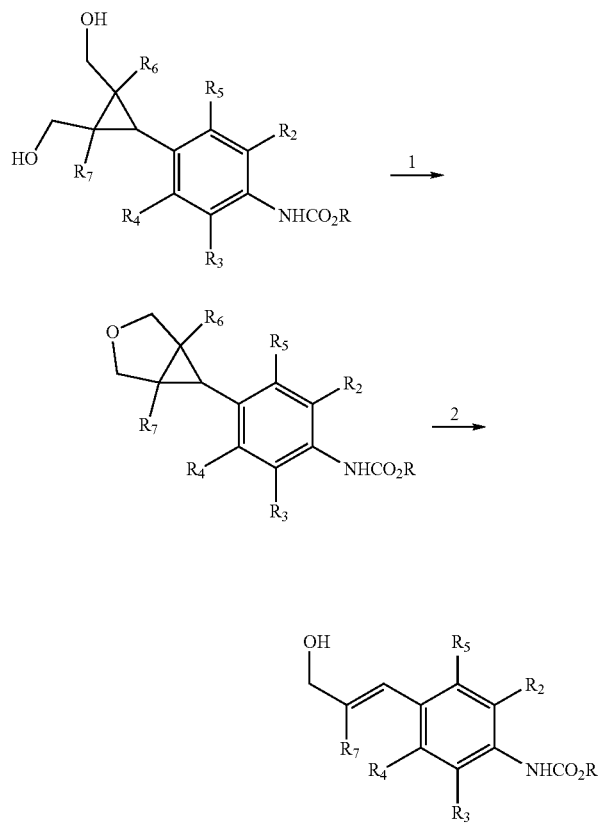

-continued

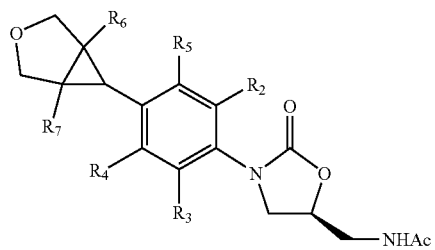

Step 2 of Scheme V involves construction of the oxazolidinone ring. This transformation is conducted as described above for step 3 of Scheme III.

Scheme VI describes the preparation of claimed structures in which Y is —N($R^8$)— and W is C=O. Step 1 of Scheme VI represents a step or steps for converting the allylic alcohol described in Scheme II to an allylic amine. This well-known transformation may be performed by initial activation of the hydroxy group as an alkyl or aryl sulfonate, halide, or optionally by Mitsunobu-type activation (see Fabiano et al. *Synthesis,* 1987, p. 190). These reactions are well known to those skilled in the art and may be performed with reagents such as methanesulfonyl chloride, p-toluenesulfonyl chloride, or with dialkyl azodicarboxylates (for Mitsunobu reactions). Next the activated alcohol is reacted with a nucleophilic nitrogen source. For reactions of alkyl or aryl sulfonates this is usually accomplished by reaction with an azide salt (e.g., sodium azide) in polar solvents such as acetone or dimethyl sulfoxide (optionally with added water) and at temperatures of about 50° C. to 120° C. For Mitsunobu activation, hydrazoic acid is commonly employed as a nucleophilic nitrogen sources. Finally, the azide is reduced to the amine, a transformation that can be accomplished with a variety of inorganic reducing agents or by catalytic hydrogenation. An alternative and selective reduction of azides is accomplished by reaction with phosphines (Staudinger reaction).

In step 2 of Scheme VI, the allylic amine is converted to a diazo acetamide. This conversion may be accomplished using the procedure described by Doyle et al. (see *J. Am. Chem. Soc.* 1995, 117, pp 5763-5775) although other methods may also be employed.

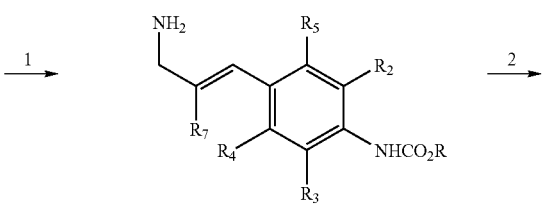

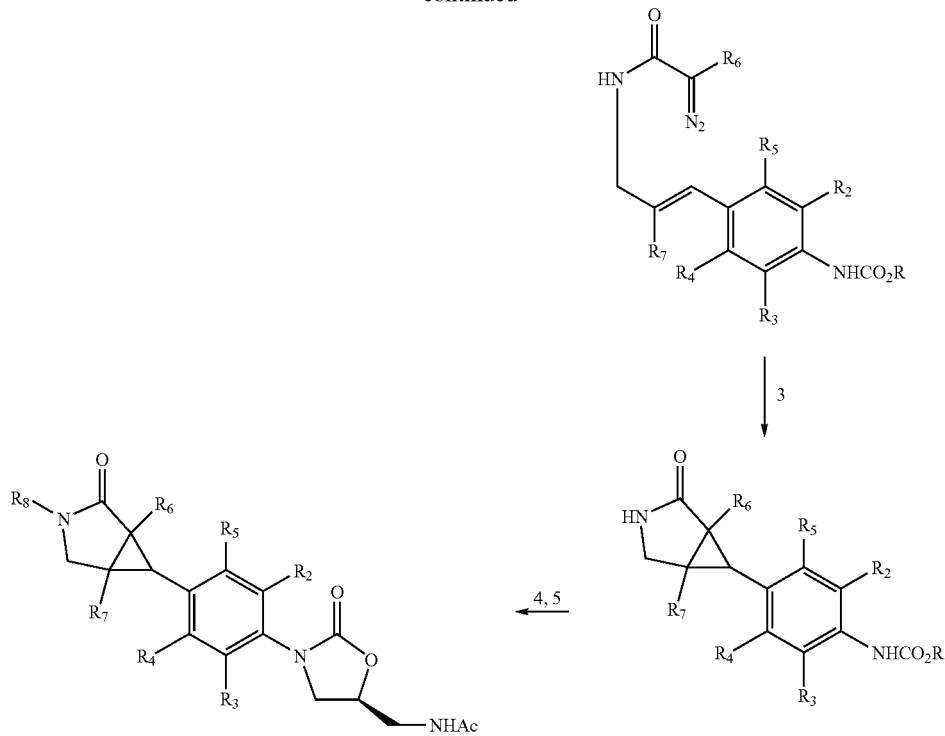

Step 3 of Scheme VI describes an intramolecular cyclopropanation reaction and may be accomplished as described above for step 4 of Scheme II.

Step 4 of Scheme VI involves construction of the oxazolidinone ring. This transformation is conducted as described above for step 3 of Scheme III.

Step 5 of Scheme VI represents an optional step or steps that may involve the introduction and further elaboration of the $R^8$ substituent. For example, these reactions may involve alkylation or similar functionalization of the lactam ring nitrogen using known processes.

Scheme VII involves an alternate route for the preparation of analogs in which the preparation of claimed structures in which Y is —N($R^8$)— and W is C=O. The starting material for this method is the lactone described in Scheme II. In step 1 of Scheme VII, the lactone is reacted with a suitable amine nucleophile such as benzyl or 4-methoxybenzylamine, opening the lactone ring to give an amide. This is a well known reaction in organic chemistry and may be accomplished in a variety of alcoholic or polar aprotic solvents at temperatures from about 25° C. to 100° C.

Step 2 of Scheme VII describes involves cyclization of the amido alcohol to reform a lactam ring. These reactions are known and are often accomplished by activating the alcohol with reagents such as mesyl chloride (e.g., see Haddad, M. et al in *J. Org. Chem.* 1998, 63, 5680-5683) or by Mitsunobu-type activation (e.g., see Ma, D. et. al. in *Tet. Lett.* 1998, 9067-9068).

Step 3 of Scheme VII involves construction of the oxazolidinone ring. This transformation is conducted as described above for step 3 of Scheme III or as described in Scheme VIII.

SCHEME VII

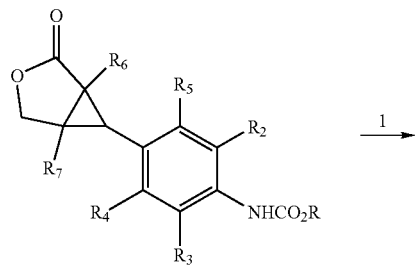

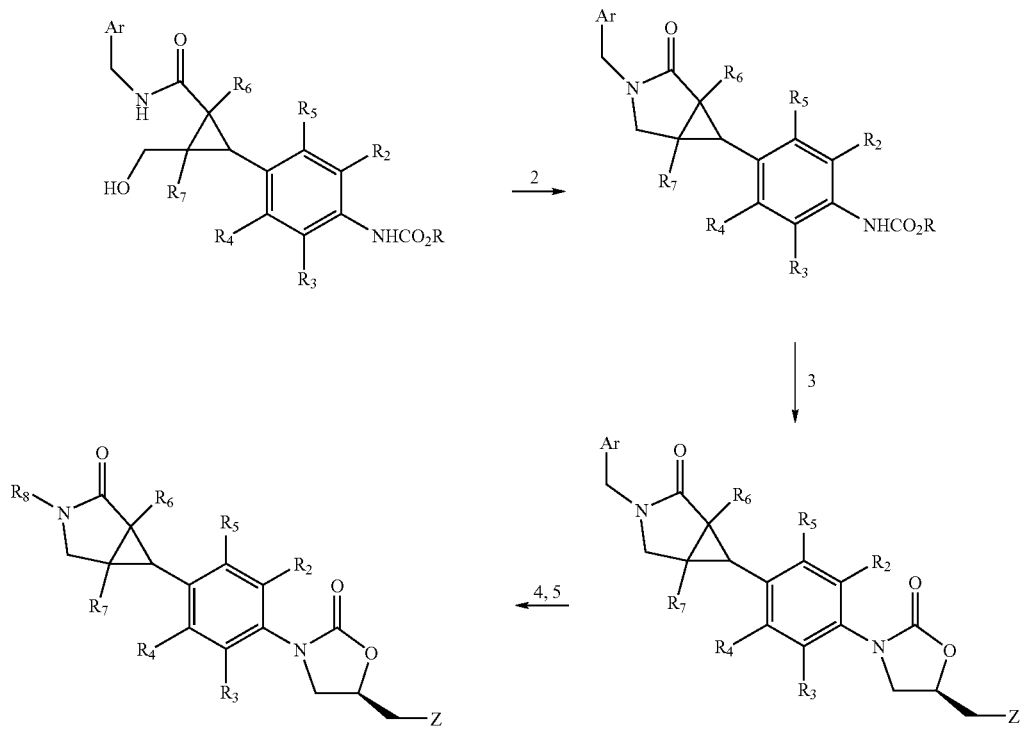

Steps 4 and 5 of Scheme VII represent an optional step or steps that may involve removal of a substituent on the amide nitrogen (e.g. a benzyl group) and the introduction and further elaboration of an $R^8$ substituent. For example, these reactions may involve alkylation or similar functionalization of the lactam ring nitrogen using known methods.

Scheme VIII describes a general synthesis of aryloxazolidinone compounds substituted at C-5 of the oxazolidinone with substituents other than simple acetylaminomethyl. In step 1 of Scheme VIII, the aryl carbamate analogs (described in Schemes III-VII) are reacted with (3-chloro-2-hydroxypropyl)-carbamic acid tert-butyl ester. This reagent is prepared from (S)-epichlorohydrin in three steps (epoxide ring opening with benzaldehyde imine, imine hydrolysis, and amine protection with di-tert-butyldicarbonate) according to the procedure described in U.S. patent application Ser. No. 09/982,157, which is incorporated herein in it entirety. The reaction of this reagent with aryl carbamates is performed in the presence of an organic base such as lithium tert-butoxide, in a polar organic solvent such as dimethylformamide, at temperatures of about 0° C. to 25° C.

In step 2 of Scheme VIII, the tert-butyl carbamate (Boc group) is removed to provide the aminomethyl analog. This transformation is conveniently accomplished with hydrochloric acid in dioxane at a temperature in the range of about 0° C. to about 25° C.; however, a person skilled in the art will recognize other deprotection conditions that may be employed.

SCHEME VIII

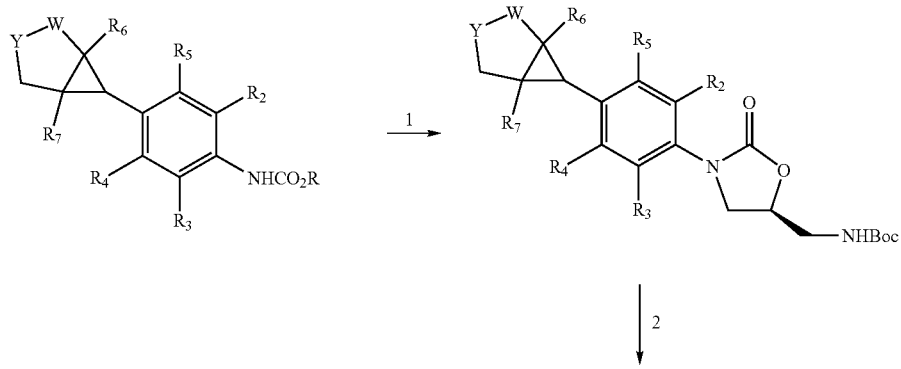

-continued

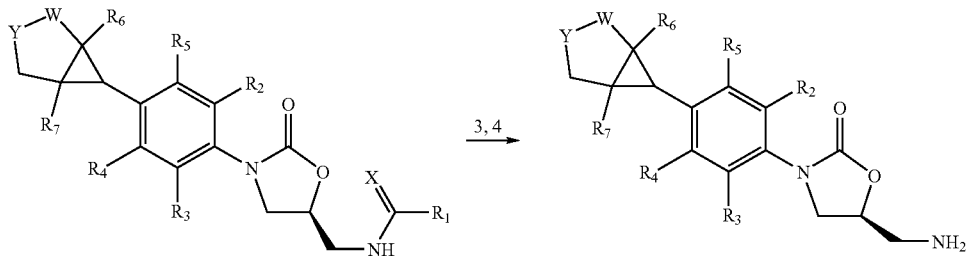

Step 3 of Scheme VIII involves acylation or thioacylation of the amine intermediate using known art. Hence, acylations can be performed by reaction of the amine with carboxylic acid anhydrides, esters or acid chlorides. These transformations are usually performed at temperatures between 0° C. and 50° C. in solvents such as dichloromethane, acetonitrile, tetrahydrofuran, dimethylformamide, methanol, or mixtures thereof. These reactions are generally performed in the presence of acid-scavenging amines such as triethylamine, pyridine, or potassium carbonate. Thioacylations are accomplished by reaction of the amines from step 2 with dithioesters or thionoesters in the presence of a tertiary amine base such as triethylamine. Preferred solvents for these reactions include tetrahydrofuran, dichloromethane or methanol and the reactions are conducted in a temperature range from 20° C. to 50° C. Other thiocarbonyl compounds of Scheme VIII can be prepared according to procedures disclosed in PCT International Publication WO 98/54161, which is incorporated herein by reference in its entirety.

Step 4 of Scheme VIII represents an optional step or steps that may involve a deprotection step or other reaction to introduce or further elaborate an $R^8$ substituent in cases where Y is —N($R^8$)—. In cases were Y is S, these optional steps may constitute oxidation steps to form sulfoxide or sulfone functionality.

Scheme DC describes the synthesis of claimed compounds that possess a carboxamide substituent at C-5 of the oxazolidinone ring (i.e., where Z is C(=O)NHR$^1$). The preparation of oxazolidinones with this particular substituent is outlined below in steps 2-4 of Scheme DC and is further described known art in U.S. Provisional Patent Application Ser. No. 60/359,495, which is incorporated herein by reference in its entirety. It will be apparent to those skilled in the art that this scheme describes a general method that may be applied in the context of any of bicyclic heterocycles described in Schemes III-VII to prepare claimed structures possessing carboxamide substituent at C-5 of the oxazolidinone ring. A person skilled in the art will also recognize that some modifications of the synthetic protocol may be required if certain functional groups are incompatible with the methods described. In these cases, suitable protecting groups may be employed to protect these functional groups from participating in undesired reactions, see "Protecting Groups" by Philip J. Kocienski (publisher: Georg Thieme Verlag: Stuttgart, 1994).

Step 1 of Scheme IX requires the removal of carbamate protection from intermediates of the type described in Schemes III-VII. The conditions employed for this reaction will depend on the carbamate employed in a particular case. For example, benzyloxycarbonyl (Cbz) groups can be removed using hydrogenolysis with palladium catalysts whereas tert-butoxycarbonyl (Boc) groups are effectively removed using hydrochloric acid in solvents such as dioxane, although other similar reagents may also be used. These examples are only illustrative and it is understood that other carbamate protecting groups and deprotection conditions may be employed.

Step 2 of Scheme DC describes the reaction of the substituted aniline intermediate with ethyl (2R)-2,3-epoxypropanoate, available from Acros, or similar reagent to provide an amino alcohol. This reaction may be conducted in the presence of a promoter such as lithium triflate and in solvents such as acetonitrile or dioxane at temperatures of about 30° C. to 100° C.

Step 3 of Scheme IX describes the formation of the oxazolidinone ring from the amino alcohol intermediate. This type of reaction is known in the art and is typically conducted with reagents such carbonyldiimidazole or phosgene, with or without the addition of acid scavenging bases such as triethylamine. The reactions can be conducted in solvents such as acetonitrile, dimethylformamide or dichloromethane and at temperatures of about 0° C. to 50° C. and are typically run for about 0.5 hours to about 48 hours, or until the reaction is complete.

SCHEME IX

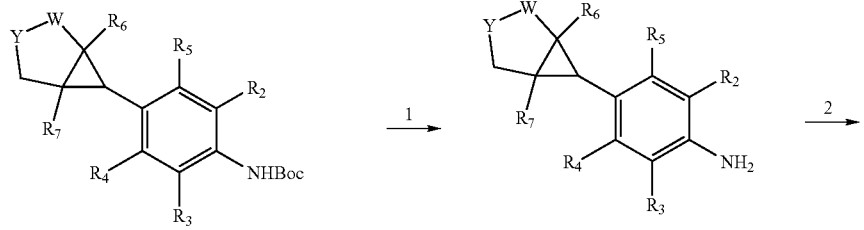

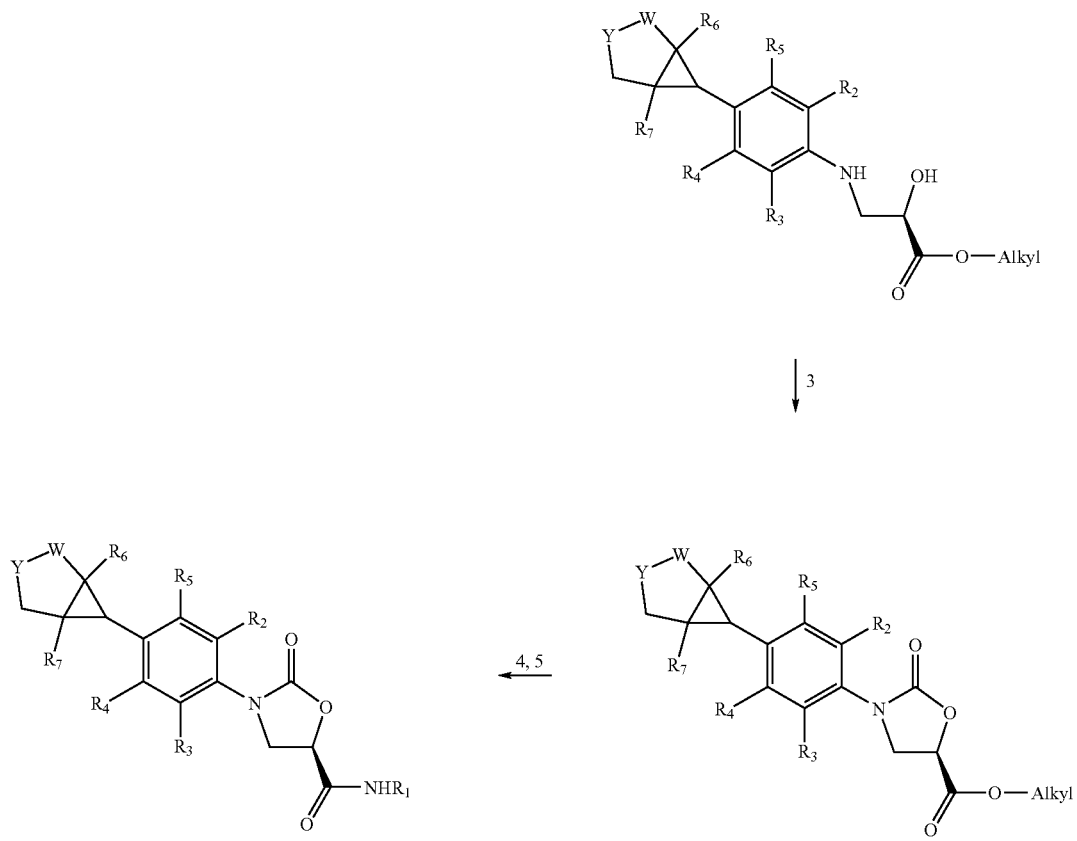

Step 4 of Scheme IX describes the reaction of ammonia or a primary amine with the ester bearing oxazolidinone formed in the previous step. Reaction of the amine with the ester group provides the desired product possessing carboxamide substitution at C-5. These reactions may be carried out with an excess of the amine in solvents such as methaol, tetrahydrofuran or mixtures thereof and at temperatures of around 0° C. to 50° C.

Step 5 of Scheme IX represents an optional step or steps that may involve a deprotection step and/or other reaction to introduce or further elaborate an $R^8$ substituent in cases where Y is —N($R^8$)—. In cases were Y is S, these optional steps may constitute oxidation steps to form sulfoxide or sulfone functionality.

Schemes X-XII below describe general methods for the preparation of claimed compounds in which Z is NH-het[1], O-het[1], S-het[1], or het[2]. The starting materials for this procedure are arylcarbamates (described in Schemes III-VII) and the conversion of these intermediates to the final compounds is known art (see Gravestock, M. B., International Publications WO 99/64417 and WO 00/21960). The structures shown are those in which A is structure (i); however it is understood that analogous procedures may be employed—with some modifications of the synthetic route—when A is structure (ii), (iii), or (iv).

Step 1 of Scheme X involves transformation of the aryl carbamate (prepared as described in Schemes III-VII) to a hydroxymethyl-substituted oxazolidinone. Transformations of this type are known to those skilled in the art (see, e.g., International Publication WO 95/07271, published on 16 Mar. 1995). This reaction is accomplished with R-(−)-glycidyl butyrate or a similar glycidyl ester. The reaction is performed in the presence of organic base such as lithium hexamethyldisilylamide in organic solvents such as tetrahydrofuran, at temperatures of about −78° C. to 25° C.

In Step 2 of Scheme X, the hydroxy group is converted to a displaceable group (Lg) such as alkyl or aryl sulfonate, or halide. These reactions are well known to those skilled in the art and may be performed with reagents such as methanesulfonyl chloride, p-toluenesulfonyl chloride, or similar reagents. The reactions may be carried out in organic solvents such as dichloromethane or tetrahydrofuran, and in the presence of acid-scavenging amines such as triethylamine or N,N-diisopropylethylamine a temperature of about 0° C. to 40° C.

SCHEME X

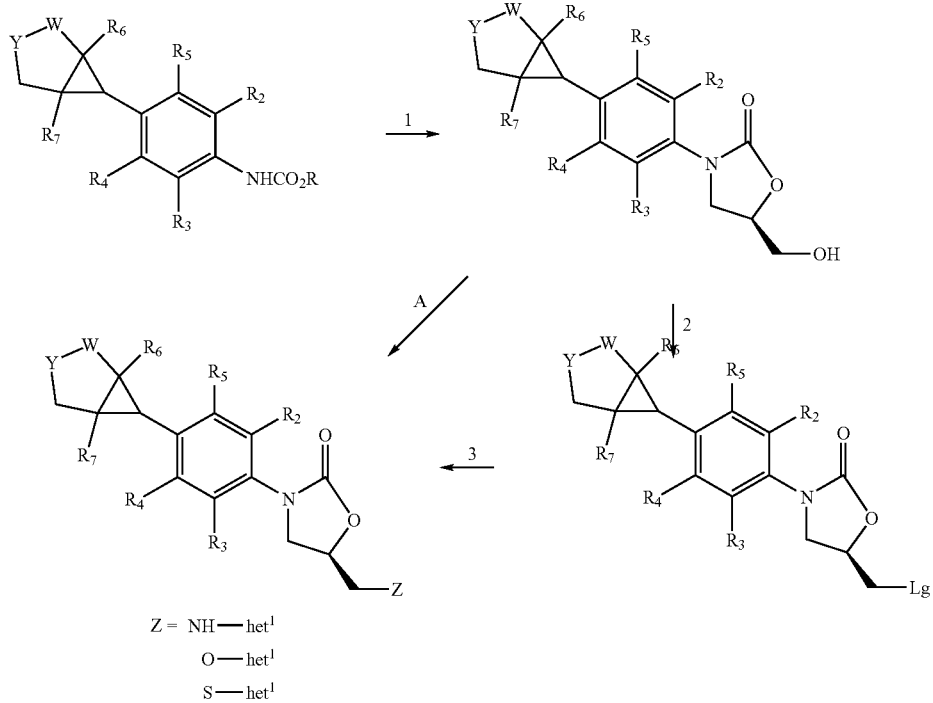

Z = NH—het¹
    O—het¹
    S—het¹

In Step 3 of Scheme X, the activated hydroxy compound is reacted with a compound of the formula HN(Pg)het¹, HOhet¹, HShet¹ or the corresponding metal alkoxide salts M-N(Pg)het¹, M-Ohet¹, M-Shet¹ where M is an alkali metal or another metal known to promote O-alkylation (e.g., silver) and "Pg" is a suitable protecting group. Alternatively, the hydroxymethyl starting material may be reacted directly with compounds of the formula HN(Pg)het¹, HOhet¹, HShet¹ (Step A) under Mitsunobu activation using a suitable dialkyl azodicarboxylate reagent and alkyl or aryl phosphine (see Fabiano et. al. *Synthesis,* 1987, p. 190). Finally, an optional step or steps may be required to introduce or further elaborate an $R^8$ substituent in cases where Y is —N($R^8$)—. In cases were Y is S, these optional steps may constitute oxidation steps to form sulfoxide or sulfone functionality.

The synthesis of analogs in which Z is het² may be accomplished as shown in Scheme XI. Preparation of these analogs from hydroxymethyl oxazolidinones is known art (see Gravestock, M. B., Betts, M. J., and Griffin, D. A., International Publications WO 01/81350). In Step 1, the hydroxy group is converted to a displaceable group (Lg) such as alkyl or aryl sulfonate, bromide, or iodide using known art. In Step 2, this intermediate is reacted with het²-H in the free base form or as the anion het²-formed from the free base. An alternative method to prepare 1,2,3-triazoles specifically involves conversion of the hydroxy group to an azide in Step A (as described for step 1 of Scheme VI), followed by cycloaddition with norbornadiene (Step B). Finally, an optional step or steps may be required to introduce or further elaborate an $R^8$ substituent in cases where Y is —N($R^8$)—. In cases were Y is S, these optional steps may constitute oxidation steps to form sulfoxide or sulfone functionality.

SCHEME XI

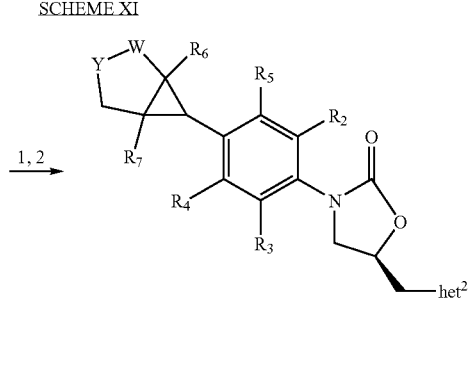

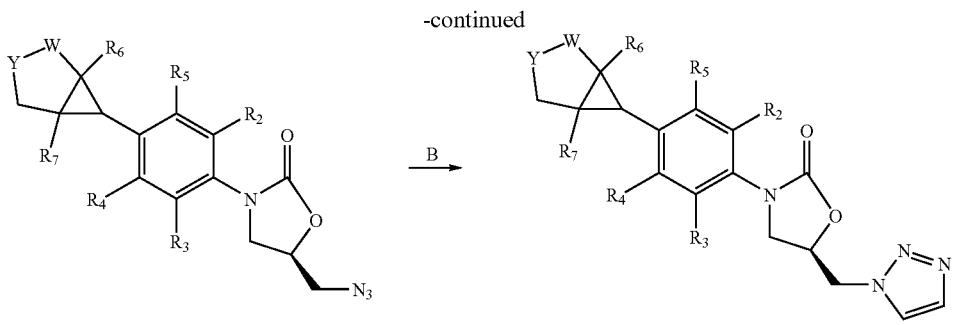

Scheme XII describes an alternative method for the preparation of the analogs described in Schemes X and XI. This method is well known in the art (see, for example, Gravestock, M. B., International Publications WO 99/64417 and WO 00/21960; Gravestock, M. B., Betts, M. J., and Griffin, D. A., International Publications WO 01/81350, which are each incorporated herein in their entirety). Reaction of aryl carbamate intermediates (described in Schemes III-VII) with epoxides of the formula $CH_2(O)CHCH_2$-$het^2$, $CH_2(O)CHCH_2$—$NHhet^1$, $CH_2(O)CHCH_2$—$O$-$het^1$, or $CH_2(O)CHCH_2$—$S$-$het^1$ provides the desired compounds. Finally, an optional step or steps may be required to introduce or further elaborate an $R^8$ substituent in cases where Y is —$N(R^8)$—. In cases were Y is S, these optional steps may constitute oxidation steps to form sulfoxide or sulfone functionality.

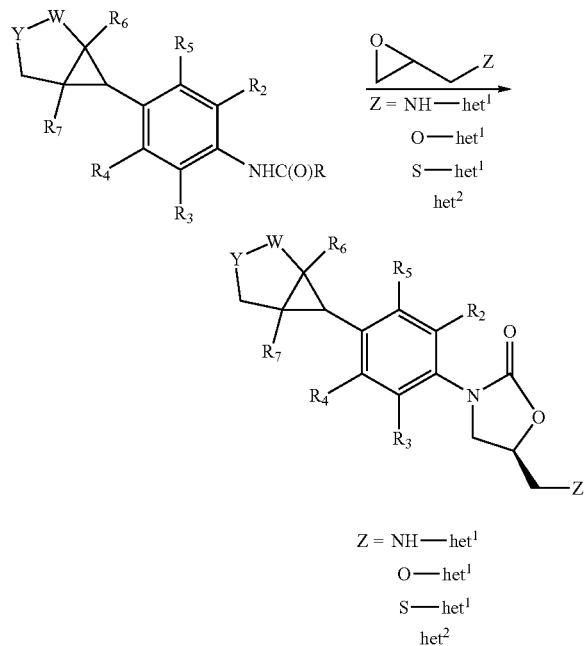

Schemes XIII-XV describe the synthesis of arylisoxazolinone and arylisoxazoline compounds bearing bicyclic rings of the type described in Schemes III-VII. It will be apparent to those skilled in the art that the following schemes describe general methods to prepare claimed structures in which A is (ii) or (iv). These methods may be employed using any of the bicyclic heterocycles described in Schemes III-VII. The starting materials required to prepare these structures are aromatic aldehydes rather than amines and therefore some modifications of the synthetic protocol will be required. The bicyclic heterocycles can be prepared as described above in Schemes III-VII but it is understood that suitable protecting groups should be employed to protect and later reveal sensitive functional groups, in particular the aromatic aldehyde function.

Scheme XIII summarizes the synthesis of the requisite substituted benzaldehyde intermediates. The starting materials for this synthesis may include commercially-available terephthaldehyde mono(diethyl acetal) or other substituted analog prepared using known art. The aldehyde starting materials are then converted to bicyclo[3.1.0]hexyl ring systems using the procedures described in Schemes III-VII. A final deprotection of the acetal then reveals the desired benzaldehyde intermediate. The removal of acetal protection can be accomplished using various reaction conditions that are well known in the art, (see "Protecting Groups" by Philip J. Kocienski; publisher: Georg Thieme Verlag: Stuttgart, 1994).

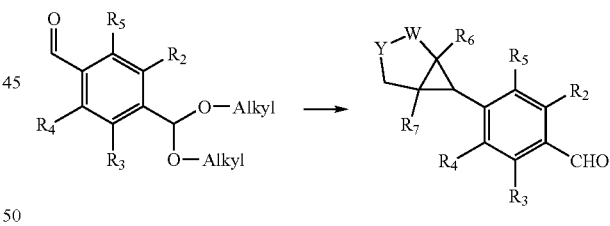

Step 1 of Scheme XIV involves reaction of the bicyclo [3.1.0]hexyl benzaldehyde intermediate with ethyl diazoacetate (as described in Mahmood et al., 1998 J. Org. Chem., 63, pgs. 3333-3336) to provide the ester aldehyde intermediate shown. Addition of hydroxylamine, followed by warming to reflux in aqueous methanol, yields the arylisoxazolinone (Step 2). This intermediate is then converted to the corresponding methylacetamide (Step 3) by reaction with N-(hydroxymethyl)acetamide acetate (prepared as described by Barnes et al. in U.S. Pat. No. 5,284,863, the disclosure of which is incorporated herein in its entirety) in a polar aprotic solvent such as DMF. In step 4, an optional step or steps may be required to introduce or further elaborate an $R^8$ substituent in cases where Y is —$N(R^8)$—. In cases were Y is S, these optional steps may constitute oxidation steps to form sulfoxide or sulfone functionality.

SCHEME XIV

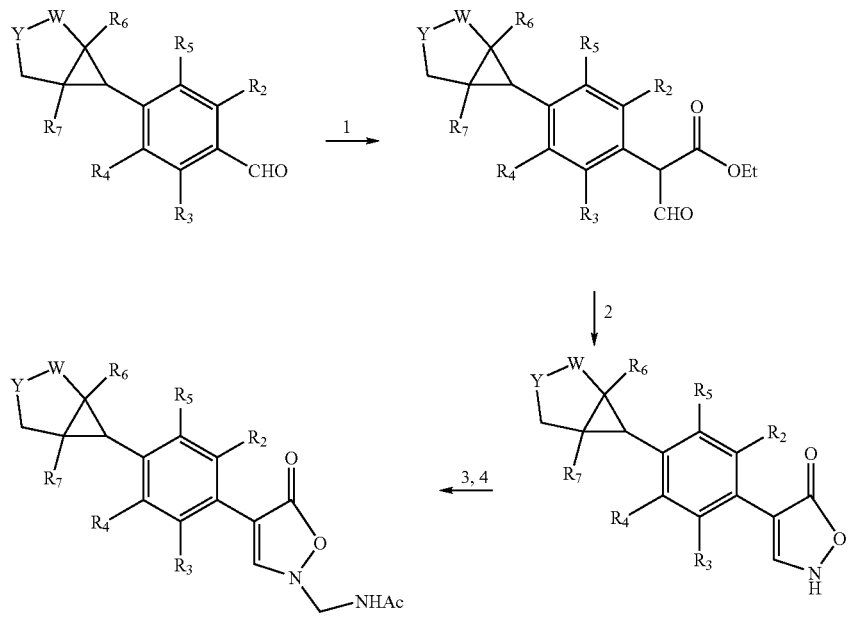

Scheme XV describes a general method for preparing arylisoxazoline compounds bearing bicyclic heterocycles of the type described in Schemes III-VII. In Step 1 of Scheme XV the substituted benzaldehyde is reacted with hydroxylamine hydrochloride in a polar protic solvent, such as methanol, in the presence of a base, such as pyridine, to afford the oxime.

In Step 2 of Scheme XV, the oxime is oxidized with N-chloro-succinamide (NCS) in an appropriate solvent, such as dichloromethane, to give the oximyl chloride. In Step 3, the oximyl chloride is reacted with an allylic compound such as allyl alcohol or N-acetylallylamine, in the presence of a base such as triethylamine and in a solvent such as dichloromethane, to provide hydroxymethyl or acetamidomethyl substituted isoxazolines. Alternatively, the oximyl chloride can be formed in situ and directly treated with the allylic compound (a combination of steps 2 and 3).

SCHEME XV

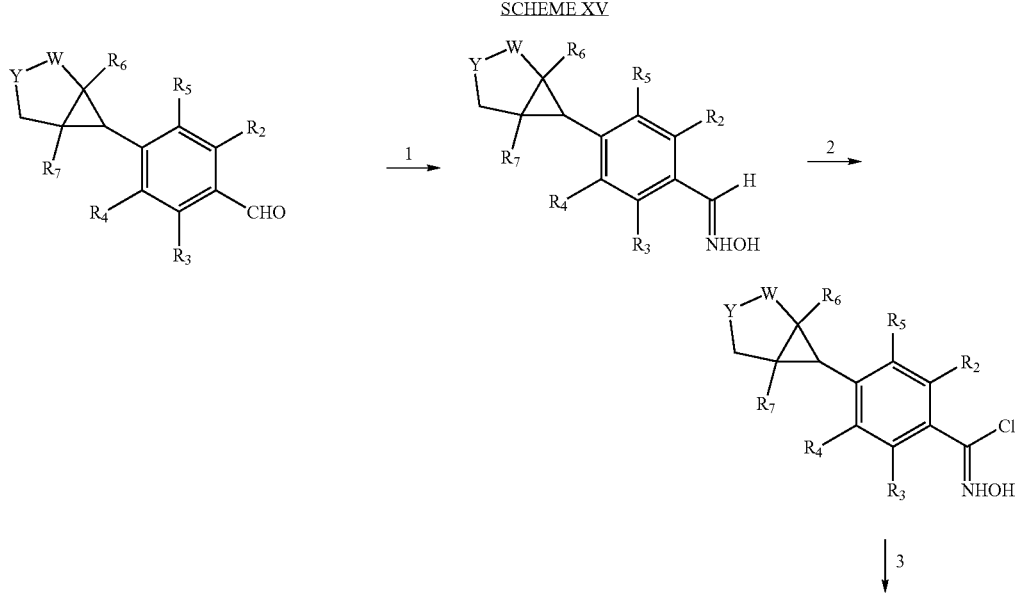

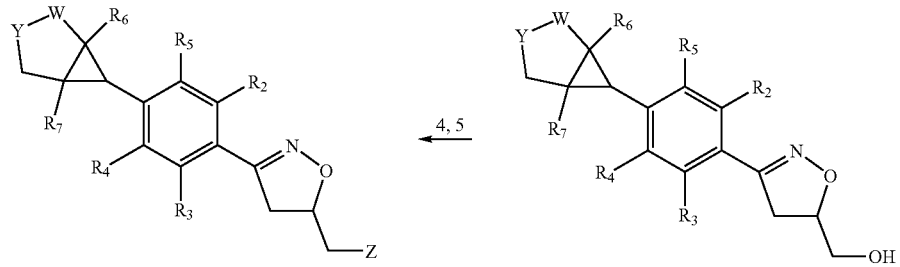

Step 4 of Scheme XV represents a step or series of steps for preparing compounds in which Z is a group other than NH(C=O)CH$_3$. First, the hydroxymethyl analog is elaborated to aminomethyl using known art (as described in step 1 of Scheme VI) and this intermediate is then converted to the desired amide or thioamide analogs (as described in step 3 of Scheme VII). Alternatively, a heterocyclic substituent (for analogs where Z is NH-het$^1$, O-het$^1$, S-het$^1$, or het$^2$) may be introduced from hydroxymethyl or azidomethyl intemediates using known art (as described in Schemes X-XII). In step 5, an optional step or steps may be required to introduce or further elaborate an R$^8$ substituent in cases where Y is —N(R$^8$)—. In cases were Y is S, these optional steps may constitute oxidation steps to form sulfoxide or sulfone functionality.

Utility and Testing

The compounds of the subject invention exhibit potent activities against a variety of organisms, including gram positive and/or gram negative bacteria. Accordingly, the compounds of the subject invention have broad antibacterial activity. Thus, the compounds of the present invention are useful antimicrobial agents and may be effective against a number of human and veterinary pathogens, including gram positive aerobic bacteria such as multiply-resistant *staphylococci* and *streptococci*, gram negative organisms such as *H. influenzae* and *M. catarrahlis*, as well as anaerobic organisms such as bacteroides and clostridia species, and acid-fast organisms such as *Mycobacterium tuberculosis* and *Mycobacterium avium*. In addition the compounds of the present invention are effective against infections in any area of the body.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," 3$^{rd}$ ed., published 1993 by the National Committee for Clinical Laboratory standards, Villanova, Pa., USA.

The in vitro MICs of test compounds may be determined by a standard agar dilution method. A stock drug solution of each analog is prepared in a preferred solvent, usually DMSO:H$_2$O (1:3). Serial 2-fold dilutions of each sample are made using 1.0 mL aliquots of sterile distilled water. To each 1.0 mL aliquot of drug is added 9 mL of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 mL drop of the cell suspension using a Steers replicator, yielding approximately 10$^4$ to 10$^5$ cells per spot. The plates are incubated overnight at 35° C.

Following incubation the Minimum Inhibitory Concentration (MIC µg/mL), the lowest concentration of drug that inhibits visible growth of the organism, is read and recorded. The data is shown in Table I. The compounds of Example 1 to Example 20 were tested using this method and all showed an MIC of 8 µg/mL or less against *S. aureus* UC9213, 2 µg/mL or less against *S. pneumoniae* UC9912 and 16 µg/mL or less against *H. influenzae* 30063, with the exception of the compounds of examples 1 and 7 which were 32 µg/mL or less and the compound of example 20 which was >64 µg/mL.

TABLE 1

Antimicrobial activity of selected compounds.

| Example # | *S. aureus* UC9213 MIC, µg/mL | *S. pneumoniae* UC9912 MIC, µg/mL | *H. influenzae* 30063 MIC, µg/mL |
|---|---|---|---|
| linezolid | 4 | 1 | 16 |
| 1 | 4 | 1 | 32 |
| 2 | 2 | 0.25 | 2 |
| 3 | 2 | 0.25 | 4 |
| 4 | 4 | 0.5 | 4 |
| 5 | 2 | 0.25 | 4 |
| 6 | 0.5 | 0.25 | 4 |
| 7 | 2 | 0.5 | 32 |
| 8 | 4 | 1 | 8 |
| 9 | 8 | 1 | 8 |
| 10 | 2 | 0.5 | 4 |
| 11 | 0.5 | 0.25 | 2 |
| 12 | 1 | 0.5 | 4 |
| 13 | 1 | 0.5 | 8 |
| 14 | 2 | 0.5 | 16 |
| 15 | 2 | 0.5 | 16 |
| 16 | 4 | 2 | 16 |
| 17 | 4 | 2 | 8 |
| 18 | 2 | 0.5 | 4 |
| 19 | 4 | 1 | 8 |
| 20 | 2 | 2 | >64 |
| 21 | 4 | 1 | 8 |
| 22 | 1 | 0.5 | 8 |
| 23 | 1 | 0.25 | 4 |
| 24 | 4 | 2 | 16 |
| 25 | 8 | 4 | 32 |
| 26 | 1 | 0.5 | 4 |
| 27 | 2 | 0.5 | 8 |
| 28 | 4 | 4 | 8 |
| 29 | 4 | 2 | 16 |
| 30 | 4 | 4 | 16 |
| 31 | 2 | 2 | 16 |

TABLE 1-continued

Antimicrobial activity of selected compounds.

| Example # | S. aureus UC9213 MIC, μg/mL | S. pneumoniae UC9912 MIC, μg/mL | H. influenzae 30063 MIC, μg/mL |
|---|---|---|---|
| 32 | 2 | 0.5 | 8 |
| 33 | 2 | 2 | 16 |
| 34 | 2 | 1 | 8 |
| 35 | 8 | 2 | 16 |
| 36 | 8 | 4 | 32 |
| 37 | 1 | 0.5 | 8 |
| 38 | 2 | 2 | 8 |
| 39 | 0.5 | 1 | 4 |
| 40 | 4 | 2 | 16 |
| 41 | 4 | 2 | 32 |
| 42 | 8 | 4 | 32 |
| 43 | 4 | 1 | 32 |
| 44 | 16 | 32 | 64 |
| 45 | 4 | 4 | 16 |
| 46 | 8 | 2 | 16 |
| 47 | 4 | 1 | 8 |
| 48 | 4 | 1 | 16 |
| 49 | >64 | >64 | >64 |
| 50 | 2 | 1 | 4 |
| 51 | 2 | 1 | 8 |
| 52 | 4 | 1 | 4 |
| 53 | 4 | 2 | 4 |
| 54 | 8 | 4 | 4 |
| 55 | 8 | 2 | 16 |
| 56 | 4 | 2 | 16 |
| 57 | 8 | 2 | 32 |
| 58 | 1 | 1 | 2 |
| 59 | 1 | 1 | 4 |
| 60 | 8 | 2 | 16 |
| 61 | 2 | 1 | 8 |
| 62 | 4 | 1 | 8 |
| 63 | 2 | 1 | 8 |
| 64 | 4 | 2 | 8 |
| 65 | 2 | 2 | 16 |
| 66 | 4 | 2 | 8 |
| 67 | 4 | 4 | 4 |
| 68 | 4 | 1 | 8 |
| 69 | 4 | 4 | 8 |
| 70 | 2 | 1 | 4 |
| 71 | 4 | 2 | 4 |
| 72 | 32 | 8 | 64 |
| 73 | 2 | 1 | 4 |
| 74 | 1 | 1 | 4 |
| 75 | 2 | 2 | 4 |

Administration and Pharmaceutical Formulations

In general, the compounds of the subject invention will be administered in a therapeutically effective amount by any of the accepted modes of administration for agents that serve similar utilities. The actual amount of the compound of the subject invention, i.e., the active ingredient, will depend on a number of factors, such as the severity of the disease, i.e., the infection, to be treated, the age and relative health of the subject, the potency of the compound used, the route and form of administration, and other factors all of which are within the routine skill of the attending clinician.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

When employed as pharmaceuticals, the compounds of the subject invention are usually administered in the form of pharmaceutical compositions. These compounds can be administered by a variety of routes including oral, or parenteral, rectal, transdermal, topical, subcutaneous, intravenous, intramuscular, and intranasal routes. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions may be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. The compound of the subject invention is employed at no more than about 20 weight percent of the pharmaceutical composition, generally no more than about 15 weight percent, with the balance being pharmaceutically inert carrier(s).

The active compound is effective over a wide dosage range and is generally administered in a pharmaceutically or therapeutically effective amount. It, will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, or about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. An enteric layer can separate these two components. This layer serves to resist disintegration in the stomach and to permit the inner component to pass intact into the duodenum or to provide for delayed release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions may be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered orally or nasally, from devices that deliver the formulation in an appropriate manner.

Suitable formulations for use in the present invention can be found in *Remington's Pharmaceutical Sciences*, Mace Publishing Company, Philadelphia, Pa., 17th ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

| | |
|---|---|
| bm = | broad multiplet |
| bd = | broad doublet |
| bs = | broad singlet |
| bt = | broad triplet |
| ca. = | about |
| CDI = | $_{1,1}$'carbodiimidazole |
| d = | doublet |
| dd = | doublet of doublets |
| dt = | doublet of triplets |
| DMF = | dimethylformamide |
| DMSO = | dimethyl sulfoxide |
| eq. = | equivalents |
| g = | grams |
| h = | hours |

-continued

| | |
|---|---|
| hept = | heptuplet |
| HPLC = | high pressure liquid chromatography |
| HATU = | N-[(dimethylamino)-1H-1,2,3-triazolo-[4,5-b]pyridin-1-yl-methylene]-N-methylmethanaminium hexafluorophosphate N-oxide |
| LiOtBu = | lithium tert-butoxide |
| m = | multiplet |
| M = | molar |
| mg = | milligram |
| mL = | milliliter |
| mm = | millimeter |
| mmol = | millimol |
| q = | quartet |
| s = | singlet |
| t = | triplet |
| tt = | triplet of triplets |
| TFA = | trifluoroacetic acid |
| THF = | tetrahydrofuran |
| TLC = | thin layer chromatography |
| p-TLC = | preparative thin layer chromatography |
| µM = | micromolar |
| N = | normality |
| MeOH = | methanol |
| DCM = | dichloromethane |
| HCl = | hydrochloric acid |
| ACN = | acetonitrile |
| MS = | mass spectrometry |
| rt = | room temperature |
| EtOAc = | ethyl acetate |
| EtO = | ethoxy |
| Ac = | acetate |
| µL = | microliter |
| J = | coupling constant |
| NMR = | Nuclear magnetic resonance |
| MHz = | megahertz |
| Hz = | hertz |
| m/z = | mass to charge ratio |
| min = | minutes |
| Boc = | tert-butoxycarbonyl |
| CBZ = | benzyloxycarbonyl |
| EDCI = | 1-(3-dimethylaminopropyl)-3-ethylcarbodiimide hydrochloride |
| HOBT = | 1-hydroxybenzotriazole hydrate |
| DIEA = | N,N-diisopropylethylamine |
| BINAP = | 2,2'-bis(diphenylphosphino)-1,1'-binaphthyl |
| rac = | racemic |

All of the starting materials used in the synthesis of the compounds of the present invention are known compounds, some of which are commercially available from at least one or more of the following companies: Aldrich, Fluka, Lancaster, Sigma, Chemservice, Bachem, Maybridge, NovaBiochem, Alfa and TCI. Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Acros" indicates that the compound or reagent used in the following procedures is commercially available from Acros Organics distributed by Fisher Scientific 2000 Park Lane Drive, Pittsburgh, Pa. 15275; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate St., Portland, Oreg., 97203, OR, USA; the term "Alfa" indicates that the compound or reagent is commercially available from Johnson Matthey Catalog Company, Inc. 30 Bond Street, Ward Hill, Mass. 01835-0747; and the term "Nova Biochem" indicates that the compound or reagent is commercially available from NovaBiochem USA, 10933 North Torrey Pines Road, P.O. Box 12087, La Jolla Calif. 92039-2087.

In the examples below, all temperatures are in degrees Celsius (unless otherwise indicated) and the following general procedures were used to prepare the compounds as indicated.

Example 1

N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide

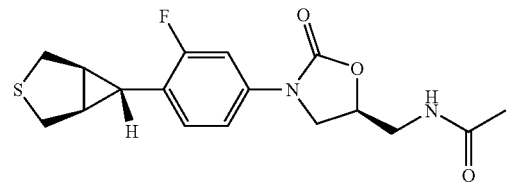

Lithium butoxide solution (3.0 mL of a 1.0 M THF solution, 3.0 mmol) was added to a cooled (0° C.) solution of benzyl 3-fluoro-4-[exo-(1R,5S)-3-thiabicyclo[3.1.0]hex-6-yl]phenylcarbamate (0.35 g, 1.0 mmol) in DMF (0.7 mL) and MeOH (0.081 mL, 2.0 mmol). Solid (S)-acetic acid 2-acetylamino-1-chloromethyl-ethyl ester (0.39 g, 2.0 mmol) was then added and the solution allowed to warm to room temperature and stirred for 20 h. Saturated aqueous ammonium chloride (2 mL) was added, along with 10 mL of H$_2$O and 10 mL of brine. The solution was extracted with three portions of dichloromethane and the combined organic phases dried (MgSO$_4$), filtered and concentrated. The crude residue was purified by column chromatography (0-3% MeOH-DCM) to provide the title compound.

Yield 0.24 g (68%). MS (m/z): [M+H]=351 $^1$H NMR (300 MHz, CDCl$_3$): 1.93 (m, 2H), 2.02 (m, 3H), 2.47 (t, J=4 Hz, 1H), 3.08-3.21 (m, 4H), 3.59-3.77 (m, 3H), 4.02 (t, J=9 Hz, 1H), 4.75-4.80 (m, 1H), 6.14 (t, J=6 Hz, 1H), 6.94 (t, J=8 Hz, 1H), 7.09 (dd, J=8, 2 Hz, 1H), 7.35 (dd, J=12, 2 Hz, 1H) mp=177-178° C.

Intermediates for the preparation of example 1 were synthesized as follows.

I. benzyl 3-fluoro-4-formylphenylcarbamate

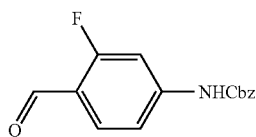

Ammonium chloride (38 g, 0.71 mol) was added to a solution of 2-fluoro-4-nitrobenzaldehyde (12 g, 0.071 mol, prepared as described by Gordeev, et. al., U.S. Pat. No. 6,239,152, which is incorporated herein by reference in its entirety) in 2:1 ethanol-$H_2O$ (300 mL). The mixture was heated to 80° C. and treated with iron metal in 6 portions over 1 hour (11.9 g total, 0.212 mmol). After the addition was complete the reaction mixture was stirred another hour and the warm solution filtered with the aid of more water and ethanol. The filtrate was then concentrated to remove ethanol and the resulting aqueous solution extracted thrice with ethyl acetate. The combined organic phases were washed with water, brine, and dried ($MgSO_4$), filtered, and concentrated to provide 9.6 g of the crude amine.

The crude amine (9.6 g, 0.069 mol) was dissolved in dichloromethane (230 mL) and pyridine (11.1 mL, 0.138 mol) and the solution cooled to 0° C. The solution was then treated with benzyl chloroformate (11.8 mL, 0.083 mol) dropwise and the solution stirred at room temperature for 18 h. The reaction mixture was then diluted with more dichloromethane and the organic solution washed thrice with water, once with brine, and dried ($MgSO_4$), filtered, and concentrated. Trituration with hexane provided the title compound as a yellow solid.

Yield 15 g (77%). $^1$H NMR (300 MHz, $CDCl_3$): 5.23 (s, 2H), 6.99 (bs, 1H), 7.03 (dd, J=9, 2 Hz, 1H), 7.37-7.42 (m, 5H), 7.57 (dd, J=13, 2 Hz, 1H), 7.81 (t, J=9 Hz, 1H), 10.23 (s, 1H).

II. methyl(2E)-3-(4-{[(benzyloxy)carbonyl]amino}-2-fluorophenyl)acrylate

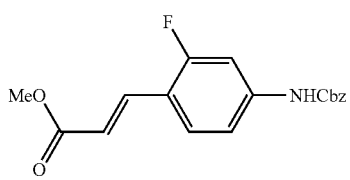

Sodium hydride (0.513 g of a 60% dispersion, 12.8 mmol) was placed in a flask and washed three times with hexane. The resulting solid was suspended in DMF (10 mL) and cooled to 0° C. Trimethyl phosphonoacetate (2.2 mL, 13.5 mmol) was added dropwise to this suspension to give a clear homogeneous solution. After stirring for another 15 minutes at 0° C., a solution of benzyl 3-fluoro-4-formylphenylcarbamate (3.5 g, 12.8 mmol) in DMF (10 mL) was added dropwise. The resulting orange suspension was allowed to warm slowly to room temperature and stirred for 16 hours. The reaction mixture was poured into 0.5 N HCl and extracted with three portions of dichloromethane. Combined organic phases were washed with saturated $NaHCO_3$, $H_2O$, brine, and dried ($MgSO_4$) filtered and concentrated. The resulting orange solid was washed sequentially with hexane and then 30% ethyl acetate-hexane to provide the title compound as a yellow-orange solid (2.7 g). The washings were concentrated and purified by column chromatography (0-30% ethyl acetate-hexane) to provide an additional 0.95 g of the product.

Yield 3.66 g (87%). $^1$H NMR (300 MHz, $d_6$-DMSO): 3.71 (s, 3H), 5.17 (s, 2H), 6.55 (dd, J=16, 1 Hz, 1H), 7.26 (d, J=9 Hz, 1H), 7.35-7.50 (m, 6H), 7.63 (d, J=16 Hz, 1H), 7.79 (t, J=9 Hz, 1H), 10.3 (bs, 1 H) mp=157-158° C.

III. benzyl 3-fluoro-4-[(1E)-3-hydroxyprop-1-enyl]phenylcarbamate

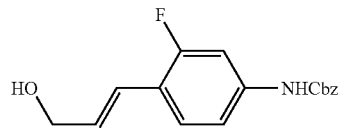

A THF solution of $LiAlH_4$ (10.2 mL of a 1.0 M solution, 10.2 mmol) was added to a cooled (-78° C.) solution of methyl (2E)-3-(4-{[(benzyloxy)carbonyl]amino}-2-fluorophenyl)acrylate (3.35 g, 10.2 mmol) in TBF (50 mL). The solution was allowed to warm slowly to -20° C. and maintained at that temperature for 2 hours. The reaction mixture was quenched by slow addition of saturated $NH_4Cl$ and then treated with 30 mL of dilute citric acid. The resulting solution was stirred for 15 minutes and then extracted with three portions of ethyl acetate. Combined organic phases were washed with $H_2O$, brine and dried ($MgSO_4$), filtered and concentrated to give a red oil. The crude product was purified by column chromatography (25-50% ethyl acetate-hexane) to provide the title compound as a yellow solid.

Yield 2.14 g (70%). $^1$H NMR (300 MHz, $CDCl_3$): 1.43 (t, J=6 Hz, 1H), 4.33 (t, J=6 Hz, 2H), 5.28 (s, 2H), 6.37 (dt, J=15, 6 Hz, 1H), 6.69 (d, J=16 Hz, 1H), 6.70 (s, 1H), 6.99 (d, J=9 Hz, 1H), 7.20-7.39 (m, 7H) mp=105-106° C.

IV. (2E)-3-(4-{[(benzyloxy)carbonyl]amino}-2-fluorophenyl)prop-2-enyl diazoacetate

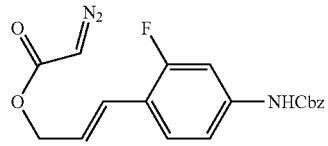

Glyoxylic acid chloride p-toluenesulfonylhydrazone (2.2 g, 8.5 mmol, prepared as described by C. J. Blankley, F. J. Sauter and H. O. House, *Organic Syntheses,* Coll. Vol. V, p. 258; John Wiley, New York (1973)) was added to a suspension of benzyl 3-fluoro-4-[(1E)-3-hydroxyprop-1-enyl]phenylcarbamate (2.14 g, 7.1 mmol) in dichloromethane (55 mL). The mixture was cooled to 0° C. and treated with N,N-dimethylaniline (1.0 mL, 7.81 mmol). After 30 minutes, triethylamine (4.9 mL, 35.5 mmol) was added and the mixture stirred 30 minutes at 0° C. and 15 minutes at room temperature. The reaction mixture was then concentrated to about 15 mL and 50 mL of water added. The mixture was extracted with two portions of diethyl ether and the combined organic solutions washed with saturated NaHCO$_3$, brine and dried (MgSO$_4$), filtered and concentrated. Purification by column chromatography (0-25% ethyl acetate-hexane) provided the title compound as a yellow solid.

Yield 2.30 g (88%). $^1$H NMR (300 MHz, CDCl$_3$): 4.80 (s, 2H), 4.83 (s, 1H), 5.21 (s, 2H), 6.29 (dt, J=16, 6 Hz, 1H), 6.72 (d, J=16 Hz, 1H), 6.73 (s, 1H), 6.98 (d, J=8 Hz, 1H), 7.25-7.40 (m, 7H) mp=93-96° C.

V. (racemic)benzyl 3-fluoro-4-[(1S,5R,6R)-2-oxo-3-oxabicyclo[3.1.0]hex-6-yl]phenylcarbamate

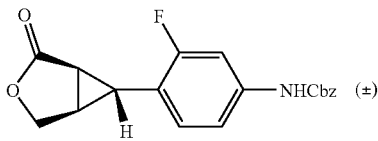

A solution of (2E)-3-(4-{[(benzyloxy)carbonyl]amino}-2-fluorophenyl)prop-2-enyl diazoacetate (2.26 g, 6.12 mmol) in toluene (125 mL) was added dropwise over 14 h to a refluxing solution of bis-(N-t-butylsalicylaldiminato)copper(II) (0.254 g, 0.61 mmol, prepared as described by R. G. Charles, *J. Org. Chem.* 1957, 22, 677) in 125 mL of toluene. After the addition was complete, the reaction mixture was heated another hour at reflux, then cooled, filtered and concentrated. The crude oil was purified by column chromatography (0-0.5% MeOH-DCM) to provide the title compound as a yellow solid.

Yield 1.57 g (75%). $^1$H NMR (300 MHz, CDCl$_3$): 2.33-2.39 (m, 2H), 2.49-2.53 (m, 1H), 4.4 (m, 2H), 5.18 (s, 2H), 6.82 (t, J=9 Hz, 1H), 7.0 (d, J=8 Hz, 1H), 7.01 (s, 1H), 7.25-7.38 (m, 6H); mp=141-142° C.

VI. benzyl 4-[exo-(2R,3S)-2,3-bis(hydroxymethyl)cyclopropyl]-3-fluorophenylcarbamate

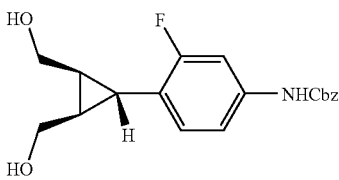

A THF solution of LiAlH$_4$ (2.5 mL of a 1.0M solution, 2.5 mmol) was added dropwise to a solution of benzyl 3-fluoro-4-[(1S,5R,6R)-2-oxo-3-oxabicyclo[3.1.0]hex-6-yl]phenylcarbamate (0.86 g, 2.5 mmol) in THF (20 mL) cooled at 0° C. The solution was stirred at 0° C. for 1 h and then treated with more LiAlH$_4$ solution (1.25 mL, 1.25 mmol) and allowed to warm to room temperature. After another hour at room temperature, the solution was quenched by the slow addition of saturated NH$_4$Cl (15 mL) followed by H$_2$O (30 mL) and saturated citric acid (10 mL). The solution was concentrated to remove THF and the resulting aqueous solution extracted with three portions of ethyl acetate. The combined organic phases were then washed with H$_2$O, brine, and dried (MgSO$_4$), filtered and concentrated to an oil. Purification by column chromatography (0-3% MeOH-DCM) provided the title compound as a white foam.

Yield 0.55 g (63%). $^1$H NMR (300 MHz, CDCl$_3$): 1.65-1.72 (m, 2H), 1.90 (t, J=5 Hz, 1H), 2.72 (bs, 2H), 3.48 (m, 2H), 4.23 (m, 2H), 5.19 (s, 2H), 6.75 (s, 1H), 6.82 (t, J=8 Hz, 1H), 6.93 (dd, J=9, 2 Hz, 1H), 7.30-7.41 (m, 6H).

VII. benzyl 4-[exo-(2R,3S)-2,3-bis(methanesulfonyloxymethyl)cyclopropyl]-3-fluorophenylcarbamate

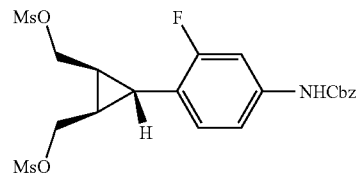

Methanesulfonic anhydride (1.51 g, 8.7 mmol) was added to a cooled (0° C.) solution of benzyl 4-[exo-(2R,3S)-2,3-bis(hydroxymethyl)cyclopropyl]-3-fluorophenylcarbamate (1.0 g, 2.9 mmol) in dichloromethane (36 mL) and triethylamine (1.61 mL, 11.6 mmol). The solution was allowed to warm to room temperature and stirred for 2 h. The solution was then diluted with 30 mL dichloromethane and washed with two portions of saturated NaHCO$_3$, brine, and dried (MgSO$_4$). The crude product was passed through a short pad of SiO$_2$ (eluting with ethyl acetate) to provide the title compound as a white solid that was used directly in the next reation.

Yield 1.4 g (96%). $^1$H NMR mp=85-95° C. dec.

VIII. benzyl 3-fluoro-4-[exo-(1R,5S)-3-thiabicyclo[3.1.0]hex-6-yl]phenylcarbamate

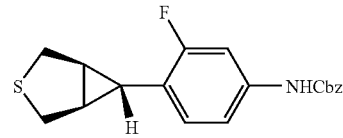

Sodium sulfide (0.65 g, 8.4 mmol) was added to a solution of benzyl 4-[exo-(2R,3S)-2,3-bis(methanesulfonyloxymethyl)cyclopropyl]-3-fluorophenylcarbamate (1.4 g, 2.8 mmol) in DMSO (5.5 mL). The reaction mixture was stirred at room temperature for 2 h. The resulting yellow suspension was then diluted with 30 mL of H$_2$O and extracted with three portions of diethyl ether. The combined organic extracts were dried (MgSO$_4$), filtered and concentrated to provide the title compound as a white solid.

Yield 0.87 g (91%). $^1$H NMR (300 MHz, CDCl$_3$): 1.91 (m, 2H), 2.44 (m, 1H), 3.09 (d, J=11 Hz, 2H), 3.18 (d, J=11 Hz, 2H), 5.20 (s, 2H), 6.61 (s, 1H), 6.91 (t, J=8 Hz, 1H), 6.94 (d, J=8 Hz, 1H), 7.19-7.40 (m, 6H) mp=121-122° C.

Example 2

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide

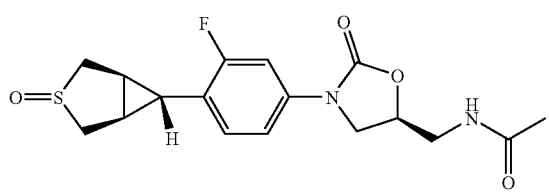

A solution of sodium periodate (0.087 g, 0.41 mmol) in water (1.5 mL) was added to a suspension of N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide (0.136 g, 0.39 mmol) in methanol (5 mL) and stirred at 4° C. for 24 h. The resulting suspension was filtered with the aid of chloroform and the filtrate concentrated. The resulting solution was diluted with 5 mL of water and extracted with five portions of chloroform. The combined organic phases were dried (MgSO$_4$) filtered and concentrated. Purification by column chromatography (10% ACN-5% MeOH-DCM) provided the title compound as a separable mixture of sulfoxide diastereomers (ca. 1:1 ratio).

Yield (total for both isomers) 0.095 g (65%). Low Rf ("syn") isomer: $^1$H NMR (300 MHz, CD$_3$OD): 1.95 (s, 3H), 2.24 (t, J=4 Hz, 1H), 2.58 (m, 2H), 3.10 (d, J=15 Hz, 2H), 3.33-3.38 (m, 2H), 3.54 (d, J=5 Hz, 2H), 3.78 (dd, J=6, 3 Hz, 1H), 4.11 (t, J=9 Hz, 1H), 4.74-4.81 (m, 1H), 7.03 (t, J=8 Hz, 1H), 7.19 (dd, J=9, 2 Hz, 1H), 7.46 (dd, J=13, 2 Hz, 1H) High Rf ("anti") isomer: $^1$H NMR (300 MHz, CD$_3$OD): 1.95 (s, 3H), 2.31 (m, 2H), 2.74 (t, J=4 Hz, 1H), 3.24 (d, J=15 Hz, 2H), 3.46-3.55 (m, 4H), 3.78 (dd, J=6, 3 Hz, 1H), 4.11 (t, J=9 Hz, 1H), 4.75-4.81 (m, 1H), 7.06 (t, J=8 Hz, 1H), 7.20 (dd, J=8, 2 Hz, 1H), 7.44 (dd, J=13, 2 Hz, 1H).

Example 3

N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]acetamide

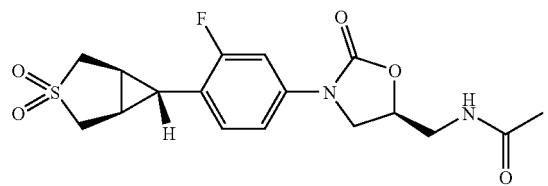

Peracetic acid (0.18 mL of a 32% aqueous solution, 0.856 mmol) was added to a solution of N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide (0.10 g, 0.285 mmol) in THF (9 mL) cooled at 0° C. The reaction mixture was stirred for 2 h at room temperature, treated with more peracetic acid (0.050 mL) and stirred another 3 h. The reaction was quenched by the addition of saturated Na$_2$S$_2$O$_3$ (2 mL) and water (5 mL). The THF was then removed on the rotary evaporator and the resulting solution extracted with three portions of ethyl acetate. Combined organic extracts were then washed with dilute NaHCO$_3$, brine, and dried (MgSO$_4$). The crude product was purified by column chromatography (0-4% MeOH-DCM) to provide the title compound as a foam.

Yield 0.089 g (82%). MS (m/z): [M+Na]=405 $^1$H NMR (300 MHz, d$_6$-DMSO): 1.82 (s, 3H), 2.10 (m, 2H), 2.33 (t, J=4 Hz, 1H), 3.01 (d, J=13 Hz, 2H), 3.33-3.41 (m, 2H), 3.59 (m, 2H), 3.71 (t, J=7 Hz, 1H), 4.09 (t, J=9 Hz, 1H), 4.71 (m, 1H), 7.12 (t, J=8 Hz, 1H), 7.22 (d, J=8 Hz, 1H), 7.47 (d, J=13 Hz, 1H), 8.24 (t, J=5 Hz, 1H).

Example 4

N-[((5S)-3-{3-fluoro-4-[exo-(1R,5S)-3-oxabicyclo[3.1.0]hex-6-yl]phenyl}-2-oxo-1,3-oxazolidin-5-yl)methyl]acetamide

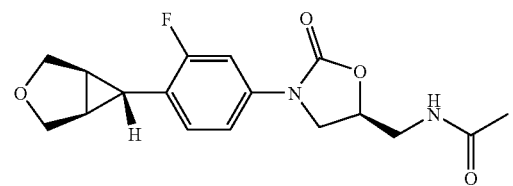

A solution of benzyl 3-fluoro-4-[exo-(1R,5S)-3-oxabicyclo[3.1.0]hex-6-yl]phenylcarbamate (0.072 g, 0.22 mmol) in DMF (0.15 mL) and MeOH (0.018 mL, 0.44 mmol) was cooled at 0° C. and treated with LiOtBu solution (0.66 mL, 0.66 mmol) dropwise. The solution was then treated in one portion with (S)-acetic acid 2-acetylamino-1-chloromethylethyl ester (0.085 g, 0.44 mmol). The reaction mixture was slowly warmed to room temperature and stirred for 20 h. The solution was then treated with 1.0 mL of saturated NH$_4$Cl was added followed by 5 mL of water and 5 mL of brine. The mixture was extracted with three portions of dichloromethane and the combined organic phases washed with water, brine, and dried (MgSO$_4$), filtered and concentrated to an oil. Purification by column chromatography (0→3% MeOH-DCM) provided the title compound.

Yield 52 mg (70%). MS (m/z): [M+H]=335 $^1$H NMR (300 MHz, d$_6$-DMSO): 1.81 (m, 1H), 1.82 (s, 3H), 2.01 (m, 2H), 3.40 (t, J=5 Hz, 2H), 3.68 (d, J=8 Hz, 2H), 3.70 (m, 1H), 3.89 (d, J=8 Hz, 2H), 4.09 (t, J=9 Hz, 1H), 4.71 (m, 1H), 7.10 (t, J=9 Hz, 1H), 7.20 (dd, J=9, 2 Hz, 1H), 7.44 (dd, J=13, 2 Hz, 1H), 8.24 (t, J=6 Hz, 1H).

Intermediates for the preparation of example 4 were synthesized as follows.

I. benzyl 3-fluoro-4-[exo-(1R,5S)-3-oxabicyclo[3.1.0]hex-6-yl]phenylcarbamate

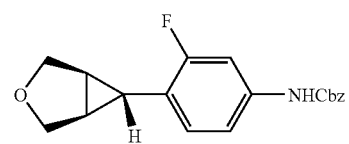

A solution of benzyl 4-[exo-(2R,3S)-2,3-bis(hydroxymethyl)cyclopropyl]-3-fluorophenylcarbamate (0.18 g, 0.52 mmol,) in THF (5 mL) was cooled to −50° C. An n-BuLi solution (0.72 mL, 1.14 mmol) was added and the resulting yellow suspension was stirred for 10 min and then methanesulfonyl chloride (0.088 mL, 1.14 mmol) was added. This produced a homogeneous solution that was stirred for 10 min and then treated with more n-BuLi (0.36 mL, 0.57 mmol). The solution was allowed to warm to −30° C. over one hour and then quenched by the addition of water and then dilute $NaHCO_3$. THF was removed in vacuo and the resulting aqueous solution was then extracted with ethyl acetate three times. The combined organic phases were then washed with brine and dried ($MgSO_4$), filtered and concentrated. The crude product was purified by column chromatography (0→30% ethyl acetate/hexane) to provide the title compound.

Yield 73 mg (43%). $^1$H NMR (300 MHz, $CDCl_3$): 1.89 (m, 2H), 1.98 (t, J=4 Hz, 1H), 3.80 (d, J=8 Hz, 2H), 4.02 (d, J=8 Hz, 2H), 5.20 (s, 2H), 6.63 (bs, 1H), 6.87 (t, J=8 Hz, 1H), 6.95 (d, J=8 Hz, 1H), 7.25 (d, J=12 Hz, 1H), 7.35–7.41 (m, 5H) mp=118-119° C.

Example 5

N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]acetamide

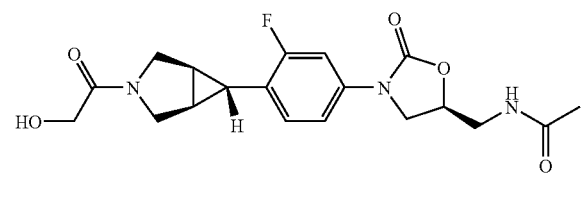

A solution of N-[((5S)-3-{3-fluoro-4-[exo-(1R,5S)-3-(2-benzyloxyacetyl)-3-azabicyclo[3.1.0]hex-6-yl]phenyl}-2-oxo-1,3-oxazolidin-5-yl)methyl]acetamide (0.089 g, 0.185 mmol) in 2:1 methanol-dichloromethane (6 mL) was stirred under a hydrogen atmosphere in the presence of 10% Pd/C (0.025 g) for 1.5 h and then filtered through celite. The filtrate was concentrated to provide the title compound.

Yield 0.069 g (95%). $^1$H NMR (300 MHz, $d_6$-DMSO): 1.72 (t, J=4 Hz, 1H), 1.82 (s, 3H), 1.93 (m, 1H), 2.06 (m, 1H), 3.35–3.47 (m, 3H), 3.53–3.88 (m, 4H), 3.90–4.12 (m, 3H), 4.56 (t, J=6 Hz, 1H), 4.69–4.74 (m, 1H), 7.08 (t, J=9 Hz, 1H), 7.20 (dd, J=9, 2 Hz, 1H), 7.45 (dd, J=13, 2 Hz, 1H), 8.24 (t, J=6 Hz, 1H).

Intermediates for the preparation of example 5 were synthesized as follows.

I. benzyl 3-fluoro-4-[exo-(1R,5S)-3-(4-methoxybenzyl)-3-azabicyclo[3.1.0]hex-6-yl]phenylcarbamate

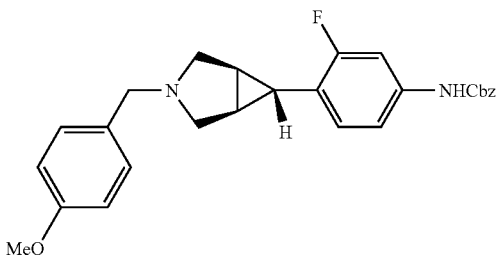

Benzyl 4-[exo-(2R,3S)-2,3-bis(methanesulfonyloxymethyl)cyclopropyl]-3-fluorophenylcarbamate (1.05 g, 2.1 mmol) was dissolved in 4-methoxybenzylamine (4.2 mL, 32 mmol) and stirred at room temperature for 16 h. The resulting solution was then diluted with 125 mL of ethyl aceate and washed with 2.5% $NaHCO_3$, dilute aqueous HCl (32 mL of a 1 N solution diluted to 100 mL with $H_2O$), again with 2.5% $NaHCO_3$, brine, and dried ($MgSO_4$), filtered and concentrated. The crude product was then purified by silica gel column chromatography (gradient 0-25% ethyl acetate-hexane—1% $Et_3N$) to provide the title compound as a white solid.

Yield 0.75 g (79%). $^1$H NMR (300 MHz, $CDCl_3$): 1.65 (bs, 2H), 2.44 (d, J=9 Hz, 2H), 2.47 (m, 1H), 3.09 (d, J=9 Hz, 2H), 3.58 (s, 2H), 3.80 (s, 3H), 5.19 (s, 2H), 6.60 (bs, 1H), 6.77-6.93 (m, 4H), 7.21-7.41 (m, 8H).

II. N-[((5S)-3-{3-fluoro-4-[exo-(1R,5S)-3-(4-methoxybenzyl)-3-azabicyclo[3.1.0]hex-6-yl]phenyl}-2-oxo-1,3-oxazolidin-5-yl)methyl]acetamide Benzyl 3-fluoro-4-[exo-(1R,5S)-3-(4-methoxybenzyl)-3-azabicyclo[3.1.0]hex-6-yl]phenylcarbamate (0.75 g, 1.7 mmol) was dissolved in DMF (1.1 mL) and methanol (0.137 mL, 3.4 mmol), cooled at 0° C. and treated with lithium butoxide solution dropwise over 5 minutes (5.1 mL of a 1.0 M THF solution, 5.1 mmol). Solid (S)-acetic acid 2-acetylamino-1-chloromethyl-ethyl ester (0.66 g, 3.4 mmol) was then added and the solution allowed to warm to room temperature and stirred for 20 h. Saturated aqueous ammonium chloride (4 mL) was added, along with 20 mL of $H_2O$ and 20 mL of brine. The solution was extracted with three portions of dichloromethane and the combined organic phases dried ($MgSO_4$), filtered and concentrated. The crude product was purified by column chromatography (0-5% MeOH-DCM) to provide the title compound.

Yield 0.49 g (64%). ¹H NMR (300 MHz, CDCl₃): 1.66 (bs, 2H), 2.02 (s, 3H), 2.44 (d, J=8 Hz, 2H), 2.50 (m, 1H), 3.10 (d, J=9 Hz, 2H), 3.51-3.78 (m, 3H), 3.56 (s, 2H), 3.80 (s, 3H), 4.00 (t, J=9 Hz, 1H), 4.72-4.79 (m, 1H), 6.20 (bs, 1H), 6.83-6.88 (m, 3H), 7.06 (dd, J=9, 2 Hz, 1H), 7.22 (d, J=9 Hz, 2H), 7.31 (dd, J=12, 2 Hz, 1H).

III. N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide

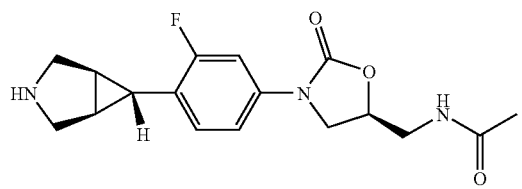

A solution of N-[((5S)-3-{3-fluoro-4-[exo-(1R,5S)-3-(4-methoxybenzyl)-3-azabicyclo[3.1.0]hex-6-yl]phenyl}-2-oxo-1,3-oxazolidin-5-yl)methyl]acetamide (0.49 g, 1.08 mmol) in 1:1 ethyl acetate-methanol (50 mL) was stirred under a hydrogen atmosphere in the presence of 20% Pd(OH)₂/C (0.5 g) for 16 h and then filtered through celite. The filtrate was concentrated to provide the title compound which was used directly in the next reaction.

VI. N-[((5S)-3-{3-fluoro-4-[exo-(1R,5S)-3-(2-benzyloxyacetyl)-3-azabicyclo[3.1.0]hex-6-yl]phenyl}-2-oxo-1,3-oxazolidin-5-yl)methyl]acetamide

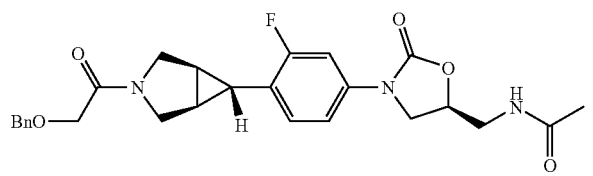

A solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.082 g, 0.25 mmol) in dichloromethane (5 mL) and triethylamine (0.081 mL, 0.58 mmol) was cooled to 0° C. Benzyloxyacetyl chloride (0.050 mL, 0.32 mmol) was added to the solution and the mixture stirred for 1.5 h at room temperature. More dichloromethane was added and the solution extracted with 2.5% NaHCO₃ (back extracting with more dichloromethane). The combined organic phases were then washed with brine and dried (MgSO₄), filtered, and concentrated. Purification by silica gel column chromatography (0-2% MeOH—CH₂Cl₂) provided the title compound.

Yield 0.089 g (74% over two steps). ¹H NMR (300 MHz, CDCl₃): 1.78 (bs, 1H), 1.91 (bs, 2H), 2.02 (s, 3H), 3.54-3.78 (m, 6H), 3.99-4.09 (m, 2H), 4.10 (s, 2H), 4.63 (s, 2H), 4.73-4-81 (m, 1H), 6.25 (m, 1H), 6.89 (t, J=8 Hz, 1H), 7.11 (d, J=8 Hz, 1H), 7.27-7.38 (m, 6H).

Example 6

2,2-difluoro-N-[((5S)-3-{3-fluoro-4-[exo-(1R,5S)-3-gycoloyl-3-azabicyclo[3.1.0]hex-6-yl]phenyl}-2-oxo-1,3-oxazolidin-5-yl)methyl]ethanethioamide

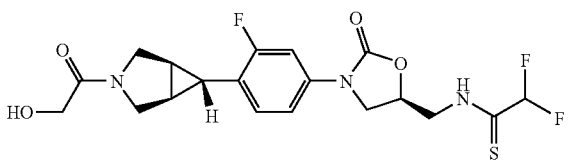

A solution of (5S)-5-(aminomethyl)-3-{3-fluoro-4-[exo-(1R,5S)-3-glycoloyl-3-azabicyclo[3.1.0]hex-6-yl]phenyl}-1,3-oxazolidin-2-one (0.32 mmol) in methanol (3 mL) and triethylamine (0.13 mL, 0.96 mmol) was treated with difluoroacetic acid 3,3-diphenyl-1-propanol ester (0.15 g, 0.13 mL, 0.48 mmol) as a solution in 0.7 mL of dichloromethane. The mixture was stirred at room temperature for 20 h and concentrated. The residue was dissolved in ethyl acetate and washed with 2.5% NaHCO₃, brine, and dried (MgSO₄). Purification by column chromatography (0→2% MeOH—CH₂Cl₂) provided the title compound.

Yield 0.113 g (75% over three steps). ¹H NMR (300 MHz, d₆-DMSO): 1.73 (t, J=3 Hz, 1H), 1.93 (m, 1H), 2.06 (m, 1H), 3.42 (dd, J=12, 4 Hz, 1H), 3.55 (dd, J=11, 5 Hz, 1H), 3.65-4.09 (m, 7H), 4.16 (t, J=9 Hz, 1H), 4.56 (t, J=5 Hz, 1H), 5.02 (m, 1H), 6.49 (t, J=55 Hz, 1H), 7.09 (t, J=9 Hz, 1H), 7.21 (dd, J=9, 2 Hz, 1H), 7.45 (dd, J=13, 2 Hz, 1H), 11.14 (bs, 1H).

Intermediates for the preparation of example 6 were synthesized as follows.

I. tert-butyl((5S)-3-{3-fluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate

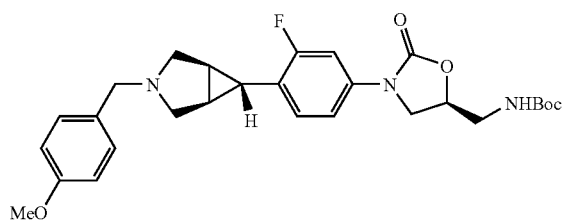

A solution of lithium t-butoxide (1.85 mL, 1.85 mmol) was added to a cooled (0° C.) solution of benzyl 3-fluoro-4-[exo-(1R,5S)-3-(4-methoxybenzyl)-3-azabicyclo[3.1.0]hex-6-yl]phenylcarbamate (0.33 g, 0.74 mmol) and (S)-(3-chloro-2-hydroxy-propyl)-carbamic acid tert-butyl ester (0.20 g, 0.96 mmol, prepared according to the procedure described in U.S. patent application Ser. No. 09/982,157, incorporated herein in its entirety) in DMF (0.5 mL). The resulting solution was stirred overnight and then quenched by the addition of saturated NH₄Cl, water, and brine. The solution was extracted with two portions of dichloromethane and the combined organics washed with water, brine, and dried (MgSO₄), filtered and concentrated. The crude product was purified by column chromatography (0-50% ethyl acetate—hexane—1% Et₃N) to provide the title compound.

Yield 0.28 g (73%). $^1$H NMR (300 MHz, CDCl$_3$): 1.44 (s, 9H), 1.66 (m, 2H), 2.45 (d, J=8 Hz, 2H), 2.50 (t, J=3 Hz, 1H), 3.10 (d, J=9 Hz, 2H), 3.48-3.53 (m, 2H), 3.58 (s, 2H), 3.78 (m, 1H), 3.79 (s, 3H), 3.99 (t, J=9 Hz, 1H), 4.72-4.76 (m, 1H), 4.99 (bt, 1H), 6.83-6.89 (m, 3H), 7.09 (dd, J=9, 2 Hz, 1H), 7.21-7.24 (m, 2H), 7.32 (dd, J=12, 2 Hz, 1H).

II. tert-butyl((5S)-3-{3-fluoro-4-[exo-(1R,5S)-3-azabicyclo[3.1.0]hex-6-yl]phenyl}-2-oxo-1,3-oxazolidin-5-yl)methylcarbamate

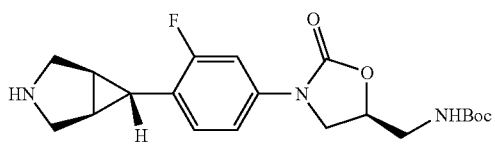

A solution of tert-butyl ((5S)-3-{3-fluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate (0.275 g, 0.54 mmol) in 1:1 ethyl acetate—methanol (6 mL) was stirred under a hydrogen atmosphere in the presence of Pd(OH)$_2$/C (0.16 g). After 20 h the solution was filtered through celite and the filtrate concentrated to provide 0.217 g of the title compound which was used directly in the next reaction.

III. tert-butyl((5S)-3-{3-fluoro-4-[exo-(1R,5S)-3-(2-benzyloxyacetyl)-3-azabicyclo[3.1.0]hex-6-yl]phenyl}-2-oxo-1,3-oxazolidin-5-yl)methylcarbamate

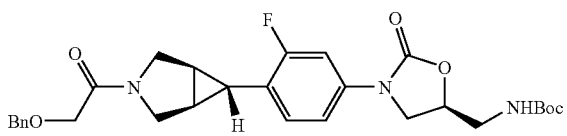

A solution of tert-butyl ((5S)-3-{3-fluoro-4-[exo-(1R,5S)-3-azabicyclo[3.1.0]hex-6-yl]phenyl}-2-oxo-1,3-oxazolidin-5-yl)methylcarbamate (0.217 g, 0.54 mmol) in dichloromethane (11 mL) and triethylamine (0.189 mL, 1.35 mmol) was cooled to 0° C. Benzyloxyacetyl chloride (0.10 mL, 0.65 mmol) was added to the solution and the mixture stirred for 2 h at room temperature. More dichloromethane was added and the solution extracted with 2.5% NaHCO$_3$ (back extracting with more dichloromethane). The combined organic phases were then washed with brine and dried (MgSO$_4$), filtered, and concentrated. Purification by column chromatography (0→2% MeOH—CH$_2$Cl$_2$) provided the title compound.

Yield 0.25 g (86% over two steps). $^1$H NMR (300 MHz, CDCl$_3$): 1.41 (s, 9H), 1.78 (t, J=4 Hz, 1H), 1.91 (M, 2H), 3.49-3.66 (m, 4H), 3.75-3.84 (m, 2H), 3.70-4.09 (m, 2H), 4.10 (s, 2H), 4.64 (s, 2H), 4.75 (m, 1H), 5.04 (bt, 1H), 6.89 (t, J=8 Hz, 1H), 7.14 (d, J=8 Hz, 1H), 7.31-7.38 (m, 6H).

VI. (5S)-5-(aminomethyl)-3-{3-fluoro-4-[exo-(1R,5S)-3-glycoloyl-3-azabicyclo[3.1.0]hex-6-yl]phenyl}-1,3-oxazolidin-2-one

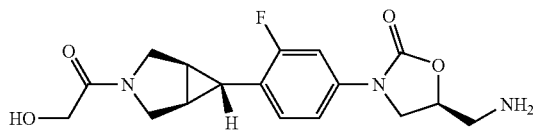

A solution of tert-butyl ((5S)-3-{3-fluoro-4-[exo-(1R,5S)-3-(2-benzyloxyacetyl)-3-azabicyclo[3.1.0]hex-6-yl]phenyl}-2-oxo-1,3-oxazolidin-5-yl)methylcarbamate (0.185 g, 0.34 mmol) was dissolved in 2:1 methanol-dichloromethane (12 mL) and stirred under a hydrogen atmosphere in the presence of 10% Pd/C (0.09 g). After 2 h the solution was filtered through celite and the filtrate concentrated. The residue was dissolved in dioxane (6 mL) and treated with 4 N HCl in dioxane solution (6 mL). After stirring for 4 h the suspension was concentrated to give the title compound as the HCl salt and this material was used directly in the next reaction.

Example 7 methyl exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxylate

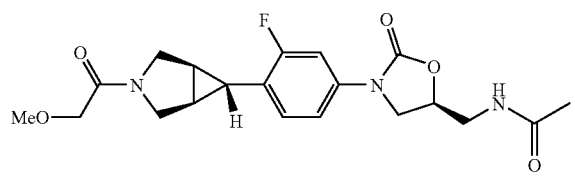

A solution of N-[((5S)-3-{4-[exo-(1R,5S)-3-azabicyclo[3.1.0]hex-6-yl]-3-yl]-3-fluorophenyl}-2-oxo-1,3-oxazolidin-5-yl)methyl]acetamide (0.055 g, 0.165 mmol) was dissolved in DMF (0.75 mL) and triethylamine (0.069 mL, 0.5 mmol), cooled to 0° C. and treated with methyl chloroformate (0.019 mL, 0.25 mmol). After 2 h, the reaction mixture was diluted with ethyl acetate, washed with 2.5% NaHCO$_3$ (back-extracting once) and the combined organic extracts washed with brine and dried (MgSO$_4$), filtered and concentrated. The crude material was purified by silica gel column chromatography (0-2% methanol-dichloromethane) to provide the title compound.

Yield 0.045 g (74%). MS (m/z): [M+H]=392 $^1$H NMR (300 MHz, d$_6$-DMSO): 1.73 (t, J=4 Hz, 1H), 1.82 (s, 3H), 1.95 (m, 2H), 3.20-3.48 (m, 5H), 3.58 (s, 3H), 3.61-3.73 (m, 2H), 4.09 (t, J=9 Hz, 1H), 4.69-4.74 (m, 1H), 7.08 (t, J=9 Hz, 1H), 7.20 (dd, J=8, 2 Hz, 1H), 7.44 (dd, J=13, 2 Hz, 1H), 8.24 (t, J=6 Hz, 1H).

Example 8

N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]acetamide

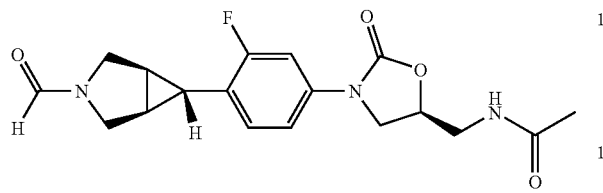

A solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.010 g, 0.03 mmol) was dissolved in acetic anhydride (0.25 mL) and formic acid (0.50 mL) and stirred at room temperature. After 3 days the solution was concentrated and the residue purified by preparative HPLC to give the title compound.

Yield 4 mg (40%). MS (m/z): [M+H]=362 ¹H NMR (300 MHz, d₆-DMSO): 1.68 (t, J=4 Hz, 1H), 1.82 (s, 3H), 1.91-1.97 (m, 2H), 3.20-3.40 (m, 3H), 3.60-3.73 (m, 2H), 3.83 (d, J=10 Hz, 2H), 4.09 (t, J=9 Hz, 1H), 4.71 (m, 1H), 7.09 (t, J=8 Hz, 1H), 7.21 (dd, J=9, 2 Hz, 1H), 7.45 (dd, J=13, 2 Hz, 1H), 8.14 (s, 1H), 8.24 (t, J=6 Hz, 1H).

Example 9

N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]acetamide

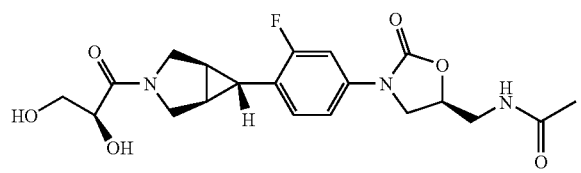

A solution of N-[((5S)-3-{3-fluoro-4-[exo-(1R,5S)-3-({(4S)-2,2-dimethyl-1,3-dioxolan-4-yl}carbonyl)-3-azabicyclo[3.1.0]hex-6-yl]phenyl}-2-oxo-1,3-oxazolidin-5-yl)methyl]acetamide (8 mg, 0.017 mmol) in 1 mL of 1:1 trifluoroacetic acid-water was stirred for 2 hours. The solution was then concentrated and the resulting aqueous solution lyophilized. The resulting crude product was then purified by preparative HPLC to provide the title compound.

Yield 4 mg (50%). MS (m/z): [M+H]=422 ¹H NMR (300 MHz, CD₃OD): 1.82 (m, 1H), 1.95 (s, 3H), 2.03 (m, 2H), 3.50-4.14 (m, 11H), 4.33 (m, 1H), 4.78 (m, 1H), 7.04 (t, J=8 Hz, 1H), 7.19 (d, J=8 Hz, 1H), 7.45 (dd, J=13, 2 Hz, 1H).

Intermediates for the preparation of example 9 were synthesized as follows.

I. N-[((5S)-3-{3-fluoro-4-[exo-(1R,5S)-3-({(4S)-2,2-dimethyl-1,3-dioxolan-4-yl}carbonyl)-3-azabicyclo[3.1.0]hex-6-yl]phenyl}-2-oxo-1,3-oxazolidin-5-yl)methyl]acetamide

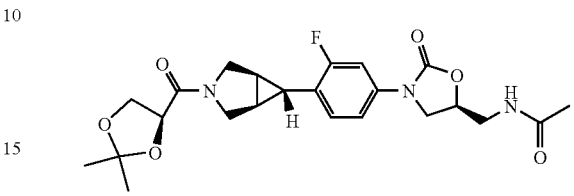

A solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.010 g, 0.03 mmol) was dissolved in 0.25 mL of DMF. To the solution was added a premixed (for 15 min) solution of HATU (0.03 g, 0.075 mmol), diisopropylethylamine (0.026 mL, 0.15 mmol) and (S)-2,2-dimethyl-1,3-dioxolane-4-carboxylic acid (0.009 g, 0.06 mmol) in 0.25 mL of DMF. After stirring overnight the solution was diluted with ethyl acetate and washed with 2.5% NaHCO₃, dilute citric acid, 2.5% NaHCO₃, brine and dried (MgSO₄). The solution was filtered and concentrated under vacuum and the residue purified by preparative TLC (6% methanol-dichloromethane) to provide the title compound.

Yield 8 mg (60%). ¹H NMR (300 MHz, CD₃OD): 1.37-1.42 (m, 6H), 1.77 (m, 1H), 1.95 (s, 3H), 2.02 (m, 2H), 3.50-3.96 (m, 7H), 4.08-4.26 (m, 4H), 4.72-4.78 (m, 1H), 7.04 (t, J=8 Hz, 1H), 7.19 (d, J=9 Hz, 1H), 7.44 (dd, J=13, 2 Hz, 1H).

Example 10 exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxamide

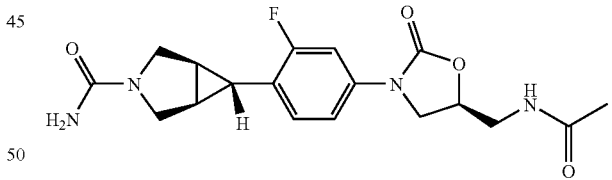

A solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (5 mg, 0.015 mmol) in dichloromethane (0.1 mL) and triethylamine (4 µL, 0.03 mmol) was treated with trimethylsilyl isocyanate in portions until the starting material had been consumed (a total of 6 eq. added over 1.5 h). The reaction mixture was then treated with methanol and the solution concentrated and purified by preparative HPLC to provide the title compound.

Yield: 2 mg (40%). MS (m/z): [M+H]=377 ¹H NMR (300 MHz, d₆-DMSO): 1.68 (t, J=3 Hz, 1H), 1.82 (s, 3H), 1.92 (bs, 2H), 3.20-3.40 (m, 4H), 3.60 (d, J=11 Hz, 2H), 3.70 (m, 1H), 4.09 (t, J=9 Hz, 1H), 4.70 (m, 1H), 5.80 (s, 2H), 7.07 (t, J=8 Hz, 1H), 7.20 (dd, J=8, 2 Hz, 1H), 7.44 (dd, J=13, 2 Hz, 1H), 8.24 (t, J=6 Hz, 1H).

Example 11 exo-(1R,5S)-6-[4-((5S)-5-{[(2,2-difluoroethaneth-ioyl)amino]methyl}-2-oxo-1,3-oxazolidin-3-yl)-2-fluorophenyl]-3-azabicyclo[3.1.0]hexane-3-carboxamide

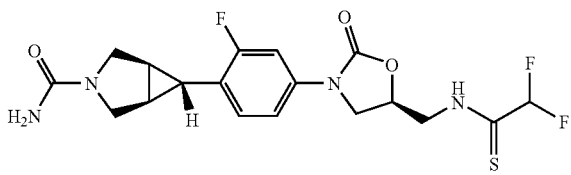

A solution of tert-butyl ((5S)-3-{4-[exo-(1R,5S)-3-(aminocarbonyl)-3-azabicyclo[3.1.0]hex-6-yl]-3-fluorophenyl}-2-oxo-1,3-oxazolidin-5-yl)methylcarbamate (0.2 g, 0.45 mmol) was dissolved in 4 mL of dioxane and treated with a dioxane solution of HCl (8 mL of a 4 M solution). The solution was stirred for 4 hours at room temperature and the resulting suspension concentrated to give an off-white solid. This material was then dissolved in methanol (4.5 mL) and triethylamine (0.19 mL, 1.35 mmol) and treated with difluoroacetic acid 3,3-diphenyl-1-propanol ester (0.206 g, 0.68 mmol) dissolved in 0.75 mL of dichloromethane. The mixture was stirred at room temperature for 2 h and then concentrated. The residue was dissolved in ethyl acetate and washed with 2.5% NaHCO$_3$, brine, and dried (MgSO$_4$). Purification by preparative TLC (gradient 0-5% methanol-dichloromethane/10% acetonitrile) provided the title compound.

Yield 0.16 g (84% overall). MS (m/z): [M+H]=429 $^1$H NMR (300 MHz, d$_6$-DMSO): 1.70 (m, 1H), 1.92 (bs, 2H), 3.32 (d, J=11 Hz, 2H), 3.60 (d, J=11 Hz, 2H), 3.83 (m, 1H), 3.98 (m, 2H), 4.16 (t, J=9 Hz, 1H), 5.01 (m, 1H), 5.80 (s, 2H), 6.49 (t, J=55 Hz, 1H), 7.07 (t, J=9 Hz, 1H), 7.21 (d, J=9 Hz, 1H), 7.44 (d, J=13 Hz, 1H), 11.13 (bt, 1H).

Intermediates for the preparation of example 11 were synthesized as follows.

I. tert-butyl((5S)-3-{4-[exo-(1R,5S)-3-(aminocarbonyl)-3-azabicyclo[3.1.0]hex-6-yl]-3-fluorophenyl}-2-oxo-1,3-oxazolidin-5-yl)methylcarbamate

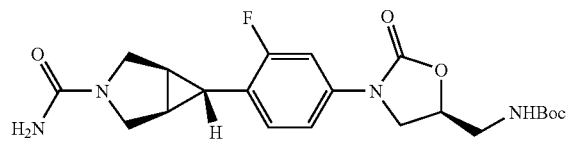

A solution of tert-butyl ((5S)-3-{3-fluoro-4-[exo-(1R,5S)-3-azabicyclo[3.1.0]hex-6-yl]phenyl}-2-oxo-1,3-oxazolidin-5-yl)methylcarbamate (0.275 g, 0.72 mmol) in dichloromethane (15 mL) and triethylamine (0.15 mL, 1.1 mmol) was treated with trimethylsilyl isocyanate in portions until the starting material had been consumed (a total of 14 eq. added over 24 h). The reaction mixture was then treated with methanol and the solution concentrated. The residue was passed through a short column of silica gel (5% methanol-dichloromethane) to give the title compound, which was used without further purification.

Example 12

N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide

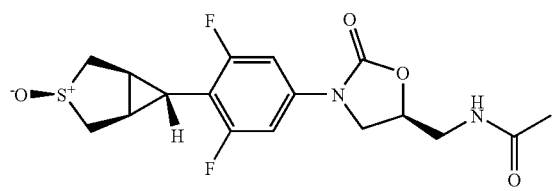

An aqueous solution of NaIO$_4$ (0.101 g, 0.47 mmol) was added to a solution of N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]acetamide (0.16 g, 0.43 mmols) in 8 mL of MeOH—H$_2$O (3:1) and stirred at 0° C. for 20 h. The reaction mixture was filtered with the aid of chloroform and the filtrate concentrated. Purification by column chromatography (0-5% MeOH-10% ACN-dichloromethane) provided the title compound which elutes first, ahead of the other sulfoxide isomer.

Yield 50 mg (30%). MS (m/z): [M+H]=385. HPLC (SYMMETRY C$_{18}$ 3.5 μM, 4.6×30 mm column; gradient elution 2%-98% MeCN with 0.1% TFA over 5 min; 2 mL/min rate): retention time=1.67 min. $^1$H NMR (300 MHz, CDCl$_3$): 2.00 (s, 3H), 2.35 (bs, 2H), 2.62(t, J=4.5 Hz, 1H), 3.30-(s, 4H), 3.54-3.72 (m, 3H), 3.97(t, J=9.0 Hz, 1H), 4.72-4.80 (m, 1H), 6.01 (bs, 1H), 7.06 (d, J=10.2 Hz, 2H).

Intermediates for the preparation of example 12 were synthesized as follows.

I. Isopropyl 3,5-difluoro-phenylcarbamate

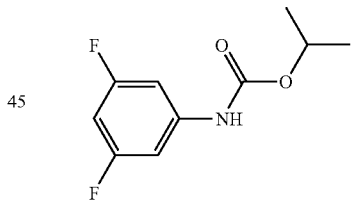

Lithium bis(trimethylsilyl) amide (1.0 M solution in tetrahydrofuran, 542 mL, 0.542 mol) was added to a solution of 3,5-difluoroaniline (35 g, 0.271 mol) in THF (60 mL) at 0° C. Isopropyl chloroformate (1M solution in toluene, 406 mL, 0.406 mol) was then added dropwise at 0° C. and the mixture allowed to warm to room temperature over 2 h. The reaction mixture was diluted with ether and washed with 1N hydrochloric acid, water, saturated aqueous sodium bicarbonate, brine and dried (MgSO$_4$). Solvent was removed under vacuum and the residue was triturated in hexanes to obtain the title compound.

Yield 48 g (82%). MS (m/z): [M+H]=216. HPLC (SYMMETRY C$_{18}$ 3.5 μM, 4.6×30 mm column; gradient elution 2%-98% MeCN with 0.1% TFA over 5 min; 2 mL/min rate): retention time=3.04 min. $^1$H NMR (300 MHz, CD$_3$OD): 1.21 (d, J=6.3 Hz, 6H), 4.96-5.04 (m, 1H), 6.71 (dd, J=7.2 Hz, 2.1 Hz, 2H), 6.8 (tt, J=9.0 Hz, 2.1 Hz, 1H).

II. isopropyl 3,5-difluoro-4-formylphenylcarbamate

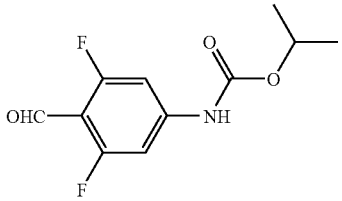

n-Butyllithium (2.5M in hexane, 112 mL, 0.279 mol) was added dropwise at −78° C. to a solution of isopropyl 3,5-difluoro-phenylcarbamate (20 g, 0.093 mol) and N,N,N,N-tetramethylethylenediamine (32 mL, 0.214 mol) in 93 mL of THF, and stirred for 30 min. Dimethylformamide (10.8 mL, 0.140 mol) was then added dropwise at −78° C., stirred for 1 h, and allowed to warm to −20° C. The reaction was then quenched with saturated aqueous ammonium chloride (100 mL). The reaction mixture was extracted with ethyl acetate, the extracts washed with brine, dried (MgSO$_4$), and concentrated. The crude product was triturated with hexane to provide the title compound. The combined hexane washings were concentrated and purified by flash column chromatography (30% ethyl acetate/hexane) to provide additional product.

Yield=7.0 g (31%). MS (m/z): [M+H]=244. HPLC (SYMMETRY C$_{18}$ 3.5 μM, 4.6×30 mm column; gradient elution 2%-98% MeCN with 0.1% TFA over 5 min; 2 mL/min rate): retention time=2.72 min. $^1$H NMR (300 MHz, CDCl$_3$): 1.29, (d, J=6.3 Hz, 6H), 5.02 (hept, J=6.3 Hz, 1H), 6.85 (bs, 1H), 7.08 (d, J=10.8 hz, 2H), 10.18 (s, 1H).

III. methyl(2E)-3-{2,6-difluoro-4-[(isopropoxycarbonyl)amino]phenyl}acrylate

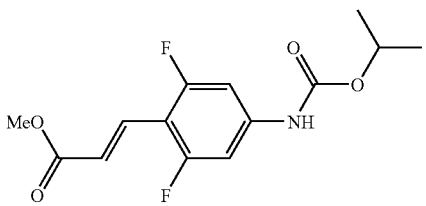

Sodium hydride (1.4 g of 60% dispersion, 35 mmol) was placed in a flask and washed three times with hexane. The resulting solid was suspended in DMF (29 mL) and cooled to 0° C. Trimethyl phosphonoacetate (5.95 mL, 36.75 mmol) was added dropwise to this suspension to give a clear homogeneous solution. After stirring for another 15 minutes at 0° C., a solution of isopropyl 3,5-difluoro-4-formylphenylcarbamate (8.51 g, 35 mmol) in DMF (25 mL) was added dropwise. The resulting orange suspension was allowed to warm slowly to room temperature and stirred for 16 hours. The reaction mixture was then poured into 0.5 N HCl and extracted with three portions of dichloromethane. Combined organic phases were washed with saturated NaHCO$_3$, H$_2$O, brine, and dried (MgSO$_4$) filtered and concentrated. The resulting orange solid was washed with hexane, 30% ethyl acetate-hexane, and then purified by column chromatography (15-30% ethyl acetate-hexane) to provide title compound.

Yield 7.8 g (75%). MS (m/z): [M+H]=300. HPLC (SYMMETRY C$_{18}$ 3.5 μM, 4.6×30 mm column; gradient elution 2%-98% MeCN with 0.1% TFA over 5 min; 2 mL/min rate): retention time=3.28 min. $^1$H NMR (300 MHz, CDCl$_3$): 1.28 (d, J=6.0 Hz, 6H), 3.78 (s, 3H), 5.00 (hept, J=6.3 Hz, 1H), 6.62 (d, J=16.5 Hz, 1H), 6.77 (s, 1H), 7.05 (d, J=10.8 hz, 2H), 7.69 (d, J=16.2 Hz, 1H).

IV. isopropyl 3,5-difluoro-4-[(1E)-3-hydroxyprop-1-enyl]phenylcarbamate

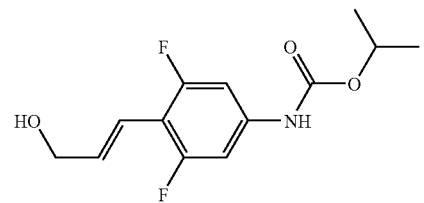

A solution of LiAlH$_4$ (26 mL of a 1.0 M THF solution, 26 mmol) was added to a cooled (−78° C.) solution of methyl (2E)-3-{2,6-difluoro-4-[(isopropoxycarbonyl)amino]phenyl}acrylate (7.77 g, 26 mmol) in THF (130 mL). The solution was allowed to warm slowly to −20° C. and maintained at that temperature for 2 hours. The reaction mixture was then quenched by slow addition of saturated NH$_4$Cl and then treated with 30 mL of dilute citric acid. The resulting mixture was stirred for 15 minutes and then extracted with three portions of ethyl acetate. Combined organic phases were washed with H$_2$O, brine and dried (MgSO$_4$), filtered and concentrated to give a red oil. The crude product was purified by column chromatography (0-1% methanol-dichloromethane) to afford the title compound as a yellow oil.

Yield 4.6 g (65%). MS (m/z): [M+H]=272. HPLC (SYMMETRY C$_{18}$ 3.5 μM, 4.6×30 mm column; gradient elution 2%-98% MeCN with 0.1% TFA over 5 min; 2 mL/min rate): retention time=2.59 min $^1$H NMR (300 MHz, CDCl$_3$): 1.27 (d, J=6.3 Hz, 6H), 4.31 (s, 2H), 4.99 (hept, J=6.3 Hz, 1H), 6.56 (s, 2H), 6.59 (s, 1H), 6.97 (d, J=10.5 Hz, 2H).

V. (2E)-3-{2,6-difluoro-4-[(isopropoxycarbonyl)amino]phenyl}prop-2-enyl diazoacetate

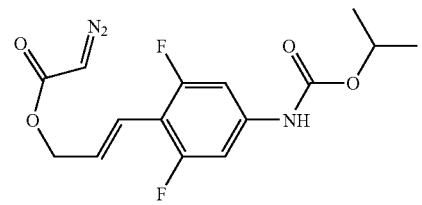

Glyoxylic acid chloride p-toluenesulfonylhydrazone (4.64 g, 17.8 mmol) was added to a suspension of isopropyl 3,5-difluoro-4-[(1E)-3-hydroxyprop-1-enyl]phenylcarbamate (2.68 g, 9.89 mmol) in dichloromethane (66 mL). The mixture was cooled to 0° C. and treated with N,N-dimethylaniline (2.26 mL, 17.8 mmol). After 30 minutes, triethylamine (6.89 mL, 49.5 mmol) was added and the mixture stirred 30 minutes at 0° C. and 15 minutes at room temperature. The reaction mixture was then concentrated to ca.

15 mL and 50 mL of water added. The mixture was extracted with two portions of diethyl ether and the combined organic solutions washed with saturated NaHCO₃, brine, and dried (MgSO₄), filtered and concentrated. Purification by column chromatography (0-25% ethyl acetate-hexane) provided the title compound a yellow solid.

Yield 2.44 g (73%). MS (m/z): [M+H]=340. HPLC (SYMMETRY $C_{18}$ 3.5 μM, 4.6×30 mm column; gradient elution 2%-98% MeCN with 0.1% TFA over 5 min; 2 mL/min rate): retention time=3.22 min. ¹H NMR (300 MHz, CDCl₃): 1.28 (d, J=6.3 Hz, 6H), 4.79 (s, 2H), 4.81 (s, 1H), 4.99 (hept, J=6.3 Hz, 1H), 6.47 (dt, J=16.2, 5.7 Hz, 1H), 6.59 (d, J=16.2 Hz, 1H), 6.62 (s, 1H), 6.98 (d, J=10.5 Hz, 2H).

VI. (racemic)isopropyl 3,5-difluoro-4-[(1S,5R,6R)-2-oxo-3-oxabicyclo[3.1.0]hex-6-yl]phenylcarbamate

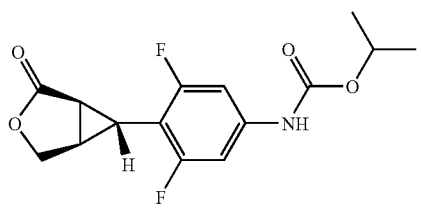

(±)

A solution of (2E)-3-{2,6-difluoro-4-[(isopropoxycarbonyl)amino]phenyl}prop-2-enyl diazoacetate (2.4 g, 7.07 mmol) in 170 mL of toluene/dichloromethane (1:2) was added dropwise over 14 h to a refluxing solution of bis-(N-t-butylsalicylaldiminato) copper(II) (0.147 g, 0.35 mmol) in 120 mL of toluene. After the addition was complete, the reaction mixture was heated another hour at reflux, then cooled, filtered and concentrated. The crude oil was purified by column chromatography (15-40% EtOAc-hexanes) to provide the title compound (a racemic mixture) as a yellow solid.

Yield 1.62 g (75%). MS (m/z): [M+H]=312. HPLC (SYMMETRY $C_{18}$ 3.5 μM, 4.6×30 mm column; gradient elution 2%-98% MeCN with 0.1% TFA over 5 min; 2 mL/min rate): retention time=2.77 min. ¹H NMR (300 MHz, CDCl₃): 1.27 (d, J=6.3 Hz, 6H), 2.23 (dd, J=4.2, 3.3 Hz, 1H), 2.54 (dd, J=6.0, 3.3 Hz, 1H), 2.74-2.79 (m, 1H), 4.37-4.46 (m, 2H), 4.98 (hept, J=6.3 Hz, 1H), 6.57 (s, 1H), 6.97 (d, J=10.2 Hz, 2H).

VII. isopropyl 4-[exo-(2R,3S)-2,3-bis(hydroxymethyl)cyclopropyl]-3,5-difluorophenylcarbamate

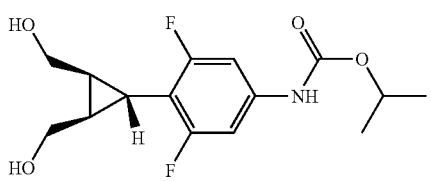

A solution of LiAlH₄ (5.2 mL of a 1.0 M THF solution, 5.2 mmol) was added dropwise to a solution of isopropyl 3,5-difluoro-4-[(1S,5R,6R)-2-oxo-3-oxabicyclo[3.1.0]hex-6-yl]phenylcarbamate (1.61 g, 5.17 mmol) in THF (41 mL) cooled at 0° C. The solution was stirred at 0° C. for 1 h and then treated with more LiAlH₄ solution (2.5 mL, 2.5 mmol) and allowed to warm to room temperature. After another hour at room temperature, the solution was quenched by the slow addition of saturated NH₄Cl (15 mL) followed by H₂O (30 mL) and saturated citric acid (10 mL). The solution was concentrated to remove THF and the resulting aqueous solution extracted with three portions of ethyl acetate. The combined organic phases were then washed with H₂O, brine, and dried (MgSO₄), filtered and concentrated to an oil. Purification by column chromatography (0-3% MeOH-dichloromethane) provided the title compound as a white solid.

Yield 1.16 g (72%). MS (m/z): [M+H]=316. HPLC (SYMMETRY $C_{18\ 3.5}$ μM, 4.6×30 mm column; gradient elution 2%-98% MeCN with 0.1% TFA over 5 min; 2 mL/min rate): retention time=2.26 min. ¹H NMR (300 MHz, CD₃OD): 1.27 (d, J=6.3 Hz, 6H), 1.63-1.75 (m, 3H), 3.55-3.62 (m, 2H), 3.93 (dd, J=5.7, 11.7 Hz, 2H), 4.93 (hept, J=6.0 Hz, 1H), 7.01 (d, J=10.2 Hz, 2H).

VIII. isopropyl 3,5-difluoro-4-[exo-(1R,5S)-3-thiabicyclo[3.1.0]hex-6-yl]phenylcarbamate

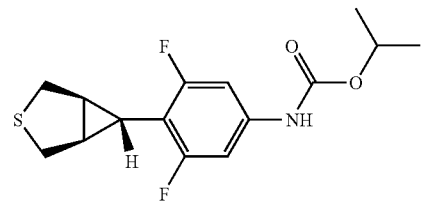

Methanesulfonic anhydride (0.696 g, 4.00 mmol) was added to a suspension of isopropyl 4-[exo-(2R,3S)-2,3-bis(hydroxymethyl)cyclopropyl]-3,5-difluorophenylcarbamate (0.50 g, 1.6 mmol) in dichloromethane (20 mL) and triethylamine (0.848 mL, 6.4 mmol) cooled at 0° C. The solution was stirred at 0° C. for 45 minutes and then diluted with more dichloromethane, washed with saturated NaHCO₃ solution, water, brine, dried (MgSO₄) and concentrated in an ice-cooled bath. The resulting white foam was dissolved in DMSO (4 mL), treated with Na₂S (0.375 g, 4.8 mmol) and allowed to stir overnight. The resulting suspension was dissolved in H₂O and extracted with ether thrice. The combined organic phases were dried (MgSO₄), filtered and concentrated to provide the title compound as a yellow solid.

Yield 0.450 g (90%). MS (m/z): [M+H]=314. HPLC (SYMMETRY $C_{18}$ 3.5 μM, 4.6×30 mm column; gradient elution 2%-98% MeCN with 0.1% TFA over 5 min; 2 mL/min rate): retention time 3.66 min. ¹H NMR (300 MHz, CDCl₃): 1.27 (d, J=6.3 Hz, 6H), 2.06 (bs, 2H), 2.18(t, J=4.2 Hz, 1H), 3.06-3.17 (m, 4H), 4.98 (q, J=6.3 Hz, 1H), 6.49 (bs, 1H), 6.90 (d, J=9.9 Hz, 2H).

IX. N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]acetamide

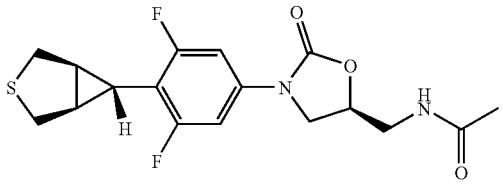

Lithium butoxide (2.07 mL of a 1.0 M THF solution, 2.07 mmol) was added to a cooled (0° C.) solution of isopropyl 3,5-difluoro-4-[exo-(1R,5S)-3-thiabicyclo[3.1.0]hex-6-yl] phenylcarbamate (0.217 g, 0.69 mmol) in DMF (0.46 mL) and MeOH (0.061 mL, 1.52 mmol). Solid (S)-acetic acid 2-acetylamino-1-chloromethyl-ethyl ester (0.267 g, 1.38 mmol) was then added and the solution allowed to warm to room temperature and stirred for 20 h. Saturated aqueous ammonium chloride (2 mL) was added, along with 10 mL of $H_2O$ and 10 mL of brine. The solution was extracted with three portions of dichloromethane and the combined organic phases dried ($MgSO_4$), filtered and concentrated. The crude product was purified by column chromatography (0-1% MeOH-dichloromethane) to provide the title compound.

Yield 0.16 g (62%). MS (m/z): [M+H]=369 MS (ESPOS): 369 (M+1) HPLC (SYMMETRY $C_{18}$ 3.5 µM, 4.6×30 mm column; gradient elution 2%-98% MeCN with 0.1% TFA over 5 min; 2 mL/min rate): retention time=2.70 min. $^1$H NMR (300 MHz, $CDCl_3$): 2.00 (s, 3H), 2.09 (bs, 2H), 2.22 (t, J=4.2 Hz, 1H), 3.07-3.17 (m, 4H), 3.54-3.72 (m, 3H), 3.97(t, J=9.0 Hz,1H), 4.71-4.80 (m, 1H), 5.94 (bs, 1H), 7.04 (d, J=10.2 Hz, 2H).

Example 13

N-[((5S)-3-{4-[exo-(1R,5S)-3,3-dioxido-3-thiabicyclo[3.1.0]hex-6-yl]-3,5-difluorophenyl}-2-oxo-1,3-oxazolidin-5-yl)methyl]acetamide

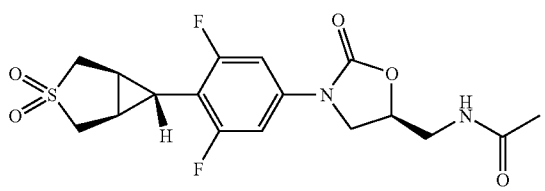

A solution of peracetic acid (0.24 mL, 0.99 mmol) was added to a solution of N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]acetamide (0.12 g, 0.33 mmol) in THF (16.5 mL) and the reaction mixture allowed to stir for 20 h at room temperature. The reaction mixture was quenched with 5 mL of saturated $Na_2S_2O_3$ and water was added. The mixture was concentrated to remove THF and the resulting aqueous solution extracted with ethyl acetate. The organic layer was washed with brine and dried ($MgSO_4$), filtered, and concentrated. The residue was purified by pTLC (7% MeOH-dichloromethane) to provide the title compound.

Yield 120 mg (91%). MS (m/z): [M+H]=401 HPLC (SYMMETRY $C_{18}$ 3.5 µM, 4.6×30 mm column; gradient elution 2%-98% MeCN with 0.1% TFA over 5 min; 2 mL/min rate): retention time=1.90 min. $^1$H NMR (300 MHz, $CDCl_3$): 1.97-2.01 (m, 4H), 2.22 (t, J=4.8 Hz, 2H), 3.07 (d, J=14.1 Hz, 2H), 3.50-3.72 (m, 5H), 3.97 (t, J=9.0 Hz, 1H), 4.72-4.81 (m, 1H), 6.36 (t, J=6 Hz, 1H), 7.08 (d, J=10.2 Hz, 2H).

Example 14

N-[((5S)-3-{3,5-difluoro-4-[exo-(1R,5S)-3-oxabicyclo[3.1.0]hex-6-yl]phenyl}-2-oxo-1,3-oxazolidin-5-yl)methyl]acetamide

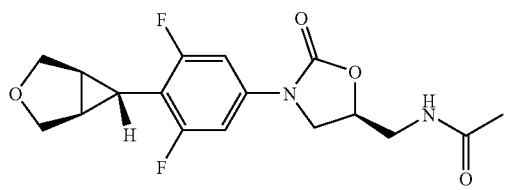

A solution of isopropyl 3,5-difluoro-4-[exo-(1R,5S)-3-oxabicyclo[3.1.0]hex-6-yl]phenylcarbamate (0.063 g, 0.21 mmol) in DMF (0.14 mL) and MeOH (0.017 mL, 0.42 mmol) was cooled at 0° C. and treated with LiOtBu solution (0.64 mL, 0.64 mmol) dropwise. The solution was then treated in one portion with (S)-acetic acid 2-acetylamino-1-chloromethyl-ethyl ester (0.082 g, 0.42 mmol). The reaction mixture was slowly warmed to room temperature and stirred for 20 h. The solution was then treated with 1.0 mL of saturated $NH_4Cl$ was added followed by 5 mL of water and 5 mL of brine. The mixture was extracted with three portions of dichloromethane and the combined organic phases washed with water, brine, and dried ($MgSO_4$), filtered and concentrated to an oil. Purification by column chromatography (0→2% MeOH-DCM) provided the title compound.

Yield 53 mg (71%). MS (m/z): [M+H]=353 $^1$H NMR (300 MHz, DMSO-$d_6$): 1.61 (t, J=4 Hz, 1H), 1.82 (s, 3H), 2.13 (m, 2H), 3.40 (t, J=5 Hz, 2H), 3.66 (d, J=8 Hz, 2H), 3.70 (m, 1H), 3.89 (d, J=8 Hz, 2H), 4.08 (t, J=9 Hz, 1H), 4.74 (m, 1H), 7.26 (d, J=11 Hz, 2H), 8.24 (t, J=6 Hz, 1H).

Intermediates for the preparation of example 14 were synthesized as follows.

I. isopropyl 3,5-difluoro-4-[exo-(1R,5S)-3-oxabicyclo[3.1.0]hex-6-yl]phenylcarbamate

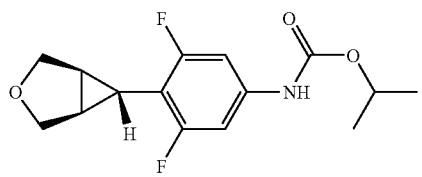

A solution of isopropyl 4-[exo-(2R,3S)-2,3-bis(hydroxymethyl)cyclopropyl]-3,5-difluorophenylcarbamate (0.16 g, 0.51 mmol,) in THF (4.5 mL) was cooled to −50° C. An n-BuLi solution (0.58 mL, 1.6 M in hexane, 0.924 mmol) was added and the resulting yellow suspension was stirred for 10 min and then methanesulfonyl chloride (0.045 mL, 0.57 mmol) was added. This produced a homogeneous solution that was stirred for 10 min and then treated with more n-BuLi (0.41 mL, 0.57 mmol). The solution was allowed to warm to −30° C. over one hour and then quenched by the addition of water and then dilute NaHCO₃. THF was removed in vacuo and the resulting aqueous solution was then extracted with ethyl acetate three times. The combined organic phases were then washed with brine and dried (MgSO₄), filtered and concentrated. The crude product was purified by column chromatography (0-30% ethyl acetate/hexane) to provide the title compound.

Yield 72 mg (47%). $^1$H NMR. mp=125-127° C.

Example 15

N-[((5S)-3-{3,5-difluoro-4-[exo-(1R,5S)-3-gly-coloyl-3-azabicyclo[3.1.0]hex-6-yl]phenyl}-2-oxo-1,3-oxazolidin-5-yl)methyl]acetamide

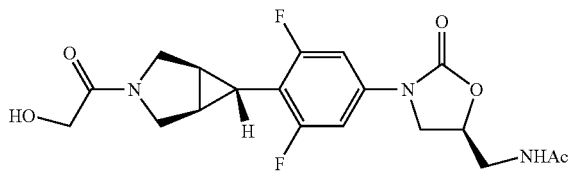

To a solution of N-[((5S)-3-{3,5-difluoro-4-[exo-(1R,5S)-3-(2-benzyloxyacetyl)-3-azabicyclo[3.1.0]hex-6-yl]phenyl}-2-oxo-1,3-oxazolidin-5-yl)methyl]acetamide (0.105 g, 0.21 mmol) in MeOH (7 mL) was added 10% Pd/C (0.35 g) and the reaction mixture stirred under an H₂ atmosphere for 1.5 hr. The reaction mixture was then filtered through celite and concentrated. Purification by flash chromatography (0-3% MeOH-dichloromethane) provided the title compound.

Yield 0.073 g (85%). MS (m/z): [M+H]⁺=410.4. $^1$H NMR (300 MHz, DMSO): 1.52 (t, J=4 Hz,1H), 1.81 (s, 3H), 2.01-2.06 (m, 1H), 2.13-2.18 (m, 1H), 3.36-3.43 (m, 3H), 3.53 (dd, J=4.2, 10 Hz, 1H), 3.63-3.71 (m, 2H) 3.77 (d, J=12 Hz, 1H), 3.86-4.10 (m, 3H), 4.54 (br t, 1H), 4.68-4.76 (m, 1H), 7.25 (d, J=1 Hz, 2H), 8.23 (t, J=6 Hz, 1H).

Intermediates for the preparation of example 15 were synthesized as follows.

I. isopropyl 3,5-difluoro-4-[exo-(1R,5S)-3-azabicyclo[3.1.0]hex-6-yl]phenylcarbamate

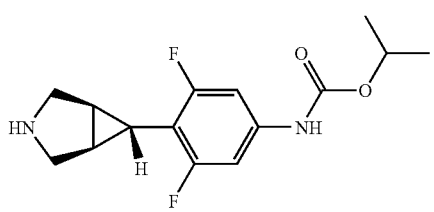

Methanesulfonic anhydride (1.325 g, 7.62 mmol) was added to a suspension of isopropyl 4-[exo-(2R,3S)-2,3-bis(hydroxymethyl)cyclopropyl]-3,5-difluorophenylcarbamate (0.80 g, 2.54 mmol) in dichloromethane (50 mL) and triethylamine (1.41 mL, 10.6 mmol) cooled at 0° C. The solution was stirred at 0° C. for 1 h and then treated with more Methanesulfonic anhydride (0.442 g, 2.54 mmol) and allowed to warm to room temperature. After another hour at room temperature, the reaction mixture was diluted with more dichloromethane and washed with saturated NaHCO₃ solution, water, brine, and dried (MgSO₄), filtered and concentrated. The resulting white foam was dissolved in MeOH (50 mL), treated with NH₄OH (50 mL) and allowed to stir overnight. The mixture was then extracted with ethyl acetate thrice. The combined organic phases were then washed with H₂O, brine, and dried (MgSO₄), filtered and concentrated to provide the title compound as an oil. This material was used in the next step without further purification.

HPLC (SYMMETRY C₁₈ 3.5 μM, 4.6×30 mm column; gradient elution 2%-98% MeCN with 0.1% TFA over 5 min; 2 mL/min rate): retention time=1.96 min.

II. isopropyl 3,5-difluoro-4-[exo-(1R,5S)-3-(2-benzyloxyacetyl)-3-azabicyclo[3.1.0]hex-6-yl]phenylcarbamate

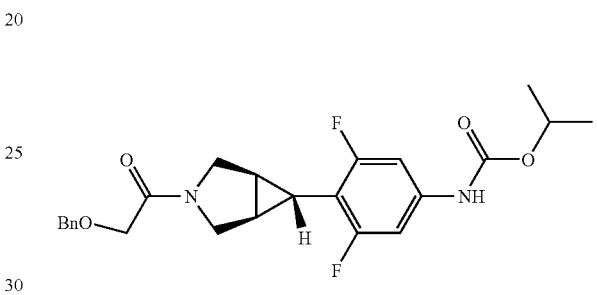

Benzyloxyacetyl chloride (0.519 mL, 3.3 mmol) was added to a solution of isopropyl 3,5-difluoro-4-[exo-(1R,5S)-3-azabicyclo[3.1.0]hex-6-yl]phenylcarbamate (ca. 2.5 mmol, crude) in ethyl acetate (50 mL) and 10% NaHCO₃ (100 mL). This mixture was stirred vigorously for 1 hr. The aqueous layer was maintained at basic pH and more benzyloxyacetyl chloride (0.519 mL, 3.3 mmol) was added. When most of the starting material had been consumed, the layers were separated and the aqueous layer extracted with more ethyl acetate. The combined organic layers were washed with 1N HCl, saturated aqueous NaHCO₃, water, brine, and dried (MgSO₄), filtered and concentrated. Purification by flash chromatography (0-2% MeOH-dichloromethane) and then by pTLC (20% EtOAc-hexanes) provided the title compound.

Yield 0.46 g (41% over 2 steps). MS (m/z): [M+H]=445.5. $^1$H NMR (300 MHz, DMSO): 1.23 (d, J=6 Hz, 6H), 1.47 (t, J=4 Hz, 1H), 1.97-2.02 (m, 1H), 2.08-2.14 (m, 1H), 3.32-3.79 (m, 4H), 4.03-4.17 (m, 2H), 4.50 (bs, 2H) 4.87 (q, J=6 Hz, 1H), 7.10 (d, J=11 Hz, 2H), 7.33 (bs, 5H), 9.91 (s, 1H).

III. N-[((5S)-3-{3,5-difluoro-4-[exo-(1R,5S)-3-(2-benzyloxyacetyl)-3-azabicyclo[3.1.0]hex-6-yl]phenyl-2-oxo-1,3-oxazolidin-5-yl)methyl]acetamide

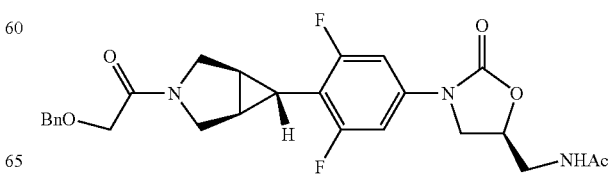

Lithium butoxide solution (1.02 mL of a 1.0 M THF solution, 1.02 mmol) was added to a cooled (0° C.) solution of isopropyl 3,5-difluoro-4-[exo-(1R,5S)-3-(2-benzyloxy-acetyl)-3-azabicyclo[3.1.0]hex-6-yl]phenylcarbamate (0.150 g, 0.34 mmol) in DMF (0.23 mL) and MeOH (0.027 mL, 0.68 mmol). Solid (S)-acetic acid 2-acetylamino-1-chloromethyl-ethyl ester (0.131 g, 0.68 mmol) was then added and the solution stirred at room temperature for 20 h. Saturated aqueous ammonium chloride (2 mL) was then added, along with 10 mL of H₂O and 10 mL of brine. The solution was extracted with three portions of dichloromethane and the combined organic phases dried (MgSO₄), filtered and concentrated. The crude product was purified by column chromatography (0-2% MeOH-dichloromethane) to provide the title compound.

Yield 0.06 g (35%). MS (m/z): [M+H]=500.5. ¹H NMR (300 MHz, CDCl₃): 1.53 (m, 1H), 1.99 (bs, 3H), 2.07-2.11 (m, 2H), 3.49-3.76 (m, 6H), 3.93-4.07 (m, 4H), 4.60 (s, 2H) 4.75 (m, 1H), 6.01 (m, 1H), 7.06 (d, J=10 Hz, 2H), 7.33-7.35 (m, 5H).

Example 16

N-[((5S)-3-{4-[exo-(1R,5S)-3-oxabicyclo[3.1.0]hex-6-yl]phenyl}-2-oxo-1,3-oxazolidin-5-yl)methyl]acetamide

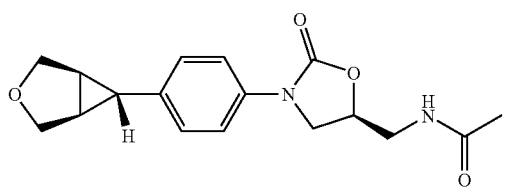

A solution of tert-butyl ((5S)-3-{4-[exo-(1R,5S)-3-oxabicyclo[3.1.0]hex-6-yl]phenyl}-2-oxo-1,3-oxazolidin-5-yl)methylcarbamate (0.068 g, 0.18 mmol) in 20% TFA-dichloroethane (1.0 mL) was stirred at room temperature for 2 h. The reaction mixture was concentrated to provide the free amine as a TFA salt. This material (10 mg, 0.03 mmol) was taken in pyridine (0.05 mL, 0.6 mmol). To this solution, acetic anhydride (0.007 mL, 0.06 mmol) was added and the mixture was stirred at room temperature for 16 h. The reaction mixture was concentrated and the title compound was isolated by pTLC (5% MeOH/DCM).

Yield 5 mg (56%). MS (m/z): [M+H]⁺=317.4. ¹H NMR (300 MHz, DMSO-d₆): 1.71 (s, 1H), 1.81(s, 3H), 1.91 (s, 2H), 3.30-3.40 (m, 2H), 3.65-3.71 (m, 3H), 3.87(d, J=9 Hz, 2H), 4.06 (t, J=9 Hz, 1H), 4.68 (m, 1H), 7.10 (d, J=9 Hz, 2H), 7.38-7.41 (d, J=9 Hz, 2H), 8.23 (bt, 1H).

Intermediates for the preparation of example 16 were synthesized as follows.

I. benzyl 4-formylphenylcarbamate

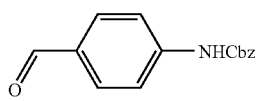

Benzyl 4-bromophenylcarbamate (20 g, 65.3 mmol) was taken in anhydrous THF (440 mL) and cooled to −78° C. To this solution, n-BuLi (55 mL, 137.2 mmol) was added dropwise and stirred for 0.5 h at −78° C. To this mixture, DMF (7.6 mL) was added dropwise and the reaction was allowed to warm to room temperature over a period of 5 h. The reaction mixture was quenched with 1 N HCl and then concentrated to remove THF, followed by addition of water. The mixture was extracted with three portions of ethyl acetate. The combined organic phases were washed with H₂O, brine, and dried (MgSO₄) filtered and concentrated. Trituration with hexanes and then with 20% ethyl acetate in hexanes afforded the title compound as a yellow solid.

Yield 8.75 g (52%). ¹H NMR.

II. methyl (2E)-3-(4-{[(benzyloxycarbonyl]amino}phenyl)acrylate

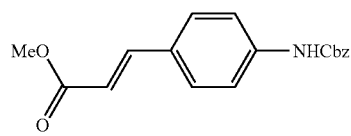

Sodium hydride (0.36 g of a 60% dispersion, 9.0 mmol) was placed in a flask and washed three times with hexane. The resulting solid was suspended in DMF (7 mL) and cooled to 0° C. Trimethyl phosphonoacetate (1.53 mL, 9.46 mmol) was added dropwise to this suspension to give a clear homogeneous solution. After stirring for another 20 minutes at 0° C., a solution of benzyl 4-formylphenyl-carbamate (2.3 g, 9.0 mmol) in DMF (7 mL) was added dropwise. The resulting orange suspension was allowed to warm slowly to room temperature and stirred for 15 h. The reaction mixture was poured into 0.5 N HCl and extracted with three portions of DCM. Combined organic phases were washed with saturated NaHCO₃, H₂O, brine, and dried (MgSO₄) filtered and concentrated. Purification by silica gel column chromatography (gradient 0-30% EtOAC/hexanes) provided the title compound.

Yield 2.5 g (89%). ¹H NMR (300 MHz, CDCl₃): 3.79(s, 3H), 5.21 (s, 2H), 6.33-6.38 (d, J=16 Hz, 1H), 6.78 (s, 1H), 7.31-7.46 (m, 9H), 7.61-7.66 (d, J=16 Hz, 1H).

III. benzyl 4-[(1E)-3-hydroxyprop-1-enyl]phenylcarbamate

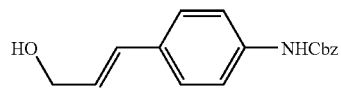

A THF solution of LiAlH₄ (6.75 mL of a 1.0 M solution, 6.75 mmol) was added to a cooled (−78° C.) solution of methyl (2E)-3-(4-{[(benzyloxy)carbonyl]amino}phenyl)acrylate (2.1 g, 6.75 mmol) in TBF (34 mL). The solution was allowed to warm slowly to −20° C. and maintained at that temperature for 2 hours. The reaction mixture was quenched by slow addition of saturated NH₄Cl and then treated with dilute citric acid. The resulting solution was stirred for 15 minutes and then extracted with three portions of ethyl acetate. The combined organic phases were washed with H₂O, brine and dried (MgSO₄), filtered and concentrated to give an oil. The crude product was purified by column chromatography (20-50% ethyl acetate-hexane) to provide the title compound as a yellow solid.

Yield 1.0 g (52%). ¹H NMR (300 MHz, CDCl₃): 4.28-4.30 (d, J=6 Hz, 2H), 5.18 (s, 2H), 6.22-6.31 (m, 1H), 6.52-6.57 (d, J=16 Hz, 1H), 6.64 (s, 1H), 7.32-7.40 (m, 9H).

IV. (2E)-3-(4-{[(benzyloxy)carbonyl]amino}phenyl)prop-2-enyl diazoacetate

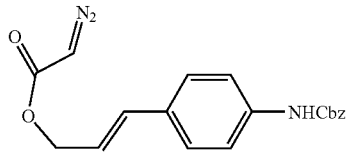

Glyoxylic acid chloride p-toluenesulfonylhydrazone (1.66 g, 6.35 mmol) was added to a suspension of benzyl 4-[(1E)-3-hydroxyprop-1-enyl]phenylcarbamate (1.0 g, 3.53 mmol) in dichloromethane (25 mL). The mixture was cooled to 0° C. and treated with N,N-dimethylaniline (0.8 mL, 6.35 mmol). After 0.5 h, triethylamine (2.5 mL, 17.6 mmol) was added and the mixture stirred 2 h at 0° C. and warmed to room temperature. The reaction mixture was then concentrated and water was added. The mixture was extracted with two portions of diethyl ether and the combined organic solutions washed with saturated NaHCO₃, brine and dried (MgSO₄), filtered and concentrated. Purification by silica gel column chromatography (gradient 0-25% EtOAc-hexane) provided the title compound.

Yield 0.65 g (52%). ¹H NMR (300 MHz, d₆-DMSO): 4.72-4.74 (d, J=6 Hz, 2H), 5.13 (s, 2H), 6.18-6.28 (m, 1H), 6.56-6.62 (d, J=16 Hz, 1H), 7.32-7.45 (m, 10H), 9.85 (s, 1H).

V. (racemic)benzyl 4-[(1S,5R,6R)-2-oxo-3-oxabicyclo[3.1.0]hex-6-yl]phenylcarbamate

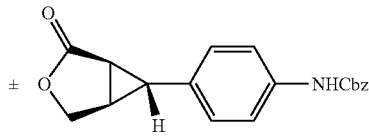

A solution of (2E)-3-(4-{[(benzyloxy)carbonyl]amino}phenyl)prop-2-enyl diazoacetate (0.7 g, 2.0 mmol) in dichloromethane (20 mL) was added dropwise over 18 h to a refluxing solution of bis-(N-t-butylsalicylaldiminato)copper(II) (0.041 g, 0.01 mmol) in 80 mL of toluene. After the addition was complete, the reaction mixture was heated for another 2 h at reflux and stirred at room temperature for 36 hours. Then the reaction mixture was cooled, filtered and concentrated. The crude oil was purified by silica gel column chromatography (gradient 0-1.5% MeOH-DCM) to provide the title compound and its enantiomer as a racemic mixture.

Yield 0.55 g (85%). ¹H NMR (300 MHz, CDCl₃): 2.26-2.28 (d, J=6 Hz, 2H), 2.47 (m, 1H), 4.37-4.46 (m, 2H), 5.17 (s, 2H), 6.64 (s, 1H), 6.98-7.00 (d, J=6 Hz, 2H), 7.30-7.39 (m, 7H).

VI. benzyl 4-[exo-(2R,3S)-2,3-bis(hydroxymethyl)cyclopropyl]phenylcarbamate

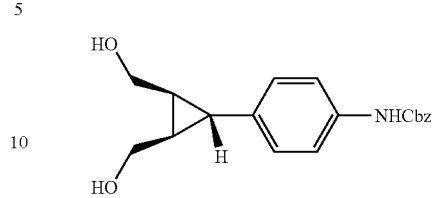

A THF solution of LiAlH₄ (2.4 mL of a 1.0M solution, 2.4 mmol) was added dropwise to a solution of benzyl 4-[(1S,5R,6R)-2-oxo-3-oxabicyclo[3.1.0]hex-6-yl]phenylcarbamate (0.51 g, 1.58 mmol) in THF (12.5 mL) cooled at 0° C. The solution was stirred at 0° C. for 1 h and at room temperature for 1 h and then the solution was quenched by the slow addition of saturated NH₄Cl (50 mL) followed by H₂O and saturated citric acid. The solution was concentrated to remove THF and the resulting aqueous solution extracted with three portions of ethyl acetate. The combined organic phases were then washed with H₂O, brine, and dried (MgSO₄), filtered and concentrated to an oil. Purification by silica gel column chromatography (gradient 0-3.5% MeOH-DCM) provided the title compound as a white foam.

Yield 0.3 g (58%). MS (m/z): [M+H]⁺=350.4. ¹H NMR (300 MHz, CDCl₃): 1.65-1.77 (m, 3H), 2.61 (s, 2H), 3.42-3.49 (m, 2H), 4.19-4.25 (m, 2H), 5.19 (s, 2H), 6.62 (s, 1H), 6.98 (d, J=7 Hz, 2H), 7.26-7.41 (m, 7H).

VII. benzyl 4-[exo-(1R,5S)-3-oxabicyclo[3.1.0]hex-6-yl]phenylcarbamate

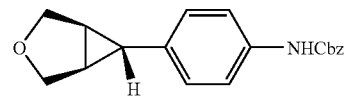

A solution of benzyl 4-[exo-(2R,3S)-2,3-bis(hydroxymethyl)cyclopropyl]phenylcarbamate (0.23 g, 0.7 mmol) in THF (7 mL) was cooled to −50° C. The n-BuLi solution (0.83 mL, 1.33 mmol) was added and the resulting yellow suspension was stirred for 10 min and then methanesulfonyl chloride (0.081 mL, 1.05 mmol) was added. This produced a homogeneous solution that was stirred for 10 min and then treated with more n-BuLi (0.57 mL, 0.91 mmol). The solution was allowed to warm to −30° C. over 1 h and then quenched by the addition of water and then dilute NaHCO₃. THF was removed in vacuo and the resulting aqueous solution was then extracted with EtOAc thrice. The combined organic phases were then washed with brine and dried (MgSO₄), filtered and concentrated. The crude product was purified by column chromatography (0-20% EtOAc/hexanes) to give the title compound.

Yield 80 mg (37%). ¹H NMR (300 MHz, CDCl₃): 1.78-1.82 (m, 3H), 3.78 (d, J=8 Hz, 2H), 3.96 (d, J=8 Hz, 2H), 5.17 (s, 2H), 6.58 (s, 1H), 6.97 (d, J=8 Hz, 2H), 7.23-7.39 (m, 7H).

VIII. tert-butyl((5S)-3-{4-[exo-(1R,5S)-3-oxabicyclo[3.1.0]hex-6-yl]phenyl}-2-oxo-1,3-oxazolidin-5-yl)methylcarbamate

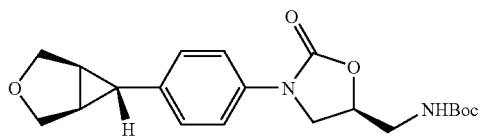

A solution of benzyl 4-[exo-(1R,5S)-3-oxabicyclo[3.1.0]hex-6-yl]phenylcarbamate (0.075 g, 0.24 mmol) and (S)-(3-chloro-2-hydroxy-propyl)-carbamic acid tert-butyl ester (0.065 g, 0.31 mmol) in DMF (0.15 mL) was stirred at 0° C. The mixture was treated with LiOtBu solution (1.0 M in THF, 0.58 mL, 0.58 mmol) dropwise. The reaction mixture was slowly warmed to room temperature and stirred for 18 h. The solution was then was quenched with saturated NH$_4$Cl, followed by addition of water and brine. The mixture was extracted with three portions of ethyl acetate and the combined organic phases washed with water, brine, and dried (MgSO$_4$), filtered and concentrated. The title compound was isolated by pTLC (5% MeOH/DCM).

Yield 69 mg (78%). $^1$H NMR (300 MHz, CDCl$_3$): 1.31 (s, 9H), 1.73 (m, 3H), 3.35-3.41 (m, 2H), 3.65-3.70 (m, 3H), 3.85-3.90 (m, 3H), 4.60-4.63 (m, 1H), 4.93 (s, 1H), 6.92-6.96 (d, J=12 Hz, 2H), 7.26-7.30 (d, J=12 Hz, 2H).

Example 17

N-[((5S)-3-{4-[exo-(1R,5S)-3-glycoloyl-3-azabicyclo[3.1.0]hex-6-yl]phenyl}-2-oxo-1,3-oxazolidin-5-yl)methyl]acetamide

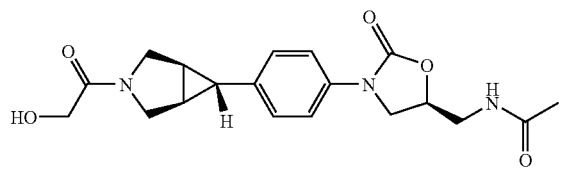

A solution of N-[((5S)-3-{4-[exo-(1R,5S)-3-(2-acetoxyacetyl)-3-azabicyclo[3.1.0]hex-6-yl]phenyl}-2-oxo-1,3-oxazolidin-5-yl)methyl]acetamide (0.075 g, 0.18 mmol) was dissolved in THF/water (16 mL, 3:1) and treated with 0.1 M LiOH in MeOH (3.6 mL, 0.36 mmol). The mixture was stirred at room temperature for 24 h and then concentrated to remove methanol. The resulting aqueous solution was then extracted with ethyl acetate thrice. The combined organic layers were washed with water, brine, dried (MgSO$_4$), filtered and concentrated. The title compound was isolated by pTLC (5% MeOH/dichloromethane).

Yield 40 mg (60%). MS (m/z): [M+H]$^+$=374.4 $^1$H NMR (300 MHz, CDCl$_3$): 1.62-1.64 (t, 1H), 1.86-1.89 (m, 2H), 1.99 (s, 3H), 3.46 (s, 1H), 3.54-3.77 (m, 6H), 3.98-4.07 (m, 4H), 4.72-4.76 (m, 1H), 6.10 (m, 1H), 6.99-7.02 (d, J=9 Hz, 2H), 7.38-7.41 (d, J=9 Hz, 2H).

Intermediates for the preparation of example 17 were synthesized as follows.

I. benzyl 4-[exo-(1R,5S)-3-(4-methoxybenzyl)-3-azabicyclo[3.1.0]hex-6-yl]phenylcarbamate

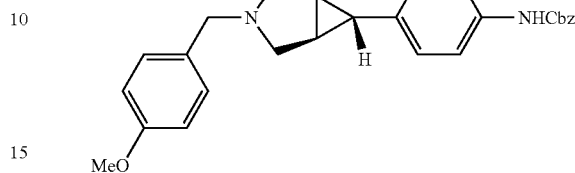

A solution of benzyl 4-[exo-(2R,3S)-2,3-bis(hydroxymethyl)cyclopropyl]phenylcarbamate (0.35 g, 1.07 mmol) in dichloromethane (13.5 mL) and triethylamine (0.6 mL, 4.28 mmol,) was cooled to 0° C. Methanesulfonic acid anhydride (0.56 g, 3.2 mmol) was then added and the reaction mixture stirred at 0° C. for 1 hour. The solution was then diluted with 20 mL of dichloromethane, washed with water, saturated NaHCO$_3$, brine, dried (MgSO$_4$), filtered and concentrated. The residue obtained was dissolved in 4-methoxybenzylamine (2.1 mL, 16.0 mmol) and stirred at room temperature for 18 h. The reaction mixture was diluted with ethyl acetate and washed with dilute NaHCO$_3$, dilute HCl (32 mL of 1N HCl in 100 mL water), dilute NaHCO$_3$, brine, dried (MgSO$_4$), filtered and concentrated. The title compound was isolated by silica gel column chromatography (gradient 0-25% EtOAc/hexanes/1% triethylamine).

Yield 290 mg (63%). MS (m/z): [M+H]$^+$=429.4. $^1$H NMR (300 MHz, CDCl$_3$): 2.51 (s, 1H), 2.65-2.68 (d, J=9 Hz, 2H), 3.28-3.31 (d, J=9 Hz, 2H), 3.79 (s, 2H), 4.00-4.02 (m, 5H), 5.39 (s, 2H), 6.78 (s, 1H), 7.04-7.07 (d, J=9 Hz, 2H), 7.16-7.19 (d,J=9 Hz, 2H), 7.41-7.59 (m, 9H).

II. N-[((5S)-3-{4-[exo-(1R,5S)-3-(4-methoxybenzyl)-3-azabicyclo[3.1.0]hex-6-yl]phenyl}-2-oxo-1,3-oxazolidin-5-yl)methyl]acetamide

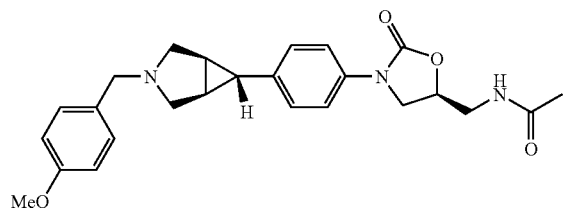

A solution of benzyl 4-[exo-(1R,5S)-3-(4-methoxybenzyl)-3-azabicyclo[3.1.0]hex-6-yl]phenylcarbamate (0.35 g, 0.82 mmol) in DMF (0.15 mL) and MeOH (0.066 mL) and cooled to 10° C. This mixture was treated with LiOtBu (2.45 mL of 1M solution in THF, 2.45 mmol) dropwise and cooled to 0° C. To this mixture, (S)-acetic acid 2-acetylamino-1-chloromethyl-ethyl ester (0.32 g, 1.63 mmol) was added and the reaction mixture was slowly warmed to room temperature and stirred for 18 h. The solution then was quenched with saturated NH$_4$Cl, followed by addition of water and brine. The mixture was extracted with three portions of ethyl acetate and the combined organic phases washed with water, brine, and dried (MgSO$_4$), filtered and concentrated. The title compound was isolated by silica gel column chromatography (gradient 0-4% MeOH/dichloromethane).

Yield 70 mg (20%). MS (m/z): [M+H]⁺=436.5. ¹H NMR (300 MHz, CDCl₃): 1.98 (s, 3H), 2.31 (s, 1H), 2.44-2.47 (d, J=9 Hz, 2H), 3.07-3.10 (d, J=9 Hz, 3H), 3.57-3.75 (m, 6H), 3.78 (s, 3H), 3.96-4.02 (t, J=9 Hz, 1H), 4.71-4.73 (m, 1H), 6.20 (br t, 1H), 6.82-6.85 (d, J=9 Hz, 2H), 6.98-7.01 (d, J=9 Hz, 2H), 7.19-7.22 (d, J=9 Hz, 2H), 7.32-7.35 (d, J=9 Hz, 2H).

III. N-[((5S)-3-{4-[exo-(1R,5S)-3-(2-acetoxyacetyl)-3-azabicyclo[3.1.0]hex-6-yl]phenyl}-2-oxo-1,3-oxazolidin-5-yl)methyl]acetamide

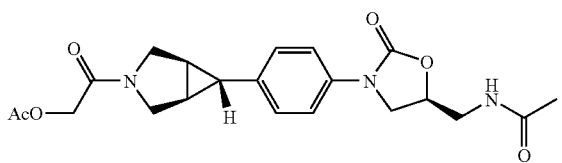

A solution of N-[((5S)-3-{4-[exo-(1R,5S)-3-(4-methoxybenzyl)-3-azabicyclo[3.1.0]hex-6-yl]phenyl}-2-oxo-1,3-oxazolidin-5-yl)methyl]acetamide (0.11 g, 0.25 mmol) in dichloromethane (1.0 mL) and triethylamine (0.035 mL, 0.25 mmol) and stirred at 0° C. To this, 1-chloroethyl chloroformate (0.055 mL, 0.5 mmol) was added and the reaction mixture stirred at 0° C. for 30 min. The reaction mixture was then concentrated, dissolved in methanol and heated at reflux for 45 min. The reaction mixture was then concentrated and triturated with diethyl ether to provide N-[((5S)-3-{4-[exo-(1R,5S)-3-azabicyclo[3.1.0]hex-6-yl]phenyl}-2-oxo-1,3-oxazolidin-5-yl)methyl]acetamide as a yellow powder. This intermediate was dissolved in dichloromethane (6.0 mL) and triethylamine (0.1 mL, 0.75 mmol) and cooled to 0° C. To this solution, acetoxyacetyl chloride (0.04 mL, 0.36 mmol) was added and the mixture was stirred at 0° C. for 30 min. The reaction mixture was then washed with water, brine, dried (MgSO₄), filtered and concentrated. The title compound was isolated by pTLC (5% MeOH/dichloromethane).

Yield 75 mg (72%). MS (m/z): [M+H]⁺=416.4. ¹H NMR (300 MHz, CDCl₃): 1.65-1.68 (br t, 1H), 1.82-1.88 (m, 2H), 1.99 (s, 3H), 2.16 (s, 3H), 3.52-3.77 (m, 6H), 3.96-4.04 (m, 2H), 4.57-4.60 (d, J=9 Hz, 2H), 4.72-4.76 (m, 1H), 6.15 (s, 1H), 6.99-7.02 (d, J=9 Hz, 2H), 7.38-7.41 (d, J=9 Hz, 2H).

Example 18

N-[((5S)-3-{4-[exo-(1R,5S)-3-oxido-3-thiabicyclo[3.1.0]hex-6-yl]phenyl}-2-oxo-1,3-oxazolidin-5-yl)methyl]acetamide

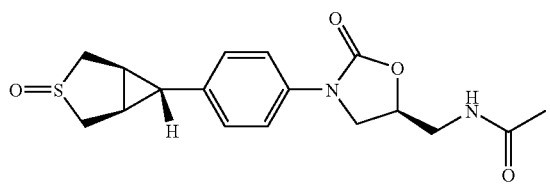

An aqueous solution of NaIO₄ (0.128 g, 0.60 mmol) was added to a solution of N-[((5S)-3-{4-[exo-(1R,5S)-3-thiabicyclo[3.1.0]hex-6-yl]phenyl}-2-oxo-1,3-oxazolidin-5-yl)methyl]acetamide (0.19 g, 0.57 mmol) in MeOH:H₂O (3:1, 10 mL) and stirred at 4° C. for 20 h. The reaction mixture was filtered with the aid of chloroform. The filtrate was extracted with 5 additional portions of chloroform and the combined organic layers were dried (MgSO₄), filtered and concentrated. Purification by pTLC (5% MeOH—10% ACN-DCM) provided the title compound as two separable diastereomers.

Yield (both isomers) 0.150 g (76%). MS (m/z): [M+H]⁺=349.2. HPLC (SYMMETRY C₁₈ 3.5 μM, 4.6×30 mm column; gradient elution 2%-98% MeCN with 0.1% TFA over 5 min; 2 mL/min rate): retention time=1.50 min. High Rf ("anti") isomer: ¹H NMR (300 MHz, CD₃OD): 1.95 (s, 3H), 2.23 (m, 2 H), 2.59(t, J=4.2 Hz, 1H), 3.21 (d, J=14.7 Hz, 2H), 3.46-3.55 (m, 4 H), 3.79 (dd, J=9.0, 6.3 Hz, 1H), 4.12 (t, J=9.0 Hz, 1H), 4.72-4.80 (m, 1H), 7.12 (d, J=9.0 Hz, 2H), 7.45 (d, J=9.0 Hz, 2H). Low Rf ("syn") isomer: ¹H NMR (300 MHz, CD₃OD): 1.95 (s, 3H), 2.11(t, J=4.2 Hz, 1H), 2.52 (m, 2H), 3.04-3.09 (dd, J=13, 2 Hz, 2H), 3.31-3.38 (m, 2H), 3.54 (d, J=5.1 Hz, 2H), 3.79 (dd, J=9.0, 6.3 Hz, 1H), 4.12 (t, J=9.0 Hz, 1H), 4.72-4.80 (m, 1H), 7.11 (d, J=9.0 Hz, 2H), 7.46 (d, J=9.0 Hz, 2H).

Intermediates for the preparation of example 18 were synthesized as follows.

I. benzyl 4-[exo-(1R,5S)-3-thiabicyclo[3.1.0]hex-6-yl]phenylcarbamate

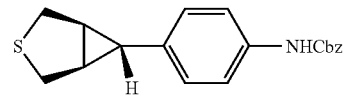

Methanesulfonic anhydride (0.92 g, 5.3 mmol) was added to a cooled (0° C.) solution of benzyl 4-[exo-(2R,3S)-2,3-bis(hydroxymethyl)cyclopropyl]phenylcarbamate (0.577 g, 1.76 mmol) in dichloromethane (22 mL) and triethylamine (0.98 mL, 7.05 mmol). The solution was allowed to warm to room temperature and stirred for 2 h. The solution was then diluted with 30 mL dichloromethane and washed with two portions of saturated NaHCO₃, brine, and dried (MgSO₄), filtered and concentrated to provide the bis-mesylate. This material was dissolved in DMSO (3.3 mL) and treated with sodium sulfide (0.39 g, 5.0 mmol). The reaction mixture was stirred at room temperature for 2 h. The resulting yellow suspension was then diluted with 30 mL of H₂O and extracted with three portions of diethyl ether. The combined organic extracts were dried (MgSO₄), filtered and concentrated to provide the title compound as a white solid.

Yield 0.45 g (79%). ¹H NMR.

II. N-[((5S)-3-{4-[exo-(1R,5S)-3-thiabicyclo[3.1.0]hex-6-yl]phenyl}-2-oxo-1,3-oxazolidin-5-yl)methyl}acetamide

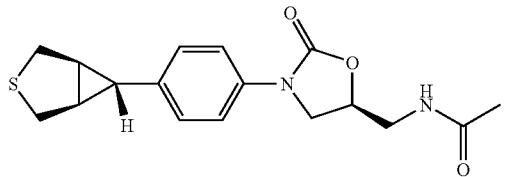

Lithium butoxide solution (4.1 mL of a 1.0 M THF solution, 4.1 mmol) was added to a cooled (0° C.) solution of benzyl 4-[exo-(1R,5S)-3-thiabicyclo[3.1.0]hex-6-yl]phenylcarbamate (0.44 g, 1.36 mmol) in DMF (0.91 mL) and MeOH (0.011 mL, 2.72 mmol). Solid (S)-acetic acid 2-acetylamino-1-chloromethyl-ethyl ester (0.53 g, 2.72 mmol) was then added and the solution allowed to warm to room temperature and stirred for 20 h. Saturated aqueous ammonium chloride (4 mL) was added, along with 20 mL of H$_2$O and 20 mL of brine. The solution was extracted with three portions of dichloromethane and the combined organic phases washed with water, brine, and dried (MgSO$_4$), filtered and concentrated. The crude residue was purified by column chromatography (0-3% MeOH-DCM) to provide the title compound.

Yield 0.19 g (41%). $^1$H NMR (300 MHz, CDCl$_3$): 1.85 (t, J=3.6 Hz, 2H), 1.99 (s, 3H), 2.29(t, J=3.9 Hz, 1H), 3.04-3.19 (m, 4H), 3.56 (dt, J=15, 6.3 Hz, 1H), 3.67 (dd, J=3.3, 6.3 Hz, 1H), 3.74 (dd, J=6.9, 9.3 Hz, 1H), 4.02 (t, J=9.3 Hz, 1H), 4.69-4.78 (m, 1H), 5.96 (t, J=6.3 Hz, 1H), 7.05 (d, J=8.7 Hz, 2H), 7.37 (d, J=8.7 Hz, 2H).

Example 19

N-[((5S)-3-{4-[exo-(1R,5S)-3,3-dioxido-3-thiabicyclo[3.1.0]hex-6-yl]phenyl}-2-oxo-1,3-oxazolidin-5-yl)methyl]acetamide

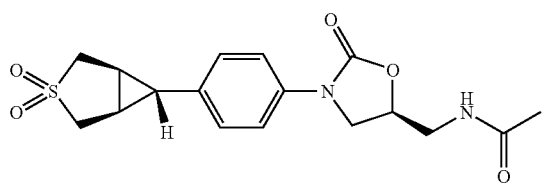

A solution of peracetic acid (0.12 mL, 0.58 mmol) was added to a solution of N-[((5S)-3-{4-[exo-(1R,5S)-3-oxido-3-thiabicyclo[3.1.0]hex-6-yl]phenyl}-2-oxo-1,3-oxazolidin-5-yl)methyl]acetamide ("syn" isomer, 0.067 g, 0.19 mmol) in THF (6.5 mL) at 0° C. and allowed to stir for 20 h. The reaction was quenched with 5 mL saturated Na$_2$S$_2$O$_3$ and diluted with water. The solution was concentrated to remove THF and the resulting aqueous solution extracted with ethyl acetate. The organic layer was washed with brine and dried (MgSO$_4$), filtered and concentrated. The residue was purified by pTLC (7% MeOH-DCM) to provide the title compound.

Yield 65 mg (92%). MS (m/z): [M+H]$^+$=401. HPLC (SYMMETRY C18 3.5 µM, 4.6×30 mm column; gradient elution 2%-98% MeCN with 0.1% TFA over 5 min; 2 mL/min rate): retention time=1.70 min. $^1$H NMR (300 MHz, CD$_3$OD): 1.95 (s, 3H), 2.08 (bs, 2H), 2.17 (bs, 1H), 3.01 (d, J=14.1 Hz, 2H), 3.52-3.59 (m, 4H), 3.80 (dd, J=6.3, 9.3 Hz, 1H), 4.12 (t, J=9.0 Hz, 1H), 4.72-4.81 (m, 1H), 7.16 (d, J=8.7 Hz, 2H), 7.47 (d, J=8.7 Hz, 2H).

Example 20

(5R)-3-{4-[exo-(1R,5S)-3,3-dioxido-3-thiabicyclo[3.1.0]hex-6-yl]-3-fluorophenyl}-2-oxo-1,3-oxazolidine-5-carboxamide

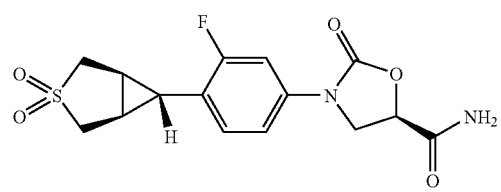

A solution of ethyl (5R)-3-{4-[exo-(1R,5S)-3,3-dioxido-3-thiabicyclo[3.1.0]hex-6-yl]-3-fluorophenyl}-2-oxo-1,3-oxazolidine-5-carboxylate (0.14 g, 0.36 mmol) in methanol (1 mL) was treated with a solution of ammonia in methanol (2.0 M, 4 mL) and stirred at room temperature for one hour to give a homogeneous solution. The reaction mixture was then concentrated and the crude product purified by column chromatography (elution with 0→3% methanol in dichloromethane) to provide the title compound.

Yield 95 mg (74%). MS (m/z): [M+H]$^+$=355.5 $^1$H NMR (300 MHz, d$_6$-DMSO): 7.86 (s, 1H), 7.62 (s, 1H), 7.50 (dd, J=13, 2 Hz, 1H), 7.29 (d, J=8 Hz, 1H), 7.13 (t, J=8 Hz, 1H), 5.02 (m, 1H), 4.26 (t, J=9 Hz, 1H), 3.99 (m, 1H), 3.59 (dd, J=14, 5 Hz, 2H), 3.02 (d, J=14 Hz, 2H), 2.34 (t, J=5 Hz, 1H), 2.08 (m, 2H).

Intermediates for the preparation of example 20 were synthesized as follows.

I. benzyl 4-[exo-(1R,5S)-3,3-dioxido-3-thiabicyclo[3.1.0]hex-6-yl]-3-fluorophenylcarbamate

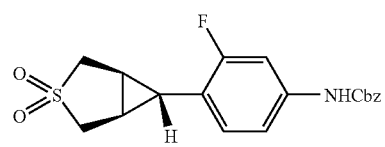

An aqueous solution of peracetic acid (0.64 mL of a 32% solution, 3.0 mmol) was added to a cooled (0° C.) solution of benzyl 4-[exo-(1R,5S)-3-thiabicyclo[3.1.0]hex-6-yl]-3-fluorophenylcarbamate (0.300 g, 0.88 mmol) in 20 mL of THF. After stirring at room temperature for 3 hours, the solution was treated with saturated Na$_2$S$_2$O$_3$ and water and the THF removed on a rotary evaporator. The resulting aqueous solution was then extracted thrice with ethyl acetate and the combined organic extracts washed with diluted NaHCO$_3$, brine and dried (MgSO$_4$), filtered and concentrated to give an oil. Purification by column chromatography (50% ethyl acetate-hexane) provided the title compound as a solid.

Yield 0.31 g (95%). mp 122-124° C. MS (m/z): [M+Na]⁺=398 ¹H NMR (300 MHz, CDCl₃): 7.24-7.41 (m, 6H), 6.97 (d, J=8 Hz, 1H), 6.88 (t, J=8 Hz, 1H), 6.69 (bs, 1H), 5.20 (s, 2H), 3.57 (dd, J=14, 5 Hz, 2H), 3.04 (d, J=13 Hz, 2H), 2.18 (t, J=4 Hz, 1H), 2.07 (m, 2H).

II. 4-[exo-(1R,5S)-3,3-dioxido-3-thiabicyclo[3.1.0]hex-6-yl]-3-fluoroaniline

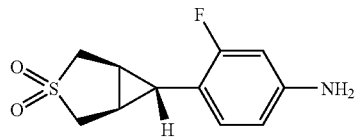

A solution of benzyl 4-[exo-(1R,5S)-3,3-dioxido-3-thiabicyclo[3.1.0]hex-6-yl]-3-fluorophenylcarbamate (0.30 g, 0.80 mmol) in 2:1 methanol-dichloromethane (7.5 mL) was treated with palladium (1.2 g of 5 wt % Pd on barium sulfate) and stirred under a hydrogen atmosphere for twenty hours. The mixture was then filtered through celite and the filtrate concentrated to give the title compound that was used without further purification.

Yield 0.18 g (91%) MS (m/z): [M+H]⁺=242 ¹H NMR (300 MHz, CD₃OD): 6.78 (m, 1H), 6.40 (m, 2H), 3.53 (d, J=14 Hz, 2H), 2.97 (d, J=14 Hz, 2H), 2.10 (bs, 1H), 2.00 (bs, 2H).

III. ethyl(2R)-3-({4-[exo-(1R,5S)-3,3-dioxido-3-thiabicyclo[3.1.0]hex-6-yl]-3-fluorophenyl}amino)-2-hydroxypropanoate

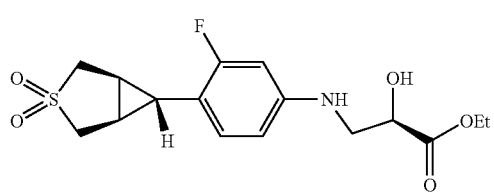

Lithium triflate (0.17 g, 1.43 mmol) was added to a suspension of 4-[exo-(1R,5S)-3,3-dioxido-3-thiabicyclo[3.1.0]hex-6-yl]-3-fluoroaniline (0.18 g, 0.75 mmol) and ethyl (2R)-2,3-epoxypropanoate (0.15 mL, 1.5 mmol) in acetonitrile (2.5 mL). The solution was heated at 60° C. for 18 hours and then treated with additional lithium triflate (70 mg) and epoxide (62 µL) and stirred at 60° C. for another 20 hours. The solution was then concentrated and purified by column chromatography (25%→50% ethyl acetate-hexane) to provide the title compound.

Yield 0.14 g (52%). MS (m/z): [M+H]⁺=358 ¹H NMR (300 MHz, CDCl₃): 6.76 (t, J=8 Hz, 1H), 6.38 (s, 1H), 6.35 (bs, 1H), 4.38 (q, J=4 Hz, 1H), 4.23-4.29 (m, 2H), 4.16 (m, 1H), 3.52-3.59 (m, 2H), 3.40-3.50 (m, 2H), 3.05 (s, 1H), 3.01 (d, J=15 Hz, 2H), 2.08 (m, 1H), 2.01 (m, 2H), 1.28-1.33 (m, 3H).

IV. ethyl(5R)-3-{4-[exo-(1R,5S)-3,3-dioxido-3-thiabicyclo[3.1.0]hex-6-yl]-3-fluorophenyl}-2-oxo-1,3-oxazolidine-5-carboxylate

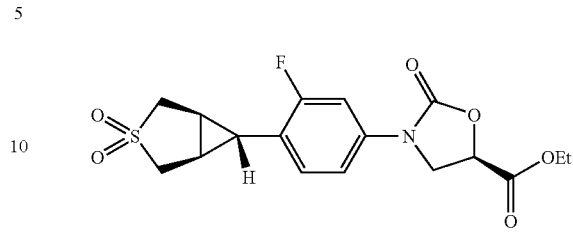

Phosgene (0.27 mL of a 20% toluene solution, 0.51 mmol) was added to a cooled (0° C.) solution of ethyl (2R)-3-({4-[exo-(1R,5S)-3,3-dioxido-3-thiabicyclo[3.1.0]hex-6-yl]-3-fluorophenyl}amino)-2-hydroxypropanoate (0.14 g, 0.40 mmol) and triethylamine (0.16 mL, 1.2 mmol) in 4 mL of dichloromethane. The reaction mixture was allowed to stir at room temperature for 2 hours and then diluted with more dichloromethane and washed with dilute NaHCO₃, brine and dried (MgSO₄), filtered and concentrated to provide the title compound that was used directly without further purification.

Yield 0.14 g (92%). MS (m/z): [M+H]⁺=384.5 ¹H NMR (300 MHz, CDCl₃): 7.42 (d, J=12 Hz, 1H), 7.19 (d, J=8 Hz, 1H), 6.97 (t, J=8 Hz,1H), 5.05 (m, 1H), 4.22-4.37 (m, 3H), 4.10 (m, 1H), 3.58 (dd, J=14, 4 Hz, 2H), 3.06 (d, J=14 Hz, 2H), 2.23 (t, J=4, 1H). 2.10 (bs, 2H), 1.37 (t, J=7 Hz, 3H).

Example 21

N-[((5S)-3-{4-[exo-(1R,5S)-3-azabicyclo[3.1.0]hex-6-yl]-3-fluorophenyl}-2-oxo-1,3-oxazolidin-5-yl)methyl]proyanamide

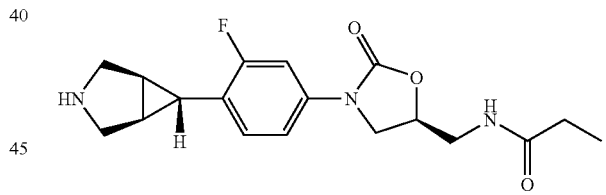

To a solution of N-[((5S)-3-{3-fluoro-4-[exo-(1R,5S)-3-(4-methoxybenzyl)-3-azabicyclo[3.1.0]hex-6-yl]phenyl}-2-oxo-1,3-oxazolidin-5-yl)methyl]propanamide (2.76 g, 5.9 mmol, 1 equiv.) in MeOH (86 mL) and EtOAc (138 mL) at 23° C. was added 20% Pd(OH)₂/C (1.7 g). The reaction mixture was stirred under a hydrogen atmosphere for 17 hours and then the mixture was filtered through celite with the aid of methanol. The filtrate was evaporated to dryness. This material could be used directly in subsequent reactions. A portion of the crude product (300 mg) was purified by chromatography on a silica gel column, eluting with a gradient increasing in polarity from 0 to 5% methanol in methylene chloride (contain 1% Et₃N). Relevant fractions were combined to give the title compound.

Yield 0.18 g (60%). MS (m/z): [M+H]⁺=348. HPLC (SYMMETRY C₁₈ 3.5 µM, 4.6×30 mm column; gradient elution 2%-98% MeCN with 0.1% TFA over 5 min; 2 mL/min rate): retention time=1.38 min. ¹H NMR (300 MHz, DMSO-d₆): 0.93 (t, J=7.8 Hz, 3H), 1.73 (s, 2H), 1.94 (m, 1H), 2.09 (q, J=7.5 Hz, 2H), 2.83 (d, J=11.1 Hz, 2H), 3.04 (d, J=11.4 Hz, 2H), 3.39 (m, 2H), 3.70 (m, 1H), 4.07 (t, J=9.0 Hz, 1H), 4.71 (m, 1H), 7.03 (t, J=9.0 Hz, 1H), 7.15 (m, 1H), 7.40 (d, J=12.9 Hz, 1H), 8.17 (t, J=5.4 Hz, 1H).

Intermediates for the preparation of example 21 were synthesized as follows.

I. Benzyl 3-fluoro-4-formylphenylcarbamate

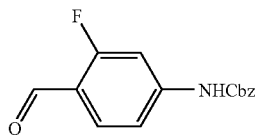

To an oven dried flask was added 4-bromo-2-fluorobenzaldehyde (50 g, 0.247 mol, 1.0 equiv.), benzyl carbarmate (45 g, 0.297 mol, 1.2 equiv.), rac-BINAP (12.5 g, 0.020 mol, 0.08 equiv.), Cs$_2$CO$_3$ (115 g, 0.353 mol, 1.42 equiv.) and Pd$_2$(dba)$_3$ (9.15 g, 0.01 mol, 0.04 equiv.). Then, the flask was degassed and refilled with nitrogen. Anhydrous toluene (500 mL) was transferred into flask by cannula. The resulting suspension was stirred at 95°-100° C. for 24 hours and cooled down to 23° C. The reaction mixture was diluted with NH$_4$Cl aqueous (1000 mL) and extracted with EtOAc (3×300 mL). The combined organic layers were washed (brine), dried (Na$_2$SO$_4$), filtered and evaporated to dry. The residue was purified by chromatography on a silica gel column, eluting with a gradient increasing in polarity from 0 to 20% ethyl acetate in hexane. Relevant fractions were combined to give the desired compound.

Yield 44.7 g (66%). HPLC (SYMMETRY C$_{18}$ 3.5 µM, 4.6×30 mm column; gradient elution 2%-98% MeCN with 0.1% TFA over 5 min; 2 mL/min rate): retention time=2.87 min. $^1$H NMR (300 MHz, CDCl$_3$): 5.23 (s, 2H), 6.98 (bs, 1H), 7.02 (d, J=8.4 Hz, 1H), 7.40 (bs, 5H), 7.57 (d, J=12.6 Hz, 1H), 7.80 (t, J=7.8 Hz, 1H), 10.23 (s, 1H).

II. Methyl (2E)-3-(4-{[(benzyloxy)carbonyl]amino}-2-fluorophenyl)acrylate

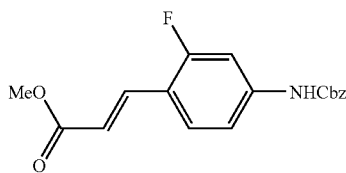

Sodium hydride (7.2 g of a 60% dispersion, 0.188 mol) was placed in a flask and washed three times with hexane. The resulting solid was suspended in DMF (140 mL) and cooled to 0° C. Trimethyl phosphonoacetate (30.7 mL, 0.190 mol) was added dropwise to this suspension to give a clear homogeneous solution. After stirring for another 20 minutes at 0° C., a solution of benzyl 3-fluoro-4-formylphenylcarbamate (2) (48 g, 0.176 mol) in DMF (140 mL) was added dropwise. The resulting orange suspension was allowed to warm slowly to room temperature and stirred for 16 hours. The reaction mixture was poured into 0.5 N HCl (1.5 L) and extracted with three 300 mL portions of dichloromethane. Combined organic phases were washed with saturated NaHCO$_3$, twice with H$_2$O, brine, and dried (Na$_2$SO$_4$). While concentrating the solution on a rotary evaporator, the product precipitated from solution and these solids were collected on a filter (33.4 g). The filtrate was concentrated to give more solids that were washed with ether (additional 8.4 g obtained).

Yield 41.8 g (72%). $^1$H NMR (300 MHz, d$_6$-DMSO): 3.71 (s, 3H), 5.17 (s, 2H), 6.55 (dd, J=16, 1 Hz, 1H), 7.26 (d, J=9 Hz, 1H), 7.35-7.50 (m, 6H), 7.63 (d, J=16 Hz, 1H), 7.79 (t, J=9 Hz, 1H), 10.3 (bs, 1H) mp=157-158° C.

III. Benzyl 3-fluoro-4-[(1E)-3-hydroxyprop-1-enyl]phenylcarbamate

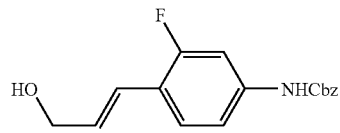

A THF solution of diisobutylaluminum hydride (522 mL of a 1.0 M solution, 522 mmol) was added to a cooled (−78° C.) solution of methyl (2E)-3-(4-{[(benzyloxy)carbonyl]amino}-2-fluorophenyl)acrylate (43 g, 130 mmol) in THF (900 mL). After stirring for one hour at −78° C., additional diisobutylaluminum hydride solution was added (140 mL of a 1.0 M solution, 140 mmol). After another 30 minutes, aqueous citric acid and ethyl acetate were added and the mixture allowed to warm slowly to room temperature. The layers were separated and the aqueous phase extracted with more ethyl acetate. Combined organic phases were washed with H$_2$O, brine and dried (MgSO$_4$), filtered and concentrated to give a red oil. The crude product was purified by column chromatography (0-40% ethyl acetate-hexane) to provide the title compound as a yellow solid.

Yield 36 g (92%). $^1$H NMR (300 MHz, CDCl$_3$): 1.43 (t, J=6 Hz, 1H), 4.33 (t, J=6 Hz, 2H), 5.28 (s, 2H), 6.37 (dt, J=15, 6 Hz, 1H), 6.69 (d, J=16 Hz, 1H), 6.70 (s, 1H), 6.99 (d, J=9 Hz, 1H), 7.20-7.39 (m, 7H) mp=105-106° C.

IV. (2E)-3-(4-{[(benzyloxy)carbonyl]amino}-2-fluorophenyl)prop-2-enyl diazoacetate

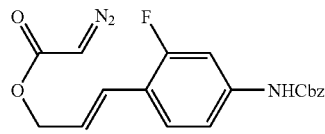

To a suspension of glyoxylic acid p-toluenesulfonylhydrazone (24 g, 0.10 mol, prepared as described by C. J. Blankley, F. J. Sauter and H. O. House, *Organic Syntheses*, Coll. Vol. V, p. 258; John Wiley, New York (1973)) in CH$_2$Cl$_2$ (600 mL) at 23° C. was added commercially available 1-chloro-N,N,2-trimethyl-1-propenylamine (15 mL, 0.114 mol, 1.14 equiv.) over 5 min. The reaction mixture was stirred at the same temperature for 40 min. The reaction mixture was then cooled to 0° C. and benzyl 3-fluoro-4-[(1E)-3-hydroxyprop-1-enyl]phenylcarbamate (23 g, 0.077 mol) was added in one portion followed by the addition of N,N-dimethylaniline (12 mL, 0.095 mol). After 30 minutes, triethylamine (53 mL, 0.385 mol) was added and the mixture stirred for 30 minutes at 0° C. and 15 minutes at room temperature. The reaction mixture was then concentrated to a volume of about 100 mL and 500 mL of water added. The mixture was extracted with two portions of diethyl ether and the combined organic solutions washed with saturated NaHCO$_3$, brine, and dried (MgSO$_4$), filtered and concentrated. Purification by column chromatography (0-25% ethyl acetate-hexane) provided the title compound as a yellow solid.

Yield 23.8 g (84%). $^1$H NMR (300 MHz, CDCl$_3$): 4.80 (s, 2H), 4.83 (s, 1H), 5.21 (s, 2H), 6.29 (dt, J=16, 6 Hz, 1H), 6.72 (d, J=16 Hz, 1H), 6.73 (s, 1H), 6.98 (d, J=8 Hz, 1H), 7.25-7.40 (m, 7H) mp=93-96° C.

V. (racemic)benzyl 3-fluoro-4-[(1S,5R,6R)-2-oxo-3-oxabicyclo[3.1.0]hex-6-yl]phenylcarbamate

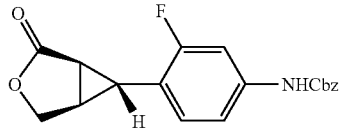

(±)

A solution of (2E)-3-(4-{[(benzyloxy)carbonyl]amino}-2-fluorophenyl)prop-2-enyl diazoacetate (13.9 g, 37.5 mmol) in 1,2-dichloroethane (150 mL) was added dropwise over 14 h to a refluxing solution of bis-(N-t-butylsalicyla-ldiminato)copper(II) (0.82 g, 1.9 mmol, prepared as described by R. G. Charles, *J. Org. Chem.* 1957, 22, 677) in 1.5 L of toluene. After the addition was complete, the reaction mixture was heated another hour at reflux, then cooled, filtered and concentrated. The crude oil was purified by column chromatography (0-50% ethyl acetate-hexanes) to provide the (racemic) title compound as a yellow solid.

Yield 9.3 g (73%). $^1$H NMR (300 MHz, CDCl$_3$): 2.33-2.39 (m, 2H), 2.49-2.53 (m, 1H), 4.4 (m, 2H), 5.18 (s, 2H), 6.82 (t, J=9 Hz, 1H), 7.0 (d, J=8 Hz, 1H), 7.01 (s, 1H), 7.25-7.38 (m, 6H); mp=141-142° C.

VI. Benzyl 4-[exo-(2R,3S)-2,3-bis(hydroxymethyl)cyclopropyl]-3-fluorophenylcarbamate

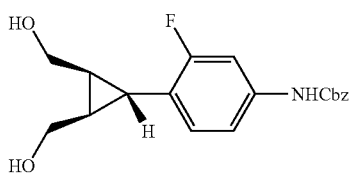

Solid LiBH$_4$ (2.6 g, 119 mmol) was added in one portion to a solution of racemic benzyl 3-fluoro-4-[(1S,5R,6R)-2-oxo-3-oxabicyclo[3.1.0]hex-6-yl]phenylcarbamate (8.3 g, 24.3 mmol) in THF (170 mL) cooled at 0° C. The solution was allowed to warm to room temperature and stirred for 14 hours. The solution was then re-cooled to 0° C. and quenched by the addition of aqueous citric acid solution. The solution was extracted with three portions of ethyl acetate. The combined organic phases were then washed with H$_2$O, brine, and dried (MgSO$_4$), filtered and concentrated. Purification by column chromatography (20-75% ethyl acetate-hexanes) provided the title compound as a white foam.

Yield 6.4 g (81%). $^1$H NMR (300 MHz, CDCl$_3$): 1.65-1.72 (m, 2H), 1.90 (t, J=5 Hz, 1H), 2.72 (bs, 2H), 3.48 (m, 2H), 4.23 (m, 2H), 5.19 (s, 2H), 6.75 (s, 1H), 6.82 (t, J=8 Hz, 1H), 6.93 (dd, J=9, 2 Hz, 1H), 7.30-7.41 (m, 6H).

VII. Benzyl 4-[exo-(2R,3S)-2,3-bis(methanesulfonyloxmethyl)cyclopropyl]-3-fluorophenylcarbamate

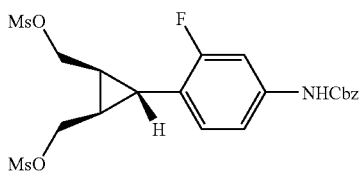

Methanesulfonic anhydride (9.85 g, 56.5 mmol) was added to a cooled (0° C.) solution of benzyl 4-[exo-(2R,3S)-2,3-bis(hydroxymethyl)cyclopropyl]-3-fluorophenylcarbamate (6.5 g, 18.8 mmol) in dichloromethane (220 mL) and triethylamine (10.6 mL, 76 mmol). The solution was allowed to warm to room temperature and stirred for 1 h. The solution was then diluted with 250 mL dichloromethane and washed with two portions of saturated NaHCO$_3$, brine, and dried (Na$_2$SO$_4$). The crude product was passed through a short pad of SiO$_2$ (eluting with ethyl acetate) to provide the title compound as a white solid that was used directly in the next reation.

$^1$H NMR

VIII. Benzyl 3-fluoro-4-[exo-(1R,5S)-3-(4-methoxybenzyl)-3-azabicyclo[3.1.0]hex-6-yl]phenylcarbamate

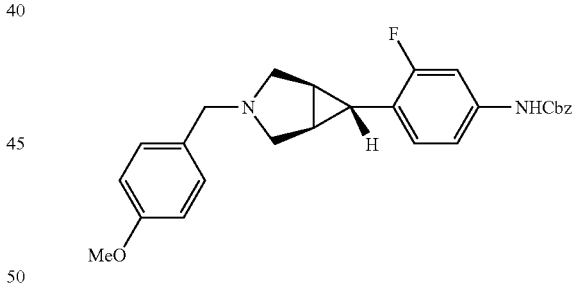

Crude benzyl 4-[exo-(2R,3S)-2,3-bis(methanesulfonyloxymethyl)cyclopropyl]-3-fluorophenylcarbamate (18.8 mmol) was dissolved in 4-methoxybenzylamine (50 g, 360 mmol) and stirred at room temperature for 16 h. The resulting solution was then diluted with of ethyl aceate and washed with 2.5% NaHCO$_3$, dilute aqueous HCl (360 mL of a 1 N solution diluted to 1.0 L with H$_2$O), again with 2.5% NaHCO$_3$, brine, and dried (MgSO$_4$), filtered and concentrated. The crude product was then purified by silica gel column chromatography (gradient 0-30% ethyl acetate-hexane—1% Et$_3$N) to provide the title compound as a white solid.

Yield 7.7 g (92% over 2 steps). $^1$H NMR (300 MHz, CDCl$_3$): 1.65 (bs, 2H), 2.44 (d, J=9 Hz, 2H), 2.47 (m, 1H), 3.09 (d, J=9 Hz, 2H), 3.58 (s, 2H), 3.80 (s, 3H), 5.19 (s, 2H), 6.60 (bs, 1H), 6.77-6.93 (m, 4H), 7.21-7.41 (m, 8H).

IX. Tert-butyl ((5S)-3-{3-fluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate

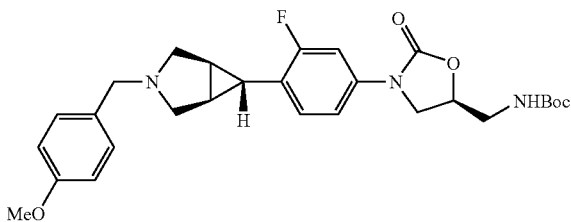

To a suspension of benzyl 3-fluoro-4-[exo-(1R,5S)-3-(4-methoxybenzyl)-3-azabicyclo[3.1.0]hex-6-yl]phenylcarbamate (3.6 g, 8.06 mmol) and (S)-(3-chloro-2-hydroxypropyl)-carbamic acid tert-butyl ester (2.5 g, 12.0 mmol, 1.5 equiv.) in DMF (5.5 mL) at 0° C., was added lithium tert-butoxide (24 mL, 1.0 M in THF, 24 mmol, 3.0 equiv.). The reaction mixture was continued to stir at 0° C. for 1 hour and then 23° C. for 18 hours. Then, the reaction mixture was diluted with saturated NH$_4$Cl aqueous and extracted with CH$_2$Cl$_2$ (4×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 50% EtOAc in hexane (contain 1% Et$_3$N). Relevant fractions were combined to give the title compound.

Yield 3.3 g (80%). $^1$H NMR (300 MHz, CDCl$_3$): 1.40 (s, 9H), 2.45 (d, J=8.7 Hz, 2H), 2.49 (t, J=3.0 Hz, 1H), 3.10 (d, J=8.7 Hz, 2H), 3.50 (m, 2H), 3.58 (s, 2H), 3.79 (m, 5H), 3.99 (t, J=8.7 Hz, 1H), 4.73 (m, 1H), 4.96 (m, 1H), 6.87 (m, 3H), 7.08 (m, 1H), 7.21-7.33 (m, 3H).

X. N-[((5S)-3-{3-fluoro-4-[exo-(1R,5S)-3-(4-methoxybenzyl)-3-azabicyclo[3.1.0]hex-6-yl]phenyl}-2-oxo-1,3-oxazolidin-5-yl)methyl]propanamide

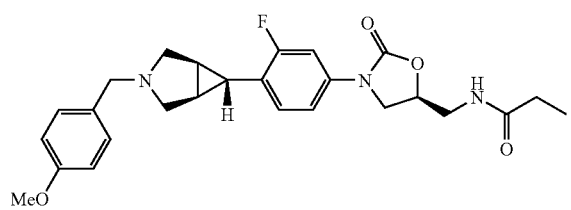

To a suspension of tert-butyl ((5S)-3-{3-fluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate (3.0 g, 5.86 mmol, 1 equiv.) in MeOH (50 mL) at 23° C., was added HCl/dioxane (4.0 M, 90 mL). After being stirred at 23° C. for 1 hour, solvent was evaporated to give the aminomethyl intermediate as the HCl salt. This material was directly used in the next step without further purification.

To a cold suspension of the amine salt (5.86 mmol, 1 equiv.) in CH$_2$Cl$_2$ (200 mL) at 0° C., was added DIEA (10 mL, 57.4 mmol, 10 equiv.), followed by propionic anhydride (1.5 mL, 11.7 mmol, 2.0 equiv.). After being stirred at 0° C. for 10 min and 23° C. for 40 min, the reaction mixture was diluted with CH$_2$Cl$_2$ (400 mL), washed with (NaHCO$_3$ aqueous, H$_2$O, brine), dried (Na$_2$SO$_4$), filtered and evaporated to give the crude title compound (2.7 g, 100%). This material could be used directly in the next step. For an analytical sample, a small portion of the crude product was purified by chromatography on a silica gel column (0-100% EtOAc in hexanes with 1% Et$_3$N). Relevant fractions were combined to give the title compound.

Crude Yield 2.7 g (quant.) $^1$H NMR (300 MHz, CDCl$_3$): 1.13 (t, J=7.5 Hz, 3H), 1.68 (s, 2H), 2.23 (q, J=7.5 Hz, 2H), 2.50 (m, 3H), 3.11 (d, J=8.7 Hz, 2H), 3.60 (s, 2H), 3.62-3.77 (m, 3H), 3.80 (s, 3H), 4.01 (t, J=9.0 Hz, 1H), 4.76 (m, 1H), 6.01 (t, J=5.4 Hz, 1H), 6.84-6.89 (m, 3H), 7.06 (m, 1H), 7.22 (d, J=8.4 Hz, 2H), 7.28-7.35 (m, 1H).

Example 22

N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]propanamide

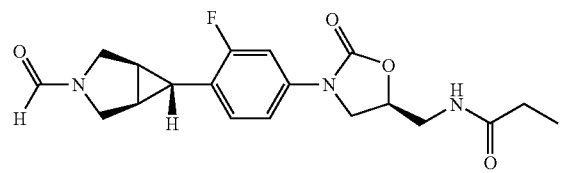

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.3 g, 0.86 mmol, 1 equiv.) in formic acid (4.5 mL) at 23° C. was added acetic anhydride (1.3 mL, 13.8 mmol, 16.0 equiv.). The reaction mixture was stirred at the same temperature for 80 min, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.20 g (62%). MS (m/z): [M+H]$^+$=376. HPLC (SYMMETRY C$_{18}$ 3.5 μM, 4.6×30 mm column; gradient elution 2%-98% MeCN with 0.1% TFA over 5 min; 2 mL/min rate): retention time=1.81 min. $^1$H NMR (300 MHz, DMSO-d$_6$): 0.93 (t, J=7.5 Hz, 3H), 1.67 (m, 1H), 1.93 (m, 2H), 2.07 (q, J=7.5 Hz, 2H), 3.23 (dd, J=3.3 Hz, 11.7 Hz, 1H), 3.42 (m, 2H), 3.63 (dd, J=3.3 Hz, 10.8 Hz, 1H), 3.70 (m, 1H), 3.80 (dd, J=2.1 Hz, 10.5 Hz, 2H), 4.08 (t, J=8.7 Hz, 1H), 4.71 (m, 1H), 7.08 (t, J=8.4 Hz, 1H), 7.19 (m, 1H), 7.42 (dd, J=12.9 Hz, 1.8 Hz, 1H), 8.13 (s, 1H), 8.16 (t, J=5.7 Hz, 1H).

Example 23 exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-carboxamide

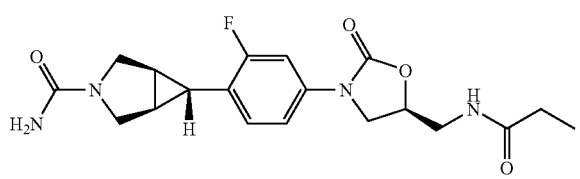

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.3 g, 0.86 mmol, 1 equiv.) in CH$_2$Cl$_2$ (15 mL) at 23° C. was added triethylamine (0.18 mL, 0.13 mmol, 1.5 equiv.), followed by trimethylsilyl isocyanate (0.27 mL, 1.73 mmol, 2.0 equiv.). After being stirred at the same temperature for 1 hour, more trimethylsilyl isocyanate (0.13 mL, 0.86 mmol, 1.0 equiv.) was added. After another hour, trimethylsilyl isocyanate (0.13 mL, 0.86 mmol, 1.0 equiv.) was added again. The reaction mixture was continued to stir at 23° C. for 17 hours, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.16 g (62%). MS (m/z): [M+H]$^+$=391. HPLC (SYMMETRY C$_{18}$ 3.5 µM, 4.6×30 mm column; gradient elution 2%-98% MeCN with 0.1% TFA over 5 min; 2 mL/min rate): retention time=1.67 min. $^1$H NMR (300 MHz, DMSO-d$_6$): 0.93 (t, J=7.8 Hz, 3H), 1.67 (s, 1H), 1.91 (s, 2H), 2.06 (q, J=7.8 Hz, 2H), 3.30 (m, 2H), 3.40 (m, 2H), 3.58 (d, J=10.2 Hz, 2H), 3.71 (m, 1H), 4.08 (t, J=9.0 Hz, 1H), 4.70 (m, 1H), 5.79 (s, 2H), 7.05 (t, J=8.4 Hz, 1H), 7.18 (m, 1H), 7.42 (d, J=12.9 Hz, 1H), 8.16 (t, J=6.0 Hz, 1H).

Example 24 exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-methylcarboxamide

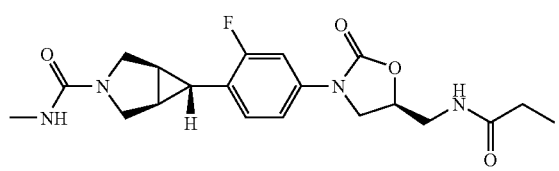

To a cold solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.34 mmol, 1 equiv.) in DMF (5 mL) at 0° C. was added DIEA (0.071 mL, 0.4 mmol, 1.2 equiv.), followed by 4-nitrophenyl chloroformate (82 mg, 0.41 mmol, 1.2 equiv.). The reaction mixture was continued to stir at 0° C. for 120 min, MeNH$_2$ (2.0 M in THF, 0.2 mL, 0.4 mmol, 1.17 equiv.) was added. Then, the reaction mixture was stirred at 23° C. for 2 hours. Another batch of MeNH$_2$ (2.0 M in THF, 0.6 mL, 1.2 mmol, 3.5 equiv.) was added. After 19 hours, the reaction mixture was diluted with CH$_2$Cl$_2$ (200 mL), washed (NaHCO$_3$ aqueous, H$_2$O, brine), dried (Na$_2$SO$_4$), filtered and evaporated to dryness. The crude product was purified by prep TLC to give the title compound.

Yield 0.02 g (15%). MS (m/z): [M+H]$^+$=405. HPLC (SYMMETRY C$_{18}$ 3.5 µM, 4.6×30 mm column; gradient elution 2%-98% MeCN with 0.1% TFA over 5 min; 2 mL/min rate): retention time=1.76 min. $^1$H NMR (300 MHz, DMSO-d$_6$): 0.93 (t, J=7.8 Hz, 3H), 1.67 (m, 1H), 1.92 (m, 2H), 2.08 (q, J=7.2 Hz, 2H), 2.54 (d, J=4.2 Hz, 3H), 3.40 (m, 4H), 3.58 (d, J=10.2 Hz, 2H), 3.70 (m 1H), 4.08 (t, J=8.7 Hz, 1H), 4.71 (m, 1H), 6.10 (m, 1H), 7.05 (t, J=8.4 Hz, 1H), 7.17 (m, 1H), 7.42 (dd, J=12.9 Hz, 1.8 Hz, 1H), 8.15 (t, J=5.4 Hz, 1H).

Example 25 exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-ethylcarboxamide

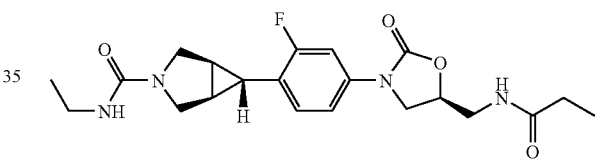

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.3 g, 0.86 mmol, 1 equiv.) in CH$_2$Cl$_2$ (15 mL) at 23° C. was added triethylamine (0.18 mL, 0.13 mmol, 1.5 equiv.), followed by ethyl isocyanate (0.14 mL, 1.77 mmol, 2.0 equiv.). After being stirred at the same temperature for 1 hour, more ethyl isocyanate (0.14 mL, 1.77 mmol, 2.0 equiv.) was added. The reaction mixture was continued to stir at 23° C. for 17 hours, diluted with CH$_2$Cl$_2$ (300 mL), washed (0.5 M HCl aqueous, H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.206 g (57%). MS (m/z): [M+H]$^+$=419. HPLC (SYMMETRY C$_{18}$ 3.5 µM, 4.6×30 mm column; gradient elution 2%-98% MeCN with 0.1% TFA over 5 min; 2 mL/min rate): retention time=1.91 min. $^1$H NMR (300 MHz, DMSO-d$_6$): 0.93 (t, J=7.8 Hz, 3H), 0.99 (t, J=7.2 Hz, 3H), 1.68 (t, J=3.6 Hz, 1H), 1.91 (s, 2H), 2.09 (q, J=7.8 Hz, 2H), 3.06 (m, 2H), 3.29 (m, 2H), 3.45 (m, 2H), 3.58 (d, J=10.2 Hz, 2H), 3.71 (m, 1H), 4.08 (t, J=9.0 Hz, 1H), 4.70 (m, 1H), 6.15 (t, J=5.4 Hz, 1H), 7.05 (t, J=8.4 Hz, 1H), 7.19 (m, 1H), 7.42 (dd, J=12.9 Hz, 2.1 Hz, 1H), 8.16 (t, J=5.4 Hz, 1H).

Example 26

N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]propanamide

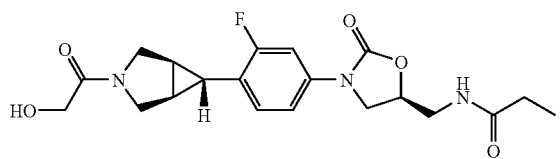

To a cold solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.3 g, 0.86 mmol, 1 equiv.) in CH$_2$Cl$_2$ (20 mL) at 0° C. was added Et$_3$N (0.3 mL, 2.15 mmol, 2.5 equiv.), followed by benzyloxyacetyl chloride (0.16 mL, 1.03 mmol, 1.2 equiv.). The reaction mixture was stirred at 23° C. for 30 min, diluted with CH$_2$Cl$_2$ (200 mL), washed (NaHCO$_3$ aqueous, H$_2$O, brine), dried (Na$_2$SO$_4$), filtered and evaporated to dryness. The crude product was used directly in next step without further purification.

To a solution of above compound (assumed 0.86 mmol, 1 equiv.) in methanol (20 mL) and CH$_2$Cl$_2$ (10 mL) at 23° C. was added 10% Pd/C (220 mg). The reaction mixture was stirred at the same temperature for 120 min under H$_2$ atmosphere, filtered through celite with aid of methanol. The filtrate was evaporated to dryness. The crude product was purified by chromatography on a silica gel column, eluting with a gradient increasing in polarity from 0 to 5% methanol in methylene chloride. Relevant fractions were combined to give the title compound.

Yield 0.18 g (52%). MS (m/z): [M+H]$^+$=406. HPLC (SYMMETRY C$_{18}$ 3.5 μM, 4.6×30 mm column; gradient elution 2%-98% MeCN with 0.1% TFA over 5 min; 2 mL/min rate): retention time=1.69 min. $^1$H NMR (300 MHz, DMSO-d$_6$): 0.93 (t, J=7.5 Hz, 3H), 1.71 (m, 1H), 1.91 (m, 2H), 2.07 (q, J=7.5 Hz, 2H), 3.39 (m, 3H), 3.55 (m, 1H), 3.63-3.80 (m 3H), 3.92 (m, 1H), 4.01 (d, J=5.4 Hz, 1H), 4.08 (t, J=8.7 Hz, 1H), 4.54 (t, J=5.4 Hz, 1H), 4,71 (m, 1H), 7.03 (t, J=8.7 Hz, 1H), 7.17 (m, 1H), 7.42 (d, J=12.6 Hz, 1H), 8.16 (t, J=5.4 Hz, 1H).

Example 27

N-[((5S)-3-{3-fluoro-4-[exo-(1R,5S)-3-methoxyacetyl-3-azabicyclo[3.1.0]hex-6-yl]phenayl}-2-oxo-1,3-oxazolidin-5-yl)methyl]propanamide

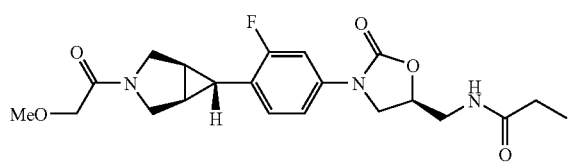

To a cold solution of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.245 g, 0.71 mmol, 1 equiv.) in CH$_2$Cl$_2$ (16 mL) at 0° C. was added Et$_3$N (0.25 mL, 1.77 mmol, 2.5 equiv.), followed by methoxyacetyl chloride (0.077 mL, 0.85 mmol, 1.2 equiv.). The reaction mixture was stirred at 23° C. for 60 min, diluted with CH$_2$Cl$_2$ (200 mL), washed (NaHCO$_3$ aqueous, H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.18 g (61%). MS (m/z): [M+H]$^+$=420. $^1$H NMR (300 MHz, DMSO-d$_6$): 0.93 (t, J=7.2 Hz, 3H), 1.71 (m, 1H), 1.91 (m, 1H), 2.07 (m, 3H), 3.28 (s, 3H), 3.40 (m, 3H), 3.57 (m, 1H), 3.66-3.79 (m 3H), 3.98 (q, J=12.3 Hz, 2H), 4.08 (m, 1H), 4.71 (m, 1H), 7.06 (t, J=8.7 Hz, 1H), 7.17 (m, 1H), 7.42 (d, J=12.6 Hz, 1H), 8.15 (t, J=6.0 Hz, 1H).

Example 28

N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]propanamide

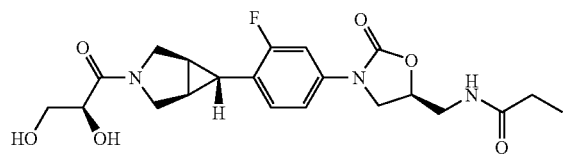

To a cold solution of N-[((5S)-3-{3-fluoro-4-[exo-(1R,5S)-3-({(4S)-2,2-dimethyl-1,3-dioxolan-4-yl}carbonyl)-3-azabicyclo[3.1.0]hex-6-yl]phenyl}-2-oxo-1,3-oxazolidin-5-yl)methyl]propanamide (0.21 g, 0.44 mmol, 1 equiv.) in CH$_2$Cl$_2$ (40 mL) at 0° C. was added H$_2$O (3.0 mL), followed by CF$_3$COOH (0.5 mL, 6.49 mmol, 14.75 equiv.) The reaction mixture was stirred at 0° C. for 60 min, then at 23° C. for 24 hours, diluted with CH$_2$Cl$_2$ (400 mL), washed (H$_2$O, brine), dried (Na$_2$SO$_4$), filtered and evaporated to dryness. The crude product was purified by chromatography on a silica gel column, eluting with a gradient increasing in polarity from 0 to 20% methanol in methylene chloride. Relevant fractions were combined to give the title compound.

Yield 0.17 g (89%). MS (m/z): [M+H]$^+$=436. HPLC (SYMMETRY C$_{18}$ 3.5 μM, 4.6×30 mm column; gradient elution 2%-98% MeCN with 0.1% TFA over 5 min; 2 mL/min rate): retention time=1.60 min. $^1$H NMR (300 MHz, DMSO-d$_6$): 0.93 (t, J=7.5 Hz, 3H), 1.70-175 (m, 1H), 1.90 (m, 1H), 2.00 (m, 1H), 2.09 (q, J=7.5 Hz, 2H), 3.39-3.51 (m, 5H), 3.62-3,87 (m, 3H), 3.95 (m 1H), 4.12 (m, 2H), 4.72 (m, 2H), 4.93 (q, J=3.6 Hz, 1H), 7.06 (t, J=8.7 Hz, 1H), 7.17 (m, 1H), 7.44 (d, J=13.2 Hz, 1H), 8.16 (t, J=5.4 Hz, 1H).

Intermediates for the synthesis of example 28 were prepared as follows.

I. N-[((5S)-3-{3-fluoro-4-[exo-(1R,5S)-3-({(4S)-2,2-dimethyl-1,3-dioxolan-4-yl}carbonyl)-3-azabicyclo[3.1.0]hex-6-yl]phenyl}-2-oxo-1,3-oxazolidin-5-yl)methyl]propanamide

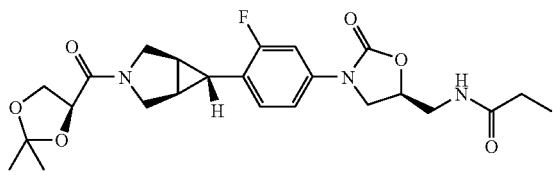

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide (0.30 g, 0.86 mmol, 1 equiv.), HOBT (147 mg, 1.09 mmol, 126 equiv.), EDCI (230 mg, 1.2 mmol, 1.4 equiv.) and (S)-2,2-dimethyl-1,3-dioxolane-4-carboxylic acid (183 mg, 0.99 mmol, 1.15 equiv.) at 23° C. was added DMF (5 mL), followed by DIEA (0.6 mL, 3.45 mmol, 4.0 equiv.). The reaction mixture was stirred at the same temperature for 17 hours, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude material was purified by chromatography on a silica gel column, eluting with a gradient increasing in polarity from 0 to 3% methanol in methylene chloride. Relevant fractions were combined to give N-[((5S)-3-{3-fluoro-4-[exo-(1R,5S)-3-({(4S)-2,2-dimethyl-1,3-dioxolan-4-yl}carbonyl)-3-azabicyclo[3.1.0]hex-6-yl]phenyl}-2-oxo-1,3-oxazolidin-5-yl)methyl]propanamide(210 mg, 51%).

$^1$H NMR

Example 29

N-[((5S)-3-{3-fluoro-4-[exo-(1R, 5S)-3-(2-(S)-hydroxypropanoyl)-3-azabicyclo[3.1.0]hex-6-yl]phenyl}-2-oxo-1,3-oxazolidin-5-yl)methyl]acetamide

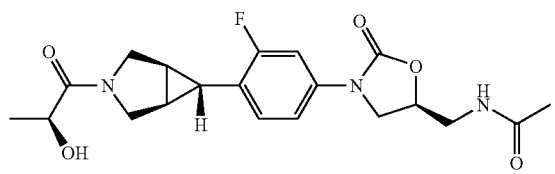

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) in CH$_2$Cl$_2$ (20 mL) at 23° C. was added triethyl amine (0.22 mL, 1.58 mmol, 4.0 equiv.), followed by (S)-(−)-2-acetoxypropionyl chloride (0.07 mL, 0.55 mmol, 1.4 equiv.). The reaction mixture was stirred at the same temperature for 30 min, diluted with saturated NaHCO$_3$ aqueous and extracted with CH$_2$Cl$_2$ (3×100 mL). The combined organic layers were washed (H$_2$, brine), dried (Na$_2$SO$_4$), filtered and evaporated to dryness. The crude acetoxy-protected intermediate was used directly in the next step without further purification.

The crude compound was dissolved in ammonia methanol solution (2.0 M, 10.0 mL) at 23° C. and stirred at the same temperature for 17 hours. The solvent was evaporated and the residue was purified by chromatography on a silica gel column, eluting with a gradient increasing in polarity from 0 to 5% methanol in methylene chloride. Relevant fractions were combined to give the title compound.

Yield 98 mg (62%). MS (m/z): [M+H]$^+$=406 $^1$H NMR (300 MHz, DMSO-d$_6$): 1.15 (m, 3H), 1.68 (bs, 1H), 1.81 (s, 3H), 1.89 (m, 1H), 2.04 (m, 1H), 3.38 (m, 3H), 3.58-3.98 (m, 4H), 4.08 (t, J=9.0 Hz, 1H), 4.20 (m, 1H), 4.70 (m, 1H), 4.90 (m, 1H), 7.07 (t, J=8.7 Hz, 1H), 7.19 (m, 1H), 7.44 (m, 1H), 8.24 (t, J=5.4 Hz, 1H).

Example 30

N-[((5S)-3-{3-fluoro-4-[exo-(1R,5S)-3-cyclopropanecarbonyl-3-azabicyclo[3.1.0]hex-6-yl]phenyl}-2-oxo-1,3-oxazolidin-5-yl)methyl]acetamide

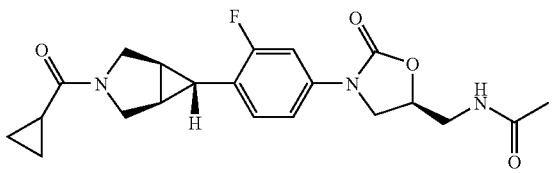

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) in CH$_2$Cl$_2$ (20 mL) at 23° C. was added triethylamine (0.22 mL, 1.58 mmol, 4.0 equiv.), followed by cyclopropanecarbonyl chloride (0.05 mL, 0.5 mmol, 1.4 equiv.). The reaction mixture was stirred at the same temperature for 25 min, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 110 mg (71%). MS (m/z): [M+H]$^+$=402 $^1$H NMR (300 MHz, DMSO-d$_6$): 0.69 (m, 4H), 1.74 (m, 2H), 1.81 (s, 3H), 1.89 (m, 1H), 2.05 (m, 1H), 3.39 (m, 3H), 3.74 (m, 3H), 4.98 (d, J=10.2 Hz, 1H), 4.08 (t, J=9.0 Hz, 1H), 4.71 (m, 1H), 7.08 (t, J=8.7 Hz, 1H), 7.20 (m, 1H), 7.44 (dd, J=2.1 Hz, 12.9 Hz, 1H), 8.24 (t, J=5.4 Hz, 1H).

Example 31

N-[((5 S)-3-{3-fluoro-4-[exo-(1R,5S)-3-(1-hydroxy-cyclopropanecarbonyl)-3-azabicyclo[3.1.0]hex-6-yl]phenyl}-2-oxo-1,3-oxazolidin-5-yl)methyl]acetamide

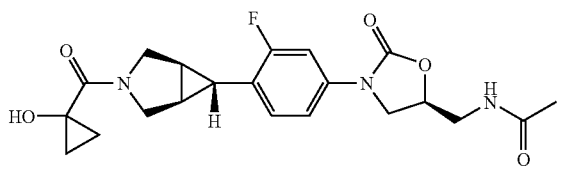

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HATU (178 mg, 0.47 mmol, 1.2 equiv.) and 1-hydroxy-1-cyclopropanecarboxylic acid (40 mg, 0.39 mmol, 1.0 equiv.) at 23° C. was added DMF (5 mL), followed by DIEA (0.34 mL, 1.96 mmol, 5.0 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 10% methanol in methylene chloride. Relevant fractions were combined to give the title compound.

Yield 32.4 mg (20%). MS (m/z): [M+H]$^+$=418 $^1$H NMR (300 MHz, DMSO-d$_6$): 0.73-0.99 (m, 4H), 1.64 (m, 1H), 1.81 (s, 3H), 1.91 (m, 1H), 2.48 (m, 1H), 3.41 (m, 3H), 3.70-3.87 (m, 3H), 4.08 (t, J=9.0 Hz, 1H), 4.28 (m, 1H), 4.71 (m, 1H), 6.17 (s, 1H), 7.08 (t, J=9.0 Hz, 1H), 7.19 (m, 1H), 7.44 (dd, J=2.4 Hz, 12.9 Hz, 1H), 8.24 (t, J=5.7 Hz, 1H).

Example 32

N-[((5S)-3-{3-fluoro-4-[exo-(1R,5S)-3-(2-hydroxy-2-methyl-propanoyl)-3-azabicyclo[3.1.0]hex-6-yl]phenyl}-2-oxo-1,3-oxazolidin-5-yl)methyl]acetamide

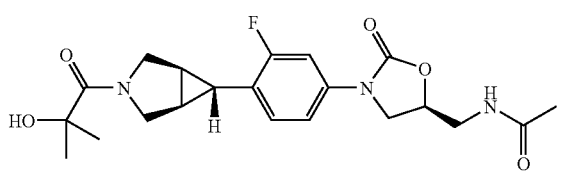

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) in CH$_2$Cl$_2$ (20 mL) at 23° C. was added triethylamine (0.22 mL, 1.58 mmol, 4.0 equiv.), followed by 1-chlorocarbonyl-1-methylethyl acetate (0.08 mL, 0.56 mmol, 1.44 equiv.). The reaction mixture was stirred at the same temperature for 30 min, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude acetoxy intermediate was used directly in the next step without further purification.

To a solution of crude acetoxy compound in methanol (3.0 mL) and THF (3.0 mL) at 23° C. was added aqueous LiOH (92 mg, 2.19 mmol, 5.6 equiv. in H$_2$O 3.0 mL). The reaction mixture was continued to stir at the same temperature for 1 hour, diluted with saturated 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The residue was purified by chromatography on a silica gel column, eluting with a gradient increasing in polarity from 0 to 10% methanol in methylene chloride. Relevant fractions were combined to give the title compound.

Yield 67 mg (41%). MS (m/z): [M+H]$^+$=420 $^1$H NMR (300 MHz, DMSO-d$_6$): 1.26 (s, 6H), 1.68 (m, 1H), 1.81 (s, 3H), 1.85 (m, 1H), 1.99 (m, 1H), 3.38 (m, 3H), 3.65-3.72 (m, 2H), 3.84 (d, J=12.3 Hz, 1H), 4.08 (t, J=9.0 Hz, 1H), 4.40 (d, J=11.4 Hz, 1H), 4.70 (m, 1H), 5.21 (s, 1H), 7.05 (t, J=8.4 Hz, 1H), 7.19 (m, 1H), 7.44 (dd, J=2.1 Hz, 12.9 Hz, 1H), 8.23 (t, J=5.7 Hz, 1H).

Example 33

N-[((5S)-3-{3-fluoro-4-[exo-(1R,5S)-3-(3,3,3-trifluoro-2-(S)-hydroxypropanoyl)-3-azabicyclo[3.1.0]hex-6-yl]phenyl}-2-oxo-1,3-oxazolidin-5-yl)methyl]acetamide

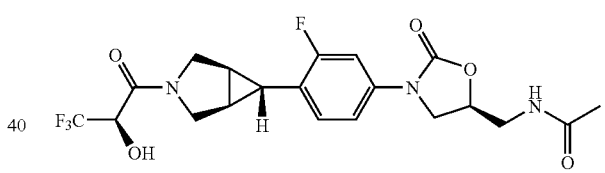

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HOBT (74 mg, 0.54 mmol, 1.4 equiv.), EDCI (120 mg, 0.626 mmol, 1.61 equiv.) and (S)-(−)-trifluorolactic acid (56 mg, 0.39 mmol, 1.0 equiv.) at 23° C. was added DMF (5 mL), followed by DIEA (0.3 mL, 1.7 mmol, 4.42 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 59.2 mg (33%). MS (m/z): [M+H]$^+$=460 $^1$H NMR (300 MHz, DMSO-d$_6$): 1.72 (m, 1H), 1.81 (s, 3H), 1.95 (m, 1H), 2.06 (m, 1H), 3.37-3.47 (m, 4H), 3.64-4.11 (m, 4H), 4.70 (m, 1H), 4.89 (m, 1H), 6.80 (m, 1H), 7.07 (t, J=9.0 Hz, 1H), 7.19 (m, 1H), 7.44 (dd, J=12.9 Hz, 1.5 Hz, 1H), 8.24 (t, J=6.0 Hz, 1H).

Example 34

N-[((5S)-3-{3-fluoro-4-[exo-(1R,5S)-3-difluoro-acetyl-3-azabicyclo[3.1.0]hex-6-yl]phenyl}-2-oxo-1,3-oxazolidin-5-yl)methyl]acetamide

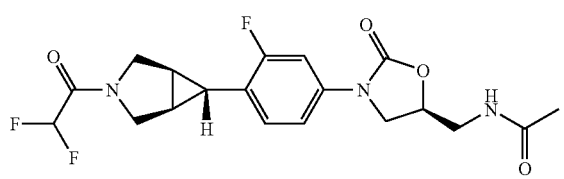

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HOBT (74 mg, 0.54 mmol, 1.4 equiv.), EDCI (120 mg, 0.626 mmol, 1.61 equiv.) and difluoroacetic acid (45 mg, 0.47 mmol, 1.2 equiv.) at 23° C. was added DMF (5 mL), followed by DIEA (0.3 mL, 1.7 mmol, 4.42 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride. Relevant fractions were combined to give the title compound.

Yield 88.4 mg (55%). MS (m/z): [M+H]$^+$=412 $^1$H NMR (300 MHz, DMSO-d$_6$): 1.78 (m, 1H), 1.81 (s, 3H), 1.98 (m, 1H), 2.09 (m, 1H), 3.39 (t, J=5.4 Hz, 2H), 3.50 (m, 1H), 3.70 (m, 2H), 3.82-3.93 (m, 2H), 4.08 (t, J=9.0 Hz, 1H), 4.71 (m, 1H), 6.52 (t, J=53.1 Hz, 1H), 7.08 (t, J=8.7 Hz, 1H), 7.19 (m, 1H), 7.44 (d, J=13.2 Hz, 1H), 8.24 (t, J=5.7 Hz, 1H).

Example 35

N-[((5S)-3-{3-fluoro-4-[exo-(1R,5S)-3-aminoacetyl-3-azabicyclo[3.1.0]hex-6-yl]phenyl}-2-oxo-1,3-oxazolidin-5-yl)methyl]acetamide

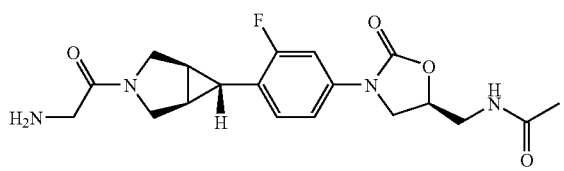

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.11 g, 0.33 mmol, 1 equivalent), HOBT (74 mg, 0.54 mmol, 1.64 equiv.), EDCI (120 mg, 0.626 mmol, 1.89 equiv.) and carbobenzyloxyglycine (96, 0.46 mmol, 1.39 equiv.) at 23° C. was added DMF (5 mL), followed by DIEA (0.3 mL, 1.7 mmol, 5.15 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dryness. The residue was purified by chromatography on a silica gel column, eluting with a gradient increasing in polarity from 0 to 5% methanol in methylene chloride. Relevant fractions were combined to give the benzyloxycarbonyl-protected intermediate which was used directly in the next step.

The benzyloxycarbonyl-protected intermediate was dissolved in methanol (20 mL) and methylene chloride (10 mL) at 23° C. Then, 10% Pd/C (100 mg) was added and the reaction mixture stirred at the same temperature for 1 hour under a hydrogen atmosphere. The reaction mixture was filtered through celite with aid of methanol. The solvent was evaporated and the residue was freeze-dried to give the title compound.

Yield 90.6 mg (70%). MS (m/z): [M+H]$^+$=391 $^1$H NMR (300 MHz, DMSO-d$_6$): 1.70 (m, 1H), 1.81 (s, 3H), 1.92 (m, 1H), 2.05 (m, 1H), 2.99 (bs, 3H), 3.39 (m, 3H), 3.52-3.78 (m, 6H), 4.08 (t, J=9.0 Hz, 1H), 4.70 (m, 1H), 7.07 (t, J=8.7 Hz, 1H), 7.19 (m, 1H), 7.42 (m, 1H), 8.25 (t, J=5.4 Hz, 1H).

Example 36

N-[((5S)-3-{3-fluoro-4-[exo-(1R,5S)-3-acetylaminoacetyl-3-azabicyclo[3.1.0]hex-6-yl]phenyl}-2-oxo-1,3-oxazolidin-5-yl)methyl]acetamide

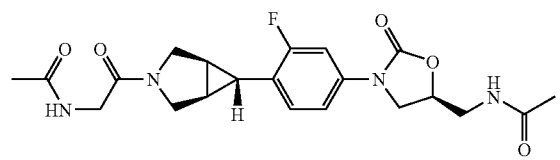

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HATU (178 mg, 0.47 mmol, 1.2 equiv.) and N-acetylglycine (50 mg, 0.43 mmol, 1.1 equiv.) at 23° C. was added DMF (5 mL), followed by DIEA (0.34 mL, 1.96 mmol, 5.0 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 10% methanol in methylene chloride. Relevant fractions were combined to give the title compound.

Yield 78.5 mg (47%). MS (m/z): [M+H]$^+$=433 $^1$H NMR (300 MHz, DMSO-d$_6$): 1.73 (m, 1H), 1.81 (s, 3H), 1.85 (s, 3H), 1.92 (m, 1H), 2.07 (m, 1H), 3.39 (m, 3H), 3.60-3.88 (m, 6H), 4.08 (m, 1H), 4.70 (m, 1H), 7.07 (t, J=9.0 Hz, 1H), 7.19 (m, 1H), 7.44 (d, J=13.2 Hz, 1H), 7.97 (t, J=5.4 Hz, 1H), 8.24 (t, J=6.0 Hz, 1H).

Example 37

N-[((5S)-3-{3-fluoro-4-[exo-(1R,5S)-3-(isoxazole-5-carbonyl)-3-azabicyclo[3.1.0]hex-6-yl]phenyl}-2-oxo-1,3-oxazolidin-5-yl)methyl]acetamide

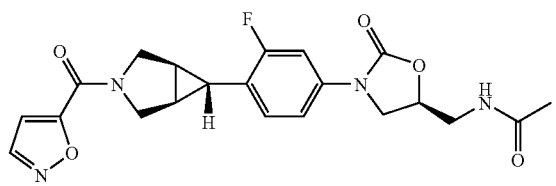

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) in CH₂Cl₂ (20 mL) at 23° C. was added triethylamine (0.22 mL, 1.58 mmol, 4.0 equiv.), followed by isoxazole-5-carbonyl chloride (140 mg, 1.07 mmol, 2.7 equiv.). The reaction mixture was stirred at the same temperature for 30 min, diluted with saturated NaHCO₃ aqueous and extracted with CH₂Cl₂ (3×100 mL). The combined organic layers were washed (H₂O, brine), dried (Na₂SO₄), filtered and evaporated to dry. The crude product was purified by chromatography on a silica gel column, eluting with a gradient increasing in polarity from 0 to 5% methanol in methylene chloride. Relevant fractions were combined to give the title compound.

Yield 110 mg (66%). MS (m/z): [M+H]⁺=429 ¹H NMR (300 MHz, DMSO-d₆): 1.81 (s, 3H), 1.83 (m, 1H), 2.04 (m, 1H), 2.10 (bs, 1H), 3.38 (t, J=7.2 Hz, 2H), 3.67 (m, 2H), 3.98 (m, 3H), 4.08 (t, J=9.0 Hz, 1H), 4.71 (m, 1H), 7.04 (m, 1H), 7.09 (m, 1H), 7.21 (m, 1H), 7.44 (dd, J=1.8 Hz, 12.9 Hz, 1H), 8.24 (t, J=6.0 Hz, 1H), 8.75 (dd, J=0.6 Hz, 2.1 Hz, 1H).

Example 38

N-[((5S)-3-{3-fluoro-4-[exo-(1R,5S)-3-(1H-pyrazole-3-carbonyl)-3-azabicyclo[3.1.0]hex-6-yl]phenyl}-2-oxo-1,3-oxazolidin-5-yl)methyl]acetamide

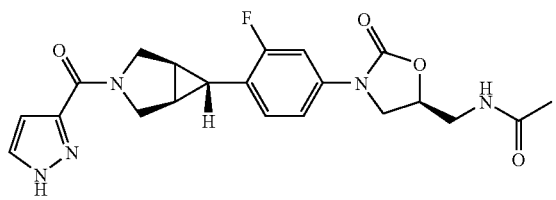

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HOBT (74 mg, 0.54 mmol, 1.4 equiv.), EDCI (120 mg, 0.626 mmol, 1.61 equiv.) and 3-pyrazolecarboxylic acid (52 mg, 0.46 mmol, 1.2 equiv.) at 23° C. was added DMF (5 mL), followed by DIEA (0.3 mL, 1.7 mmol, 4.42 equiv.). The reaction mixture was stirred at the same temperature for 17 hours, diluted with saturated NaHCO₃ aqueous and extracted with CH₂Cl₂ (3×100 mL). The combined organic layers were washed (H₂O, brine), dried (Na₂SO₄), filtered and evaporated to dry. The crude product was purified by chromatography on a silica gel column, eluting with a gradient increasing in polarity from 0 to 5% methanol in methylene chloride. Relevant fractions were combined to give the title compound.

Yield 84.3 mg (51%). MS (m/z): [M+H]⁺=428 ¹H NMR (300 MHz, DMSO-d₆): 1.69 (m, 1H), 1.81 (s, 3H), 1.99 (m, 1H), 2.04 (m, 1H), 3.39 (t, J=5.4 Hz, 2H), 3.55 (m, 1H), 3.70 (m, 1H), 3.90 (m, 1H), 4.02 (d, J=12.0 Hz, 1H), 4.08 (t, J=9.0 Hz, 1H), 4.79 (d, J=11.7 Hz, 1H), 4.70 (m, 1H), 6.64 (m, 1H), 7.09 (t, J=8.4 Hz, 1H), 7.19 (m, 1H), 7.44 (dd, J=12.9 Hz, 2.4 Hz, 2.4 Hz, 1H), 7.80 (m, 1H), 8.24 (t, J=5.7 Hz, 1H).

Example 39

N-[((5S)-3-{3-fluoro-4-[exo-(1R,5S)-3-(1H-imidazole-4-carbonyl)-3-azabicyclo[3.1.0]hex-6-yl]phenyl}-2-oxo-1,3-oxazolidin-5-yl)methyl]acetamide

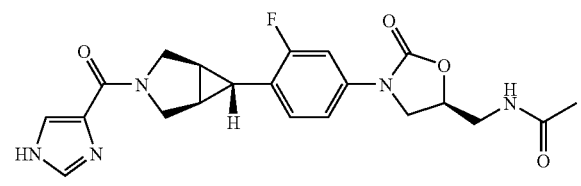

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.157 g, 0.47 mmol, 1 equivalent), HOBT (85 mg, 0.63 mmol, 1.3 equiv.), EDCI (120 mg, 0.626 mmol, 1.3 equiv.) and 4-imidazolecarboxylic acid (68 mg, 0.61 mmol, 1.3 equiv.) at 23° C. was added DMF (5 mL), followed by DIEA (0.7 mL, 4.0 mmol, 8.6 equiv.). The reaction mixture was stirred at the same temperature for 17 hours, diluted with saturated NaHCO₃ aqueous and extracted with CHCl₃ (9×50 mL). The combined organic layers were washed (H₂O, brine), dried (Na₂SO₄), filtered and evaporated to dry. The crude product was purified by chromatography on a silica gel column, eluting with a gradient increasing in polarity from 0 to 10% methanol in methylene chloride (containing 1% Et₃N). Relevant fractions were combined to evaporate and residue was dissolved in CHCl₃ (300 mL). The organic layer were washed (NaHCO₃ aqueous, brine), dried (Na₂SO₄), filtered and evaporated to dryness. The residue was freeze-dried to give the title compound.

Yield 65.6 mg (33%). MS (m/z): [M+H]⁺=428 ¹H NMR (300 MHz, DMSO-d₆): 1.68 (s, 1H), 1.82 (s, 3H), 1.98 (bs, 1H), 2.05 (bs, 1H), 3.39 (t, J=5.4 Hz, 2H), 3.53 (m, 1H), 3.70 (m, 1H), 3.88 (m, 1H), 4.00 (d, J=12.0 Hz, 1H), 4.08 (t, J=8.7 Hz, 1H), 4.48 (m, 1H), 4.71 (m, 1H), 7.09 (t, J=8.7 Hz, 1H), 7.19 (m, 1H), 7.44 (d, J=12.9 Hz, 1H), 7.59 (s, 1H), 7.72 (d, J=1.2 Hz, 8.24 (t, J=5.4 Hz, 1H).

Example 40

N-[((5S)-3-{3-fluoro-4-[exo-(1R,5S)-3-(1H-pyrazole-4-carbonyl)-3-azabicyclo[3.1.0]hex-6-yl]phenyl}-2-oxo-1,3-oxazolidin-5-yl)methyl]acetamide

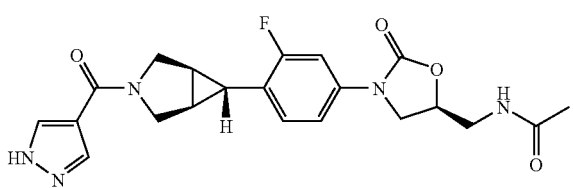

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.12 g, 0.36 mmol, 1 equivalent), HOBT (74 mg, 0.54 mmol, 1.5 equiv.), EDCI (120 mg, 0.626 mmol, 1.74 equiv.) and 4-pyrazolecarboxylic acid (47 mg, 0.42 mmol, 1.2 equiv.) at 23° C. was added DMF (5 mL), followed by DIEA (0.3 mL, 1.7 mmol, 4.7 equiv.). The reaction mixture was stirred at the same temperature for 17 hours, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.059 g (38%). MS (m/z): [M+H]$^+$=428. HPLC (SYMMETRY C$_{18}$ 3.5 μM, 4.6×30 mm column; gradient elution 2%-98% MeCN with 0.1% TFA over 5 min; 2 mL/min rate): retention time=1.71 min. $^1$H NMR (300 MHz, DMSO-d$_6$): 1.69 (m, 1H), 1.81 (s, 3H), 1.99 (bs, 1H), 2.07 (bs, 1H), 3.39 (t, J=5.4 Hz, 2H), 3.52 (m, 1H), 3.69 (m, 1H), 3.98 (m, 3H), 4.08 (t, J=8.7 Hz, 1H), 4.71 (m, 1H), 7.09 (t, J=8.7 Hz, 1H), 7.19 (m, 1H), 7.44 (dd, J=12.9 Hz, 2.1 Hz, 1H), 7.82 (s, 1H), 8.16 (s, 1H), 8.24 (t, J=6.0 Hz, 1H).

Example 41

N-[((5S)-3-{3-fluoro-4-[exo-(1R,5S)-3-(tetrahydrofuran-2-(R)-carbonyl)-3-azabicyclo[3.1.0]hex-6-yl]phenyl}-2-oxo-1,3-oxazolidin-5-yl)methyl]acetamide

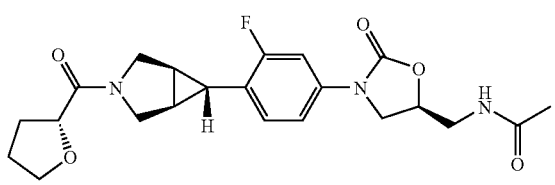

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.11 g, 0.33 mmol, 1 equivalent), HOBT (74 mg, 0.54 mmol, 1.64 equiv.), EDCI (120 mg, 0.626 mmol, 1.89 equiv.) and (R)-(+)-tetrahydro-2-furoic acid (45 uL, 0.46 mmol, 1.39 equiv.) at 23° C. was added DMF (5 mL), followed by DIEA (0.3 mL, 1.7 mmol, 5.15 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 100 mg (70%). MS (m/z): [M+Na]$^+$=454 $^1$H NMR (300 MHz, DMSO-d$_6$): 1.68 (m, 1H), 1.81 (s, 3H), 1.91-2.07 (m, 6H), 3.37 (m, 3H), 3.41-3.95 (m, 6H), 4.08 (t, J=9.0 Hz, 1H), 4.49 (m, 1H), 4.70 (m, 1H), 7.07 (t, J=8.4 Hz, 1H), 7.19 (m, 1H), 7.44 (dd, J=13.2 Hz, 1.8 Hz, 1H), 8.24 (t, J=6.0 Hz, 1H).

Example 42

N-[((5S)-3-{3-fluoro-4-[exo-(1R,5S)-3-(tetrahydrofaran-2-(S)-carbonyl)-3-azabicyclo[3.1.0]hex-6-yl]phenyl}-2-oxo-1,3-oxazolidin-5-yl)methyl]acetamide

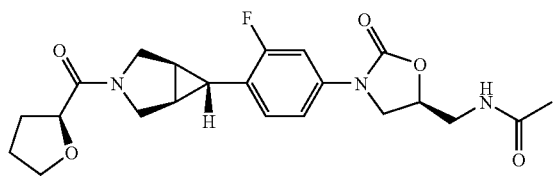

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent), HOBT (74 mg, 0.54 mmol, 1.4 equiv.), EDCI (120 mg, 0.626 mmol, 1.61 equiv.) and (S)-(−)-tetrahydro-2-furoic acid (45 uL, 0.46 mmol, 1.2 equiv.) at 23° C. was added DMF (5 mL), followed by DIEA (0.3 mL, 1.7 mmol, 4.42 equiv.). The reaction mixture was stirred at the same temperature for 17 hours, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride. Relevant fractions were combined to give the title compound.

Yield 107 mg (64%). MS (m/z): [M+H]$^+$=432 $^1$H NMR (300 MHz, DMSO-d$_6$): 1.68 (m, 1H), 1.81 (s, 3H), 1.91-2.06 (m, 6H), 3.37 (m, 3H), 3.41-3.95 (m, 6H), 4.08 (t, J=9.3 Hz, 1H), 4.49 (m, 1H), 4.70 (m, 1H), 7.07 (t, J=8.7 Hz, 1H), 7.19 (m, 1H), 7.44 (dd, J=12.9 Hz, 2.1 Hz, 1H), 8.23 (t, J=6.0 Hz, 1H).

Example 43

N-[((5S)-3-{3-fluoro-4-[exo-(1R,5S)-3-(pyrimidin-2-yl)-3-azabicyclo[3.1.0]hex-6-yl]phenyl}-2-oxo-1,3-oxazolidin-5-yl)methyl]acetamide

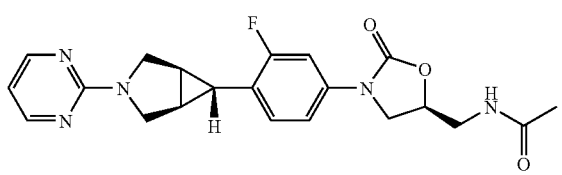

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) in DMF (5 mL) at 23° C. was added triethylamine (0.22 mL, 1.58 mmol, 4.0 equiv.), followed by 2-chloropyrimidine (67 mg, 0.585 mmol, 1.5 equiv.). The reaction mixture was stirred at 60° C. for 2.5 hours, diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride. Relevant fractions were combined to give the title compound.

Yield 55 mg (34%). MS (m/z): [M+H]$^+$=412 $^1$H NMR (300 MHz, DMSO-d$_6$): 1.76 (m, 1H), 1.81 (s, 3H), 2.08 (s, 2H), 3.38 (t, J=8.4 Hz 2H), 3.68 (d, J=9.9 Hz, 2H), 3.71 (m, 1H), 3.92 (d, J=11.4 Hz, 2H), 4.09 (t, J=9.0 Hz, 1H), 4.71 (m, 1H), 6.63 (t, J=4.8 Hz, 1H), 7.10 (t, J=8.7 Hz, 1H), 7.20 (m, 1H), 7.44 (m, 1H), 8.27 (m, 1H), 8.33 (m, 2H).

Example 44

N-[((5S)-3-{3-fluoro-4-[exo-(1R,5S)-3-(2H-tetrazol-5-yl)-3-azabicyclo[3.1.0]hex-6-yl]phenyl}-2-oxo-1,3-oxazolidin-5-yl)methyl]acetamide

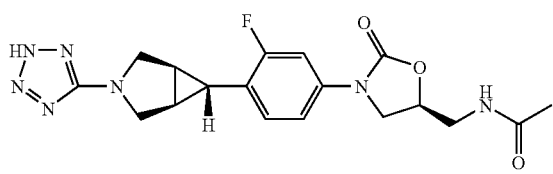

To a solid mixture of N-[((5S)-3-{3-fluoro-4-[exo-(1R,5S)-3-cyano-3-azabicyclo[3.1.0]hex-6-yl]phenyl}-2-oxo-1,3-oxazolidin-5-yl)methyl]acetamide (0.20 g, 0.56 mmol, 1 equivalent), NaN$_3$ (109 mg, 1.68 mmol, 3.0 equiv.) and NH$_4$Cl (90 mg, 1.68 mmol, 3.0 equiv.) at 23° C. was added DMF (5 mL). The reaction mixture was stirred at 100° C. for 3 hours, cooled down to 23° C., added NaNO$_3$ aqueous (200 mg in H$_2$O 4.0 mL), followed by 1.0 M HCl to adjust pH to 3. The desired product was extracted with EtOAc (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 10% methanol in methylene chloride. Relevant fractions were combined to give the title compound.

Yield 120 mg (54%). MS (m/z): [M+H]$^+$=402 $^1$H NMR (300 MHz, DMSO-d$_6$): 1.82 (s, 3H), 1.88 (m, 1H), 2.09 (s, 2H), 3.39 (t, J=5.4 Hz, 2H), 3.53 (d, J=9.3 Hz, 2H), 3.68 (d, J=7.5 Hz, 2H), 3.72 (t, J=3.9 Hz, 1H), 4.09 (t, J=9.3 Hz, 1H), 4.71 (m, 1H), 7.11 (t, J=8.7 Hz, 1H), 7.20 (m, 1H), 7.44 (dd, J=13.2 Hz, 2.4 Hz, 1H), 8.24 (t, J=5.4 Hz, 1H).

Intermediates for the preparation of example 44 were synthesized as follows.

I. N-[((5S)-3-{3-fluoro-4-[exo-(1R,5S)-3-cyano-3-azabicyclo[3.1.0]hex-6-yl]phenyl}-2-oxo-1,3-oxazolidin-5-yl)methyl]acetamide

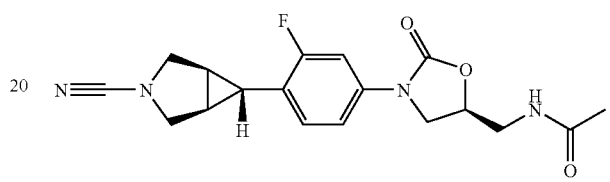

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.57 g, 1.71 mmol, 1 equivalent) in CH$_2$Cl$_2$ (30 mL) at 0° C. was added Et$_3$N (0.7 mL, 5.0 mmol, 3.0 equiv.), followed by cyanogen bromide (0.7 mL, 3.0 M solution in CH$_2$Cl$_2$, 2,1 mmol, 1.23 equiv.). The reaction mixture was stirred at the same temperature for 25 min, diluted with 0.5 M HCl aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride. Relevant fractions were combined to give the title compound.

Yield 0.25 g (41%). MS (m/z): [M+H]$^+$=359 $^1$H NMR (300 MHz, DMSO-d$_6$): 1.81 (s, 3H), 1.88 (m, 1H), 1.99 (m, 2H), 3.39 (t, J=5.4 Hz, 2H), 3.55 (s, 4H), 3.70 (m, 1H), 4.08 (t, J=9.0 Hz, 1H), 4.71 (m, 1H), 7.08 (t, J=8.7 Hz, 1H), 7.21 (m, 1H), 7.44 (dd, J=13.2 Hz, 2.4 Hz, 1H), 8.23 (t, J=5.7 Hz, 1H).

Example 45

N-[((5S)-3-{3-fluoro-4-[exo-(1R,5S)-3-(1-methyl-1H-tetrazol-5-yl)-3-azabicyclo[3.1.0]hex-6-yl]phenyl}-2-oxo-1,3-oxazolidin-5-yl)methyl]acetamide

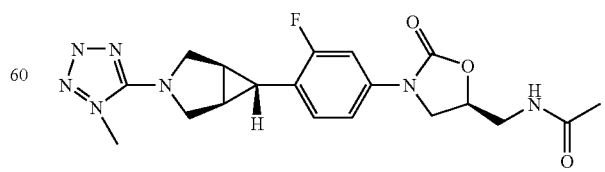

To a solution of N-[((5S)-3-{3-fluoro-4-[exo-(1R,5S)-3-(2H-tetrazol-5-yl)-3-azabicyclo[3.1.0]hex-6-yl]phenyl}-2- oxo-1,3-oxazolidin-5-yl)methyl]acetamide (0.10 g, 0.25 mmol, 1 equivalent) in DMF (5.0 mL) at 23° C. was added DIEA (0.09 mL, 0.52 mmol, 2.0 equiv.), followed by iodomethane (0.15 mL, 2.0 M solution in tert-butyl methyl ether, 0.3 mmol, 1.2 equiv.). After being stirred at the same temperature for 1 hour, more MeI (0.15 mL, 2.0 M solution in tert-butyl methyl ether, 0.3 mmol, 1.2 equiv.) was added. After another hour, the reaction mixture was diluted with saturated NH$_4$Cl aqueous and extracted with EtOAc (3×100 mL). The combined organic layers were washed (H$_2$O, brine), dried (Na$_2$SO$_4$), filtered and evaporated to dry. The crude product was purified by semi-prep HPLC to give the desired compound.

Yield 15 mg (14%). MS (m/z): [M+H]$^+$=458 $^1$H NMR (300 MHz, DMSO-d$_6$): 1.82 (s, 3H), 1.97 (m, 1H), 2.08 (m, 2H), 3.39 (t, J=5.7 Hz, 2H), 3.71 (m, 3H), 3.92 (d, J=9.9 Hz, 2H), 3.96 (s, 3H), 4.09 (m, 1H), 4.71 (m, 1H), 7.10 (t, J=8.4 Hz, 1H), 7.19 (m, 1H), 7.44 (dd, J=12.9 Hz, 2.4 Hz, 1H), 8.24 (m, 1H).

Example 46

N-[((5S)-3-{3-fluoro-4-[exo-(1R,5S)-3-(2-fluoroethyl)-3-azabicyclo[3.1.0]hex-6-yl]phenyl}-2-oxo-1,3-oxazolidin-5-yl)methyl]acetamide

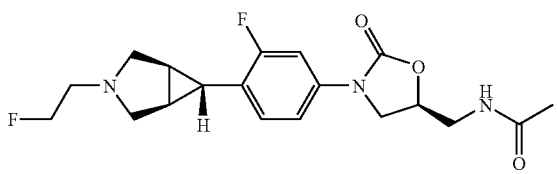

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.12 g, 0.36 mmol, 1 equivalent) and K$_2$CO$_3$ (99 mg, 0.72 mmol, 2.0 equiv.) at 23° C. was added DMF (4 mL), followed by flluoro-2-iodoethane (0.11 g, 0.63 mmol, 1.76 equiv.). After being stirred at 65° C. for 2.5 hours, more flluoro-2-iodoethane (0.11 g, 0.63 mmol, 1.76 equiv.) was added. The reaction mixture was continued to stir at 65° C. for 4 more hours, cooled down to 23° C., diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride. Relevant fractions were combined to give the title compound.

Yield 0.026 g (19%). MS (m/z): [M+H]$^+$=380. $^1$H NMR (300 MHz, DMSO-d$_6$): 1.76 (m, 2H), 1.81 (s, 3H), 2.27 (m, 1H), 2.48 (m, 2H), 2.69 (bs, 1H), 2.79 (bs, 1H), 3.14 (d, J=8.7 Hz, 2H), 3.39 (t, J=5.4 Hz, 2H) 3.68 (m, 1H), 4.07 (t, J=8.7 Hz, 1H), 4.41 (t, J=4.5 Hz, 1H), 4.57 (t, J=5.1 Hz, 1H), 4.70 (m, 1H), 7.01 (t, J=8.4 Hz, 1H), 7.18 (m, 1H), 7.42 (dd, J=12.9 Hz, 2.4 Hz, 1H), 8.23 (t, J=5.7 Hz, 1H).

Example 47

N-[((5S)-3-{3-fluoro-4-[exo-(1R,5S)-3-(2-hydroxyethyl)-3-azabicyclo[3.1.0]hex-6-yl]phenyl}-2-oxo-1,3-oxazolidin-5-yl)methyl]acetamide

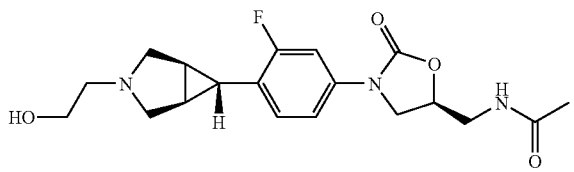

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.12 g, 0.36 mmol, 1 equivalent) in DMF (4 mL), was added DIEA (0.125 mL, 0.72 mmol, 2.0 equiv.), followed by 2-iodoethanol (0.059 mL, 0.76 mmol, 2.0 equiv.). After being stirred at 65° C. for 2 hours, cooled down to 23° C., diluted with saturated NaHCO$_3$ aqueous and extracted with CH$_2$Cl$_2$ (3×100 mL). The combined organic layers were washed (H$_2$O, brine), dried (Na$_2$SO$_4$), filtered and evaporated to dry. The crude product was purified by chromatography on a silica gel column, eluting with a gradient increasing in polarity from 0 to 10% methanol in methylene chloride. Relevant fractions were combined to give the title compound.

Yield 0.079 g (58%). MS (m/z): [M+H]$^+$=378. $^1$H NMR (300 MHz, DMSO-d$_6$): 1.75 (s, 2H), 1.81 (s, 3H), 2.30 (s, 1H), 2.53 (m, 4H), 3.32 (m, 2H), 3.39 (t, J=5.7 Hz, 2H), 3.47 (m, 2H), 3.68 (m, 1H), 4.07 (t, J=9.0 Hz, 1H), 4.46 (bs, 1H), 4.72 (m, 1H), 7.00 (t, J=8.7 Hz, 1H), 7.18 (m, 1H), 7.42 (dd, J=12.9 Hz, 2.4 Hz, 1H), 8.23 (t, J=5.4 Hz, 1H).

Example 48

N-[((5S)-3-{3-fluoro-4-[exo-(1R,5S)-3-(2-cyanoethyl)-3-azabicyclo[3.1.0]hex-6-yl]phenyl}-2-oxo-1,3-oxazolidin-5-yl)methyl]acetamide

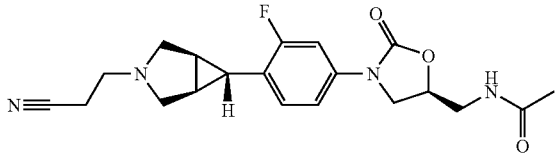

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.11 g, 0.33 mmol, 1 equivalent) in 2-propanol (4 mL), was added Et$_3$N (0.25 mL, 1.8 mmol, 5.4 equiv.), followed by acrylonitrile (0.026 mL, 0.39 mmol, 1.2 equiv.). After being stirred at 65° C. for 1.5 hours, more acrylonitrile (0.026 mL, 0.39 mmol, 1.2 equiv.) was added. After another 2.5 hours, the reaction was cooled down to 23° C. and evaporated to dryness. The crude product was purified by chromatography on a silica gel column, eluting with a gradient increasing in polarity from 0 to 5% methanol in methylene chloride. Relevant fractions were combined to give the title compound.

Yield 0.071 g (56%). MS (m/z): [M+H]⁺=387. HPLC (SYMMETRY C₁₈ 3.5 μM, 4.6×30 mm column; gradient elution 2%-98% MeCN with 0.1% TFA over 5 min; 2 mL/min rate): retention time=1.36 min. ¹H NMR (300 MHz, DMSO-d₆): 1.76 (s, 2H), 1.81 (s, 3H), 2.25 (m, 1H), 2.42 (d, J=8.4 Hz, 2H), 2.66 (m, 4H), 3.11 (d, J=8.7 Hz, 2H), 3.39 (t, J=5.4 Hz, 2H), 3.68 (m, 1H), 4.07 (t, J=9.0 Hz, 1H), 4.70 (m, 1H), 7.00 (t, J=8.4 Hz, 1H), 7.16 (m, 1H), 7.40 (dd, J=12.9 Hz, 2.1 Hz, 1H), 8.23 (t, J=5.7 Hz, 1H).

Example 49

N-[((5S)-3-{3-fluoro-4-[exo-(1R,5S)-3-dimethylamino-3-azabicyclo[3.1.0]hex-6-yl]phenyl}-2-oxo-1,3-oxazolidin-5-yl)methyl]acetamide

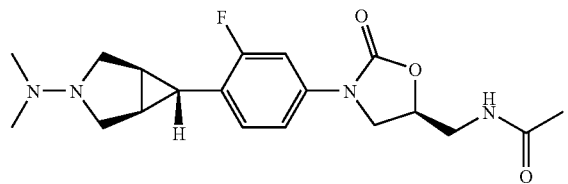

To a suspension of benzyl 3-fluoro-4-[exo-(1R,5S)-3-dimethylamino-3-azabicyclo[3.1.0]hex-6-yl]phenylcarbamate (550 mg, 1.5 mmol, 1 equiv.) in DMF (1.0 mL) at 23° C. was added MeOH (0.125 mL, 3.08 mmol, 2.11 equiv.). The resulting mixture was cooled in an ice bath. A solution of lithium t-butoxide (4.5 mL, 4.5 mmol, 3.1 equiv, 1.0 M solution in THF) was added, followed by solid (S)-acetic acid 2-acetylamino-1-chloromethyl-ethyl ester (0.59 g, 3.06 mmol, 2.11 equiv.). The resulting solution was stirred at 0° C. for 1 hour, then 23° C. for 21 hours, quenched by CF₃CO₂H (0.35 mL), diluted with CH₃CN/H₂O (1:1, 2.0 mL) and purified by semi-prep HPLC to give the title compound as its trifluoroacetic acid salt.

Yield 0.078 g (15%). MS (m/z): [M+H]⁺=377. HPLC (SYMMETRY C₁₈ 3.5 μM, 4.6×30 mm column; gradient elution 2%-98% MeCN with 0.1% TFA over 5 min; 2 mL/min rate): retention time=1.04 min. ¹H NMR (300 MHz, DMSO-d₆): 1.81 (m, 4H), 2.02 (m, 2H), 3.24 (s, 3H), 3.28 (s, 3H), 3.40 (t, J=5.1 Hz, 2H), 3.65-3.79 (m, 5H), 4.10 (t, J=8.7 Hz, 1H), 4.74 (m, 1H), 7.15-7.29 (m, 2H), 7.48 (dd, J=12.9 Hz, J=2.4 Hz, 1H), 8.27 (t, J=5.7 Hz, 1H).

Intermediates for the synthesis of example 49 were prepared as follows:

I. 3-fluoro-4-[exo-(1R,5S)-3-dimethylamino-3-azabicyclo[3.1.0]hex-6-yl]phenylcarbamate

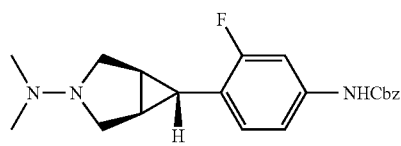

Benzyl 4-[exo-(2R,3S)-2,3-bis(methanesulfonyloxymethyl)cyclopropyl]-3-fluorophenylcarbamate (0.7 g, 1.4 mmol, 1 equiv.) was dissolved in 1,1-dimethylhydrazine (9.0 mL, 118 mmol, 85 equiv.) at 23° C. and stirred at same temperature for 17 hours. The reaction mixture was diluted with 2.0 M NaCO₃ aqueous, washed by CHCl₃. The aqueous layer was co-evaporated with toluene. The result solid was extracted with MeOH/CH₃CN/CH₂Cl₂ (1:1:8) (1000 mL), filtered through celite and concentrated. The residue was dissolved in CH₃CN/H₂O and freeze-dried. The crude product was used directly in the next step without further purification.

Example 50

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]proyanamide

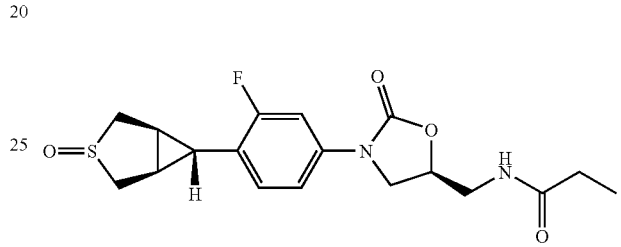

To a cold suspension of N-[((5S)-3-{3-fluoro-4-[exo-(1R,5S)-3-thiabicyclo[3.1.0]hex-6-yl]phenyl}-2-oxo-1,3-oxazolidin-5-yl)methyl]propanamide (2.45 mmol, 1 equiv.) in MeOH (35 mL) at 0° C. was added NaIO₄ aqueous (550 mg, 2.57 mmol, 1.05 equiv. in H₂O 10 mL). After being stirred at 4° C. for 14 hours, another batch of NaIO₄ (70 mg. 0.33 mmol, 0.13 equiv.) was added. After another 24 hours at 4° C., the reaction mixture was diluted with CH₂Cl₂ (300 mL), washed with (H₂O, brine), dried (Na₂SO₄), filtered and evaporated to dry. The crude product was purified by chromatography on a silica gel column, eluting with a gradient increasing in polarity from 0 to 5% methanol in methylene chloride (containing 10% CH₃CN). Relevant fractions were combined to give the title compound as two separable sulfoxide diastereomers.

Yield (both isomers) 0.64 g (69%). MS (m/z): [M+H]⁺=381.2. HPLC (SYMMETRY C₁₈ 3.5 μM, 4.6×30 mm column; gradient elution 2%-98% MeCN with 0.1% TFA over 5 min; 2 mL/min rate): retention time=1.65 min. High Rf ("anti") isomer: ¹H NMR (300 MHz, DMSO-d₆): 0.94 (t, J=7.2 Hz, 3H), 2.07 (q, J=7.5 Hz, 2H), 2.23 (s, 2H), 2.74 (t, J=3.9 Hz, 1H), 3.10 (d, J=14.7 Hz, 2H), 3.30-3.42 (m, 4H), 3.71 (m, 1H), 4.08 (t, J=9.0 Hz, 1H), 4.71 (m, 1H), 7.06 (t, J=8.7 Hz, 1H), 7.22 (m, 1H), 7.43 (dd, J=12.9 Hz, 2.1 Hz, 1H), 8.16 (t, J=5.7 Hz, 1H). Low Rf ("syn") isomer: ¹H NMR (300 MHz, DMSO-d₆): 0.94 (t, J=7.5 Hz, 3H), 2.07 (q, J=7.5 Hz, 2H), 2.22 (t, J=3.9 Hz, 1H), 2.49 (m, 2H), 3.02 (d, J=14.7 Hz, 2H), 3.14 (m, 2H), 3.39 (m, 2H), 3.70 (m, 1H), 4.08 (t, J=9.0 Hz, 1H), 4.71 (m, 1H), 7.06 (t, J=8.7 Hz, 1H), 7.21 (m, 1H), 7.43 (dd, J=12.9 Hz, 2.1 Hz, 1H), 8.16 (t, J=5.7 Hz, 1H).

113

Intermediates for the preparation of example 50 were synthesized as follows.

I. tert-butyl((5S)-3-{3-fluoro-4-[exo-(1R,5S)-3-thiabicyclo[3.1.0]hex-6-yl]phenyl}-2-oxo-1,3-oxazolidin-5-yl)methylcarbamate

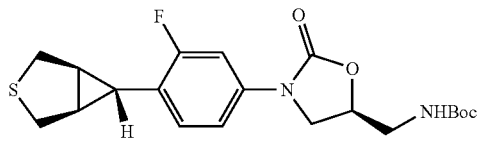

A solution of lithium t-butoxide (53 mL, 53 mmol) was added to a cooled (0° C.) solution of benzyl 3-fluoro-4-[exo-(1R,5S)-3-thiabicyclo[3.1.0]hex-6-yl]phenylcarbamate (6.1 g, 17.8 mmol) and (S)-(3-chloro-2-hydroxy-propyl)-carbamic acid tert-butyl ester (5.5 g, 26.2 mmol, prepared according to the procedure described in U.S. patent application Ser. No. 09/982,157, incorporated herein in its entirety) in DMF (12 mL). The resulting solution was stirred overnight and then quenched by the addition of saturated NH$_4$Cl, water, and brine. The solution was extracted with two portions of dichloromethane and the combined organics washed with water, brine, and dried (MgSO$_4$), filtered and concentrated. The crude product was purified by column chromatography (0-50% ethyl acetate-hexane) to provide the title compound.

Yield 5.9 g (81%). $^1$H NMR (300 MHz, CDCl$_3$): 1.40 (s, 9H), 1.93 (m, 2H), 2.47 (t, J=4.2 Hz, 1H), 3.10 (d, J=11.1 Hz, 2H), 3.17 (m, 2H), 3.54 (m, 2H), 3.80 (m, 1H), 4.00 (t, J=7.5 Hz, 1H), 4.75 (m, 1H), 4.96 (m, 1H), 6.94 (t, J=8.4 Hz, 1H), 7.12 (m, 1H), 7.33 (dd, J=12.0 Hz, 2.4 Hz, 1H).

II. N-[((5S)-3-{3-fluoro-4-[exo-(1R,5S)-3-thiabicyclo[3.1.0]hex-6-yl]phenyl}-2-oxo-1,3-oxazolidin-5-yl)methyl]propanamide

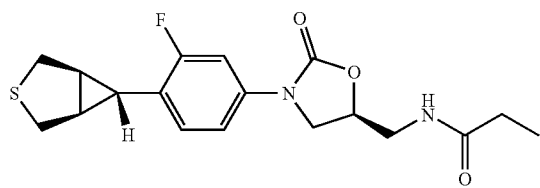

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (1.0 g, 2.45 mmol, 1 equiv.) in CH$_2$Cl$_2$ (20 mL) at 23° C., was added CF$_3$COOH (2 mL). After being stirred at 23° C. for 1 hour, the solvent was evaporated and the residue dissolved in CH$_2$Cl$_2$ (50 mL) and cooled to 0° C. DIEA (10 mL, 57.4 mmol, 23.4 equiv.) was added, followed by propionic anhydride (0.7 mL, 5.4 mmol, 2.2 equiv.). Then, the reaction mixture was stirred at 23° C. for 1.5 hours, diluted with CH$_2$Cl$_2$ (300 mL), washed with (NaHCO$_3$ aqueous, H$_2$O, brine), dried (Na$_2$SO$_4$), filtered and evaporated to dry to give the title compound (1.0 g). This product was directly used in the next step without further purification.

114

Example 51

N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]propanamide

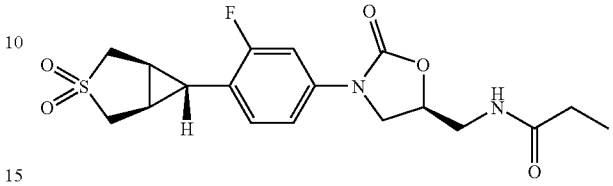

To a cold suspension of N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide (0.28 g, 0.74 mmol, 1 equiv.) in THF (15 mL) at 0° C. was added CH$_3$CO$_3$H (32% in AcOH, 0.46 mL, 2.19 mmol, 3.0 equiv.). Then, the reaction mixture was stirred at 23° C. for 90 min, diluted with CH$_2$Cl$_2$ (200 mL), washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride (containing 10% CH$_3$CN). Relevant fractions were combined to give the title compound.

Yield 0.28 g (96%). MS (m/z): [M+H]$^+$=397. HPLC (SYMMETRY C$_{18}$ 3.5 μM, 4.6×30 mm column; gradient elution 2%-98% MeCN with 0.1% TFA over 5 min; 2 mL/min rate): retention time=1.91 min. $^1$H NMR (300 MHz, DMSO-d$_6$): 0.93 (t, J=7.8 Hz, 3H), 2.07 (m, 4H), 2.32 (t, J=4.2 Hz, 1H), 3.00 (d, J=14.1 Hz, 2H), 3.40 (m, 2H), 3.59 (m, 2H), 3.71 (m 1H), 4.08 (t, J=9.0 Hz, 1H), 4.71 (m, 1H),7.11 (t, J=8.7 Hz, 1H), 7.19 (m, 1H), 7.44 (dd, J=12.9 Hz, 1.8 Hz, 1H), 8.16 (t, J=6.0 Hz, 1H).

Example 52

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide

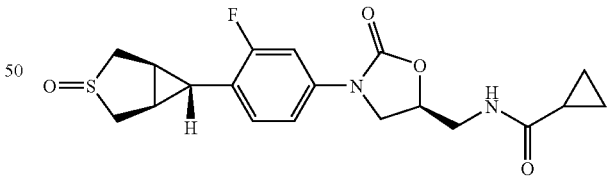

To a cold suspension of N-[((5S)-3-{3-fluoro-4-[exo-(1R,5S)-3-thiabicyclo[3.1.0]hex-6-yl]phenyl}-2-oxo-1,3-oxazolidin-5-yl)methyl]cyclopropanecarboxamide (assumed 1.23 mmol, 1 equiv.) in MeOH (18 mL) at 0° C. was added NaIO$_4$ aqueous (280 mg, 1.31 mmol, 1.06 equiv. in H$_2$O 5 mL). Two more batches of NaIO$_4$ (130 mg and 220 mg) was added during next 64 hours. Then, the reaction mixture was diluted with CH$_2$Cl$_2$ (300 mL), washed with (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride (containing 10%

CH₃CN). Relevant fractions were combined to give the title compound as two separable diastereomers.

Yield (both isomers) 0.261 g (54%). MS (m/z): [M+H]⁺=393.1. HPLC (SYMMETRY $C_{18}$ 3.5 µM, 4.6×30 mm column; gradient elution 2%-98% MeCN with 0.1% TFA over 5 min; 2 mL/min rate): retention time=1.73 min. High Rf ("anti") isomer: ¹H NMR (300 MHz, DMSO-d₆): 0.62 (m, 4H), 1.58 (m, 1H), 2.23 (m, 2H), 2.75 (t, J=3.9 Hz, 1H), 3.08 (d, J=14.7 Hz, 2H), 3.32-3.42 (m, 4H), 3.71 (m, 1H), 4.08 (t, J=9.0 Hz, 1H), 4.72 (m, 1H), 7.07 (t, J=8.7 Hz, 1H), 7.22 (m, 1H), 7.43 (dd, J=12.9 Hz, 2.4 Hz, 1H), 8.46 (t, J=5.7 Hz, 1H). Low Rf ("syn") isomer: ¹H NMR (300 MHz, DMSO-d₆): 0.62 (m, 4H), 1.58 (m, 1H), 2.23 (t, J=3.9 Hz, 1H), 2.49 (m, 2H), 3.00 (d, J=14.7 Hz, 2H), 3.14 (m, 2H), 3.42 (t, J=5.1 Hz, 2H), 3.71 (m, 1H), 4.08 (t, J=9.3 Hz, 1H), 4.72 (m, 1H), 7.06 (t, J=8.7 Hz, 1H), 7.21 (m, 1H), 7.43 (dd, J=12.9 Hz, 2.4 Hz, 1H), 8.46 (t, J=5.4 Hz, 1H).

Intermediates for the synthesis of example 52 were prepared as follows.

I. N-[((5S)-3-{3-fluoro-4-[exo-(1R,5S)-3-thiabicyclo[3.1.0]hex-6-yl]phenyl}-2-oxo-1,3-oxazolidin-5-yl)methyl]cyclopropanecarboxamide

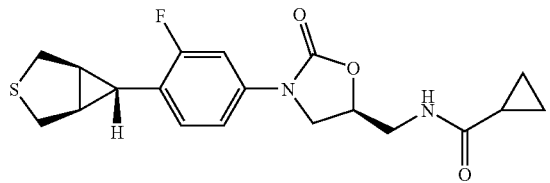

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (0.5 g, 1.23 mmol, 1 equiv.) in CH₂Cl₂ (10 mL) at 23° C., was added CF₃COOH (1.5 mL). After being stirred at 23° C. for 1.5 hour, the solvent was evaporated and the residue dissolved in CH₂Cl₂ (25 mL) and cooled to 0° C. DIEA (5 mL, 28.8 mmol, 23.4 equiv.) was added, followed by cyclopropanecarbonyl chloride (0.134 mL, 1.5 mmol, 1.2 equiv.). Then, the reaction mixture was stirred at 23° C. for 1.5 hours, diluted with CH₂Cl₂ (300 mL), washed with (NaHCO₃ aqueous, H₂O, brine), dried (Na₂SO₄), filtered and evaporated to dryness to provide the title compound which was used in the next step without further purification.

Example 53

N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide

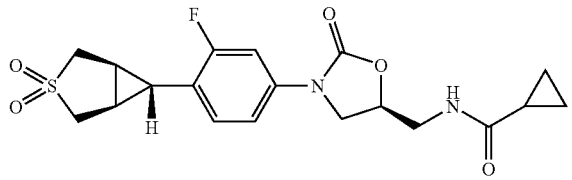

To a suspension of N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide (198 mg, 0.51 mmol, 1 equiv.) in THF (20 mL) and MeOH (4 mL) at 0° C. was added CH₃CO₃H (32% in AcOH, 0.32 mL, 1.52 mmol, 3.0 equiv.). The reaction mixture was stirred at 23° C. for 40 min, and then more CH₃CO₃H (32% in AcOH, 0.32 mL, 1.52 mmol, 3.0 equiv.) was added. After another 50 min, the reaction mixture was diluted with CHCl₃ (200 mL), washed (H₂O, brine), dried (Na₂SO₄), filtered and evaporated to dryness. The crude product was purified by chromatography on a silica gel column, eluting with a gradient increasing in polarity from 0 to 5% methanol in methylene chloride (containing 10% CH₃CN). Relevant fractions were combined to give the title compound.

Yield 0.191 g (92%). MS (m/z): [M+H]⁺=409. HPLC (SYMMETRY $C_{18}$ 3.5 µM, 4.6×30 mm column; gradient elution 2%-98% MeCN with 0.1% TFA over 5 min; 2 mL/min rate): retention time=1.97 min. ¹H NMR (300 MHz, DMSO-d₆): 0.63 (m, 4H), 1.58 (m, 1H), 2.07 (m, 2H), 2.32 (t, J=3.9 Hz, 1H), 2.98 (d, J=14.1 Hz, 2H), 3.42 (m, 2H), 3.58 (m, 2H), 3.72 (m, 1H), 4.09 (t, J=9.3 Hz, 1H), 4.72 (m, 1H), 7.12 (t, J=8.4 Hz, 1H), 7.20 (m, 1H), 7.45 (dd, J=12.9 Hz, 2.1 Hz, 1H), 8.46 (t, J=5.4 Hz, 1H).

Example 54

2,2-difluoro-N-[((5S)-3-{3-fluoro-4-[exo-(1R,5S)-3-oxido-3-thiabicyclo[3.1.0]-6-yl]phenyl}-2-oxo-1,3-oxazolidin-5-yl)methyl]propanamide

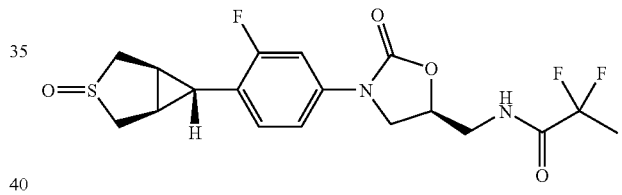

To a cold suspension of 2,2-difluoro-N-[((5S)-3-{3-fluoro-4-[exo-(1R,5S)-3-thiabicyclo[3.1.0]hex-6-yl]phenyl}-2-oxo-1,3-oxazolidin-5-yl)methyl]propanamide (400 mg, assumed 1.0 mmol, 1 equiv.) in MeOH (18 mL) at 0° C. was added NaIO₄ aqueous (225 mg, 1.06 mmol, 1.05 equiv. in H₂O 5 mL). Another batch of NaIO₄ (40 mg) was added during next 48 hours. Then, the reaction mixture was diluted with CH₂Cl₂ (300 mL), washed with (H₂O, brine), dried (Na₂SO₄), filtered and evaporated to dry. The crude product was purified by chromatography on a silica gel column, eluting with a gradient increasing in polarity from 0 to 5% methanol in methylene chloride (containing 10% CH₃CN). Relevant fractions were combined to give the title compound.

Yield (both isomers) 0.14 g (34%). MS (m/z): [M+H]⁺=417. HPLC (SYMMETRY $C_{18}$ 3.5 µM, 4.6µ30 mm column; gradient elution 2%-98% MeCN with 0.1% TFA over 5 min; 2 mL/min rate): retention time=1.87 min. High Rf ("anti") isomer: ¹H NMR (300 MHz, DMSO-d₆): 1.71 (t, J=19.5 Hz, 3H), 2.24 (m, 2H), 2.75 (t, J=3.9 Hz, 1H), 3.09 (d, J=14.7 Hz, 2H), 3.36 (m, 2H), 3.48 (t, J=5.7 Hz, 2H), 3.76 (m, 1H), 4.12 (t, J=9.0 Hz, 1H), 4.78 (m, 1H), 7.07 (t, J=8.7 Hz, 1H), 7.21 (m, 1H), 7.43 (dd, J=12.9 Hz, J=2.1 Hz, 1H), 9.03 (m, 1H). Low Rf ("syn") isomer: ¹H NMR (300 MHz, DMSO-d₆): 1.70 (t, J=19.8 Hz, 3H), 2.23 (t, J=3.9 Hz, 1H), 2.49 (m, 2H), 3.00 (m, 2H), 3.15 (m, 2H), 3.48 (t, J=5.1 Hz, 2H), 3.78 (m, 1H), 4.12 (t, J=9.0 Hz, 1H), 4.78 (m, 1H), 7.07 (t, J=8.4 Hz, 1H), 7.21 (m, 1H), 7.43 (dd, J=12.9 Hz, 2.7 Hz, 1H), 9.04 (m, 1H).

Intermediates for the synthesis of example 54 were prepared as follows.

I. 2,2-difluoro-N-[((5S)-3-{3-fluoro-4-[exo-(1R,5S)-3-thiabicyclo[3.1.0]hex-6-yl]phenyl}-2-oxo-1,3-oxazolidin-5-yl)methyl]propanamide

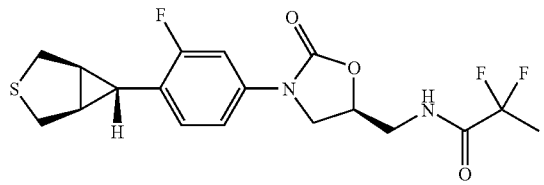

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (0.5 g, 1.23 mmol, 1 equiv.) in $CH_2Cl_2$ (10 mL) at 23° C., was added $CF_3COOH$ (1.5 mL). After being stirred at 23° C. for 1.5 hour, the solvent was evaporated and the residue dissolved in DMF (15 mL) and cooled to 0° C. Next, 2,2-difluoropropionic acid (270 mg, 2.45 mmol, 2.0 equiv.), HOBT (248 mg, 1.84 mmol, 1.5 equiv.), EDCI (408 mg, 2.13 mmol, 1.74 equiv.) and DIEA (4.26 mL, 24.5 mmol, 20 equiv.) were added. The reaction mixture was stirred at 23° C. for 17 hours, diluted with $CH_2Cl_2$ (300 mL), washed with ($NaHCO_3$ aqueous, $H_2O$, brine), dried ($Na_2SO_4$), filtered and evaporated to dryness to give the title compound which was used directly in the next step without further purification.

Example 55

2,2-difluoro-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]propanamide

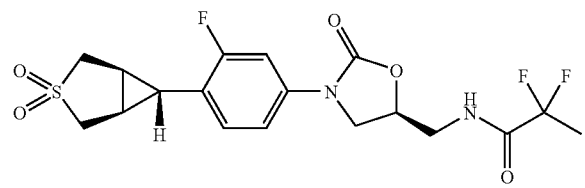

To a suspension of 2,2-difluoro-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide (60 mg, 0.14 mmol, 1 equiv.) in THF (8 mL) and MeOH (4 mL) at 0° C. was added $CH_3CO_3H$ (32% in AcOH, 0.32 mL, 1.52 mmol, 10.5 equiv.). Then, the reaction mixture was stirred at 23° C. for 90 min, the reaction mixture was diluted with $CHCl_3$ (200 mL), washed ($H_2O$, brine), dried ($Na_2SO_4$), filtered and evaporated to dry. The crude product was purified by chromatography on a silica gel column, eluting with a gradient increasing in polarity from 0 to 5% methanol in methylene chloride (containing 10% $CH_3CN$). Relevant fractions were combined to give the title compound.

Yield 0.05 g (82%). MS (m/z): $[M+Na]^+$=455. HPLC (SYMMETRY $C_{18}$ 3.5 μM, 4.6×30 mm column; gradient elution 2%-98% MeCN with 0.1% TFA over 5 min; 2 mL/min rate): retention time=2.11 min. $^1$H NMR (300 MHz, DMSO-$d_6$): 1.70 (t, J=19.5 Hz, 3H), 2.10 (m, 2H), 2.32 (t, J=4.2 Hz, 1H), 2.99 (d, J=15.1 Hz, 2H), 3.48 (t, J=5.4 Hz, 2H), 3.60 (m, 2H), 3.78 (m, 1H), 4.12 (t, J=9.0 Hz, 1H), 4.78 (m, 1H), 7.12 (t, J=8.7 Hz, 1H), 7.22 (m, 1H), 7.46 (dd, J=12.9 Hz, 1.8 Hz, 1H), 9.04 (m, 1H).

Example 56

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclobutanecarboxamide

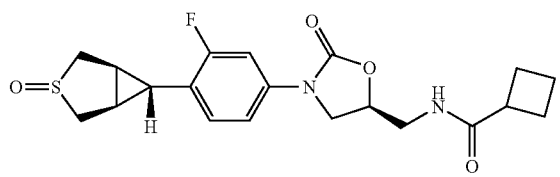

To a suspension of N-[((5S)-3-{3-fluoro-4-[exo-(1R,5S)-3-thiabicyclo[3.1.0]hex-6-yl]phenyl}-2-oxo-1,3-oxazolidin-5-yl)methyl]cyclobutanecarboxamide (1.23 mmol, 1 equiv.) in MeOH (18 mL) at 0° C. was added $NaIO_4$ aqueous (280 mg, 1.31 mmol, 1.05 equiv. in $H_2O$ 5 mL). Another batch of $NaIO_4$ (200 mg) was added during next 48 hours. Then, the reaction mixture was diluted with $CH_2Cl_2$ (300 mL), washed with ($H_2O$, brine), dried ($Na_2SO_4$), filtered and evaporated to dry. The crude product was purified by chromatography on a silica gel column, eluting with a gradient increasing in polarity from 0 to 5% methanol in methylene chloride (containing 10% $CH_3CN$). Relevant fractions were combined to give the title compound.

Yield (both isomers) 0.42 g (84%). MS (m/z): $[M+H]^+$=407. HPLC (SYMMETRY $C_{18}$ 3.5 μM, 4.6×30 mm column; gradient elution 2%-98% MeCN with 0.1% TFA over 5 min; 2 mL/min rate): retention time=1.80 min. High Rf ("anti") isomer: $^1$H NMR (300 MHz, DMSO-$d_6$): 1.69 (m, 1H), 1.70-1.95 (m, 5H), 2.11 (s, 2H), 2.74 (t, J=4.2 Hz, 1H), 3.00 (m, 1H), 3.09 (d, J=14.7 Hz, 2H), 3.32-3.44 (m, 4H), 3.72 (m, 1H), 4.08 (t, J=9.0 Hz, 1H), 4.72 (m, 1H), 7.07 (t, J=8.7 Hz, 1H), 7.21 (m, 1H), 7.43 (dd, J=12.9 Hz, J=2.1 Hz, 1H), 8.04 (t, J=6.0 Hz, 1H). Low Rf ("syn") isomer: $^1$H NMR (300 MHz, DMSO-$d_6$): 1.68 (m, 1H), 1.81-2.07 (m, 5H), 2.22 (t, J=4.2 Hz, 1H), 2.49 (m, 2H), 3.02 (m, 3H), 3.18 (m, 2H), 3.39 (m, 2H), 3.72 (m, 1H), 4.08 (t, J=9.0 Hz, 1H), 4.72 (m, 1H), 7.06 (t, J=8.4 Hz, 1H), 7.18 (m, 1H), 7.43 (dd, J=12.9 Hz, 2.4 Hz, 1H), 8.04 (t, J=5.7 Hz, 1H).

Intermediates for the synthesis of example 56 were prepared as follows.

I. N-[((5S)-3-{3-fluoro-4-[exo-(1R,5S)-3-thiabicyclo[3.1.0]hex-6-yl]phenyl}-2-oxo-1,3-oxazolidin-5-yl)methyl]cyclobutanecarboxamide

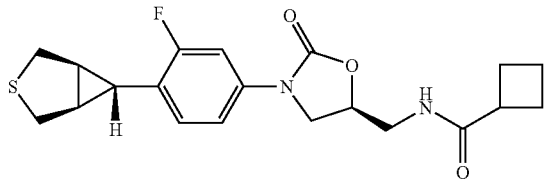

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (0.5 g, 1.23 mmol, 1 equiv.) in CH$_2$Cl$_2$ (10 mL) at 23° C., was added CF$_3$COOH (1.5 mL). After being stirred at 23° C. for 1.5 hour, the solvent was evaporated and the residue dissolved in DMF (15 mL) and cooled down to 0° C. Cyclobutanecarbonyl chloride (0.17 mL, 1.5 mmol, 1.2 equiv.) and DIEA (4.26 mL, 24.5 mmol, 20 equiv.) were then added. The reaction mixture was stirred at 23° C. for 1 hour, diluted with CH$_2$Cl$_2$ (300 mL), washed with (NaHCO$_3$ aqueous, H$_2$O, brine), dried (Na$_2$SO$_4$), filtered and evaporated to dryness to give the title compound which was used directly in the next step without further purification.

Example 57

N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclobutanecarboxamide

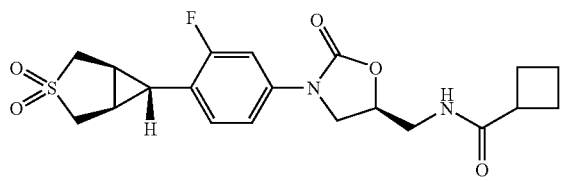

To a cold suspension of N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclobutanecarboxamide (0.25 g, 0.62 mmol, 1 equiv.) in THF (10 mL) and MeOH (5 mL) at 0° C. was added CH$_3$CO$_3$H (32% in AcOH, 0.80 mL, 3.8 mmol, 6.1 equiv.). Then, the reaction mixture was stirred at 23° C. for 90 min, the reaction mixture was diluted with CHCl$_3$ (200 mL), washed (H$_2$O, brine), dried (Na$_2$SO$_4$), filtered and evaporated to dryness. The crude product was purified by chromatography on a silica gel column, eluting with a gradient increasing in polarity from 0 to 5% methanol in methylene chloride (containing 10% CH$_3$CN). Relevant fractions were combined to give the title compound.

Yield 0.226 g (86%). MS (m/z): [M+H]$^+$=423. HPLC (SYMMETRY C$_{18}$ 3.5 μM, 4.6×30 mm column; gradient elution 2%-98% MeCN with 0.1% TFA over 5 min; 2 mL/min rate): retention time=2.11 min. $^1$H NMR (300 MHz, DMSO-d$_6$): 1.68 9 m, 1H), 1.69-1.95 (m, 5H), 2.04 (m, 2H), 2.32 (t, J=4.5 Hz, 1H), 3.02 (m, 3H), 3.40 (m, 2H), 3.60 (m, 2H), 3.72 (m, 1H), 4.08 (t, J=9.0 Hz, 1H), 4.72 (m, 1H), 7.11 (t, J=8.4 Hz, 1H), 7.22 (m, 1H), 7.46 (dd, J=12.9 Hz, 2.1 Hz, 1H), 8.04 (t, J=6.0 Hz, 1H).

Example 58

N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]propanamide

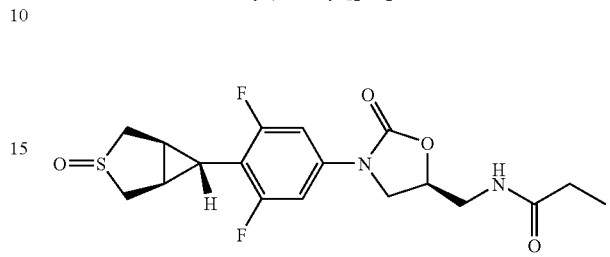

A solution of sodium periodate (0.64 g, 3.0 mmol) in water (10 mL) was added to a suspension of N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]propanamide (1.0 g, 2.61 mmol) in methanol (35 mL) and stirred at 4° C. for 48 h. The resulting suspension was filtered with the aid of chloroform and the filtrate concentrated. The resulting solution was diluted with water and extracted with chloroform. The organic phase was dried (MgSO$_4$) filtered and concentrated. Purification by column chromatography (0-5% methanol-10% acetonitrile-dichloromethane) provided the title compound as a separable mixture of sulfoxide diastereomers (ca. 1:1 ratio).

Yield (total for both isomers) 0.65 g (63%). MS (m/z): [M+Na]=421 Low ("syn") Rf isomer: $^1$H NMR (300 MHz, d$_6$-DMSO): 0.93 (t, J=9 Hz, 3H), 1.99-2.11 (m, 3H), 2.58 (s, 2H), 3.02-3.17 (m, 4H), 3.37-3.39 (m, 2H), 3.67-3.72 (m, 1H), 4.07 (t, J=9 Hz, 1H), 4.70-4.75 (m, 1H), 7.25 (d, J=12 Hz, 2H), 8.15 (t, 1H). High ("anti") Rf isomer: $^1$H NMR (300 MHz, d$_6$-DMSO): 0.93 (t, J=9 Hz, 3H), 2.07 (q, J=9 Hz, 2H), 2.36 (m, 2H), 2.52-2.55 (m, 1H), 3.11 (d, J=15 Hz, 2H), 3.36-3.40 (m, 2H), 3.67-3.72 (m, 1H), 4.07 (t, J=9 Hz, 1H), 4.70-4.75 (m, 1H), 7.25 (d, J=12 Hz, 2H), 8.15 (t, J=6 Hz, 1H).

Intermediates for the synthesis of example 58 were prepared as follows.

I. 4-Amino-2,6-difluoro-benzaldehyde

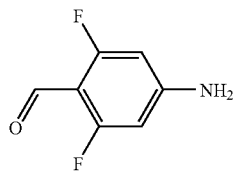

A solution of 3,5-difluoroaniline (12.9 g, 0.1 mol) in anhydrous THF (400 mL) was cooled at −78° C. and treated with nbutyllithium (2.5 M in hexane, 84 mL, 0.21 mol, 2.1 equv.) dropwise over 25 min. After stirring at −78° C. for 30 min, trimethylsilyl chloride (1.0 M in THF, 210 mL, 0.21 mol, 2.1 equiv.) was added dropwise over 30 min. The temperature was allowed to rise to 23° C. and stirred overnight. After re-cooling to −78° C., additional n-butyl-lithium (2.5 M in hexane, 44 mL, 0.11 mol, 1.1 equiv.) was added dropwise over 20 min, and the reaction mixture was stirred at that temperature for 5 hours to form the anion. Then dimethylformamide (11.6 ml, 0.15 mol, 1.5 equiv.) was added dropwise over 20 min. The temperature was allowed to rise to 23° C. and stirred overnight. The mixture was cooled in an ice-bah and acidified to pH=1 by slow addition of aqueous HCl (1.0 M, 220 mL, 0.22 mol). After stirring 15 min, the mixture was extracted with ethyl acetate (3×200 mL). The combined organic layers were washed (brine), dried ($Na_2SO_4$), filtered and evaporated to dry. The residue was purified by chromatography on a silica gel column, eluting with a gradient increasing in polarity from 0 to 50% ethyl acetate in hexane. Relevant fractions were combined to give the title compound.

Yield 8.5 g (55%). MS (m/z): $[M+Na]^+$=170. HPLC (SYMMETRY $C_{18}$ 3.5 μM, 4.6×30 mm column; gradient elution 2%-98% MeCN with 0.1% TFA over 5 min; 2 mL/min rate): retention time=1.58 min. $^1$H NMR (300 MHz, DMSO-$d_6$): 6.19 (d, J=12.3 Hz, 2H), 6.93 (bs, 2H), 9.83 (s, 1H).

II. Ethyl (2E)-3-[4-amino-2,6-difluorophenyl]acrylate

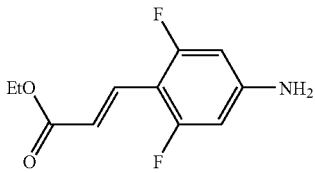

To a solid mixture of 4-amino-2,6-difluoro-benzaldehyde (6.5 g, 41.4 mmol, 1.0 equiv.) and (carbethoxymethylene)triphenylphosphorane (18.75 g, 53.8 mmol, 1.3 equiv.) at 23° C. was added ethanol (97 mL). After stirring for 25 min at 23° C., the reaction mixture was concentrated, pre-absorbed with silica gel and purified by flash column chromatography eluting with a gradient increasing in polarity from 0 to 30% ethyl acetate in hexane. Relevant fractions were combined to give the desired compound.

Yield 9.0 g (96%). HPLC (SYMMETRY $C_{18}$ 3.5 μM, 4.6×30 mm column; gradient elution 2%-98% MeCN with 0.1% TFA over 5 min; 2 mL/min rate): retention time=2.74 min. $^1$H NMR (300 MHz, CDCl$_3$): 1.32 (t, J=7.2 Hz, 3H), 4.14 (bs, 2H), 4.24 (q, J=7.2 Hz, 2H), 6.19 (d, J=10.8 Hz, 2H), 6.50 (d, J=16.2 Hz, 1H), 7.68 (d, J=16.2 Hz, 1H).

III. Ethyl (2E)-3-(4-{[(benzylox)carbonyl]amino}-2,6-difluorophenyl)acrylate

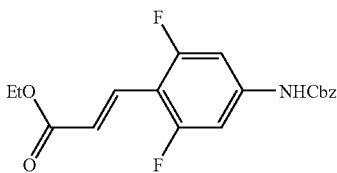

The compound ethyl (2E)-3-[4-amino-2,6-difluorophenyl]acrylate (1.7 g, 7.5 mmol) was dissolved in $CH_2Cl_2$ (100 mL) and pyridine (1.2 mL, 14.8 mmol, 2.0 equiv) and the solution was cooled in an ice-bath. The solution was then treated with benzyl chloroformate (1.3 mL, 9.1 mmol, 1.2 equiv.) dropwise and the solution was stirred at 23° C. for 17 hours. The reaction mixture was then diluted with more $CH_2Cl_2$ and the organic phase was washed (water, brine), dried ($Na_2SO_4$), filtered and evaporated to dryness. The residue was purified by chromatography on a silica gel column, eluting with a gradient increasing in polarity from 0 to 20% ethyl acetate in hexane. Relevant fractions were combined to give the title compound.

Yield 2.59 g (96%). HPLC (SYMMETRY $C_{18}$ 3.5 μM, 4.6×30 mm column; gradient elution 2%-98% MeCN with 0.1% TFA over 5 min; 2 mL/min rate): retention time=3.55 min. $^1$H NMR (300 MHz, CDCl$_3$): 1.33 (t, J=7.2 Hz, 3H), 4.26 (q, J=7.2 Hz, 2H), 5.21 (s, 2H), 6.62 (d, J=16.5 Hz, 1H), 6.90 (bs, 1H), 7.07 (d, J=10.8 Hz, 2H), 7.40 (bs, 5H), 7.70 (d, J=16.5 Hz, 1H).

IV. Benzyl 2,6-difluoro-4-[(1E)-3-hydroxyprop-1-enyl]phenylcarbamate

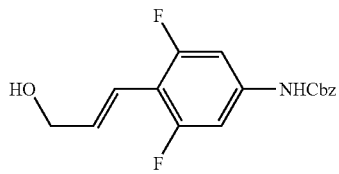

A solution of diisobutylaluminum hydride (8.3 mL, of 1.0 M hexane solution, 8.3 mmol, 3.0 equiv.) was added to a cooled (−78° C.) solution of ethyl (2E)-3-(4-{[(benzyloxy)carbonyl]amino}-2,6-difluorophenyl)acrylate (0.97 g, 2.69 mmol) in THF (20 mL) over 10 min and the cooling bath allowed to warm to −50° C. After stirring at −50° C. for 1 h, the reaction mixture was quenched by saturated NH$_4$Cl aqueous and then treated with aqueous citric acid (100 mL of a 10% solution). The resulting mixture was stirred for 15 min and then extracted with ethyl acetate (3×70 mL). Combined organic layers were washed (brine), dried (Na$_2$SO$_4$), filtered and evaporated to dryness. The residue was purified by chromatography on a silica gel column, eluting with a gradient increasing in polarity from 0 to 30% ethyl acetate in hexane. Relevant fractions were combined to give the title compound.

Yield 0.69 g (81%). HPLC (SYMMETRY $C_{18}$ 3.5 μM, 4.6×30 mm column; gradient elution 2%-98% MeCN with 0.1% TFA over 5 min; 2 mL/min rate): retention time=2.86 min. $^1$H NMR (300 MHz, CDCl$_3$): 1.54 (t, J=5.4 Hz, 1H), 4.34 (bs, 2H), 5.21 (s, 2H), 6.58 (m, 2H), 6.77 (bs, 1H), 7.00 (d, J=10.2 Hz, 2H), 7.39 (bs, 5H).

V. (2E)-3-{2,6-difluoro-4-[(benzyloxycarbonyl)amino]phenyl}prop-2-enyl diazoacetate

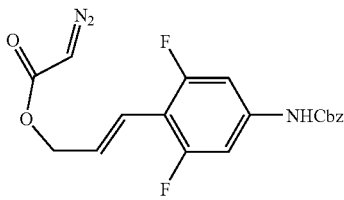

A solution of glyoxylic acid p-toluenesulfonylhydrazone (10.6 g, 43.8 mmol) and 1-chloro-N,N,2-trimethyl-1-propenylamine (7.36 mL, 55.3 mmol) in dichloromethane (300 mL) were stirred at room temperature for 2 h. The solution was cooled to 0° C., followed by the addition of allylic alcohol (10 g, 31.3 mmol) and N,N-dimethylaniline (5.55 mL, 43.8 mmol). After 45 min, triethylamine (21.7 mL, 156.5 mmol) was added and the solution was stirred at 0° C. for 30 min and room temperature for 30 min. The solution was then washed with saturated NaHCO$_3$, concentrated, diluted with water and extracted with diethyl ether. The organic phase was washed with saturated NaHCO$_3$, brine and dried (MgSO$_4$). The solution was filtered and concentrated under vacuum and the residue purified by column chromatography (0-25% ethyl acetate-hexanes) to provide the title compound.

Yield 9.7 g (80%). $^1$H NMR (300 MHz, CDCl$_3$): 4.79 (d, J=5 Hz, 2H), 4.8 (s, 1H), 5.17 (s, 2H), 6.44-6.61 (m, 2H), 6.96 (s, 1H), 7.00 (dd, J=12, 5 Hz, 2H) 7.31-7.36 (m, 5H).

VI. (racemic) Benzyl 3,5-difluoro-4-[(1S,5R,6R)-2-oxo-3-oxabicyclo[3.1.0]hex-6-yl]phenylcarbamate

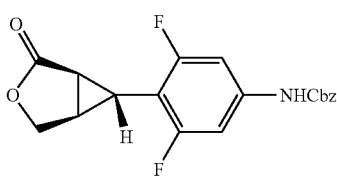

(±)

A solution of (2E)-3-{2,6-difluoro-4-[(benzyloxycarbonyl)amino]phenyl}prop-2-enyl diazoacetate (9.7 g, 25.04 mmol) in 100 mL of 1,2-dichloroethane was added dropwise over 14 h to a refluxing solution of bis-(N-t-butylsalicylaldiminato)copper(II) (0.52 g, 1.25 mmol, prepared as described by R. G. Charles, *J. Org. Chem.* 1957, 22, 677) in toluene (1000 mL). After the addition was complete, the reaction mixture was heated for another hour at reflux, then cooled, filtered and concentrated. The crude oil was purified by column chromatography (0-1% methanol-dichoromethane) to provide the title compound as a racemate.

Yield 5.5 g (61%). $^1$H NMR (300 MHz, CDCl$_3$): 2.09-2.12 (m, 1H), 2.39-2.42 (m, 1H), 2.61-2.65 (m, 1H), 4.22 (m, 2H), 5.05 (s, 2H), 6.68 (s, 1H), 6.88 (dd, J=15, 6 Hz, 2H) 7.21-7.25 (m, 5H).

VII. Benzyl 4-[exo-(2R,3S)-2,3-bis(hydroxymethyl)cyclopropyl]-3,5-difluorophenylcarbamate

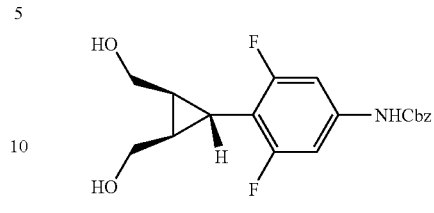

Lithium borohydride (2.97 g, 136.36 mmol) was added to a solution of racemic benzyl 3,5-difluoro-4-[(1S,5R,6R)-2-oxo-3-oxabicyclo[3.1.0]hex-6-yl]phenylcarbamate (10 g, 27.83 mmol) in THF (200 mL) cooled to 0° C. The reaction mixture was warmed to room temperature and stirred for 16 h. The reaction mixture was then cooled to 0° C., and treated with 10% aqueous citric acid solution and extraction with ethyl acetate. The organic layer was washed with brine, dried (MgSO$_4$) and concentrated. Purification by column chromatography (0-3.5% methanol-dichoromethane) provided the title compound.

Yield 8.7 g (86%). $^1$H NMR (300 MHz, CDCl$_3$): 1.57-1.61 (m, 2H), 1.80-1.85 (m, 1H), 3.41-3.49 (m, 2H), 4.20-4.26 (m, 2H), 5.16 (s, 2H), 6.67 (s, 1H), 6.91 (d, J=9 Hz, 2H) 7.34-7.38 (m, 5H).

VIII. Benzyl 3,5-difluoro-4-[exo-(1R,5S)-3-thiabicyclo[3.1.0]hex-6-yl]phenylcarbamate

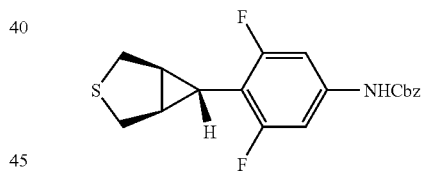

Methanesulfonic anhydride (2.18 g, 12.52 mmol) was added to a cooled (0° C.) solution of benzyl 4-[exo-(2R,3S)-2,3-bis(hydroxymethyl)cyclopropyl]-3,5-difluorophenylcarbamate (1.5 g, 4.17 mmol) in dichloromethane (42 mL) and triethylamine (2.32 mL, 16.68 mmol). After stirring at 0° C. for 30 min, the solution was diluted with dichloromethane and washed with saturated NaHCO$_3$, brine, dried (MgSO$_4$), filtered, and concentrated to provide the bis-mesylate intermediate. This residue (2.17 g, 4.17 mmol) was dissolved in DMSO (8.3 mL) and treated with sodium sulfide (0.98 g, 12.51 mmol) and the reaction mixture was stirred at room temperature for 14 h. The resulting suspension was then diluted with H$_2$O and extracted with diethyl ether. The organic extracts were dried (MgSO$_4$), filtered and concentrated to provide the title compound as a white solid that was used directly in the next reaction.

Yield 1.3 g (86%).

IX. Tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate

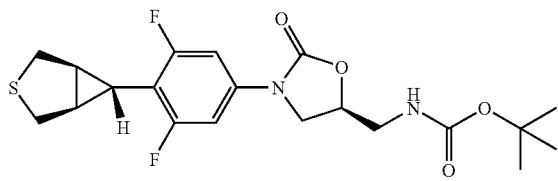

Lithium tert-butoxide solution (8.64 mL of a 1.0 M THF solution, 8.64 mmol) was added to a cooled (0° C.) solution of benzyl 3,5-difluoro-4-[exo-(1R,5S)-3-thiabicyclo[3.1.0]hex-6-yl]phenylcarbamate (1.3 g, 3.6 mmol) and (S)-(3-chloro-2-hydroxy-propyl)-carbamic acid tert-butyl ester (0.95 g, 4.53 mmol) in DMF (2.4 mL). The solution was allowed to warm to room temperature and stirred for 60 h. Saturated aqueous ammonium chloride, H$_2$O and brine were added to the reaction mixture. The solution was extracted with dichloromethane and the combined organic phases were dried (MgSO$_4$), filtered and concentrated. The crude residue was purified by column chromatography (0-40% ethyl acetate-hexanes) to provide the title compound.

Yield 1.1 g (73%). $^1$H NMR (300 MHz, CDCl$_3$): 1.39 (s, 9H), 2.08 (m, 2H), 2.20-2.23 (m, 1H), 3.10-3.19 (m, 4H), 3.47-3.49 (m, 2H), 3.74-3.79 (m, 1H), 3.95 (t, J=9 Hz, 1H), 4.72 (m, 1H), 4.92 (m, 1H), 7.05 (d, J=12 Hz, 2H).

X. N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]propanamide

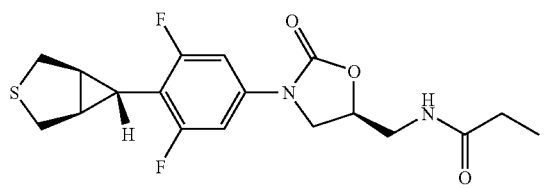

Trifluoroacetic acid (2.5 mL) was added to a solution of tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate (1.0 g, 2.34 mmol) in dichloroethane (25 mL). After stirring at room temperature for an hour, the solution was concentrated and dissolved in pyridine (0.83 mL, 10.28 mmol) and dichloromethane (25 mL). Propionic anhydride (0.66 mL, 5.14 mmol) was added to the solution and stirred at room temperature for 18 h. The solution was diluted with dichloromethane, washed with 0.1 N HCl, saturated NaHCO$_3$, and brine. The organic phase was dried (MgSO$_4$), filtered and concentrated to obtain the title compound which was used directly in the next reaction.

Yield 1.0 g (99%).

Example 59

N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide

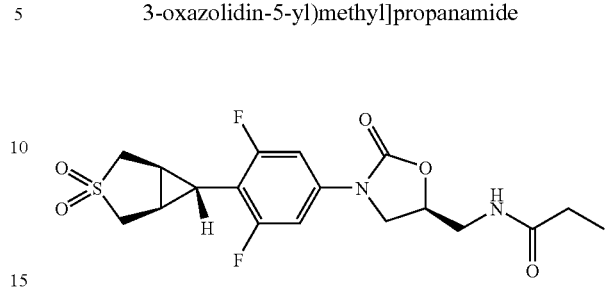

A dioxane solution of HCl (2 mL of a 4.0 M solution) was added to solid tert-butyl ((5S)-3-{3,5-difluoro-4-[exo-(1R,5S)-3,3-dioxido-thiabicyclo[3.1.0]hex-6-yl]phenyl}-2-oxo-1,3-oxazolidin-5-yl)methylcarbamate (0.19 g, 0.42 mmol). After stirring at room temperature for 4 hours, the solution was concentrated and the residue dissolved in DMF (2 mL) and pyridine (0.095 mL, 1.17 mmol) and the solution cooled at 0° C. Propionic anhydride (0.065 mL, 0.51 mmol) was added to the solution and the mixture allowed to warm to room temperature and stirred for 2 h. The solution was diluted with ethyl acetate and 2.5% aqueous NaHCO$_3$, the layers separated and the aqueous phase extracted with more ethyl acetate. The combined organic phases were washed with brine and dried (MgSO$_4$), filtered and concentrated. The crude product was purified by column chromatography (0-2% methanol in dichloromethane) to provide the title compound.

Yield 0.14 g (86%) MS (m/z): [M+H]$^+$=415.5 $^1$H NMR (300 MHz, DMSO-d6) 0.94 (t, J=8 Hz, 3H), 2.08 (q, J=8 Hz, 2H), 2.18 (m, 3H), 3.02 (d, J=13 Hz, 2H), 3.42 (m, 2H), 3.60 (m, 2H), 3.70 (m, 1H), 4.09 (t, J=9 Hz, 1H), 4.74 (m, 1H), 7.28 (d, J=12 Hz, 2H), 8.17 (t, J=6 Hz, 1H), Intermediates for the synthesis of example 59 were prepared as follows.

I. Tert-butyl ((5S)-3-{3,5-difluoro-4-[exo-(1R,5S)-3,3-dioxido-thiabicyclo[3.1.0]hex-6-yl]phenyl}-2-oxo-1,3-oxazolidin-5-yl)methylcarbamate

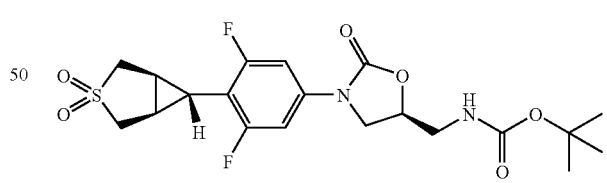

To a solution of tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate (0.19 g, 0.43 mmol, 1 equiv.) in THF (10 mL) was added CH$_3$CO$_3$H (32% in AcOH, 0.27 mL, 1.3 mmol, 3.0 equiv.). The reaction mixture was stirred at 23° C. for 90 min and then diluted with aqueous Na$_2$S$_2$O$_3$ and extracted thrice with ethyl acetate. The combined organic extracts were washed with sat NaHCO$_3$, brine and dried (MgSO$_4$), filtered and evaporated to dryness. The crude product was passed through a short pad of silica with the aid of ethyl acetate and the filtrate concentrated to provide the title compound.

Yield 0.19 g (95%) $^1$H NMR (300 MHz, CDCl$_3$): 1.40 (s, 9H), 1.45 (m, 1H), 2.27 (m, 2H), 3.10 (d, J=14 Hz, 2H), 3.51-3.60 (m, 4H), 3.84 (m, 1H), 3.98 (t, J=9 Hz, 1H)m, 4.76 (m, 1H), 4.94 (br t, 1H), 7.13 (d, J=14 Hz, 2H)

Example 60

2,2-difluoro-N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide

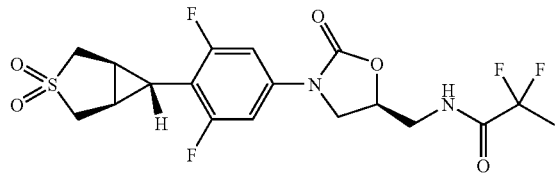

Peracetic acid (0.075 mL, 0.36 mmol) was added to a solution of 2,2-difluoro-N-[((5S)-3-{3,5-difluoro-4-[exo-(1R,5S)-3-thiabicyclo[3.1.0]hex-6-yl]phenyl}-1,3-oxazolidin-5-yl)methyl]propanamide (50 mg, 0.12 mmol) in THF (1.0 mL) and was stirred at 4° C. for 3 h. Saturated Na$_2$S$_2$O$_3$ was added to the solution and the THF was removed on a rotary evaporator. The solution was diluted with water and extracted with ethyl acetate. The organic phase was washed with brine, dried (MgSO$_4$), filtered, and concentrated. Preparative TLC (5% methanol/10% acetonitrile/dichloromethane) provided the title compound.

Yield 30 mg (56%). MS (m/z): [M+Na]$^+$=473 $^1$H NMR (300 MHz, CDCl$_3$): 1.76 (t, J=18 Hz, 3H), 2.02 (t J=6 Hz, 1H), 2.22-2.25 (m, 2H), 3.07 (d, J=15 Hz, 2H), 3.51-3.84 (m, 5H), 4.03 (t, J=9 Hz, 1H), 4.79-4.83 (m, 1H), 6.81 (bs, 1H), 7.09 (d, J=12 Hz, 2H).

Intermediates for the synthesis of example 60 were prepared as follows.

I. 2,2-difluoro-N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]propanamide

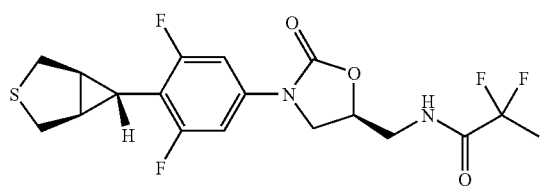

Trifluoroacetic acid (1.5 mL) was added to a solution of tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate (0.242 g, 0.57 mmol) in dichloroethane (10 mL). After stirring at room temperature for an hour, the solution was concentrated and dissolved in DMF (6 mL). To this solution was added 2,2-difluoropropanoic acid (94 mg, 0.85 mmol), N,N-diisopropylethylamine (0.4 mL, 2.28 mmol), 1-hydroxybenzotriazole (0.11 mg, 0.85 mmol), and 1-(3-dimethylaminopropyl)-3-ethylcarbodiimide hydrochloride (0.16 g, 0.85 mmol) and the mixture stirred at room temperature for 24 h. The solution was then diluted with ethyl acetate, washed with water, saturated NaHCO$_3$, and brine. The organic phase was dried (MgSO$_4$), filtered and concentrated. The title compound was obtained by preparative TLC (5% methanol/dichloromethane).

Yield 60 mg (25%). $^1$H NMR (300 MHz, CDCl$_3$): 1.75 (t, J=18 Hz, 3H), 2.08 (s, 2H), 2.22 (t, J=6 Hz, 1H), 3.06-3.17 (m, 4H), 3.59-3.81(m, 3H), 4.02 (t, J=9 Hz, 1H), 4.77-4.81 (m, 1H), 6.96-7.06 (m, 3H).

Example 61

N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide

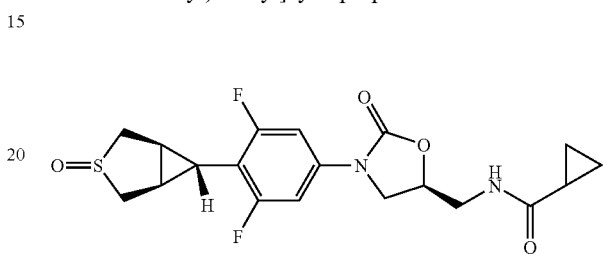

A solution of sodium periodate (0.27 g, 1.2 mmol) in water (3.0 mL) was added to a suspension of N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]cyclopropanecarboxamide (0.30 g, 0.75 mmol) in methanol (9 mL) and stirred at 4° C. for 24 h. The resulting suspension was filtered with the aid of chloroform and the filtrate concentrated. The resulting solution was diluted with water and extracted with chloroform. The organic phase was dried (MgSO$_4$) filtered and concentrated. Purification by column chromatography (0-4% methanol-10% acetonitrile-dichloromethane) provided the title compound as a separable mixture of sulfoxide diastereomers (ca. 1:1 ratio).

Yield (total for both isomers) 0.152 g (49%). MS (m/z): [M+H]=411 Low Rf ("syn") isomer: $^1$H NMR (300 MHz, CDCl$_3$): 0.73-0.96 (m, 4H), 1.32-1.37 (m, 1H), 2.35 (s, 1H), 2.60-2.68 (m, 2H), 3.13-3.29 (m, 4H), 3.64-3.75 (m, 3H), 3.95 (t, J=9 Hz, 1H), 4.76 (m, 1H), 6.07-6.09 (m, 1H). 7.06 (dd, J=3, 9 Hz, 2H).

High Rf ("anti") isomer: $^1$H NMR (300 MHz, CDCl$_3$): 0.71-0.94 (m, 4H), 1.36 (m, 1H), 2.35 (s, 2H), 2.62 (t, J=3 Hz, 1H), 3.30 (s, 4H), 3.64-3.74 (m, 3H), 3.95 (t, J=9 Hz, 1H), 4.71-4.78 (m, 1H), 6.13 (bs, 1H). 7.05 (d, J=12 Hz, 2H).

Intermediates for the preparation of example 61 were synthesized as follows.

I. N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]cyclopropanecarboxamide

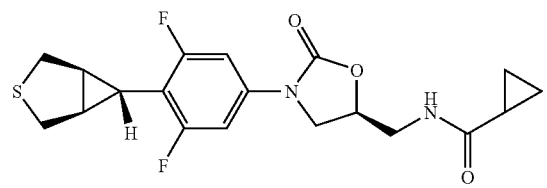

Trifluoroacetic acid (1.5 mL) was added to a solution of tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate (0.32 g, 0.75 mmol) in dichloroethane (13 mL). After stirring at room temperature for an hour, the solution was concentrated and dissolved in dichloromethane (15 mL). The solution was cooled to 0° C. and treated with triethylamine (0.52 mL, 3.75 mmol) and cyclopropyl carbonyl chloride (0.082 mL, 0.9 mmol). After stirring at 0° C. for 60 min, the solution was diluted with dichloromethane, washed with saturated NaHCO$_3$, brine, and dried (MgSO$_4$), filtered and concentrated to obtain the title compound that was used directly in the next reaction.

Yield 0.30 g (>95%).

Example 62

N-1((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide

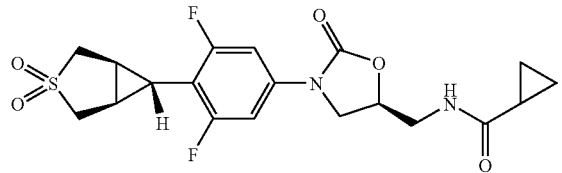

Peracetic acid (0.16 mL, 0.73 mmol) was added to a solution of N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide (0.10 g, 0.24 mmol) in THF (2.4 mL) and was stirred at 4° C. for 2 h. Saturated Na$_2$S$_2$O$_3$ was added to the solution, the THF was removed in vacuo and the solution diluted with water and extracted with ethyl acetate. The organic phase was washed with brine, dried (MgSO$_4$), filtered and concentrated. Preparative TLC (5% methanol/dichloromethane) provided the title compound.

Yield 98 mg (96%). MS (m/z): [M+Na]=449 $^1$H NMR (300 MHz, CDCl$_3$): 0.70-0.95 (m, 4H), 1.34-1.40 (m, 1H), 2.01 (t, J=6 Hz, 1H), 2.21-2.24 (m, 2H), 3.07 (d, J=12 Hz, 2H), 3.53-3.58 (m, 2H), 3.64-3.71 (m, 2H), 3.73-3.79 (m, 1H), 3.95 (t, J=9 Hz, 1H), 4.72-4.79 (m, 1H), 6.24 (bs, 1H), 7.09 (d, J=9 Hz, 2H).

Example 63 exo-(1R,5S)-6-(4-{(5S)-5-[(propanoylamino)methyl]-2-oxo-1,3-oxazolidin-3-yl}-2,6-difluorophenyl)-3-azabicyclo[3.1.0]hexane-3-carboxamide

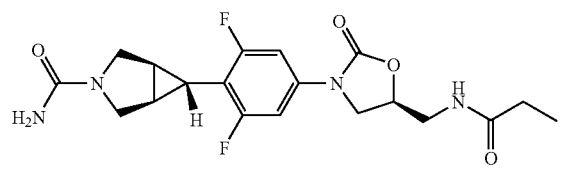

Trimethylsilyl isocyanate (0.26 mL, 1.64 mmol) was added to a solution of N-[((5S)-3-{4-[exo-(1R,5S)-3-azabicyclo[3.1.0]hex-6-yl]-3,5-difluorophenyl}-2-oxo-1,3-oxazolidin-5-yl)methyl]propanamide (0.3 g, 0.82 mmol) in dichloromethane (8 mL) and triethylamine (0.17 mL, 1.23 mmol) and stirred at room temperature for 16 h. The reaction mixture was diluted with dichloromethane and washed with 2.5% NaHCO$_3$ and brine. The organic phase was dried (MgSO$_4$) filtered and concentrated. Purification by preparative TLC (5% methanol/10% acetonitrile/dichloromethane) provided the title compound.

Yield 0.10 g (30%). MS (m/z): [M+H]=409 $^1$H NMR (300 MHz, d$_6$-DMSO): 0.93 (t, J=9 Hz, 3H), 1.48 (t, J=3 Hz, 1H), 2.03-2.11 (m, 4H), 3.29-3.39 (m, 4H), 3.59 (d, J=12 Hz, 2H), 3.66-3.72 (m, 1H), 4.07 (t, J=9 Hz, 1H), 4.70-4.75 (m, 1H), 5.79 (s, 2H), 7.24 (d, J=12 Hz, 2H), 8.17 (t, J=6Hz, 1H).

Intermediates for the synthesis of example 63 were prepared as follows.

I. Benzyl 3,5-difluoro-4-[exo-(1R,5S)-3-(4-methoxybenzyl)-3-azabicyclo[3.1.0]hex-6-yl]phenylcarbamate

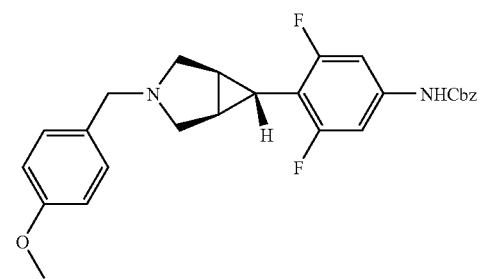

Benzyl 4-[exo-(2R,3S)-2,3-bis(methanesulfonyloxymethyl)cyclopropyl]-3,5-difluorophenylcarbamate (5 g, 9.74 mmol) was dissolved in p-methoxybenzyl amine (19 mL, 146.1 mmol) and stirred at room temperature for 16 h. The reaction mixture was diluted with ethyl acetate, washed with 0.1N HCl, dil. NaHCO$_3$ and brine. The organic extracts were dried (MgSO$_4$), filtered and concentrated. The title compound was isolated by column chromatography (0-50% ethyl acetate/hexanes/0.1% triethylamine).

Yield 3.7 g (82%). MS (m/z): [M+H]=465 $^1$H NMR (300 MHz, d$_6$-DMSO): 1.84 (s, 2H), 2.10 (s, 1H), 2.36 (d, J=9 Hz, 2H), 2.97 (d, J=9 Hz, 2H), 3.52 (s, 2H), 3.72 (s, 3H), 5.13 (s, 2H), 6.86 (d, J=9 Hz, 2H), 7.07 (d, J=9 Hz, 2H), 7.17 (d, J=9 Hz, 2H), 7.35-7.40 (m, 5H), 10.09 (s, 1H).

II. Tert-butyl ((5S)-3-{3,5-difluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate

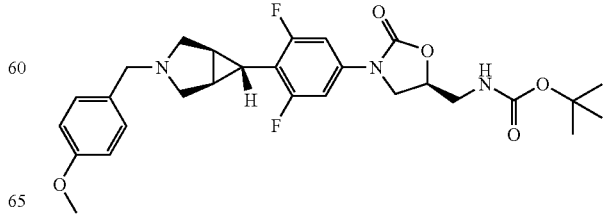

Lithium tert-butoxide solution (13.94 mL of a 1.0 M THF solution, 13.94 mmol) was added to a cooled (0° C.) solution of benzyl 3,5-difluoro-4-[exo-(1R,5S)-3-(4-methoxybenzyl)-3-azabicyclo[3.1.0]hex-6-yl]phenylcarbamate (2.7 g, 5.81 mmol) and (S)-(3-chloro-2-hydroxy-propyl)-carbamic acid tert-butyl ester (1.54 g, 7.32 mmol) in DMF (3.9 mL). The solution was allowed to warm to room temperature and stirred for 16 h. Saturated aqueous ammonium chloride, $H_2O$ and brine were added to the reaction mixture. The solution was extracted with dichloromethane and the combined organic phases were dried ($MgSO_4$), filtered and concentrated. The crude residue was purified by column chromatography (0-50% ethyl acetate/hexanes/0.1% triethylamine) to provide the title compound.

Yield 2.4 g (78%). MS (m/z): [M+H]=530 $^1$H NMR (300 MHz, CDCl$_3$): 1.37 (s, 9H), 1.98-2.15 (m, 3H), 3.48 (s, 2H), 3.75-4.01 (m, 10H), 4.54 (t, J=6 Hz, 1H), 4.69-4.76 (m, 1H), 4.92 (t, J=6 Hz, 1H), 6.86 (d, J=9 Hz, 2H), 7.06 (d, J=9 Hz, 2H), 7.29 (d, J=9 Hz, 2H).

III. N-[((5S)-3-{3,5-difluoro-4-[exo-(1R,5S)-3-(4-methoxybenzyl)-3-azabicyclo[3.1.0]hex-6-yl]phenyl}-2-oxo-1,3-oxazolidin-5-yl)methyl]propanamide

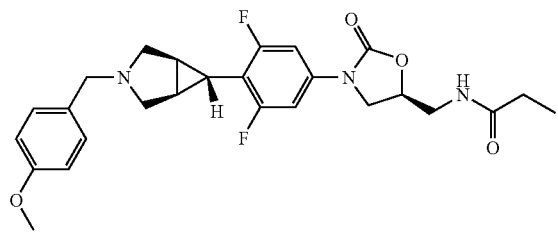

Hydrochloric acid (30 mL of a 4.0 M solution in dioxane) was added to a solution of tert-butyl ((5S)-3-{3,5-difluoro-4-[exo-(1R,5S)-3-(4-methoxyphenyl)-3-azabicyclo[3.1.0]hex-6-yl]phenyl}-2-oxo-1,3-oxazolidin-5-yl)methylcarbamate (2.4 g, 4.57 mmol) in dioxane (25 mL). After stirring at room temperature for 90 min, the solution was concentrated and the residue dissolved in pyridine (1.5 mL, 18.3 mmol) and dichloromethane (50 mL). Propionic anhydride (1.18 mL, 9.14 mmol) was added to the solution and mixture stirred at room temperature for 60 h. The reaction mixture was then diluted with dichloromethane and washed with water and brine. The organic phase was dried ($MgSO_4$), filtered and concentrated. The title compound was isolated by column chromatography (0-5% MeOH/dicholromethane/ 0.1% triethylamine).

Yield 1.62 g (74%). MS (m/z): [M+H]=486 $^1$H NMR (300 MHz, CDCl$_3$): 1.10 (t, J=9 Hz, 3H), 1.89 (s, 2H), 2.17-2.28 (m, 3H), 3.52 (d, J=9Hz, 2H), 3.16 (d, J=9 Hz 2H), 3.60-3.78 (m, 8H), 3.94 (t, J=9 Hz, 1H), 4.71-4.76 (m, 1H), 6.37 (t, J=6 Hz, 1H), 6.83 (d, J=9 Hz, 2H), 7.08 (d, J=9 Hz, 2H), 7.21 (d, J=9 Hz, 2H).

IV. N-[((5S)-3-{4-[exo-(1R,5S)-3-azabicyclo[3.1.0]hex-6-yl]-3,5-difluorophenyl]-2-oxo-1,3-oxazolidin-5-yl)methyl]propanamide

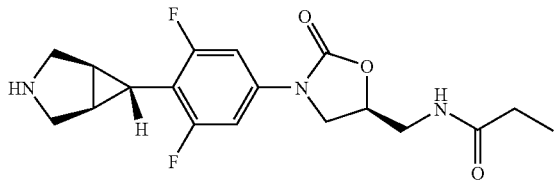

1-Chloroethyl chloroformate (0.31 mL, 2.88 mmol) was added to a solution of N-[((5S)-3-{3,5-difluoro-4-[exo-(1R,5S)-3-(4-methoxybenzyl)-3-azabicyclo[3.1.0]hex-6-yl]phenyl}-2-oxo-1,3-oxazolidin-5-yl)methyl]propanamide (0.7 g, 1.44 mmol) in dichloromethane (6.0 mL) and triethylamine (0.2 mL, 1.44 mmol) and the mixture stirred at 0° C. for 30 min. The reaction mixture was concentrated, dissolved in methanol (6 mL) and heated at reflux for 45 min. The reaction mixture was concentrated to provide the title compound as its hydrochloride salt. This material was used directly in the next reaction without further purification.

Yield 0.6 g (>95%).

Example 64

N-[((5S)-3-{3,5-difluoro-4-[exo-(1R,5S)-3-glycoloyl-3-azabicyclo[3.1.0]hex-6-yl]phenyl]-2-oxo-1,3-oxazolidin-5-yl)methyl]propanamide

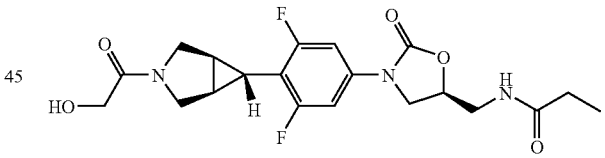

A solution of lithium hydroxide (97 mg, 2.32 mmol) in water (1.5 mL) was added to a solution of N-[((5S)-3-{3,5-difluoro-4-[exo-(1R,5S)-3-(acetoxyacetyl)-3-azabicyclo[3.1.0]hex-6-yl]phenyl}-2-oxo-1,3-oxazolidin-5-yl)methyl]propanamide (0.18 g, 0.39 mmol) in THF/methanol (8 mL, 1:1) and stirred at room temperature for 45 min. The reaction mixture was concentrated, diluted with dichloromethane, washed with 0.1N HCl, 2.5% NaHCO$_3$ and brine. The organic phase was dried (MgSO$_4$), filtered and concentrated. Purification by preparative TLC (5% methanol/10% acetonitrile/dichloromethane) provided the title compound.

Yield 0.12 g (73%). MS (m/z): [M+H]=424 $^1$H NMR (300 MHz, CDCl$_3$): 0.93 (t, J=9 Hz, 3H), 1.52 (t, J=3 Hz, 1H), 2.01-2.17 (m, 4H), 3.37-3.43 (m, 3H), 3.67-3.79 (m, 3H), 3.87-4.12 (m, 4H), 4.55 (t, J=6 Hz, 1H), 4.70-4.75 (m, 1H), 7.25 (d, J=12 Hz, 2H), 8.15 (t, J=6 Hz, 1H).

Intermediates for the synthesis of example 64 were prepared as follows

I. N-[((5S)-3-{3,5-difluoro-4-[exo-(1R,5S)-3-(acetoxyacetyl)-3-azabicyclo[3.1.0]hex-6-yl]phenyl}-2-oxo-1,3-oxazolidin-5-yl)methyl]propanamide

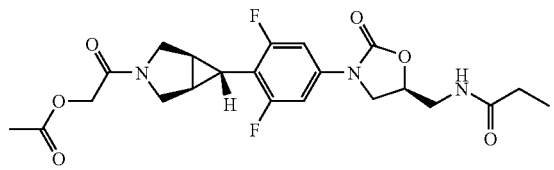

Acetoxyacetyl chloride (0.1 mL, 0.98 mmol) and N-[((5S)-3-{4-[exo-(1R,5S)-3-azabicyclo[3.1.0]hex-6-yl]-3,5-difluorophenyl}-2-oxo-1,3-oxazolidin-5-yl)methyl]propanamide (0.3 g, 0.82 mmol) were dissolved triethylamine (0.3 mL, 2.05 mmol) and dichloromethane (15 mL) and stirred at 0° C. for 45 min. The reaction mixture was diluted with dichloromethane, washed with dil. NaHCO₃ and brine. The organic extracts were dried (MgSO₄), filtered and concentrated. The title compound was isolated by preparative TLC (5% MeOH/10% acetonitrile/dichloromethane).

Yield 0.18 g (47%). MS (m/z): [M+H]=466 ¹H NMR (300 MHz, CDCl₃): 1.09 (t, J=9 Hz, 3H), 1.55-1.57 (m, 1H), 1.75 (s, 2H), 2.14-2.25 (m, 5H), 3.61-3.74 (m, 7H), 3.96 (t, J=9 Hz, 1H), 4.58 (s, 2H), 4.71-4.78 (m, 1H), 6.26 (s, 1H), 7.04 (d, J=12 Hz, 2H).

Example 65 exo-(1R,5S)-6-{2,6-difluoro-4-[(5R)-2-oxo-5-(1H-1,2,3-triazol-1-ylmethyl)-1,3-oxazolidin-3-yl]phenyl}-3-azabicyclo[3.1.0]hexane-3-carboxamide

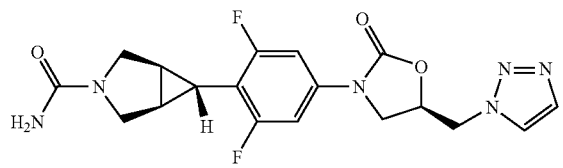

1-Chloroethyl chloroformate (0.067 mL, 0.62 mmol) was added to a cooled (0° C.) solution of (5R)-3-{4-[exo-(1R,5S)-3-(4-methoxybenzyl)-3-azabicyclo[3.1.0]hex-6-yl]-3,5-difluorophenyl}-5-(1H-1,2,3-triazol-1-ylmethyl)-1,3-oxazolidin-2-one (0.15 g, 0.31 mmol) in dichloromethane (1.5 mL) and triethylamine (0.043 mL, 0.31 mmol). After 30 min, the solution was concentrated, dissolved in methanol (1 mL) and heated at reflux for 45 min. The solution was cooled and concentrated to provide (5R)-3-{4-[exo-(1R,5S)-3-azabicyclo[3.1.0]hex-6-yl]-3,5-difluorophenyl}-5-(1H-1,2,3-triazol-1-ylmethyl)-1,3-oxazolidin-2-one as the hydrochloride salt. This material was dissolved in dichloromethane (6 mL) and triethylamine (0.086 mL, 0.62 mmol). Trimethylsilyl isocyanate (0.26 mL, 1.64 mmol) was added to the solution and stirred at room temperature for 16 h. The reaction mixture was diluted with dichloromethane and the solution was washed with 2.5% NaHCO₃ and brine. The organic phase was dried (MgSO₄), filtered and concentrated. Purification by preparative TLC (10% methanol/dichloromethane) provided the title compound.

Yield 35 mg (28%). MS (m/z): [M+H]=405 ¹H NMR (300 MHz, d₆-DMSO): 1.47 (t, J=3 Hz, 1H), 2.03 (s, 2H), 3.28-3.32 (m, 2H), 3.59, (d, J=9 Hz, 2H), 3.83-3.88 (m, 1H), 4.19 (t, J=9 Hz, 1H), 4.81 (d, J=6 Hz, 2H), 5.11-5.16 (m, 1H), 5.79 (s, 2H), 7.19 (d, J=9 Hz, 2H), 7.75 (d, J=3 Hz, 1H), 8.15 (d, J=3 Hz, 1H).

Intermediates for the synthesis of example 65 were prepared as follows.

I. 3-{3,5-difluoro-4-[exo-(1R,5S)-3-(4-methoxybenzyl)-3-azabicyclo[3.1.0]hex-6-yl]phenyl}-5-(hydroxymethyl)-1,3-oxazolidin-2-one

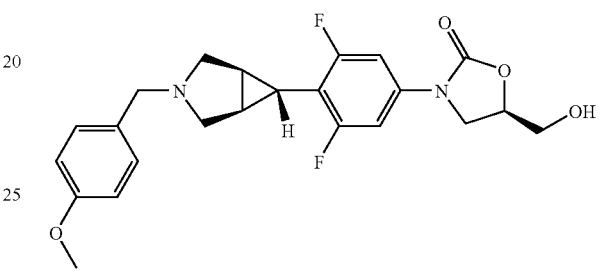

Lithium bis(trimethylsilyl)amide solution (4.3 mL of a 1.0 M THF solution, 4.3 mmol) was added to a cooled (−78° C.) solution of benzyl 3,5-difluoro-4-[exo-(1R,5S)-3-(4-methoxybenzyl)-3-azabicyclo[3.1.0]hex-6-yl]phenylcarbamate (1 g, 2.15 mmol) in THF (4.3 mL). After 90 min, R-glycidyl butyrate (0.33 mL, 2.36 mmol) was added to the solution, which was then warmed to room temperature and stirred for 36 h. Saturated aqueous ammonium chloride, H₂O and brine were added to the reaction mixture. The solution was extracted with ethyl acetate and the combined organic phases were dried (MgSO₄), filtered and concentrated to provide the title compound that was used directly in the next reaction without further purification.

II. (5R)-5-(azidomethyl)-3-{4-[exo-(1R,5S)-3-(4-methoxybenzyl)-3-azabicyclo[3.1.0]hex-6-yl]-3,5-difluorophenyl}-1,3-oxazolidin-2-one

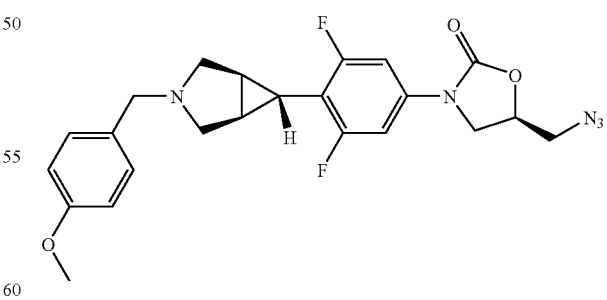

Methanesulfonyl chloride (0.16 mL, 2.1 mmol) was added to a cooled (0° C.) solution of 3-{3,5-difluoro-4-[exo-(1R,5S)-3-(4-methoxybenzyl)-3-azabicyclo[3.1.0]hex-6-yl]phenyl}-5-(hydroxymethyl)-1,3-oxazolidin-2-one (0.9 g, 2.1 mmol) in dichloromethane (10 mL) and triethylamine (0.45 mL, 3.15 mmol). After stirring at 0° C. for 45 min, the solution was diluted with dichloromethane and washed with saturated NaHCO$_3$, brine, dried (MgSO$_4$) and concentrated. This residue was dissolved in DMF (5 mL), treated with sodium azide (0.68 g, 10.5 mmol) and heated to 70° C. for 16 h. The solution was diluted with ethyl acetate and washed with water and brine, dried (MgSO$_4$), filtered and concentrated. The title compound was isolated by column chromatography (0-2% methanol/dichloromethane).

Yield 0.9 g (94%). MS (m/z): [M+H]=456 $^1$H NMR (300 MHz, CDCl$_3$): 1.87 (s, 2H), 2.29 (t, J=3 Hz, 1H), 2.44 (d, J=9 Hz, 2H), 3.10 (d, J=9 Hz, 2H), 3.57 (s, 2H), 3.65-3.77 (m, 6H), 4.01 (t, J=9 Hz, 1H), 4.71-4.79 (m, 1H), 6.82 (d, J=9 Hz, 2H), 7.03 (d, J=9 Hz, 2H), 7.20 (d, J=9 Hz, 2H).

III. (5R)-3-{4-[exo-(1R,5S)-3-(4-methoxybenzyl)-3-azabicyclo[3.1.0]hex-6-yl]-3,5-difluorophenyl}-5-(1H-1,2,3-triazol-1-ylmethyl)-1,3-oxazolidin-2-one

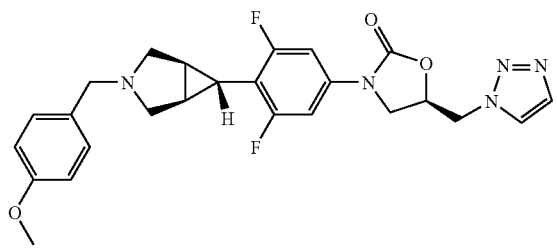

A solution of (5R)-5-(azidomethyl)-3-{4-[exo-(1R,5S)-3-(4-methoxybenzyl)-3-azabicyclo[3.1.0]hex-6-yl]-3,5-difluorophenyl}-1,3-oxazolidin-2-one (0.9 g, 1.98 mmol) and bicyclo[2.2.1]hepta-2,5-diene (0.43 mL, 3.95 mmol) in dioxane (40 mL) was stirred at 80° C. for 72 h. The reaction mixture was concentrated to provide the title compound that was used directly in the next reaction without further purification.

Example 66

N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]-2-hydroxyacetamide

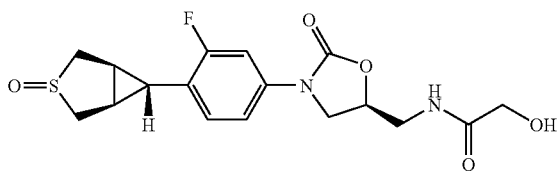

To a cold suspension of N-[((5S)-3-{3-fluoro-4-[exo-(1R,5S)-3-thiabicyclo[3.1.0]hex-6-yl]phenyl}-2-oxo-1,3-oxazolidin-5-yl)methyl]-2-hydroxyacetamide (1.23 mmol, 1 equiv.) in MeOH (18 mL) at 0° C. was added NaIO$_4$ aqueous (140 mg, 0.65 mmol, 1.06 equiv. in H$_2$O 5 mL). Another batch of NaIO$_4$ (20 mg) was added during next 48 hours. Then, the reaction mixture was diluted with CH$_2$Cl$_2$ (300 mL), washed with (H$_2$O, brine), dried (Na$_2$SO$_4$), filtered and evaporated to dry. The crude product was purified by chromatography on a silica gel column, eluting with a gradient increasing in polarity from 0 to 5% methanol in methylene chloride (contain 10% CH$_3$CN). Relevant fractions were combined to give the title compound as two separable diastereomers.

Yield (both isomers) 0.07 g (15%). MS (m/z): [2M+H]$^+$=765.2. HPLC (SYMMETRY C$_{18}$ 3.5 μM, 4.6×30 mm column; gradient elution 2%-98% MeCN with 0.1% TFA over 5 min; 2 mL/min rate): retention time=1.49 min. High Rf ("anti") isomer: $^1$H NMR (300 MHz, DMSO-d$_6$): 2.24 (s, 2H), 2.75 (t, J=4.2 Hz, 1H), 3.07 (d, J=14.4 Hz, 2H), 3.33-3.50 (m, 4H), 3.76 (m, 1H), 3.81 (d, J=5.7 Hz, 2H), 4.09 (t, J=9.0 Hz, 1H), 4.74 (m, 1H), 5.53 (t, J=5.7 Hz, 1H), 7.07 (t, J=8.4 Hz, 1H), 7.23 (m, 1H), 7.43 (d, J=13.2 Hz, 1H), 8.06 (t, J=5.4 Hz, 1H). Low Rf ("syn") isomer: $^1$H NMR (300 MHz, DMSO-d$_6$): 2.23 (t, J=3.9 Hz, 1H), 2.49 (m, 2H), 3.04 (d, J=15.0 Hz, 2H), 3.14 (m, 2H), 3.44 (m, 2H), 3.77 (m, 1H), 3.81 (d, J=5.7 Hz, 2H), 4.08 (t, J=9.0 Hz, 1H), 4.74 (m, 1H), 5.54 (t, J=5.7 Hz, 1H), 7.07 (t, J=8.7 Hz, 1H), 7.19 (m, 1H), 7.43 (dd, J=12.9 Hz, 2.1 Hz, 1H), 8.06 (t, J=6.0 Hz, 1H).

Intermediates for the synthesis of example 66 were prepared as follows.

I. N-[((5S)-3-{3-fluoro-4-[exo-(1R,5S)-3-thiabicyclo[3.1.0]hex-6-yl]phenyl}-2-oxo-1,3-oxazolidin-5-yl)methyl]-2-hydroxyacetamide

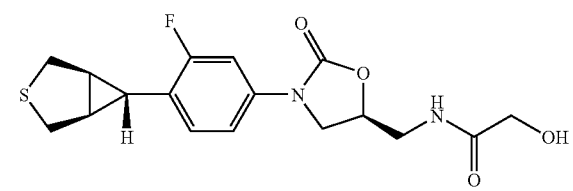

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (0.5 g, 1.23 mmol, 1 equiv.) in CH$_2$Cl$_2$ (10 mL) at 23° C., was added CF$_3$COOH (1.5 mL). After being stirred at 23° C. for 1.5 hour, solvent was evaporated and the residue dissolved in CH$_2$Cl$_2$ (25 mL) and cooled down to 0° C. Diisopropylethylamine (5 mL, 28.8 mmol, 23.4 equiv.) was added, followed by acetoxyacetyl chloride (0.157 mL, 1.46 mmol, 1.2 equiv.). The reaction mixture was stirred at 23° C. for 1.5 hours, diluted with CH$_2$Cl$_2$ (300 mL), and washed (NaHCO$_3$ aqueous, H$_2$O, brine), dried (Na$_2$SO$_4$), filtered and evaporated to dry to the title compound as its acetoxyacetamide. This material was used directly in the next step without further purification. To a solution of the acetoxy intermediate (assumed 1.23 mmol, 1 equiv.) in MeOH (12 mL) and THF (12 mL) at 23° C., was added aqueous LiOH (270 mg, 6.43 mmol, 5.25 equiv. In 12 mL of H$_2$O). After being stirred at 23° C. for 16 hour, the solution was diluted with 0.5 M HCl and extracted with CH$_2$Cl$_2$ (3×100 mL). The combined organic layers were washed with (H$_2$O, brine), dried (Na$_2$SO$_4$), filtered and evaporated to dry to give the title compound (0.22 g) which was used directly in the next step.

Example 67

N-[((5S)-3-{3-fluoro-4-{exo-(1R,5 S)-3,3-dioxido-3-thiabicyclo[3.1.0]hex-6-yl]phenyl}-2-oxo-1,3-oxazolidin-5-yl)methyl]-2-hydroxyacetamide

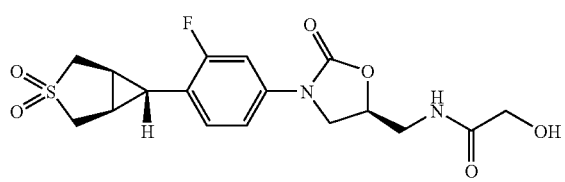

To a suspension of N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]-2-hydroxyacetamide (63 mg, 0.165 mmol, 1 equiv.) in THF (10 mL) at 0° C. was added $CH_3CO_3H$ (32% in AcOH, 0.1 mL, 0.48 mmol, 3.0 equiv.). The reaction mixture was stirred at 23° C. for 60 min and then more $CH_3CO_3H$ (32% in AcOH, 0.2 mL, 0.96 mmol, 6.0 equiv.) and MeOH (4 mL) was added. After another hour, the reaction mixture was diluted with $CHCl_3$ (200 mL) and the solution washed ($H_2O$, brine), dried ($Na_2SO_4$), filtered and evaporated to dryness. The crude product was purified by chromatography on a silica gel column, eluting with a gradient increasing in polarity from 0 to 5% methanol in methylene chloride (contain 10% $CH_3CN$). Relevant fractions were combined to give the title compound.

Yield 0.41 g (62%). MS (m/z): $[M+H]^+=399$. HPLC (SYMMETRY $C_{18}$ 3.5 µM, 4.6×30 mm column; gradient elution 2%-98% MeCN with 0.1% TFA over 5 min; 2 mL/min rate): retention time=1.66 min. $^1H$ NMR (300 MHz, DMSO-$d_6$): 2.08 (m, 2H), 2.32 (t, J=3.9 Hz, 1H), 2.99 (d, J=14.1 Hz, 2H), 3.45 (m, 2H), 3.58 (m, 2H), 3.76 (m, 1H), 3.81 (d, J=5.7 Hz, 2H, 4.09 (t, J=9.3 Hz, 1H), 4.74 (m, 1H), 5.54 (t, J=5.4 Hz, 1H), 7.12 (t, J=8.4 Hz, 1H), 7.20 (m, 1H), 7.44 (dd, J=12.9 Hz, 2.1 Hz, 1H), 8.06 (t, J=5.7 Hz, 1H).

Example 68

2-cyano-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide

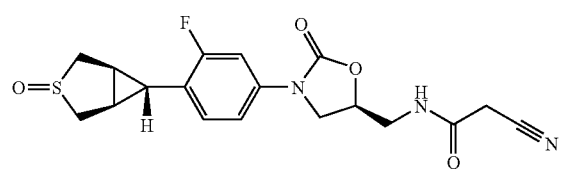

To a cold suspension of 2-cyano-N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide (1.23 mmol, 1 equiv.) in MeOH (18 mL) at 0° C. was added $NaIO_4$ aqueous (275 mg, 1.29 mmol, 1.05 equiv. in $H_2O$ 5 mL). Another batch of $NaIO_4$ (40 mg) was added during next 48 hours. Then, the reaction mixture was diluted with $CH_2Cl_2$ (300 mL), washed with ($H_2O$, brine), dried ($Na_2SO_4$), filtered and evaporated to dry. The crude product was purified by chromatography on a silica gel column, eluting with a gradient increasing in polarity from 0 to 5% methanol in methylene chloride (contain 10% $CH_3CN$). Relevant fractions were combined to give the desired compound.

Yield (both isomers) 0.174 g (36%). MS (m/z): $[M+H]^+=392$. HPLC (SYMMETRY $C_{18}$ 3.5 µM, 4.6×30 mm column; gradient elution 2%-98% MeCN with 0.1% TFA over 5 min; 2 mL/min rate): retention time=1.53 min. High Rf ("anti") isomer: $^1H$ NMR (300 MHz, DMSO-$d_6$): 2.23 (s, 2H), 2.75 (t, J=3.9 Hz, 1H), 3.07 (d, J=13.5 Hz, 2H), 3.36 (m, 2H), 3.44 (m, 2H), 3.67 (s, 2H), 3.70 (m, 1H), 4.09 (t, J=9.0 Hz, 1H), 4.74 (m, 1H), 7.07 (t, J=8.7 Hz, 1H), 7.21 (m, 1H), 7.43 (dd, J=12.9 Hz, J=2.4 Hz, 1H), 8.63 (t, J=6.3 Hz, 1H).

Low Rf ("syn") isomer: $^1H$ NMR (300 MHz, DMSO-$d_6$): 2.23 (t, J=3.9 Hz, 1H), 2.49 (m, 2H), 3.00 (m, 2H), 3.15 (m, 2H), 3.45 (m, 2H), 3.67 (s, 2H), 3.70 (m, 1H), 4.09 (m 1H), 4.74 (m, 1H), 7.07 (t, J=8.7 Hz, 1H), 7.19 (m, 1H), 7.43 (dd, J=12.9 Hz, 2.4 Hz, 1H), 8.62 (t, J=5.4 Hz, 1H).

Intermediates for the synthesis of Example 68 were prepared as follows.

I. 2-cyano-N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide

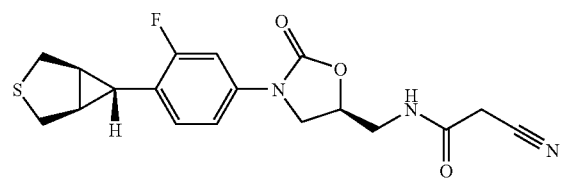

To a suspension of tert-butyl ((5S)-3-{3-fluoro-4-[exo-(1R,5S)-3-thiabicyclo[3.1.0]hex-6-yl]phenyl}-2-oxo-1,3-oxazolidin-5-yl)methylcarbamate (0.5 g, 1.23 mmol, 1 equiv.) in $CH_2Cl_2$ (10 mL) at 23° C., was added $CF_3COOH$ (1.5 mL). After being stirred at 23° C. for 1.5 hour, the solvent was evaporated and the residue dissolved in DMF (15 mL) and cooled down to 0° C. To the solution was added cyanoacetic acid (135 mg, 1.59 mmol, 1.3 equiv.), HOBT (248 mg, 1.84 mmol, 1.5 equiv.), EDCI (408 mg, 2.13 mmol, 1.74 equiv.) and DIEA (4.26 mL, 24.5 mmol, 20 equiv.). The reaction mixture was stirred at 23° C. for 17 hours and then diluted with $CH_2Cl_2$ (300 mL). The solution was then washed ($NaHCO_3$, $H_2O$, brine), dried ($Na_2SO_4$), filtered and evaporated to dryness to give the title compound which was used directly in the next step without further purification.

Example 69

2-cyano-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]acetamide

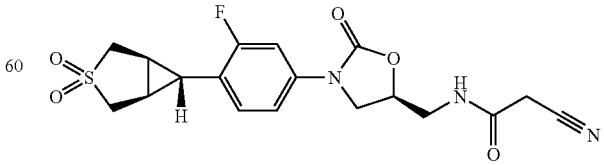

To a suspension of 2-cyano-N-[((5S)-3-{3-fluoro-4-[exo-(1R,5S)-3-oxido-3-thiabicyclo[3.1.0]hex-6-yl]phenyl}-2- oxo-1,3-oxazolidin-5-yl)methyl]acetamide (119 mg, 0.3 mmol, 1 equiv.) in THF (8 mL) and MeOH (4 mL) at 0° C. was added CH₃CO₃H (32% in AcOH, 0.32 mL, 1.52 mmol, 5.0 equiv.). The reaction mixture was stirred at 23° C. for 90 min and then diluted with CHCl₃ (200 mL). This solution was washed (H₂O, brine), dried (Na₂SO₄), filtered and evaporated to dryness. The crude product was purified by chromatography on a silica gel column, eluting with a gradient increasing in polarity from 0 to 5% methanol in methylene chloride (contain 10% CH₃CN). Relevant fractions were combined to give the title compound.

Yield 0.115 g (94%). MS (m/z): [M+H]⁺=408. HPLC (SYMMETRY C₁₈ 3.5 μM, 4.6×30 mm column; gradient elution 2%-98% MeCN with 0.1% TFA over 5 min; 2 mL/min rate): retention time=1.86 min. ¹H NMR (300 MHz, DMSO-d₆): 2.08 (m, 2H), 2.32 (t, J=4.2 Hz, 1H), 2.99 (d, J=14.1 Hz, 2H), 3.45 (m, 2H), 3.58 (m, 2H), 3.67 9s, 2H), 3.70 (m, 1H), 4.09 (t, J=9.0 Hz, 1H), 4.74 (m, 1H), 7.12 (t, J=8.7 Hz, 1H), 7.20 (m, 1H), 7.46 (dd, J=12.9 Hz, 2.4 Hz, 1H), 8.63 (t, J=5.4 Hz, 1H).

Example 70

2-cyano-N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide

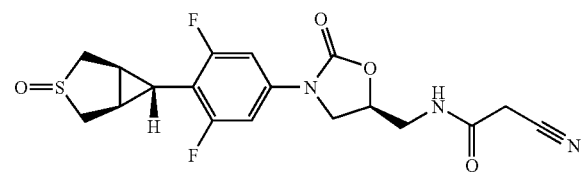

A solution of sodium periodate (0.13 g, 0.64 mmol) in water (2.4 mL) was added to a suspension of 2-cyano-N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]acetamide (0.23 g, 0.58 mmol) in methanol (7 mL) and stirred at 4° C. for 48 h. The resulting suspension was filtered with the aid of chloroform and the filtrate concentrated. The resulting solution was diluted with water and extracted with chloroform. The organic phase was dried (MgSO₄), filtered and concentrated. Purification by column chromatography (0-5% methanol-10% acetonitrile-dichloromethane) provided the title compound as a separable mixture of sulfoxide diastereomers (ca. 1:1 ratio).

Yield (total for both isomers) 0.072 g (30%). MS (m/z): [M+Na]=432 Low Rf ("syn") isomer: ¹H NMR (300 MHz, d₆-DMSO): 2.01 (t, J=6 Hz, 1H) 2.57 (s, 2H), 3.02-3.17 (m, 4H), 3.44-3.47 (m, 2H), 3.66 (m, 3H), 4.08 (t, J=6 Hz, 1H), 4.76 (m, 1H), 7.25 (d, J=9 Hz, 2H), 8.62 (t, J=6 Hz, 1H). High Rf ("anti") isomer: ¹H NMR (300 MHz, d₆-DMSO): 2.36-2.37 (m, 2H), 2.52-2.55 (m, 1H), 3.12 (d, J=15 Hz, 2H), 3.36-3.40 (m, 2H), 3.42 (m, 2H), 3.66-3.70 (m, 3H), 4.08 (t, J=9 Hz, 1H), 4.73-4.78 (m, 1H), 7.25 (d, J=12 Hz, 2H), 8.61 (t, J=6 Hz, 1H).

Intermediates for the synthesis of example 70 were prepared as follows.

I. (5S)-5-(aminomethyl)-3-{3,5-difluoro-4-[exo-(1R,5S)-3-thiabicyclo[3.1.0]hex-6-yl]phenyl}-1,3-oxazolidin-2-one

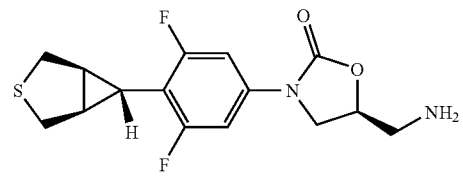

Trifluoroacetic acid (2.5 mL) was added to a solution of tert-butyl ((5S)-3-{3,5-difluoro-4-[exo-(1R,5S)-3-thiabicyclo[3.1.0]hex-6-yl]phenyl}-2-oxo-1,3-oxazolidin-5-yl)methylcarbamate (1.0 g, 2.34 mmol) in dichloroethane (25 mL). After stirring at room temperature for an hour, the solution was concentrated to obtain the title compound as a yellow solid that was used directly in the next reaction.

Yield 1.1 g (99%).

II. 2-cyano-N-[((5S)-3-{3,5-difluoro-4-[exo-(1R,5S)-3-thiabicyclo[3.1.0]hex-6-yl]phenyl}-2-oxo-1,3-oxazolidin-5-yl)methyl]acetamide

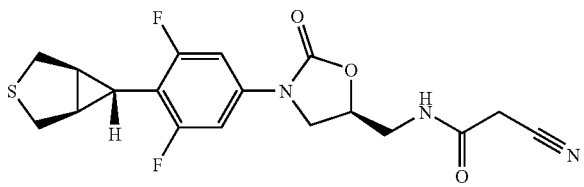

Cyano acetic acid (73 mg, 0.86 mmol) and (5S)-5-(aminomethyl)-3-{3,5-difluoro-4-[exo-(1R,5S)-3-thiabicyclo[3.1.0]hex-6-yl]phenyl}-1,3-oxazolidin-2-one (0.25 g, 0.57 mmol) were dissolved in diisopropylethylamine (1 mL, 5.7 mmol) and dichloromethane (11 mL). 1-hydroxybenzotriazole (0.11 mg, 0.86 mmol) and 1-(3-dimethylaminopropyl)-3-ethylcarbodiimide hydrochloride (0.16 g, 0.86 mmol) were added to the solution and stirred at room temperature for 18 h. The solution was diluted with dichloromethane, washed with saturated NaHCO₃, and brine. The organic phase was dried (MgSO₄), filtered and concentrated to obtain the title compound that was used directly in the next reaction.

Yield 0.2 g (89%).

Example 71

2-cyano-N-[((5S)-3-{3,5-difluoro-4-[exo-(1R,5S)-3,3-dioxide-3-thiabicyclo[3.1.0]hex-6-yl]phenyl}-2-oxo-1,3-oxazolidin-5-yl)methyl]acetamide

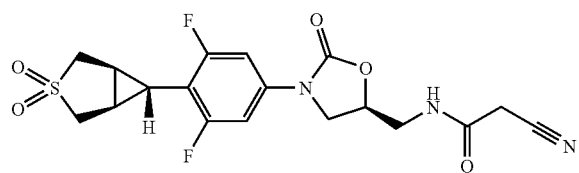

Peracetic acid (0.040 mL, 0.19 mmol) was added to a solution of 2-cyano-N-[((5S)-3-{3,5-difluoro-4-[exo-(1R,5S)-3-oxide-3-thiabicyclo[3.1.0]hex-6-yl]phenyl}-2-oxo-1,3-oxazolidin-5-yl)methyl]acetamide (26 mg, 0.064 mmol) in THF (1.0 mL) and was stirred at 4° C. for 4 h. Saturated Na$_2$S$_2$O$_3$ was added to the solution, the THF was removed in vacuo, and the resulting solution diluted with water and extracted with ethyl acetate. The organic phase was washed with brine, dried (MgSO$_4$) and concentrated. Preparative TLC (5% methanol/10% acetonitrile/dichloromethane) provided the title compound.

Yield 24 mg (88%). MS (m/z): [M+Na]=448 $^1$H NMR (300 MHz, d$_6$-DMSO): 2.15 (s, 3H), 3.01 (d, J=15 Hz, 2H), 3.43-3.45 (m, 2H), 3.59-3.70 (m, 5H), 4.09 (t, J=9 Hz, 1H), 4.75 (m, 1H) 7.27 (d, J=12 Hz, 2H), 8.61 (t, J=6Hz 1H).

Example 72

N-{[(5S)-3-(4-{exo-(1R,5S)-3-[amino(imino)methyl]-3-azabicyclo[3.1.0]hex-6-yl}-3-fluorophenyl)-2-oxo-1,3-oxazolidin-5-yl]methyl}acetamide

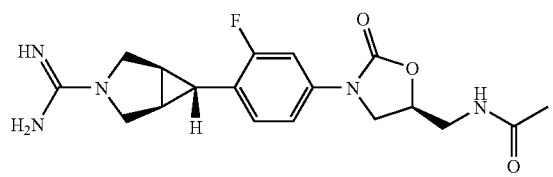

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.13 g, 0.39 mmol, 1 equivalent) and 1,3-bis(benzyloxycarbonyl)-2-methyl-2-thiopseudourea (181 mg, 0.505 mmol, 1.3 equiv.) in DMF (4.0 mL) at 23° C. was added triethyl amine (0.22 mL, 1.58 mmol, 4.0 equiv.), followed by silver triflate (140 mg, 0.54 mmol, 1.4 equiv.). The reaction mixture was stirred at the same temperature for 60 min, diluted with CH$_2$Cl$_2$ (200 mL), filtered through celite. The filtrate was washed by saturated NaHCO$_3$ aqueous, H$_2$O, brine, dried (Na$_2$SO$_4$), filtered and evaporated to dry. The residue was purified by chromatography on a silica gel column, eluting with a gradient increasing in polarity from 0 to 5% methanol in methylene chloride. Relevant fractions were combined to give the desired compound in its protected bis-benzylcarbamate form. This material (200 mg, 0.31 mmol) was dissolved in methanol (20 mL) and methylene chloride (10 mL) at 23° C. Then, 10% Pd/C (100 mg) was added and the reaction mixture was stirred at the same temperature for 1.5 hours under a hydrogen atmosphere. The reaction mixture was filtered through celite with the aid of methanol. The solvent was evaporated and the residue was dissolved in a mixture of 4.0 M HCl/dioxane (0.3 ml) and H$_2$O (10.0 mL). After being extracted with EtOAc, the aqueous solution was freeze-dried to give the desired compound as the HCl salt.

Yield 120 mg (95%). MS (m/z): [M+H]$^+$=376 $^1$H NMR (300 MHz, DMSO-d$_6$): 1.81 (bs, 4H), 2.10 (bs, 2H), 3.38 (t, J=8.4 Hz, 2H), 3.56 (m, 2H), 3.73 (m, 3H), 4.08 (t, J=9.0 Hz, 1H), 4.70 (m, 1H), 6.52 (bs, 1H), 7.10 (t, J=8.7 Hz, 1H), 7.19 (m, 1H), 7.44 (m, 4H), 8.31 (t, J=5.7 Hz, 1H).

Example 73 exo-(1R,5S)-N'-cyano-6-(4-{(5S)-5-[(acetylamino)methyl]-2-oxo-1,3-oxazolidin-3-yl}-2-fluorophenyl)-N-methyl-3-azabicyclo[3.1.0]hexane-3-carboximidamide

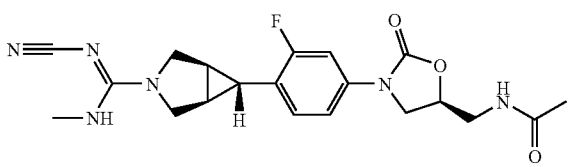

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.10 g, 0.3 mmol, 1 equivalent) and S-methyl N-cyano-N'-methylcarbamimidothioate (50 mg, 0.39 mmol, 1.3 equiv.) in DMF (4.0 mL) at 23° C. was added triethylamine (0.17 mL, 1.2 mmol, 4.0 equiv.), followed by silver triflate (100 mg, 0.39 mmol, 1.3 equiv.). The reaction mixture was stirred at the same temperature for 60 min, diluted with CH$_2$Cl$_2$ (200 mL), filtered through celite. The filtrate was washed by saturated NaHCO$_3$ aqueous, H$_2$O, brine, dried (Na$_2$SO$_4$), filtered and evaporated to dryness. The residue was purified by chromatography on a silica gel column, eluting with a gradient increasing in polarity from 0 to 10% methanol in methylene chloride. Relevant fractions were combined to give the title compound.

Yield 0.41 g (33%). MS (m/z): [M+H]$^+$=415. HPLC (SYMMETRY C$_{18}$ 3.5 μM, 4.6×30 mm column; gradient elution 2%-98% MeCN with 0.1% TFA over 5 min; 2 mL/min rate): retention time=1.84 min. $^1$H NMR (300 MHz, DMSO-d$_6$): 1.76 (t, J=3.6 Hz, 1H), 1.81 (s, 3H), 2.03 (s, 2H), 2.83 (d, J=4.2 Hz, 3H), 3.39 (t, J=5.4 Hz, 4H), 3.54 (m, 2H), 3.70 (m 1H), 3.82 (d, J=10.5 Hz, 2H), 4.08 (t, J=9.0 Hz, 1H), 4.71 (m, 1H), 6.91 (m, 1H), 7.08 (t, J=8.4 Hz, 1H), 7.18 (m, 1H), 7.42 (dd, J=12.9 Hz, 2.4 Hz, 1H), 8.23 (t, J=5.7 Hz, 1H).

Example 74 exo-(1R,5S)-N'-cyano-6-(4-{(5S)-5-[(acetylamino)methyl]-2-oxo-1,3-oxazolidin-3-yl}-2-fluorophenyl)-3-azabicyclo[3.1.0]hexane-3-carboximidamide

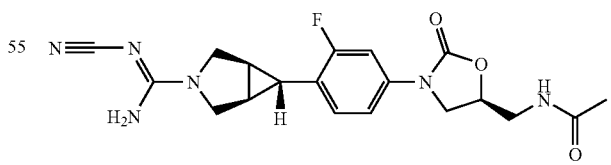

To a solid mixture of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.110 g, 0.33 mmol, 1 equivalent) and NaN(CN)$_2$ (60 mg, 0.67 mmol, 2.0 equiv.) at 23° C. was added n-BuOH (5.0 mL), followed by 1.0 M HCl (0.67 mL, 0.67 mmol, 2.0 equiv., made from 4.0 M HCl/dioxane and n-BuOH). The reaction mixture was refluxed for 2 hours, cooled down to 23° C., diluted with CH$_2$Cl$_2$ (200 mL), washed by saturated NH$_4$Cl aqueous, H$_2$O, brine, dried (Na$_2$SO$_4$), filtered and evaporated to dryness. The residue was purified by chromatography on a silica gel column, eluting with a gradient increasing in polarity from 0 to 10% methanol in methylene chloride. Relevant fractions were combined to give the title compound.

Yield 0.48 g (36%). MS (m/z): [M+H]$^+$=401. HPLC (SYMMETRY C$_{18}$ 3.5 µM, 4.6×30 mm column; gradient elution 2%-98% MeCN with 0.1% TFA over 5 min; 2 mL/min rate): retention time=1.80 min. $^1$H NMR (300 MHz, DMSO-d$_6$): 1.69 (t, J=3.6 Hz, 1H), 1.81 (s, 3H), 2.00 (s, 2H), 3.39 (m, 4H), 3.70 (m 3H), 4.08 (t, J=9.0 Hz, 1H), 4.71 (m, 1H), 7.01 (s, 2H), 7.07 (t, J=8.7 Hz, 1H), 7.18 (m, 1H), 7.42 (dd, J=12.9 Hz, 2.4 Hz, 1H), 8.24 (t, J=5.7 Hz, 1H).

Example 75

N-[((5S)-3-{3-fluoro-4-[exo-(1R,5S)-3-((E)-1-{methylamino}-2-nitrovinyl)-3-azabicyclo[3.1.0]hex-6-yl]phenyl}-2-oxo-1,3-oxazolidin-5-yl)methyl]acetamide

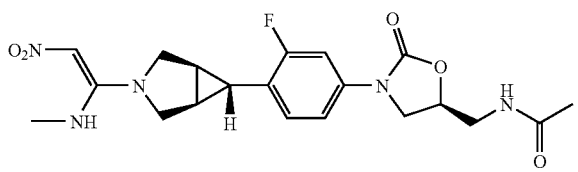

To a solution of N-[((5S)-3-{4-[exo-(1R,5S)-3-azabicyclo[3.1.0]hex-6-yl]-3-fluorophenyl}-2-oxo-1,3-oxazolidin-5-yl)methyl]acetamide (0.09 g, 0.27 mmol, 1 equivalent) and N-methyl-1-(methylthio)-2-nitro-ethenamine (52 mg, 0.35 mmol, 1.3 equiv.) in DMF (5.0 mL) at 23° C. was added triethylamine (0.15 mL, 1.1 mmol, 4.0 equiv.), followed by silver triflate (90 mg, 0.35 mmol, 1.3 equiv.). The reaction mixture was stirred at the same temperature for 90 min, diluted with CH$_2$Cl$_2$ (200 mL), filtered through celite. The filtrate was washed by saturated NaHCO$_3$ aqueous, H$_2$O, brine, dried (Na$_2$SO$_4$), filtered and evaporated to dry. The residue was purified by chromatography on a silica gel column, eluting with a gradient increasing in polarity from 0 to 10% methanol in methylene chloride. Relevant fractions were combined to give the desired compound.

Yield 0.55 g (47%). MS (m/z): [M+H]$^+$=434. HPLC (SYMMETRY C$_{18}$ 3.5 µM, 4.6×30 mm column; gradient elution 2%-98% MeCN with 0.1% TFA over 5 min; 2 mL/min rate): retention time=1.64 min. $^1$H NMR (300 MHz, DMSO-d$_6$): 1.81 (s, 3H), 1.83 (m, 1H), 2.06 (s, 2H), 2.94 (d, J=5.1 Hz, 3H), 3.39 (t, J=5.1 Hz, 4H), 3.69 (m, 2H), 3.72 (m 1H), 3.82 (d, J=10.8 Hz, 2H), 4.08 (t, J=9.6 Hz, 1H), 4.71 (m, 1H), 6.44 (s, 1H), 7.08 (t, J=8.4 Hz, 1H), 7.19 (m, 1H), 7.42 (d, J=12.3 Hz, 1H), 8.24 (t, J=5.4 Hz, 1H), 9.11 (bs, 1H).

We claim:

1. A compound of formula I:

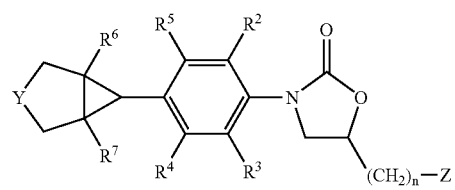

or a pharmaceutically acceptable salts thereof;

wherein Y is —SO$_m$—, —O—, or —N(R$^8$)—;

Z is C(=Q)R$^1$, —NHC(=Q)R$^1$, —C(=Q)NHR$^1$, —NHC(=NCN)R$^1$, —NHC(=NNO$_2$)R$^1$, —SO$_2$R$^1$, or —NH$_2$;

Q is oxygen or sulfur atom;

R$^1$—H, OH, —NH$_2$, —NHC$_{1-4}$alkyl, —C$_{1-4}$alkyl, —C$_{2-4}$alkenyl, —(CH$_2$)$_p$C(=O)C$_{1-4}$alkyl, —OC$_{1-4}$alkyl, —SC$_{1-4}$alkyl, —(CH$_2$)$_p$C$_{3-6}$cycloalkyl, —CH=CH-aryl, or CH$_2$C(=O)-aryl;

R$^2$ and R$^3$ are independently —H, or —F;

R$^4$ and R$^5$ are independently —H, —Cl, —F, —CH$_3$, —NH$_2$, or —OH;

R$^6$ and R$^7$ are independently —H, or —C$_{1-4}$alkyl;

R$^8$ independently —H, —OH, —CN, —NR$^9$R$^{10}$, —C$_{1-4}$alkyl, —C$_{3-6}$cycloalkyl, —C$_{1-4}$heteroalkyl, -aryl, —C$_{1-4}$alkylNR$^9$R$^{10}$, —(CH$_2$)$_p$C(=O)C$_{1-4}$alkyl, —(CH$_2$)$_p$C(=O)C$_{3-6}$cycloalkyl, —(CH$_2$)$_p$C(=O)C$_{1-4}$heteroalkyl, —C(=O)H, —(CH$_2$)$_p$C(=O)OR$^9$, —C(=O)(CH$_2$)$_p$OR$^9$, —(CH$_2$)$_p$C(=O)C$_{1-4}$alkylOR$^9$, —(CH$_2$)$_p$C(=O)(CH$_2$)$_p$NR$^9$R$^{10}$, —(CH$_2$)$_p$C(=O)NR$^9$OR$^{10}$, —(CH$_2$)$_p$CH(=NOC$_{1-4}$alkyl), —(CH$_2$)$_p$C(=NOC$_{1-4}$alkyl)C$_{1-4}$alkyl, —(CH$_2$)$_p$—SO$_2$—C$_{1-4}$alkyl, —(CH$_2$)$_p$—SO$_2$—NR$^9$R$^{10}$, CONHR$^9$, or —C(=R$^{11}$)(NR$^{12}$R$^{12}$);

each R$^9$ and R$^{10}$ are independently —H, —C$_{1-4}$alkyl, —C$_{3-6}$cycloalkyl, -aryl, —C(=O)C$_{1-4}$alkyl, —C(=O)NHC$_{1-4}$alkyl, —C(=O)aryl, —SO$_2$C$_{1-4}$alkyl, or —SO$_2$NH$_2$;

R$^{11}$ is =NH, =NCN, or CHNO$_2$;

each R$^{12}$ is independently H, or C$_{1-3}$alkyl;

each m is independently an integer equal to 0, 1, or 2;

each n is independently an integer equal to 0, or 1;

each p is an integer equal to 0, 1 or 2; and at each occurrence, C$_{1-4}$alkyl, or C$_{3-6}$cycloalkyl is optionally substituted by one to three halo, hydroxyl, —CN, OC$_{1-2}$alkyl or aryl.

2. A compound according to claim 1 which is a compound of formula IA

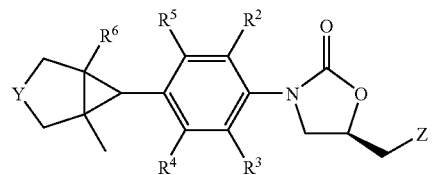

wherein Z is —NHC(=Q)R¹, or a compound of formula IB

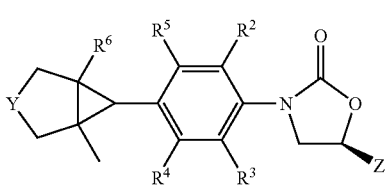

wherein Z is —C(=O)NH₂.

3. A compound of claim 2 wherein Q is oxygen atom.

4. A compound of claim 2 wherein R¹ is $C_{1-4}$alkyl, optionally substituted with one, two or three fluoro or chloro.

5. A compound of claim 2, wherein R¹ is $C_{1-4}$alkyl or $C_{3-6}$cycloalkyl, optionally substituted with —OH, or CN.

6. A compound of claim 2 wherein R¹ is —CH₃, —CHF₂, —CF₃, —CHCl₂, —CH₂CF₃, —CH₂CH₃, —CH₂CHF₂, or —CH₂CH₂F.

7. A compound of claim 2 wherein R² and R³ are —H.

8. A compound of claim 2, wherein R⁴ and R⁵ are independently —H or —F.

9. The compound of claim 2, wherein R⁶ and R⁷ are —H.

10. A compound of claim 2 wherein Y is —N(R⁸)—.

11. A compound of claim 10 wherein R⁸ is —C(=O)(CH₂)$_p$OR⁹.

12. A compound of claim 11 wherein R⁹ is H or $C_{1-4}$alkyl.

13. A compound of claim 10 wherein R⁸ is —C(=O)$C_{1-4}$alkyl, wherein the alkyl is optionally substituted with one, two, or three OH, F, or CN.

14. A compound of claim 10 wherein R⁸ is —(CH₂)$_p$C(=O)$C_{3-6}$cycloalkyl wherein the alkyl is optionally substituted with one, two, or three OH, F, or CN.

15. A compound of claim 10 wherein R⁸ is —(CH₂)$_p$C(=O)(CH₂)$_p$NR⁹R¹⁰.

16. A compound of claim 15 wherein R⁹ and R¹⁰ are independently H, $C_{1-4}$alkyl, or —C(=O)$C_{1-4}$alkyl.

17. A compound of claim 10 wherein R⁸ is —C(=O)H, —C(=O)CH₂OH, —C(=O)CH(OH)CH₂OH, —C(=O)het¹, or —C(=O)(CH₂)het².

18. A compound of claim 10 wherein R⁸ is (R¹¹=)C—NR¹²R¹², wherein R¹¹ is —NH, —NCN, or —CHNO₂; and each R¹² is independently H, or $C_{1-3}$alkyl.

19. A compound of claim 2 wherein Y is —S—, —SO—, —SO₂—, or, —O—.

20. A compound of claim 1 which is
(1) N-[((5S)-3-{3-fluoro-4-[exo-(1R,5S)-3-thiabicyclo[3.1.0]hex-6-yl]phenyl}-2-oxo-1,3-oxazolidin-5-yl)methyl]acetamide,
(2) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide,
(3) N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]acetamide,
(4) N-[((5S)-3-{3-fluoro-4-[exo-(1R,5S)-3-oxabicyclo[3.1.0]hex-6-yl]-3-oxo-1,3-oxazolidin-5-yl)methyl]acetamide,
(5) N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]acetamide,
(6) 2,2-difluoro-N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]ethanethioamide,
(7) methyl exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxylate,
(8) N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]acetamide,
(9) N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]acetamide,
(10) exo-(1R,5S)-6-(4-{(5S)-5-[(acetylamino)methyl]-2-oxo-1,3-oxazolidin-3-yl}-2-fluorophenyl)-3-azabicyclo[3.1.0]hexane-3-carboxamide,
(11) exo-(1R,5S)-6-[4-((5S)-5-{[(2,2-difluoroethanethioyl)amino]methyl}-2-oxo-1,3-oxazolidin-3-yl)-2-fluorophenyl]-3-azabicyclo[3.1.0]hexane-3-carboxamide,
(12) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide,
(13) N-[((5S)-3-{4-[exo-(1R,5S)-3,3-dioxido-3-thiabicyclo[3.1.0]hex-6-yl]-3,5-difluorophenyl}-2-oxo-1,3-oxazolidin-5-yl)methyl]acetamide,
(14) N-[((5S)-3-{3,5-difluoro-4-[exo-(1R,5S)-3-oxabicyclo[3.1.0]hex-6-yl]phenyl}-2-oxo-1,3-oxazolidin-5-yl)methyl]acetamide,
(15) N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]acetamide,
(16) N-[((5S)-3-{4-[exo-(1R,5S)-3-oxabicyclo[3.1.0]hex-6-yl]phenyl}-2-oxo-1,3-oxazolidin-5-yl)methyl]acetamide,
(17) N-[((5S)-3-{4-[exo-(1R,5S)-3-glycoloyl-3-azabicyclo[3.1.0]hex-6-yl]phenyl}-2-oxo-1,3-oxazolidin-5-yl)methyl]acetamide,
(18) N-[((5S)-3-{4-[exo-(1R,5S)-3-oxido-3-thiabicyclo[3.1.0]hex-6-yl]phenyl}-2-oxo-1,3-oxazolidin-5-yl)methyl]acetamide,
(19) N-[((5S)-3-{4-[exo-(1R,5S)-3,3-dioxido-3-thiabicyclo[3.1.0]hex-6-yl]phenyl}-2-oxo-1,3-oxazolidin-5-yl)methyl]acetamide,
(20) (5R)-3-{4-[exo-(1R,5S)-3,3-dioxido-3-thiabicyclo[3.1.0]hex-6-yl]-3-fluorophenyl}-2-oxo-1,3-oxazolidine-5-carboxamide,
(21) N-[((5S)-3-{4-[exo-(1R,5S)-3-azabicyclo[3.1.0]hex-6-yl]-3-fluorophenyl}-2-oxo-1,3-oxazolidin-5-yl)methyl]propanamide,
(22) N-[((5S)-3-{3-fluoro-4-[exo-(1R,5S)-3-formyl-3-azabicyclo[3.1.0]hex-6-yl]phenyl}-2-oxo-1,3-oxazolidin-5-yl)methyl]propanamide,
(23) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-carboxamide,
(24) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-methylcarboxamide,
(25) exo-(1R,5S)-6-(4-{(5S)-5-[(propanoylamino)methyl]-2-oxo-1,3-oxazolidin-3-yl}-2-fluorophenyl)-3-azabicyclo[3.1.0]hexane-3-ethylcarboxamide,
(26) N-[((5S)-3-{3-fluoro-4-[exo-(1R,5S)-3-glycoloyl-3-azabicyclo[3.1.0]hex-6-yl]phenyl}-2-oxo-1,3-oxazolidin-5-yl)methyl]propanamide,
(27) N-[((5S)-3-{3-fluoro-4-[exo-(1R,5S)-3-methoxyacetyl-3-azabicyclo[3.1.0]hex-6-yl]phenyl}-2-oxo-1,3-oxazolidin-5-yl)methyl]propanamide,
(28) N-[((5S)-3-{3-fluoro-4-[exo-(1R,5S)-3-((2S)-2,3-dihydroxypropanoyl)-3-azabicyclo[3.1.0]hex-6-yl]phenyl}-2-oxo-1,3-oxazolidin-5-yl)methyl]propanamide,

(29) N-[((5S)-3-{3-fluoro-4-[exo-(1R,5S)-3-(2-(S)-hydroxypropanoyl)-3-azabicyclo[3.1.0]hex-6-yl]phenyl}-2-oxo-1,3-oxazolidin-5-yl)methyl]acetamide,
(30) N-[((5S)-3-{3-fluoro-4-[exo-(1R,5S)-3-cyclopropanecarbonyl-3-azabicyclo[3.1.0]hex-6-yl]phenyl}-2-oxo-1,3-oxazolidin-5-yl)methyl]acetamide,
(31) N-[((5S)-3-{3-fluoro-4-[exo-(1R,5S)-3-(1-hydroxycyclopropanecarbonyl)-3-azabicyclo[3.1.0]hex-6-yl]phenyl}-2-oxo-1,3-oxazolidin-5-yl)methyl]acetamide,
(32) N-[((5S)-3-{3-fluoro-4-[exo-(1R,5S)-3-(2-hydroxy-2-methyl-propanoyl)-3-azabicyclo[3.1.0]hex-6-yl]phenyl}-2-oxo-1,3-oxazolidin-5-yl)methyl]acetamide,
(33) N-[((5S)-3-{3-fluoro-4-[exo-(1R,5S)-3-(3,3,3-trifluoro-2-(S)-hydroxypropanoyl)-3-azabicyclo[3.1.0]hex-6-yl]phenyl}-2-oxo-1,3-oxazolidin-5-yl)methyl]acetamide,
(34) N-[((5S)-3-{3-fluoro-4-[exo-(1R,5S)-3-difluoroacetyl-3-azabicyclo[3.1.0]hex-6-yl]phenyl}-2-oxo-1,3-oxazolidin-5-yl)methyl]acetamide,
(35) N-[((5S)-3-{3-fluoro-4-[exo-(1R,5S)-3-aminoacetyl-1,3-azabicyclo[3.1.0]hex-6-yl]phenyl}-2-oxo-1,3-oxazolidin-5-yl)methyl]acetamide,
(36) N-[((5S)-3-{3-fluoro-4-[exo-(1R,5S)-3-acetylaminoacetyl-3-azabicyclo-[3.1.0]hex-6-yl]phenyl}-2-oxo-1,3-oxazolidin-5-yl)methyl]acetamide,
(37) N-[((5S)-3-{3-fluoro-4-[exo-(1R,5S)-3-(2-fluoroethyl)-3-azabicyclo[3.1.0]hex-6-yl]phenyl}-2-oxo-1,3-oxazolidin-5-yl)methyl]acetamide,
(38) N-[((5S)-3-{3-fluoro-4-[exo-(1R,5S)-3-(2-hydroxyethyl)-3-azabicyclo[3.1.0]hex-6-yl]phenyl}-2-oxo-1,3-oxazolidin-5-yl)methyl]acetamide,
(39) N-[((5S)-3-{3-fluoro-4-[exo-(1R,5S)-3-(2-cyanoethyl)-3-azabicyclo[3.1.0]hex-6-yl]phenyl}-2-oxo-1,3-oxazolidin-5-yl)methyl]acetamide,
(40) N-[((5S)-3-{3-fluoro-4-[exo-(1R,5S)-3-dimethylamino-3-azabicyclo[3.1.0]hex-6-yl]phenyl}-2-oxo-1,3-oxazolidin-5-yl)methyl]acetamide,
(41) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide,
(42) N-[((5S)-3-{4-[exo-(1R,5S)-3,3-dioxido-3-thiabicyclo[3.1.0]hex-6-yl]-3-fluorophenyl}-2-oxo-1,3-oxazolidin-5-yl)methyl]propanamide,
(43) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide,
(44) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide,
(45) 2,2-difluoro-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]propanamide,
(46) 2,2-difluoro-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(47) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]cyclobutanecarboxamide,
(48) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]cyclobutanecarboxamide,
(49) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]propanamide,
(50) N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(51) 2,2-difluoro-N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]propanamide,
(52) N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]cyclopropanecarboxamide,
(53) N-[((5S)-3-{3,5-difluoro-4-[exo-(1R,5S)-3,3-dioxido-3-thiabicyclo[3.1.0]hex-6-yl]phenyl}-2-oxo-1,3-oxazolidin-5-yl)methyl]cyclopropanecarboxamide,
(54) exo-(1R,5S)-6-(4-{(5S)-5-[(propanoylamino)methyl]-2-oxo-1,3-oxazolidin-3-yl}-2,6-difluorophenyl)-3-azabicyclo[3.1.0]hexane-3-carboxamide,
(55) N-[((5S)-3-{3,5-difluoro-4-[exo-(1R,5S)-3-glycoloyl-3-azabicyclo[3.1.0]hex-6-yl]phenyl}-2-oxo-1,3-oxazolidin-5-yl)methyl]propanamide,
(56) N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]-2-hydroxyacetamide,
(57) N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]-2-hydroxyacetamide,
(58) 2-cyano-N-[((5S)-3-{3-fluoro-4-[exo-(1R,5S)-3-oxido-3-thiabicyclo[3.1.0]hex-6-yl]phenyl}-2-oxo-1,3-oxazolidin-5-yl)methyl]acetamide,
(59) 2-cyano-N-[((5S)-3-{3-fluoro-4-[exo-(1R,5S)-3,3-dioxido-3-thiabicyclo[3.1.0]hex-6-yl]phenyl}-2-oxo-1,3-oxazolidin-5-yl)methyl]acetamide,
(60) 2-cyano-N-[((5S)-3-{3,5-difluoro-4-[exo-(1R,5S)-3-oxido-3-thiabicyclo[3.1.0]hex-6-yl]phenyl}-2-oxo-1,3-oxazolidin-5-yl)methyl]acetamide,
(61) 2-cyano-N-[((5S)-3-{3,5-difluoro-4-[exo-(1R,5S)-3,3-dioxide-3-thiabicyclo[3.1.0]hex-6-yl]phenyl}-2-oxo-1,3-oxazolidin-5-yl)methyl]acetamide,
(62) N-{[(5S)-3-(4-{exo-(1R,5S)-3-[amino(imino)methyl]-3-azabicyclo[3.1.0]hex-6-yl}-3-fluorophenyl)-2-oxo-1,3-oxazolidin-5-yl]methyl}acetamide,
(63) exo-(1R,5S)-N'-cyano-6-(4-{(5S)-5-[(acetylamino)methyl]-2-oxo-1,3-oxazolidin-3-yl}-2-fluorophenyl)-N-methyl-3-azabicyclo[3.1.0]hexane-3-carboximidamide,
(64) exo-(1R,5S)-N'-cyano-6-(4-{(5S)-5-[(acetylamino)methyl]-2-oxo-1,3-oxazolidin-3-yl}-2-fluorophenyl)-3-azabicyclo[3.1.0]hexane-3-carboximidamide, or
(65) N-[((5S)-3-{3-fluoro-4-[exo-(1R,5S)-3-((E)-1-{methylamino}-2-nitrovinyl)-3-azabicyclo[3.1.0]hex-6-yl]phenyl}-2-oxo-1,3-oxazolidin-5-yl)methyl]acetamide.

21. A method for treating bacterial infections comprising administering to a mammal being treated a pharmaceutically effective amount of the compound of claim 1.

22. The method of claim 21 wherein the compound is administered parenterally, topically, rectally, or instranasally.

23. The method of claim 21 wherein the compound is administered orally.

24. The method of claim 21 wherein parenteral administration is subcutaneous, intravenous, intramuscular, intradermal, intrathecal, intraocular, intravetricular injection.

25. The method of claim 21 wherein said compound is administered in an amount of from about 0.1 to about 100 mg/kg of body weight/day.

26. The method of claim 21 wherein said compound is administered in an amount of from about 1 to about 50 mg/kg of body weight/day.

27. The method of claim 21 wherein said infection is skin infection.

28. The method of claim 21 wherein the infection is eye infection.

29. The method of claim 21 wherein said mammal is human.

30. The method of claim 21 wherein said mammal is an animal.

31. A pharmaceutical composition comprising a compound of claim 1 and a pharmaceutically acceptable carrier.

* * * * *